United States Patent
Parfett et al.

(10) Patent No.: US 12,201,304 B2
(45) Date of Patent: Jan. 21, 2025

(54) METHOD FOR CLOSED LOOP CONTROL OF MOTOR VELOCITY OF A SURGICAL STAPLING AND CUTTING INSTRUMENT

(71) Applicant: Cilag GmbH International, Zug (CH)

(72) Inventors: Raymond E. Parfett, Loveland, OH (US); Shane R. Adams, Lebanon, OH (US); Frederick E. Shelton, IV, Hillsboro, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/388,677

(22) Filed: Nov. 10, 2023

(65) Prior Publication Data

US 2024/0081839 A1    Mar. 14, 2024

Related U.S. Application Data

(63) Continuation of application No. 17/548,713, filed on Dec. 13, 2021, now Pat. No. 11,871,939, which is a continuation of application No. 16/752,983, filed on Jan. 27, 2020, now Pat. No. 11,213,302, which is a continuation of application No. 16/170,801, filed on
(Continued)

(51) Int. Cl.
| | | |
|---|---|---|
| *G05B 19/04* | (2006.01) | |
| *A61B 17/072* | (2006.01) | |
| *A61B 17/16* | (2006.01) | |
| *A61B 34/00* | (2016.01) | |

(Continued)

(52) U.S. Cl.
CPC .... *A61B 17/1626* (2013.01); *A61B 17/07207* (2013.01); *A61B 34/76* (2016.02); *A61B 2017/00017* (2013.01); *A61B 2017/00039* (2013.01); *A61B 2017/00398* (2013.01); *A61B 2017/07278* (2013.01); *A61B 2017/07285* (2013.01); *A61B 2017/320052* (2013.01)

(58) Field of Classification Search
CPC ...... G05B 2219/37094; A61B 17/1626; A61B 34/76; A61B 17/07207; A61B 2017/00017; A61B 2017/07285; A61B 2017/00398; A61B 2017/07278; A61B 2017/320052; A61B 2017/00039
See application file for complete search history.

(56) References Cited

U.S. PATENT DOCUMENTS

| 7,845,537 B2 | 12/2010 | Shelton, IV et al. |
| 8,210,411 B2 | 7/2012 | Yates et al. |

(Continued)

FOREIGN PATENT DOCUMENTS

| WO | WO-9710765 A1 * | 3/1997 | ............. A61B 17/14 |

*Primary Examiner* — Karen Masih

(57) ABSTRACT

A surgical system comprising an end effector, a firing driver movable during a firing stroke, a motor to drive the firing driver during the firing stroke, and a control circuit is disclosed. The control circuit is to initiate the firing stroke to drive the firing driver in a first mode, wherein, in the first mode, the motor is to drive the firing driver at a first speed; detect a first motor stall condition in the first mode; transition from the first mode to a second mode based on the detected first motor stall condition, wherein, in the second mode, the motor is to drive the firing driver at a second speed less than the first speed; detect a second motor stall condition in the second mode; and pause driving the firing driver for a period of time based on the detected second motor stall condition.

20 Claims, 73 Drawing Sheets

Related U.S. Application Data

Oct. 25, 2018, now Pat. No. 10,595,882, which is a continuation of application No. 15/628,045, filed on Jun. 20, 2017, now Pat. No. 10,307,170.

(51) Int. Cl.
 *A61B 17/00* (2006.01)
 *A61B 17/32* (2006.01)

(56) References Cited

U.S. PATENT DOCUMENTS

| | | |
|---|---|---|
| 8,967,443 B2 | 3/2015 | McCuen |
| 9,002,518 B2 | 4/2015 | Manzo et al. |
| 9,072,535 B2 | 7/2015 | Shelton, IV et al. |
| 9,345,481 B2 | 5/2016 | Hall et al. |
| 10,013,049 B2 | 7/2018 | Leimbach et al. |
| 10,307,170 B2 | 6/2019 | Parfett et al. |
| 10,327,767 B2 | 6/2019 | Shelton, IV et al. |
| 10,368,864 B2 | 8/2019 | Harris et al. |
| 10,390,841 B2 | 8/2019 | Shelton, IV et al. |
| D879,808 S | 3/2020 | Harris et al. |
| D879,809 S | 3/2020 | Harris et al. |
| 10,595,882 B2 | 3/2020 | Parfett et al. |
| 10,624,633 B2 | 4/2020 | Shelton, IV et al. |
| 10,646,220 B2 | 5/2020 | Shelton, IV et al. |
| D890,784 S | 7/2020 | Shelton, IV et al. |
| 10,779,820 B2 | 9/2020 | Harris et al. |
| 10,813,639 B2 | 10/2020 | Shelton, IV et al. |
| 10,881,396 B2 | 1/2021 | Shelton, IV et al. |
| 10,881,399 B2 | 1/2021 | Shelton, IV et al. |
| 10,888,321 B2 | 1/2021 | Shelton, IV et al. |
| 10,980,537 B2 | 4/2021 | Shelton, IV et al. |
| 11,071,554 B2 | 7/2021 | Parfett et al. |
| 11,090,046 B2 | 8/2021 | Shelton, IV et al. |
| 11,213,302 B2 | 1/2022 | Parfett et al. |
| 11,382,638 B2 | 7/2022 | Harris et al. |
| 11,517,325 B2 | 12/2022 | Shelton, IV et al. |
| 11,607,239 B2 | 3/2023 | Swensgard et al. |
| 11,653,914 B2 | 5/2023 | Shelton, IV et al. |
| 11,871,939 B2 | 1/2024 | Parfett et al. |
| 2014/0263541 A1 | 9/2014 | Leimbach et al. |
| 2014/0263552 A1 | 9/2014 | Hall et al. |
| 2018/0360456 A1 | 12/2018 | Shelton, IV et al. |

\* cited by examiner

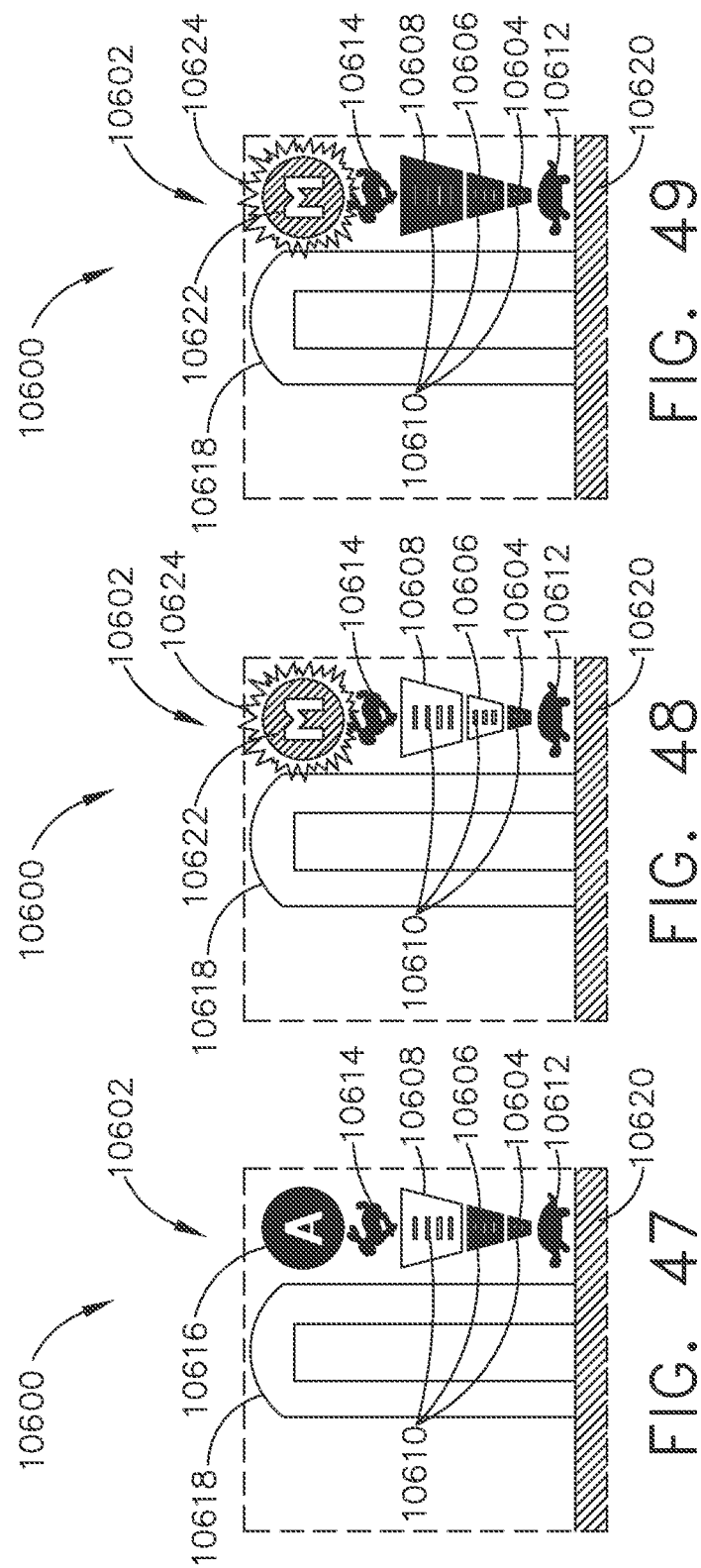

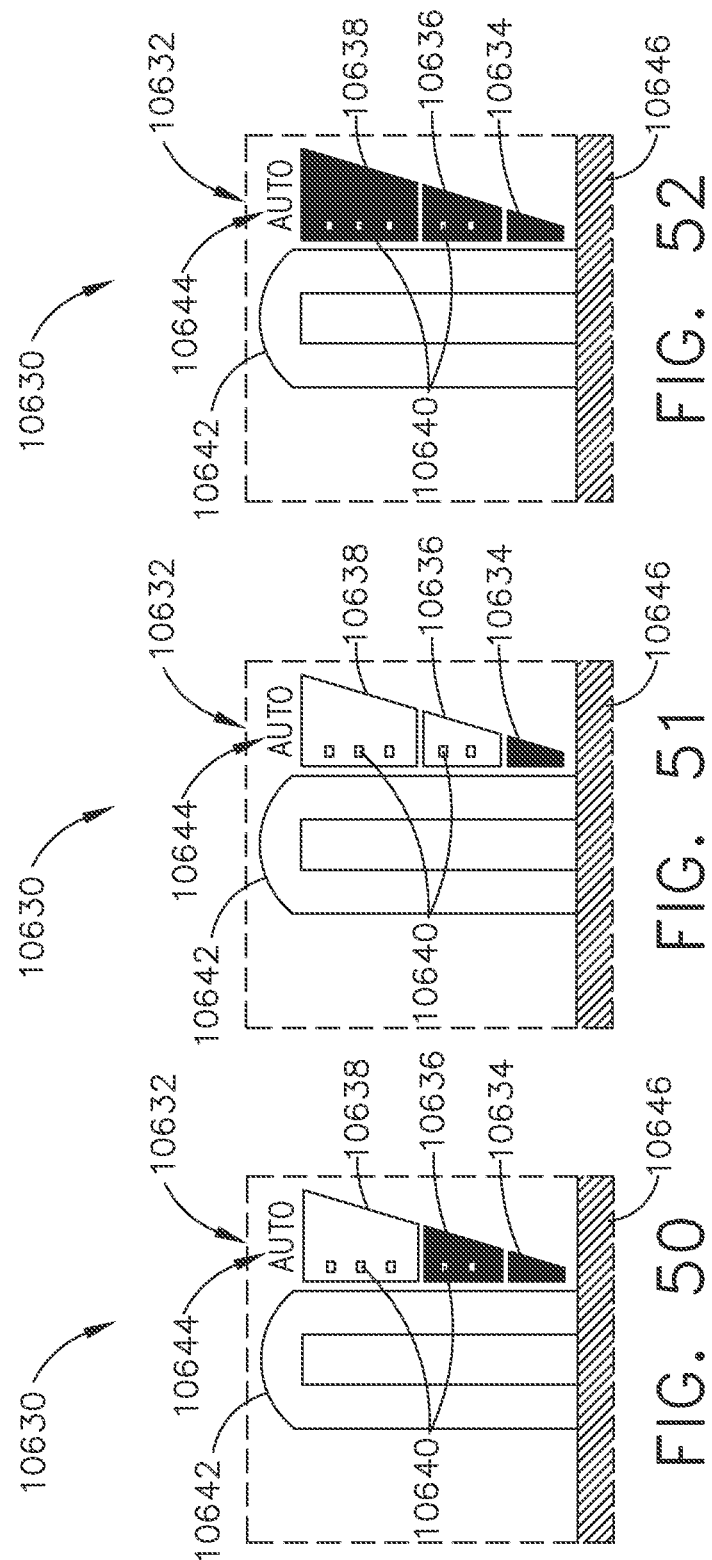

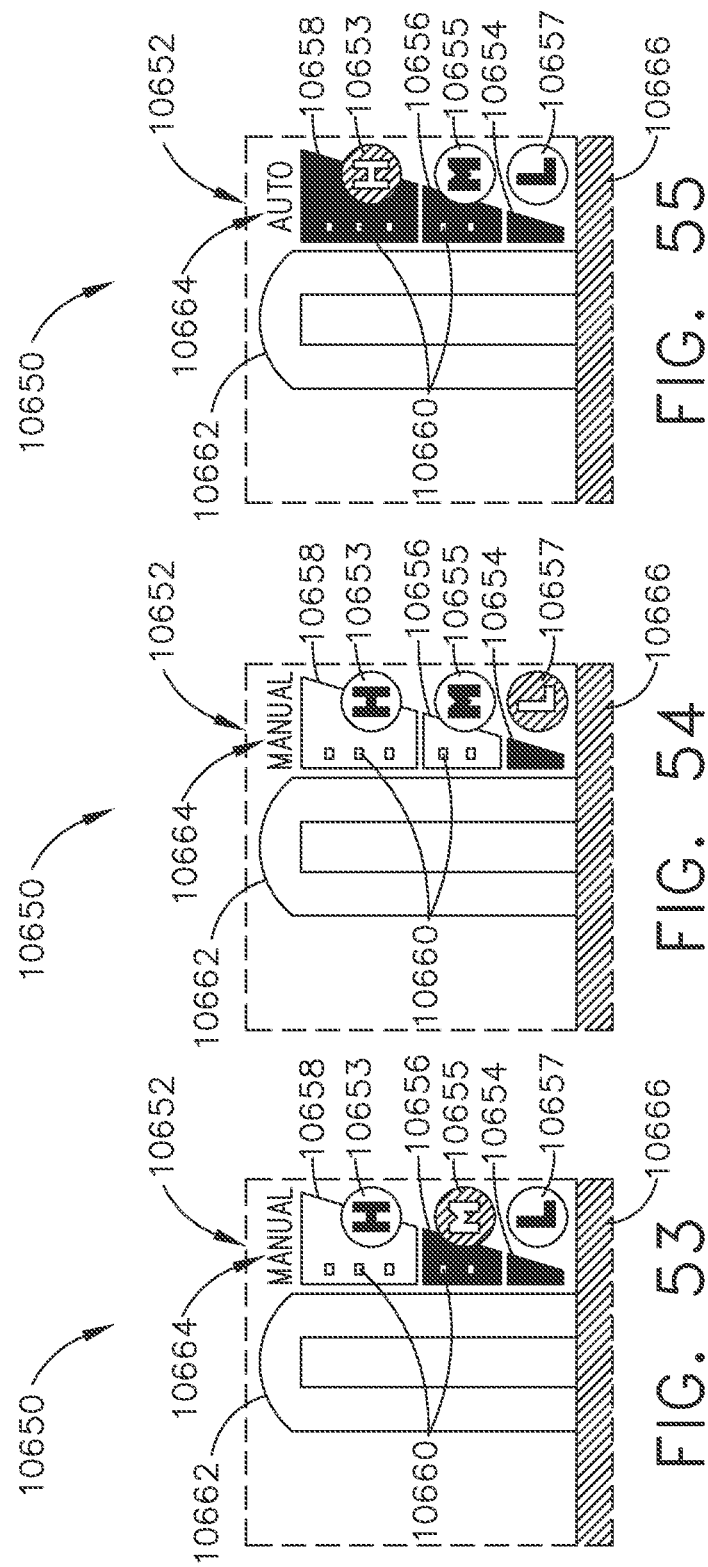

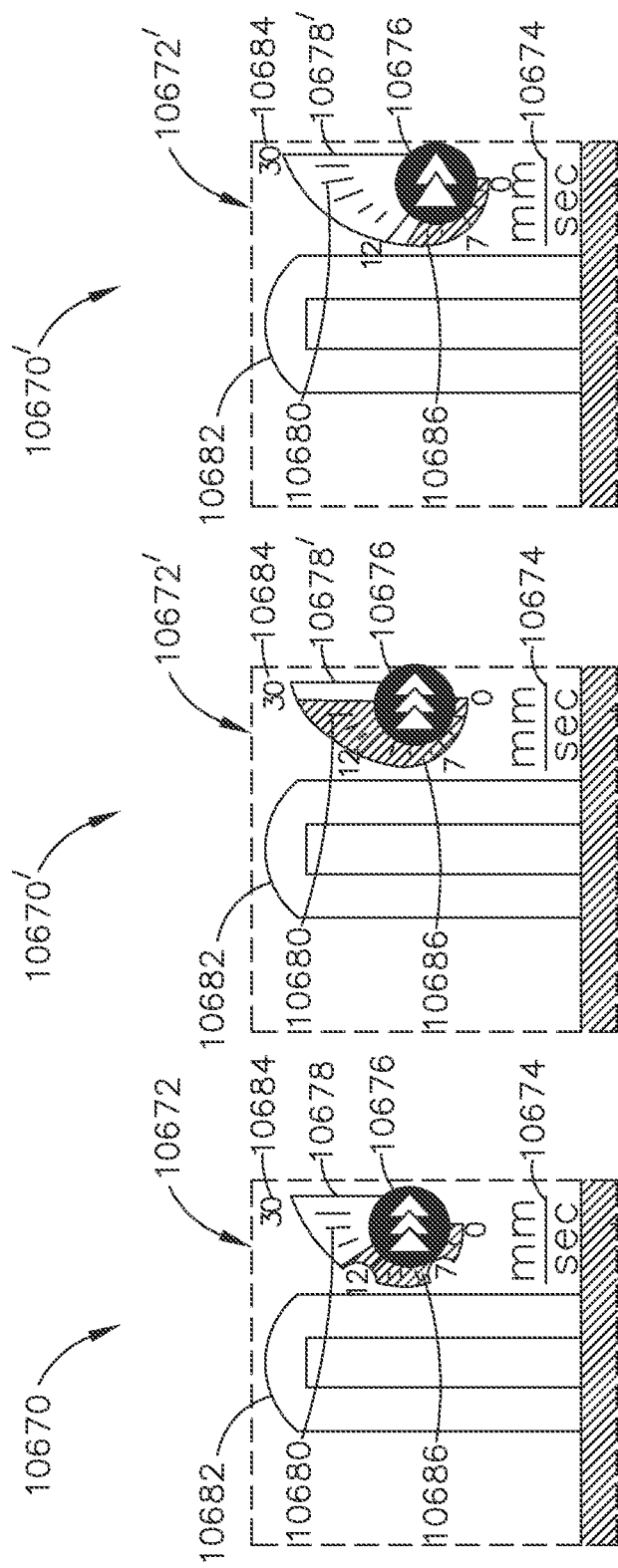

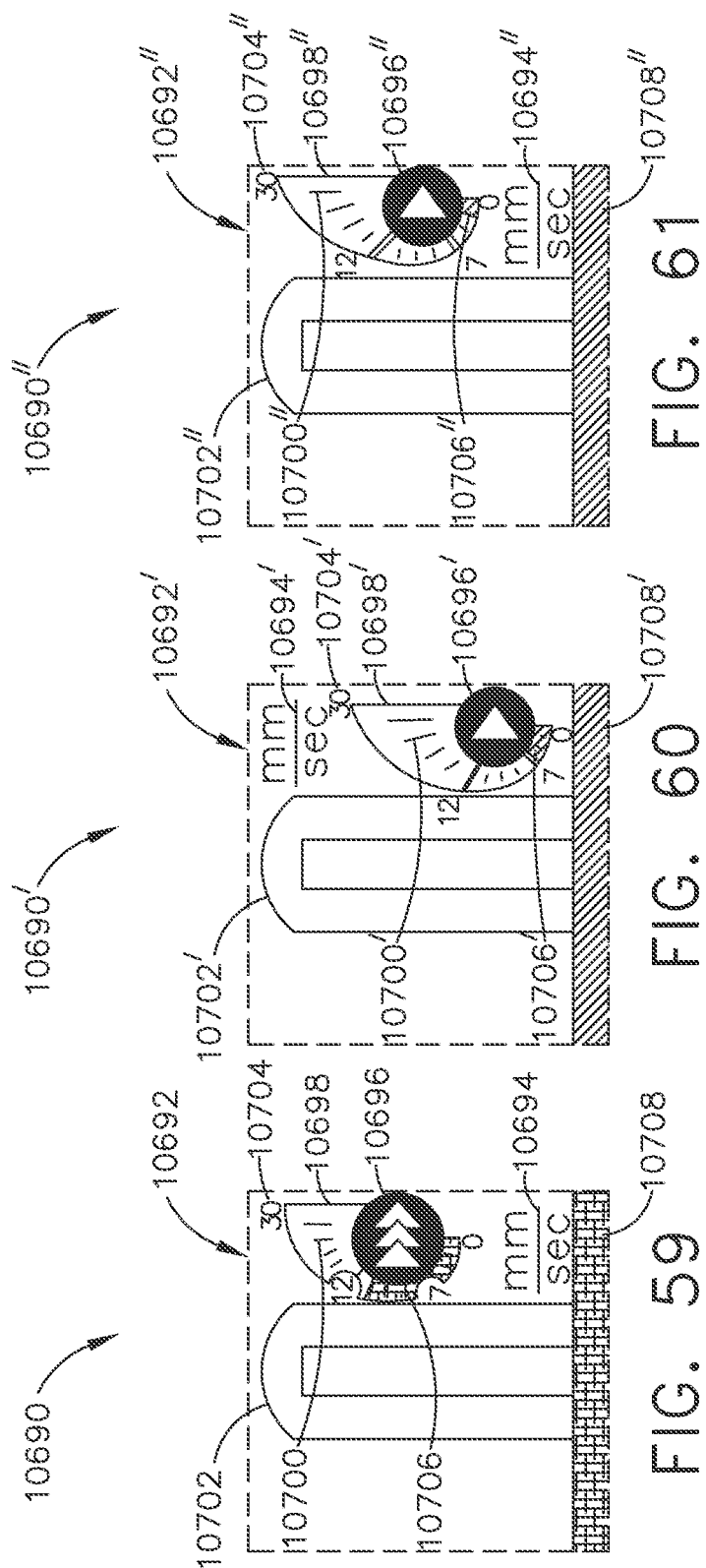

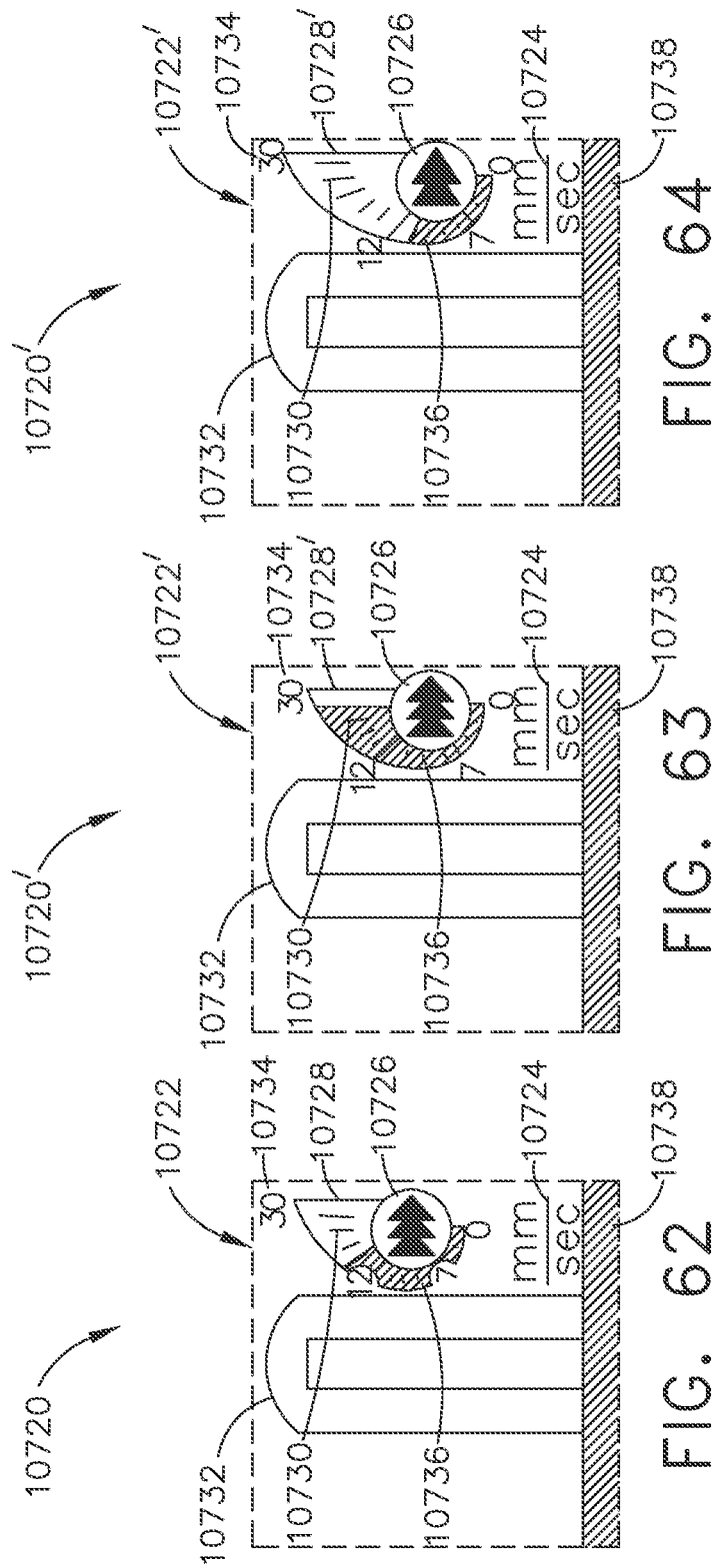

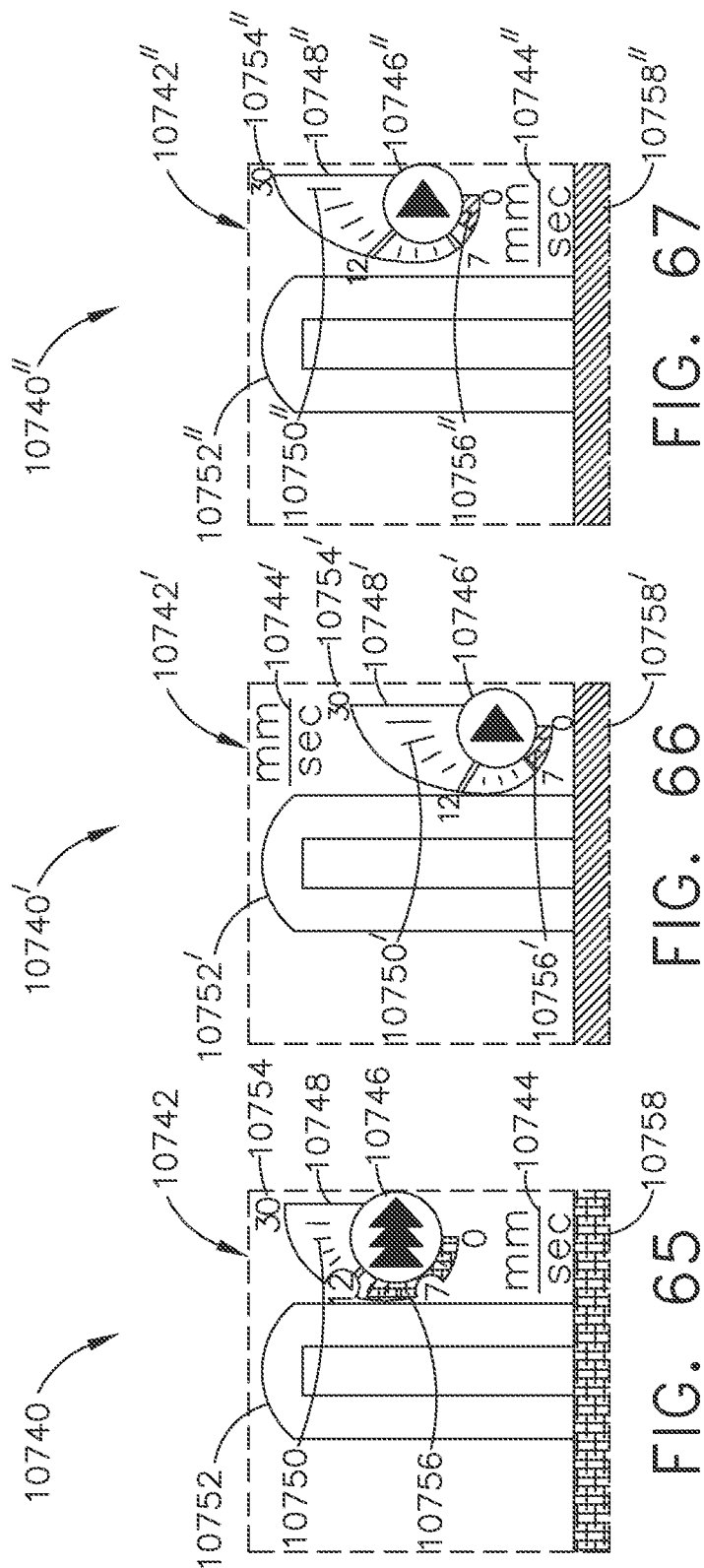

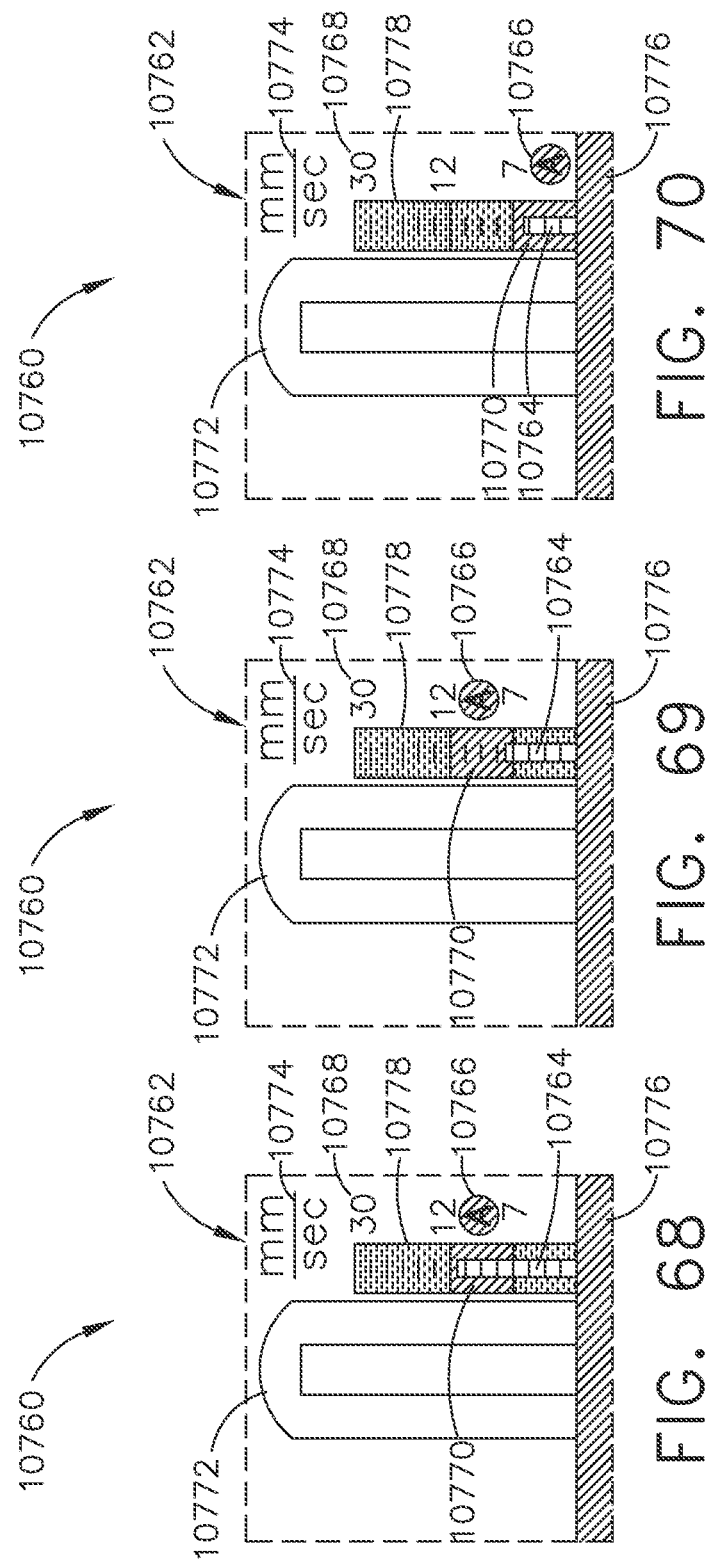

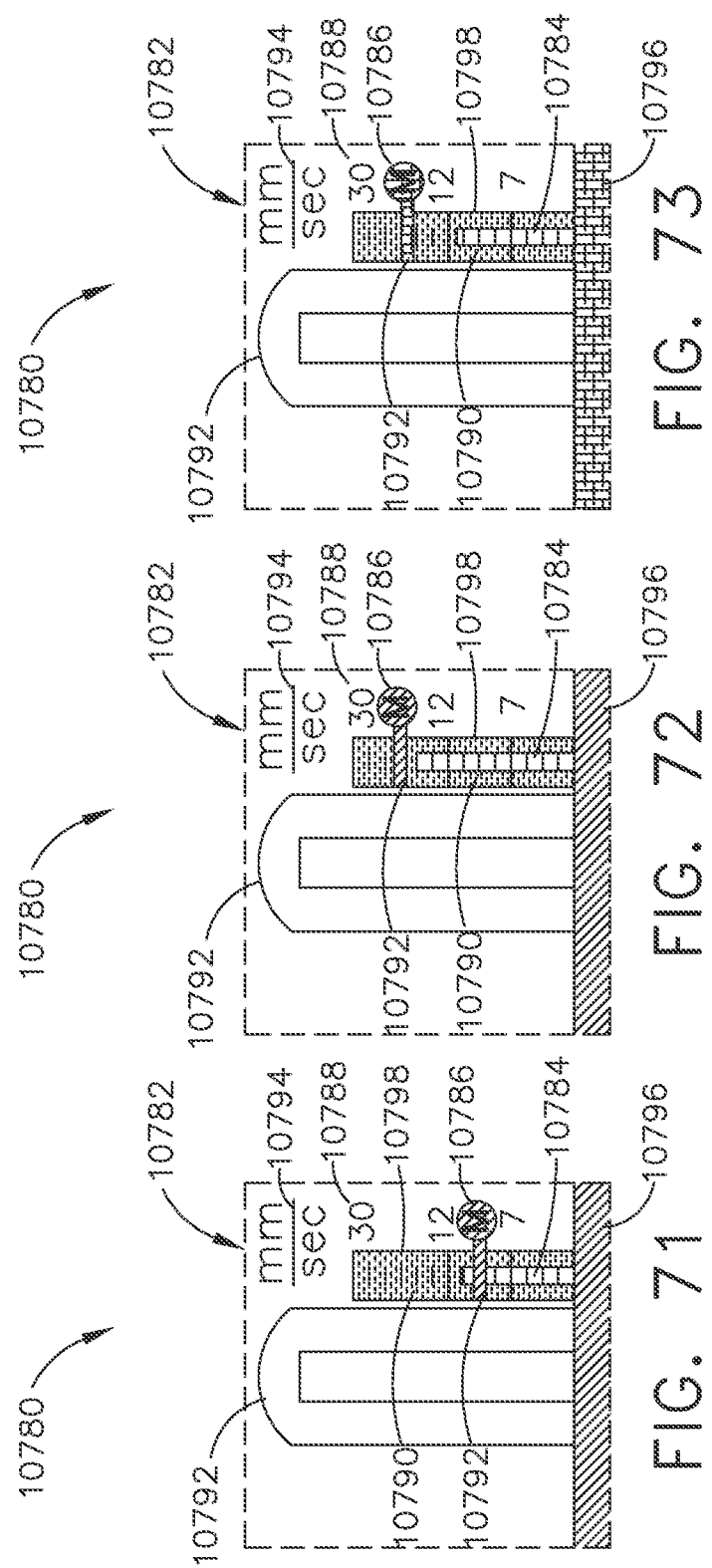

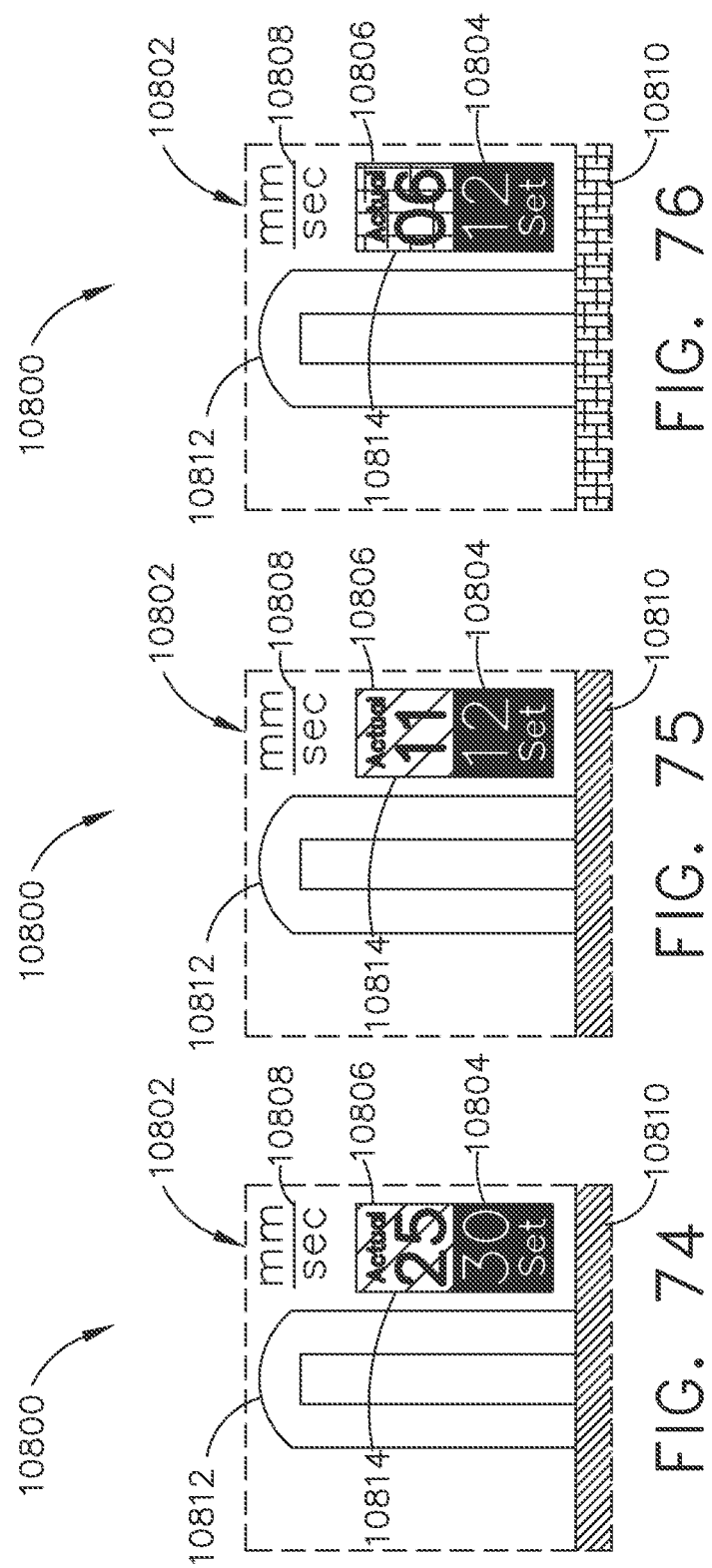

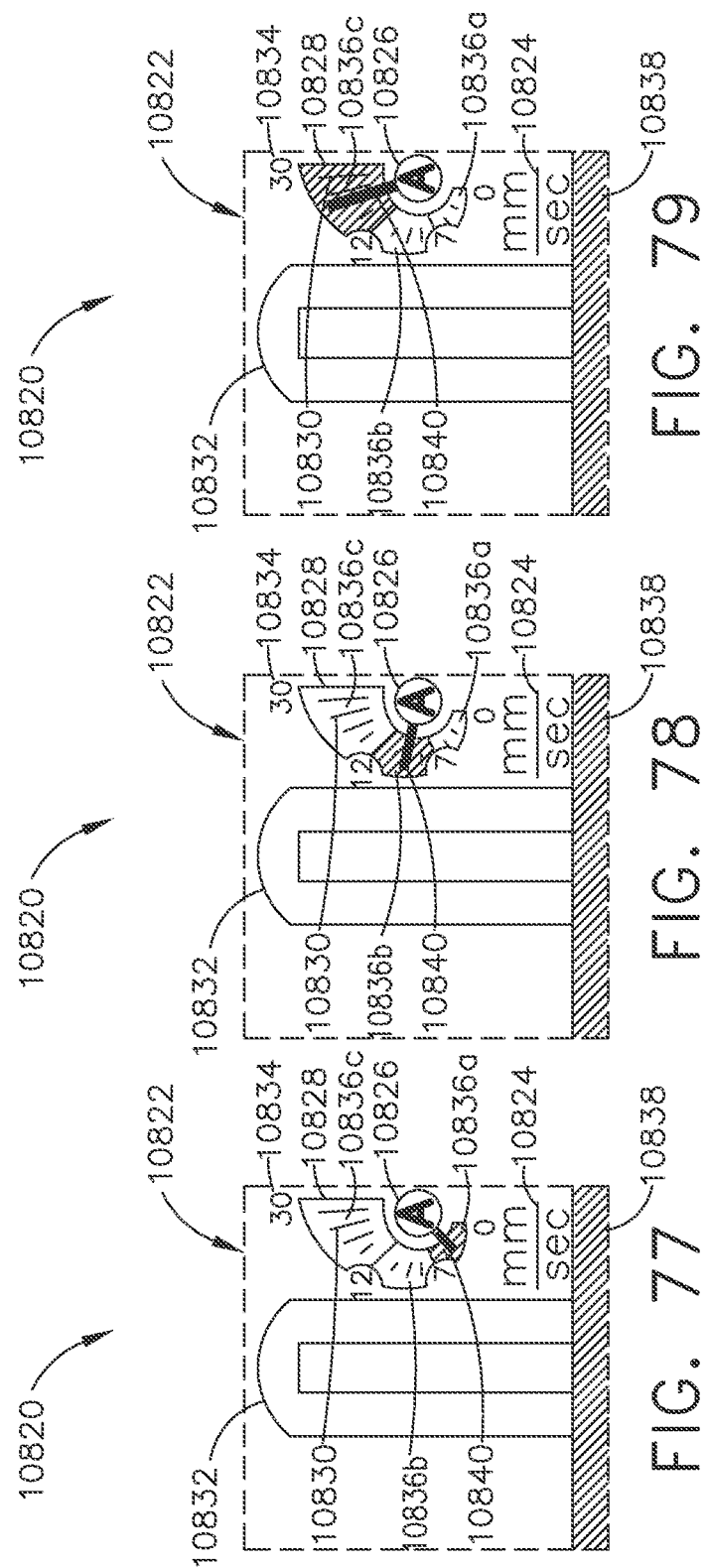

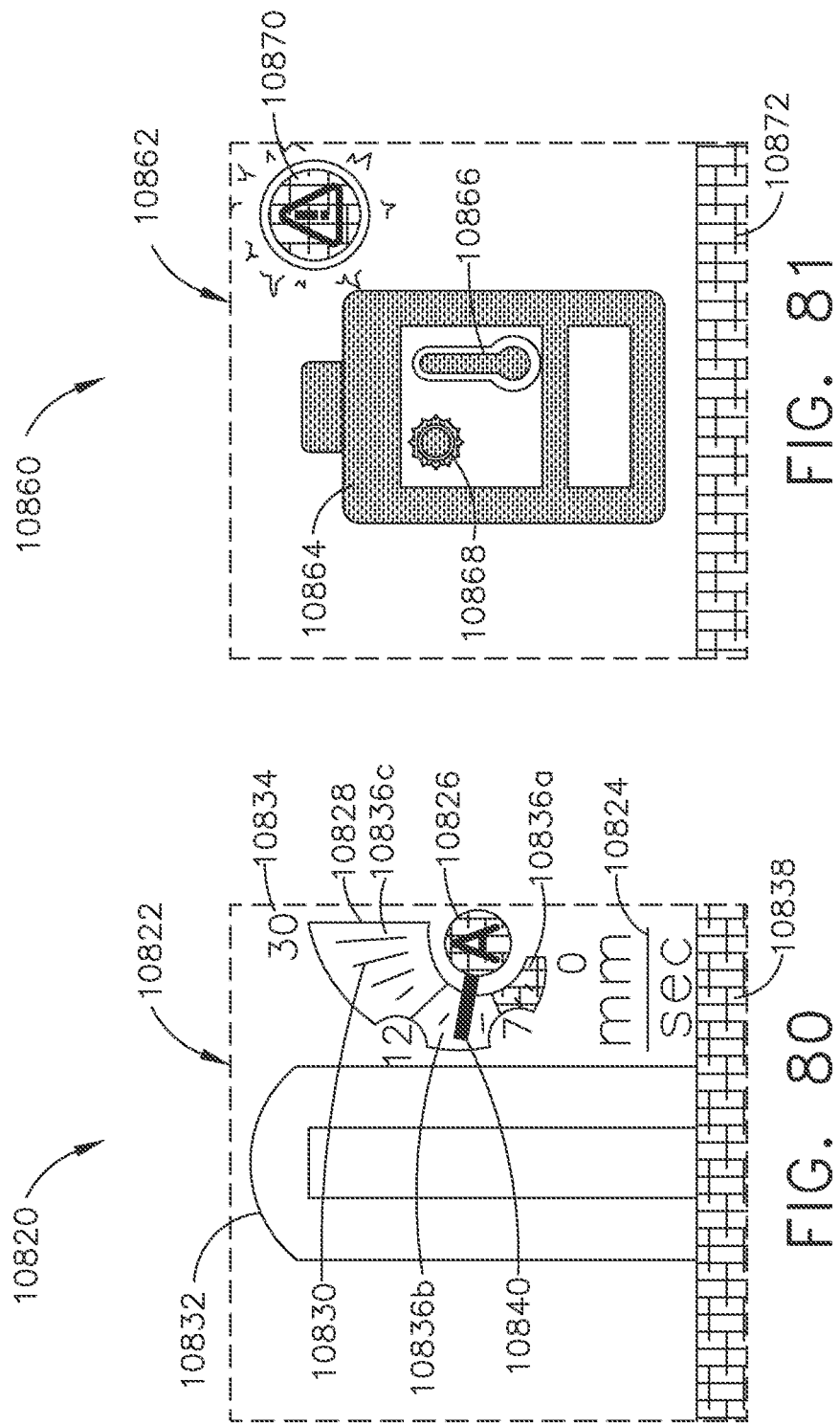

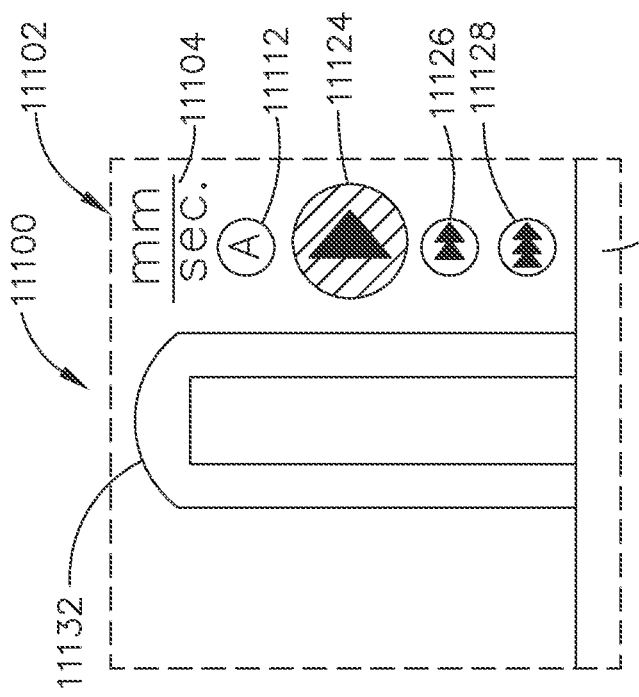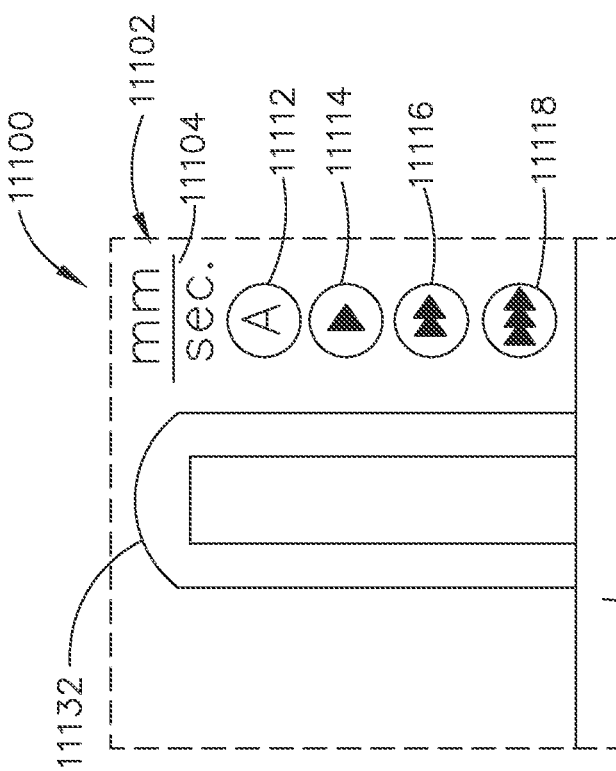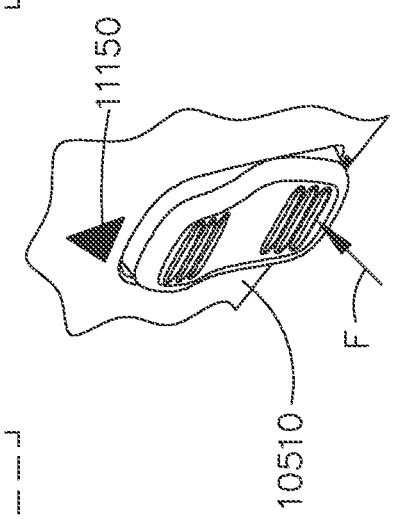
FIG. 85
FIG. 86
FIG. 87

METHOD FOR CLOSED LOOP CONTROL OF MOTOR VELOCITY OF A SURGICAL STAPLING AND CUTTING INSTRUMENT

CROSS-REFERENCE TO RELATED APPLICATIONS

This application is a continuation application claiming priority under 35 U.S.C. § 120 to U.S. patent application Ser. No. 17/548,713, entitled METHOD FOR CLOSED LOOP CONTROL OF MOTOR VELOCITY OF A SURGICAL STAPLING AND CUTTING INSTRUMENT, filed Dec. 13, 2021, which issued on Jan. 16, 2024 as U.S. Pat. No. 11,871,939, which is a continuation application claiming priority under 35 U.S.C. § 120 to U.S. patent application Ser. No. 16/752,983, entitled METHOD FOR CLOSED LOOP CONTROL OF MOTOR VELOCITY OF A SURGICAL STAPLING AND CUTTING INSTRUMENT, filed Jan. 27, 2020, which issued on Jan. 4, 2022 as U.S. Pat. No. 11,213,302, which is a continuation application claiming priority under 35 U.S.C. § 120 to U.S. patent application Ser. No. 16/170,801, entitled METHODS FOR CLOSED LOOP CONTROL OF MOTOR VELOCITY OF A SURGICAL STAPLING AND CUTTING INSTRUMENT, filed Oct. 25, 2018, which issued on Mar. 24, 2020 as U.S. Pat. No. 10,595,882, which is a continuation application claiming priority under 35 U.S.C. § 120 to U.S. patent application Ser. No. 15/628,045, entitled METHOD FOR CLOSED LOOP CONTROL OF MOTOR VELOCITY OF A SURGICAL STAPLING AND CUTTING INSTRUMENT, filed Jun. 20, 2017, which issued on Jun. 4, 2019 as U.S. Pat. No. 10,307,170, the entire disclosures of which are hereby incorporated by reference herein.

TECHNICAL FIELD

The present disclosure relates to surgical instruments and, in various circumstances, to surgical stapling and cutting instruments and staple cartridges therefor that are designed to staple and cut tissue.

BACKGROUND

In a motorized surgical stapling and cutting instrument it may be useful to control the velocity of a cutting member or to control the articulation velocity of an end effector. Velocity of a displacement member may be determined by measuring elapsed time at predetermined position intervals of the displacement member or measuring the position of the displacement member at predetermined time intervals. The control may be open loop or closed loop. Such measurements may be useful to evaluate tissue conditions such as tissue thickness and adjust the velocity of the cutting member during a firing stroke to account for the tissue conditions. Tissue thickness may be determined by comparing expected velocity of the cutting member to the actual velocity of the cutting member. In some situations, it may be useful to articulate the end effector at a constant articulation velocity. In other situations, it may be useful to drive the end effector at a different articulation velocity than a default articulation velocity at one or more regions within a sweep range of the end effector.

During use of a motorized surgical stapling and cutting instrument it is possible that a velocity controlled system error may occur between the command or directed velocity and the actual measured velocity of the cutting member or firing member. Therefore, it may be desirable to provide a closed loop feedback method of adjusting the velocity of firing based on the magnitude of one or more error terms based on the difference between an actual velocity and a command or directed velocity over a specified increment of time/distance

SUMMARY

A method of adjusting velocity in a motorized surgical instrument is provided. The surgical instrument comprises a displacement member configured to translate within the surgical instrument over a plurality of predefined zones, a motor coupled to the displacement member to translate the displacement member, and a control circuit coupled to the motor. The surgical instrument further comprises a position sensor coupled to the control circuit, the position sensor configured to measure the position of the displacement member and a timer circuit coupled to the control circuit, the timer circuit configured to measure elapsed time. The method comprises setting, by the control circuit, a directed velocity of the displacement member; determining, by the control circuit, an actual velocity of the displacement member; determining, by the control circuit, an error between the directed velocity of the displacement member and the actual velocity of the displacement member; and controlling, by the control circuit, the actual velocity of the displacement member based on the magnitude of the error.

FIGURES

The novel features of the aspects described herein are set forth with particularity in the appended claims. These aspects, however, both as to organization and methods of operation may be better understood by reference to the following description, taken in conjunction with the accompanying drawings.

Figure 26:
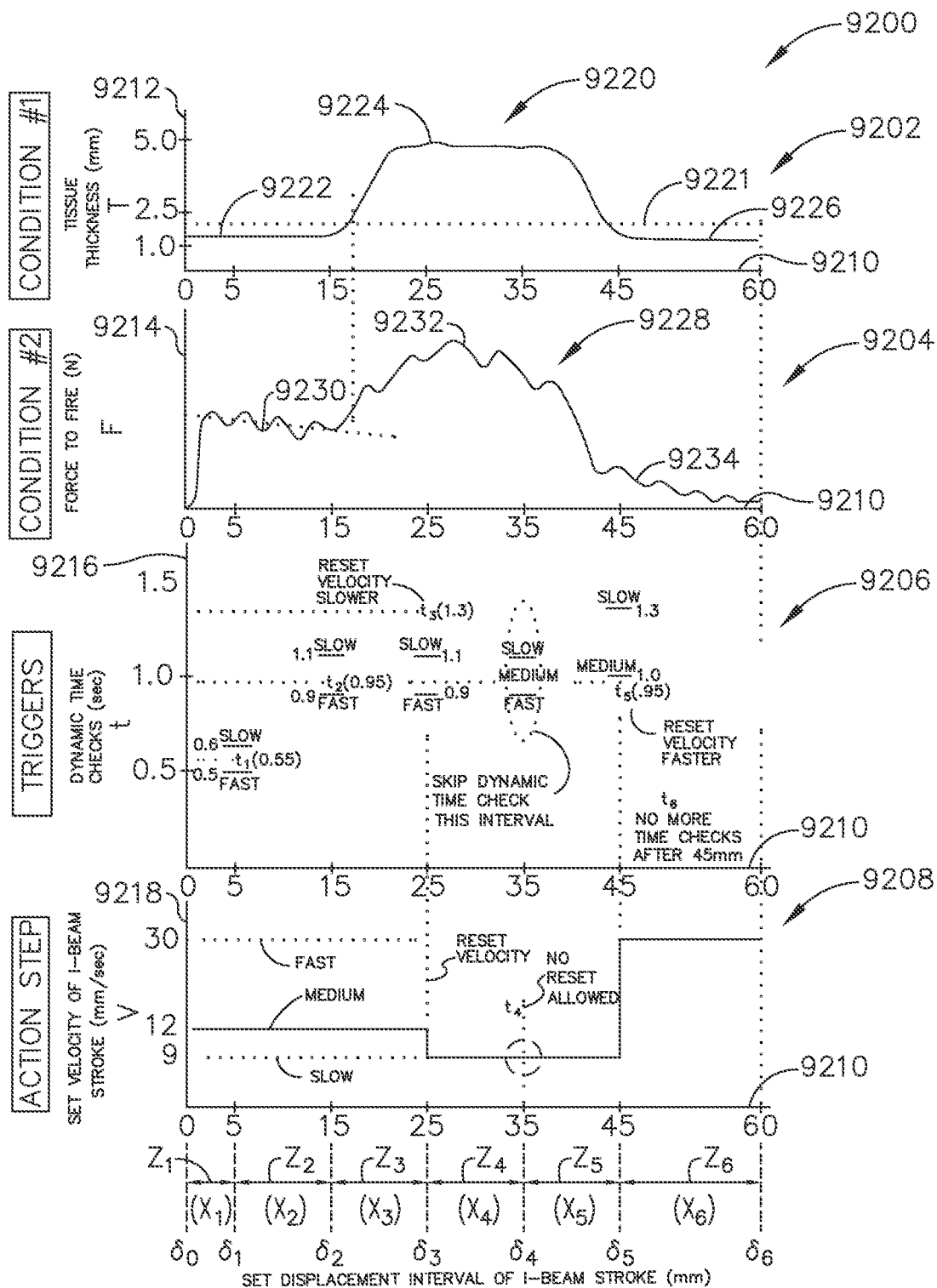

FIG. 26 is a graphical depiction comparing tissue thickness as a function of set displacement interval of I-beam stroke (top graph), force to fire as a function of set displacement interval of I-beam stroke (second graph from the top), dynamic time checks as a function of set displacement interval of I-beam stroke (third graph from the top), and set velocity of I-beam as a function of set displacement interval of I-beam stroke (bottom graph) according to one aspect of this disclosure.

Figure 27:
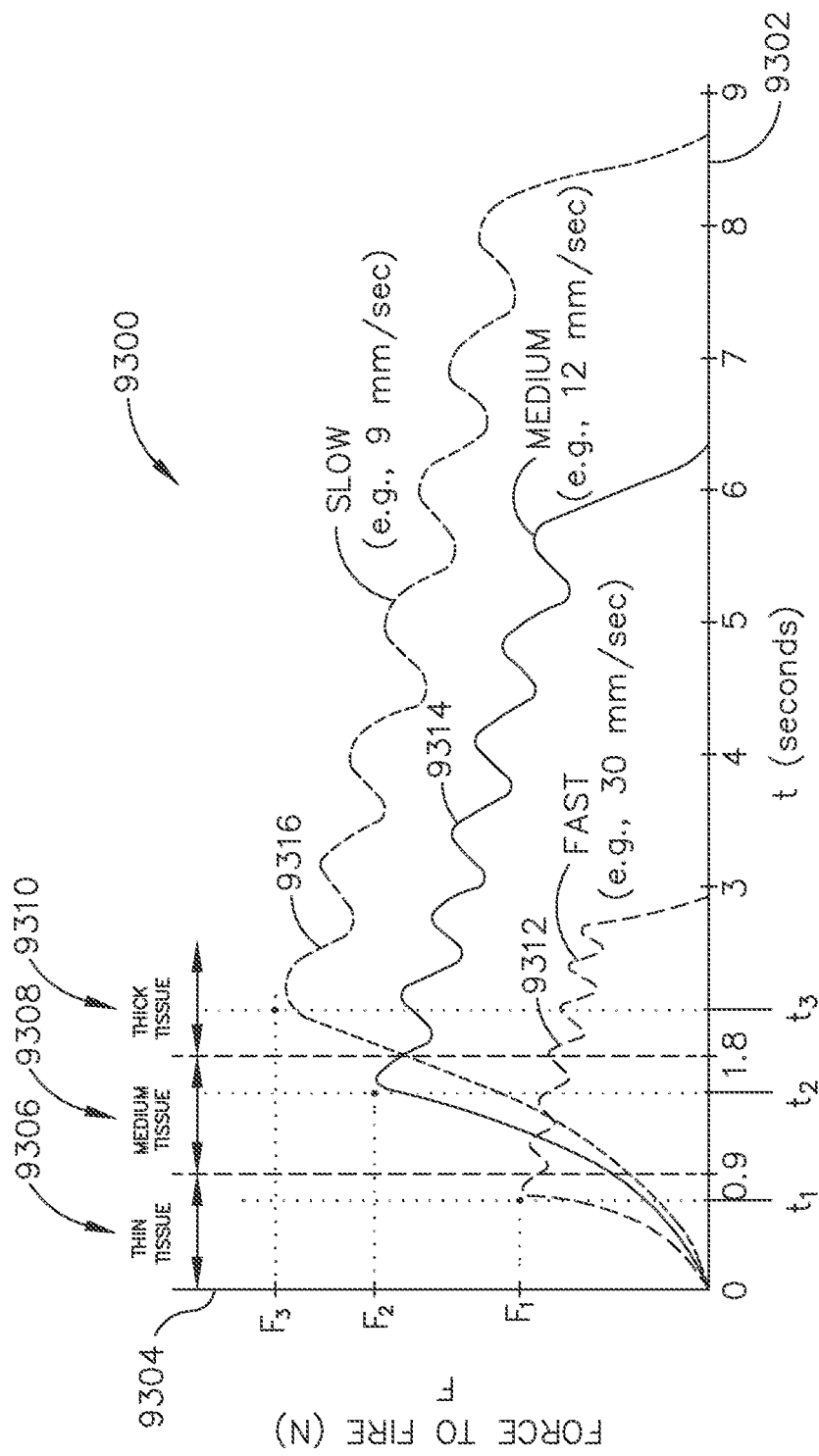

FIG. 27 is a graphical depiction of force to fire as a function of time comparing slow, medium and fast I-beam displacement velocities according to one aspect of this disclosure.

Figure 28:
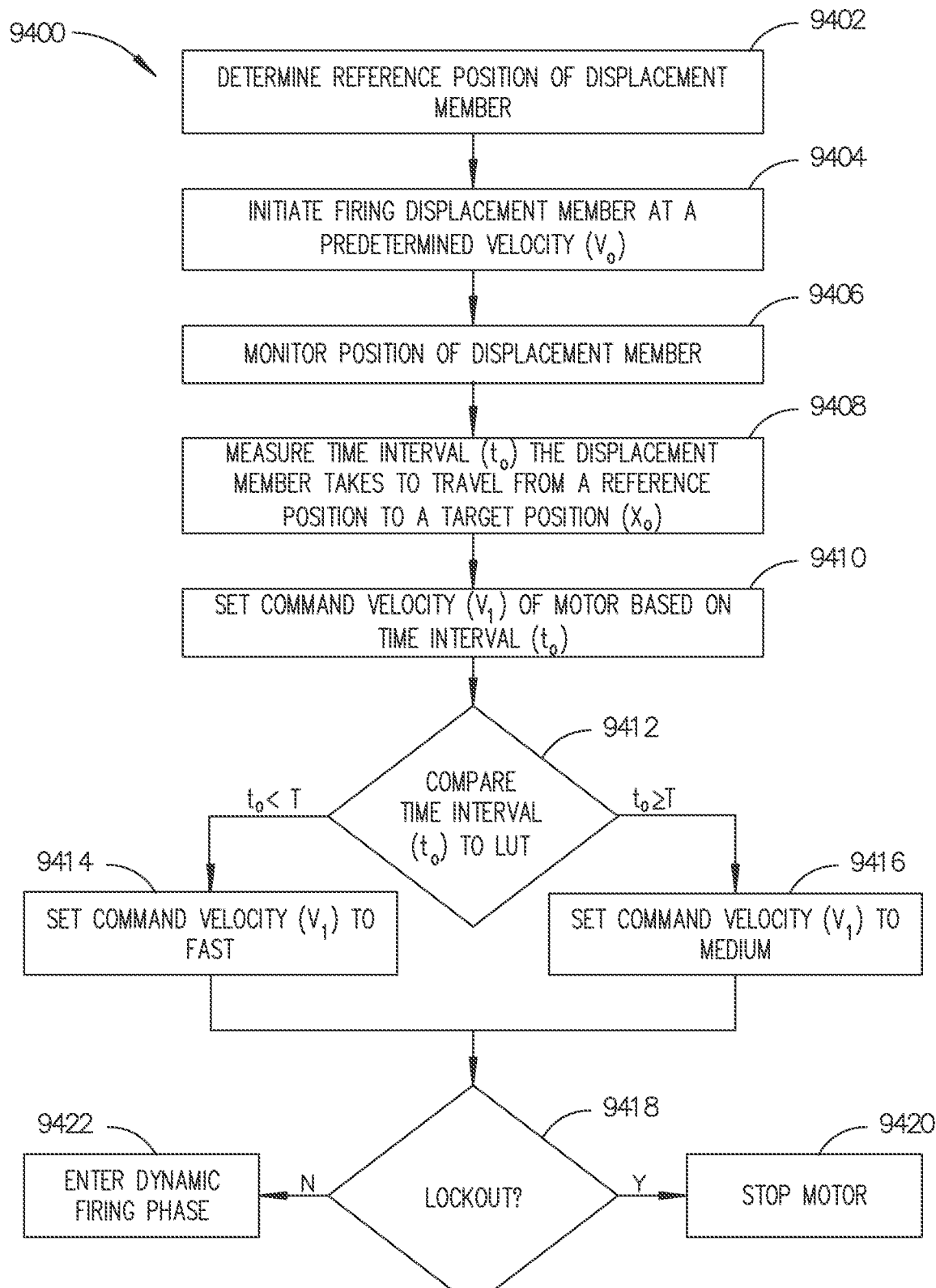

FIG. 28 is a logic flow diagram of a process depicting a control program or logic configuration for controlling command velocity in an initial firing stage according to one aspect of this disclosure.

Figure 29:
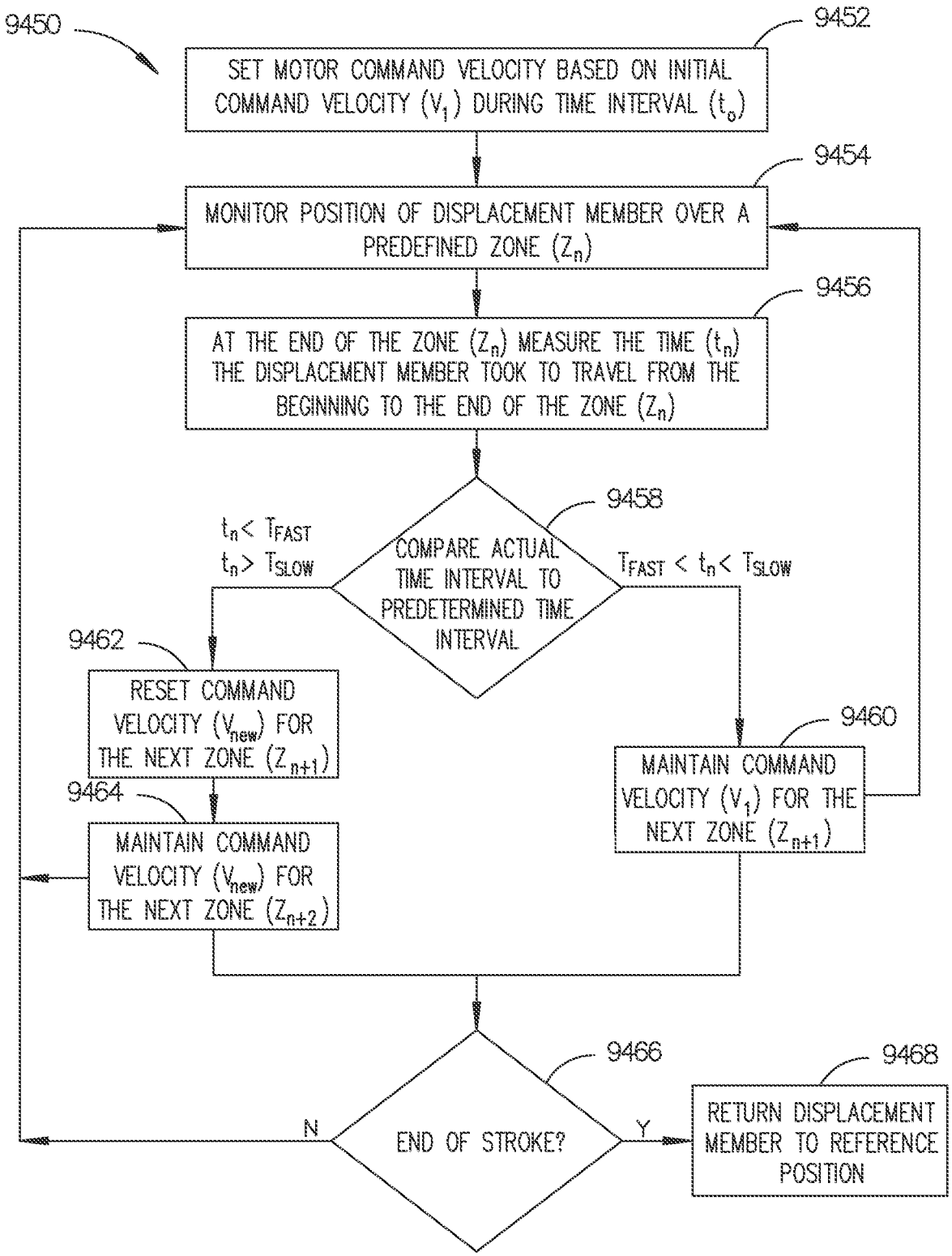

FIG. 29 is a logic flow diagram of a process depicting a control program or logic configuration for controlling command velocity in a dynamic firing stage according to one aspect of this disclosure.

Figure 30A:
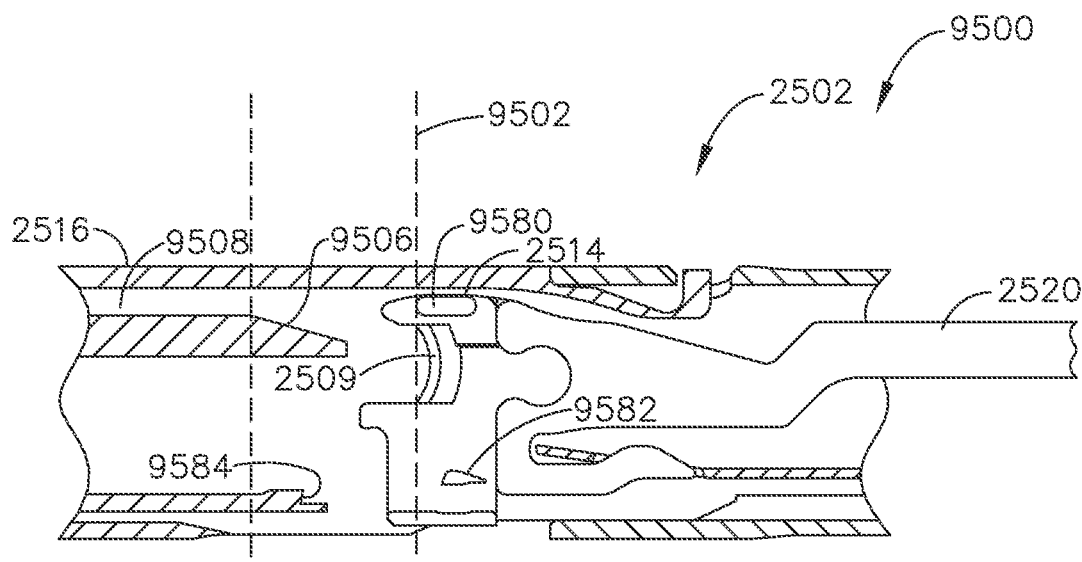

FIG. 30A illustrates an end effector comprising a firing member coupled to an I-beam comprising a cutting edge according to one aspect of this disclosure.

Figure 30B:
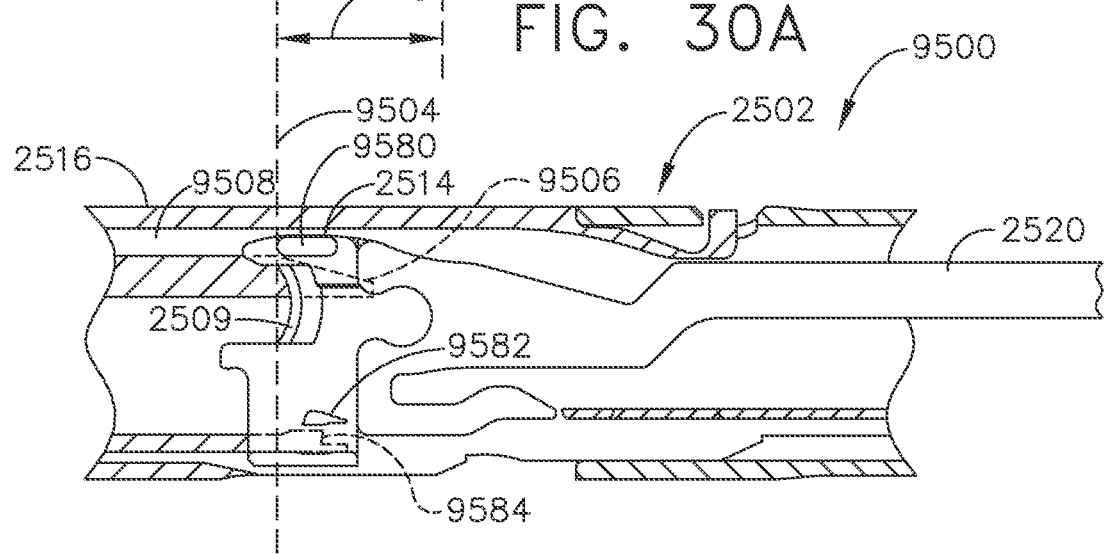

FIG. 30B illustrates an end effector where the I-beam is located in a target position at the top of a ramp with the top pin engaged in the T-slot according to one aspect of this disclosure.

Figure 31:
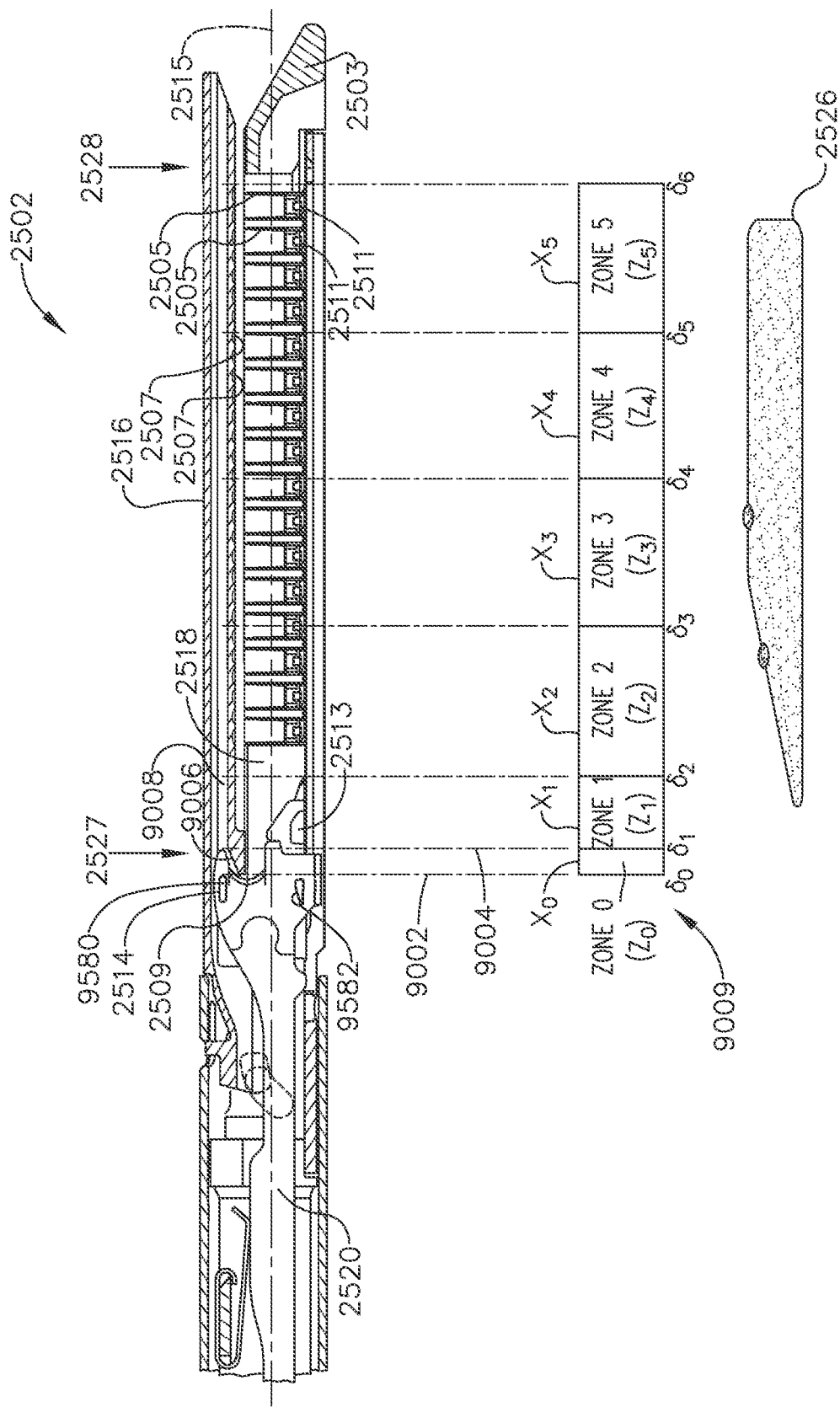

FIG. 31 illustrates the I-beam firing stroke is illustrated by a chart aligned with the end effector according to one aspect of this disclosure.

Figure 32:
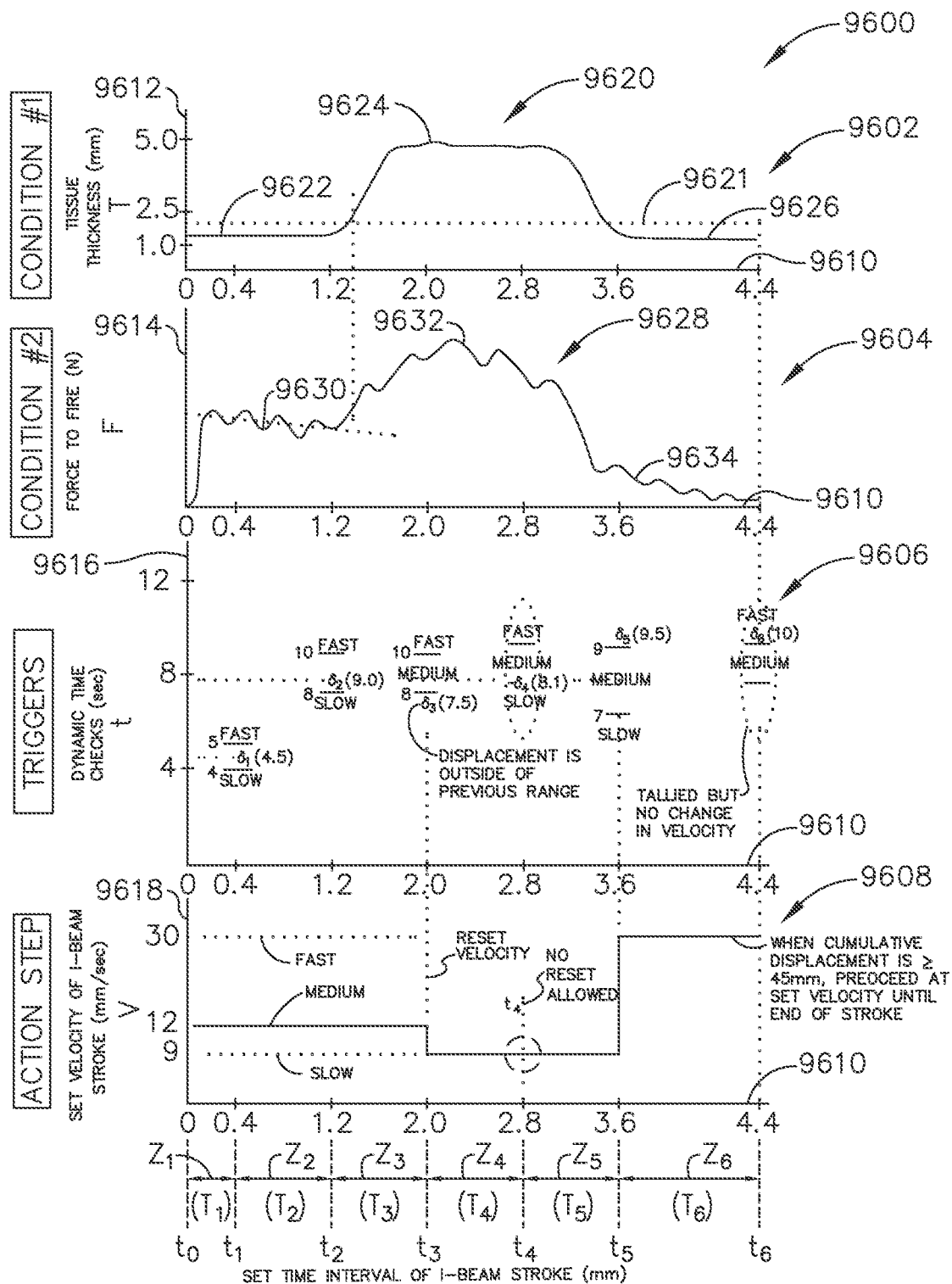

FIG. 32 is a graphical depiction comparing tissue thickness as a function of set time interval of I-beam stroke (top graph), force to fire as a function of set time interval of I-beam stroke (second graph from the top), dynamic time checks as a function of set time interval of I-beam stroke (third graph from the top), and set velocity of I-beam as a function of set time interval of I-beam stroke (bottom graph) according to one aspect of this disclosure.

Figure 33:
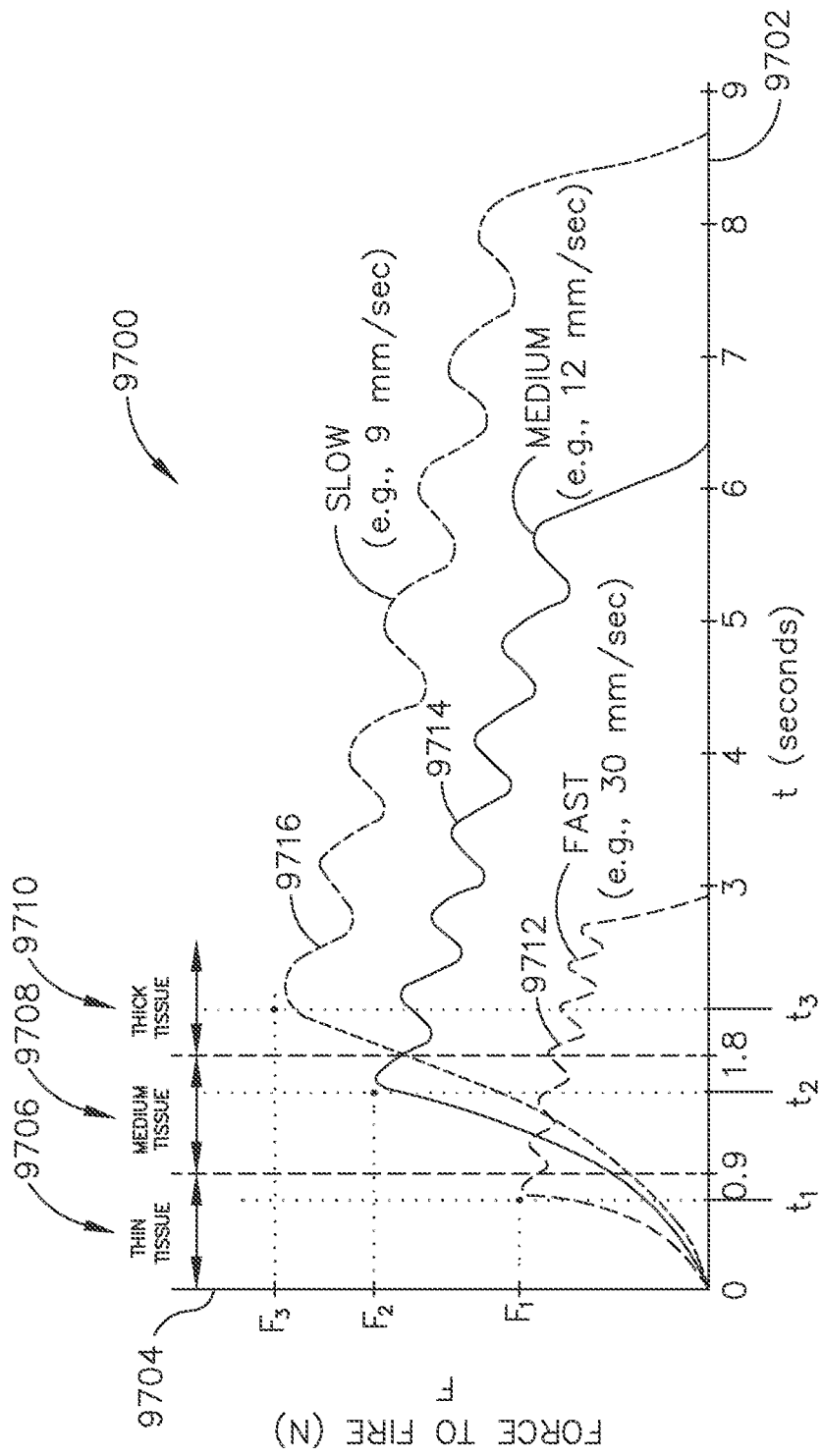

FIG. 33 is a graphical depiction of force to fire as a function of time comparing slow, medium and fast I-beam displacement velocities according to one aspect of this disclosure.

Figure 34:
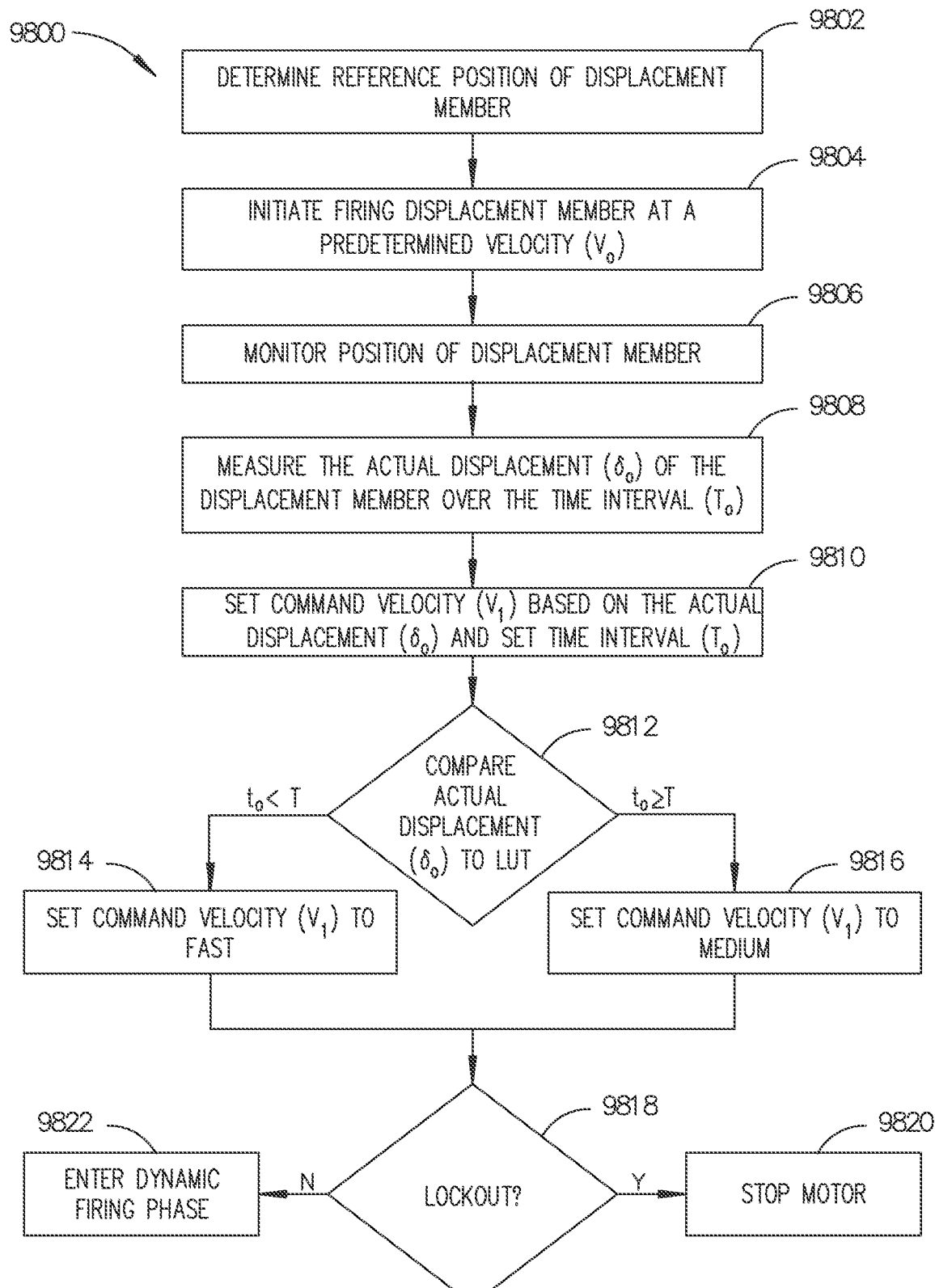

FIG. 34 is a logic flow diagram of a process depicting a control program or logic configuration for controlling command velocity in an initial firing stage according to one aspect of this disclosure.

Figure 35:
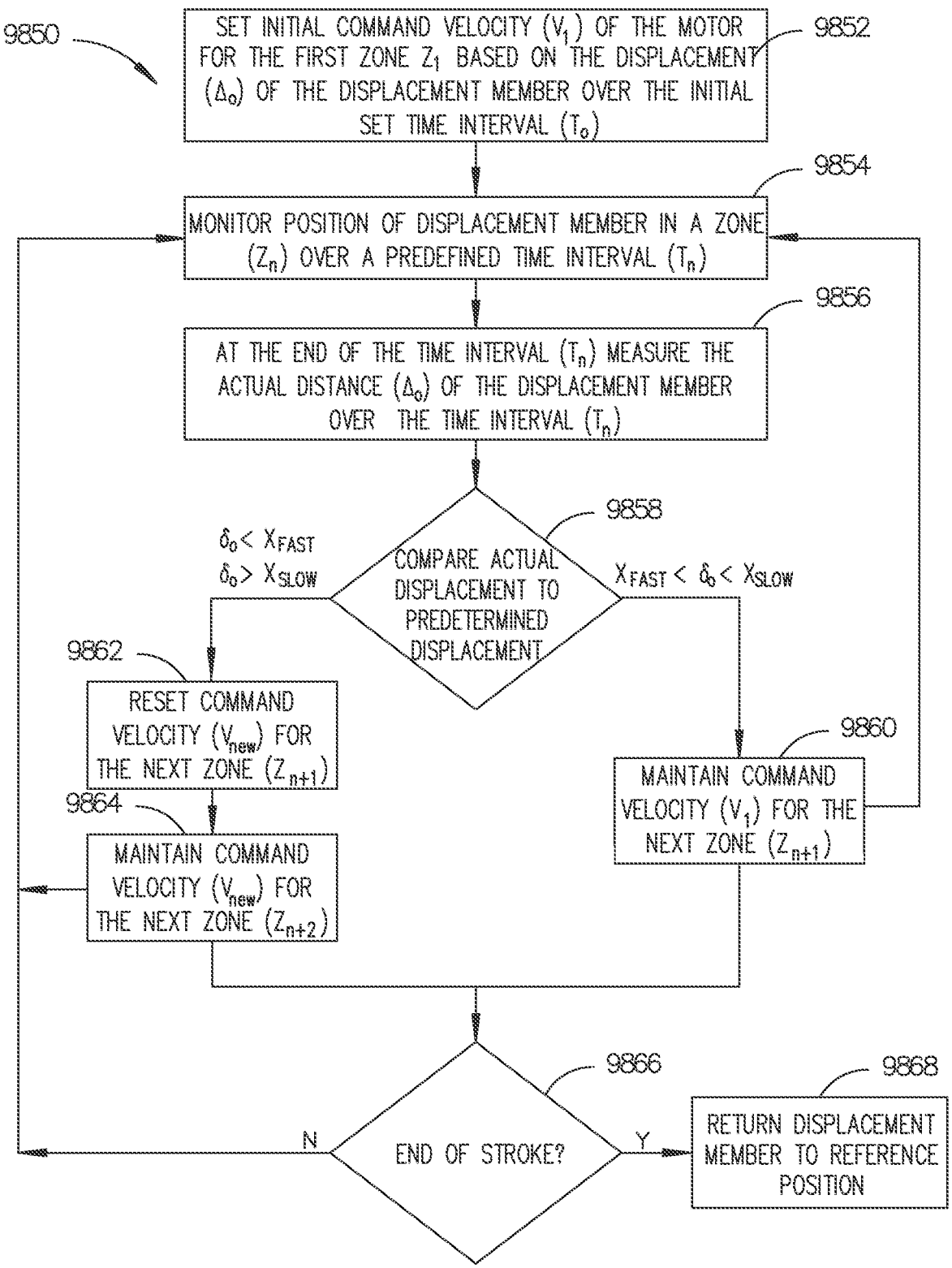

FIG. 35 is a logic flow diagram of a process depicting a control program or logic configuration for controlling command velocity in a dynamic firing stage according to one aspect of this disclosure.

Figure 36A:
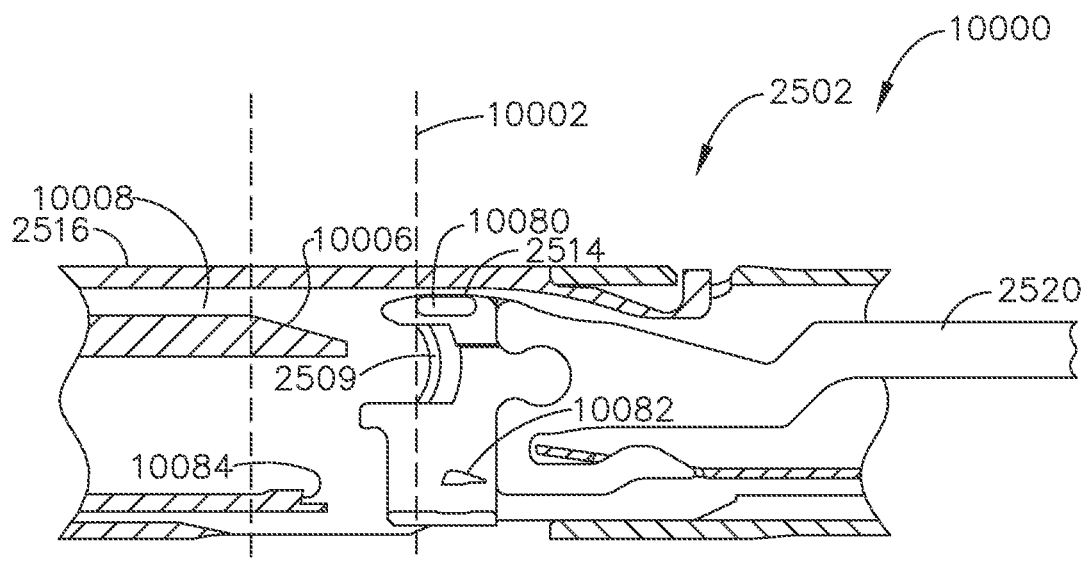

FIG. 36A illustrates an end effector comprising a firing member coupled to an I-beam comprising a cutting edge according to one aspect of this disclosure.

Figure 36B:
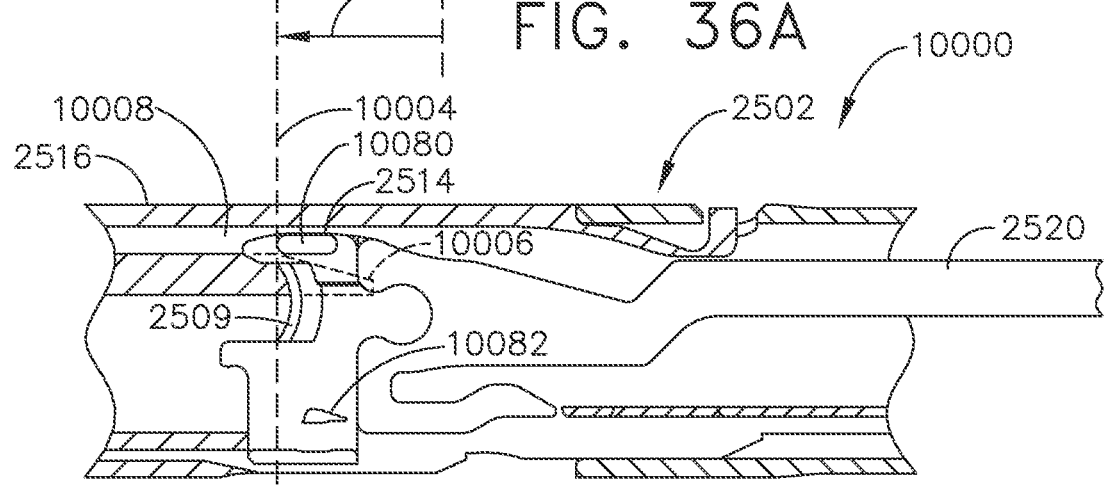

FIG. 36B illustrates an end effector where the I-beam is located in a target position at the top of a ramp with the top pin engaged in the T-slot according to one aspect of this disclosure.

Figure 37:
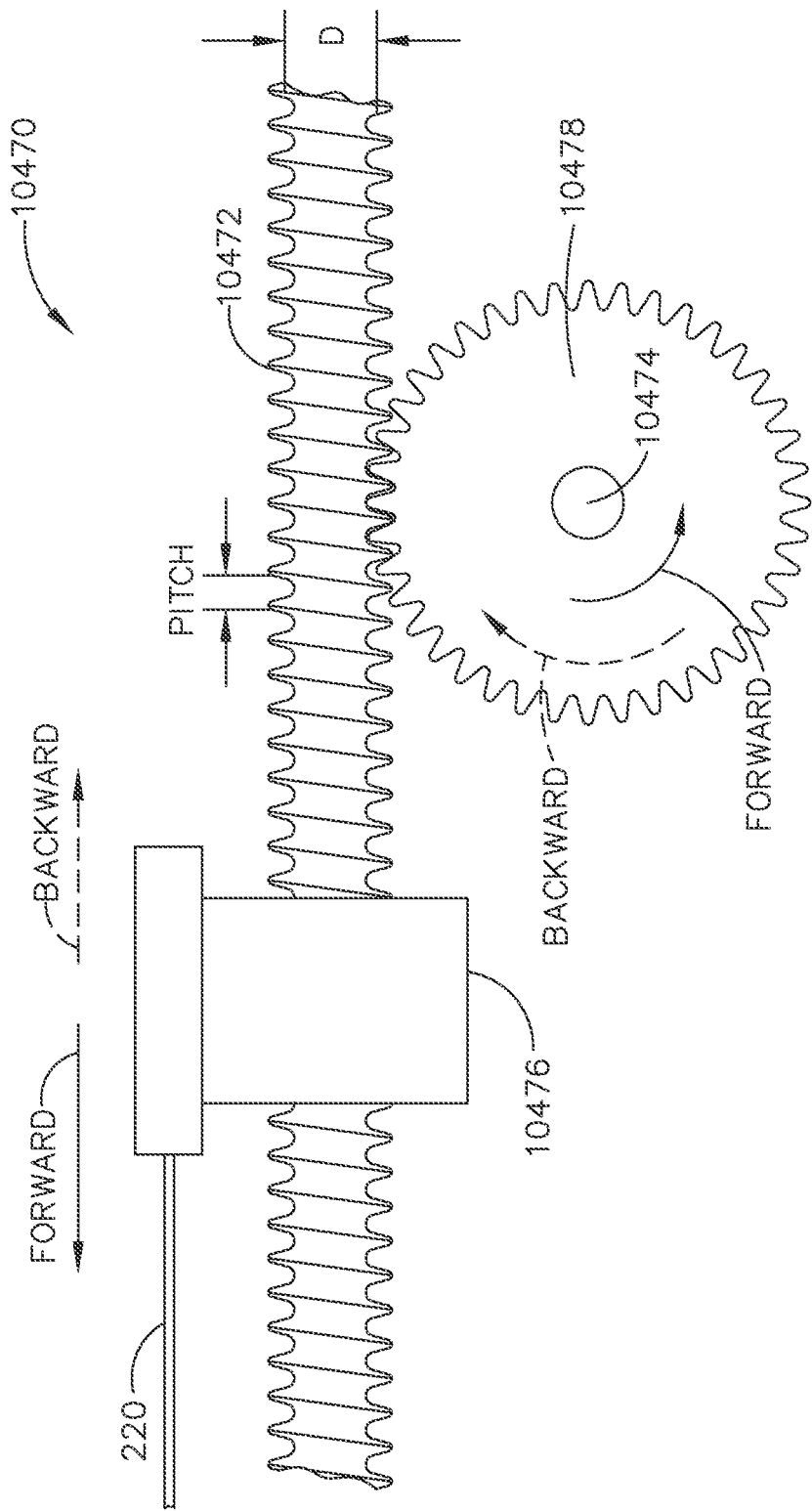

FIG. 37 illustrates a screw drive system 10470 that may be employed with the surgical instrument 10 (FIG. 1) according to one aspect of this disclosure.

Figure 38:
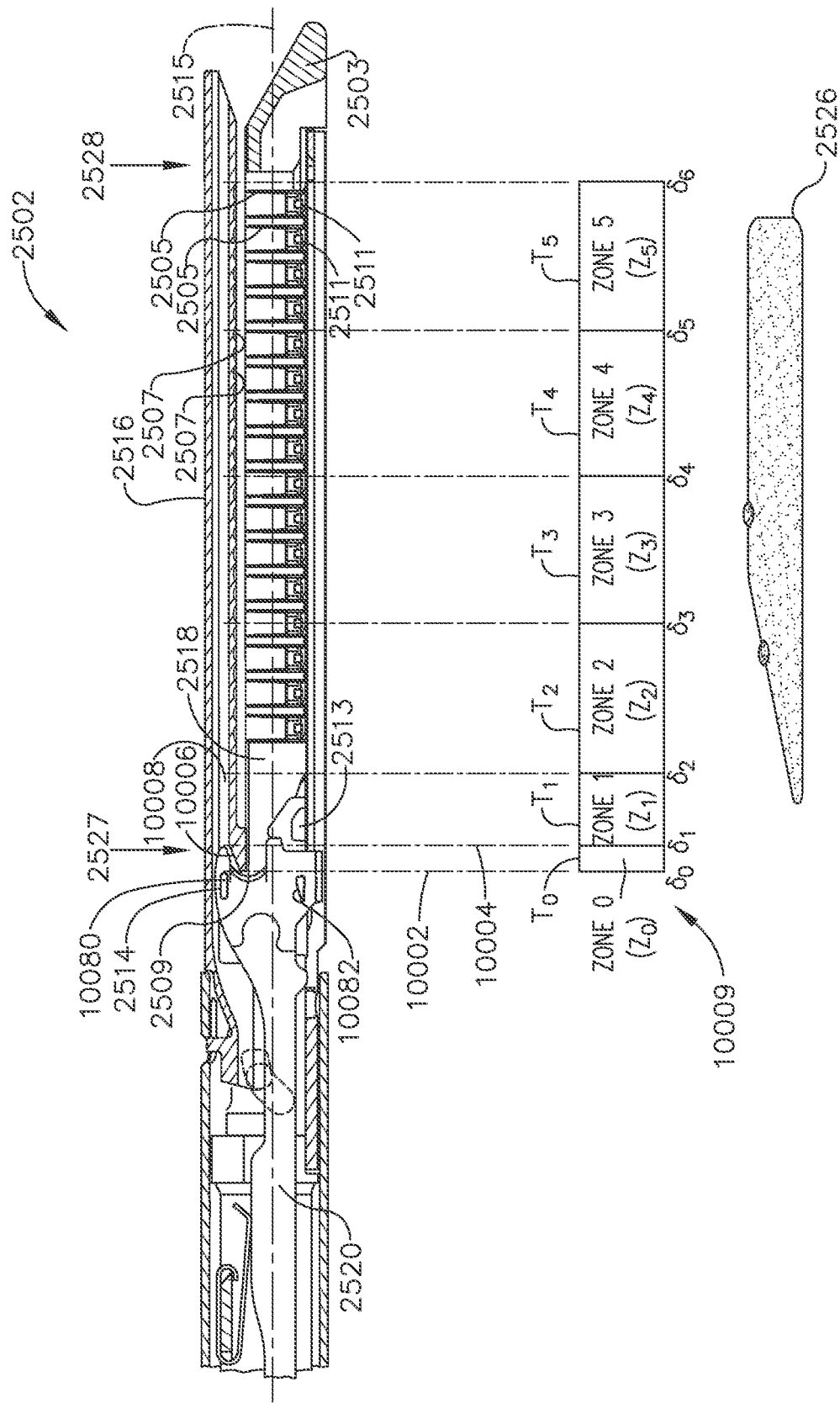

FIG. 38 illustrates the I-beam firing stroke is illustrated by a chart aligned with the end effector according to one aspect of this disclosure.

Figure 39:
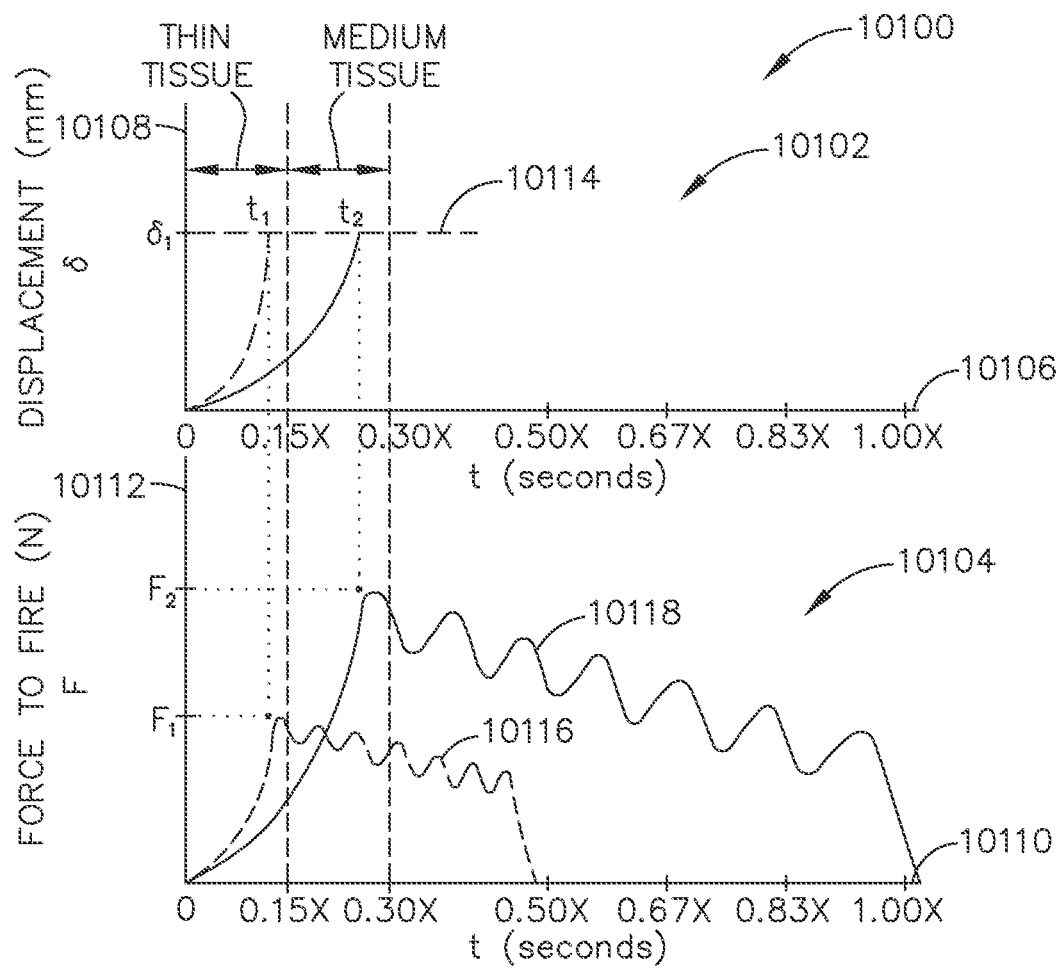

FIG. 39 is a graphical depiction comparing I-beam stroke displacement as a function of time (top graph) and expected force-to-fire as a function of time (bottom graph) according to one aspect of this disclosure.

Figure 40:
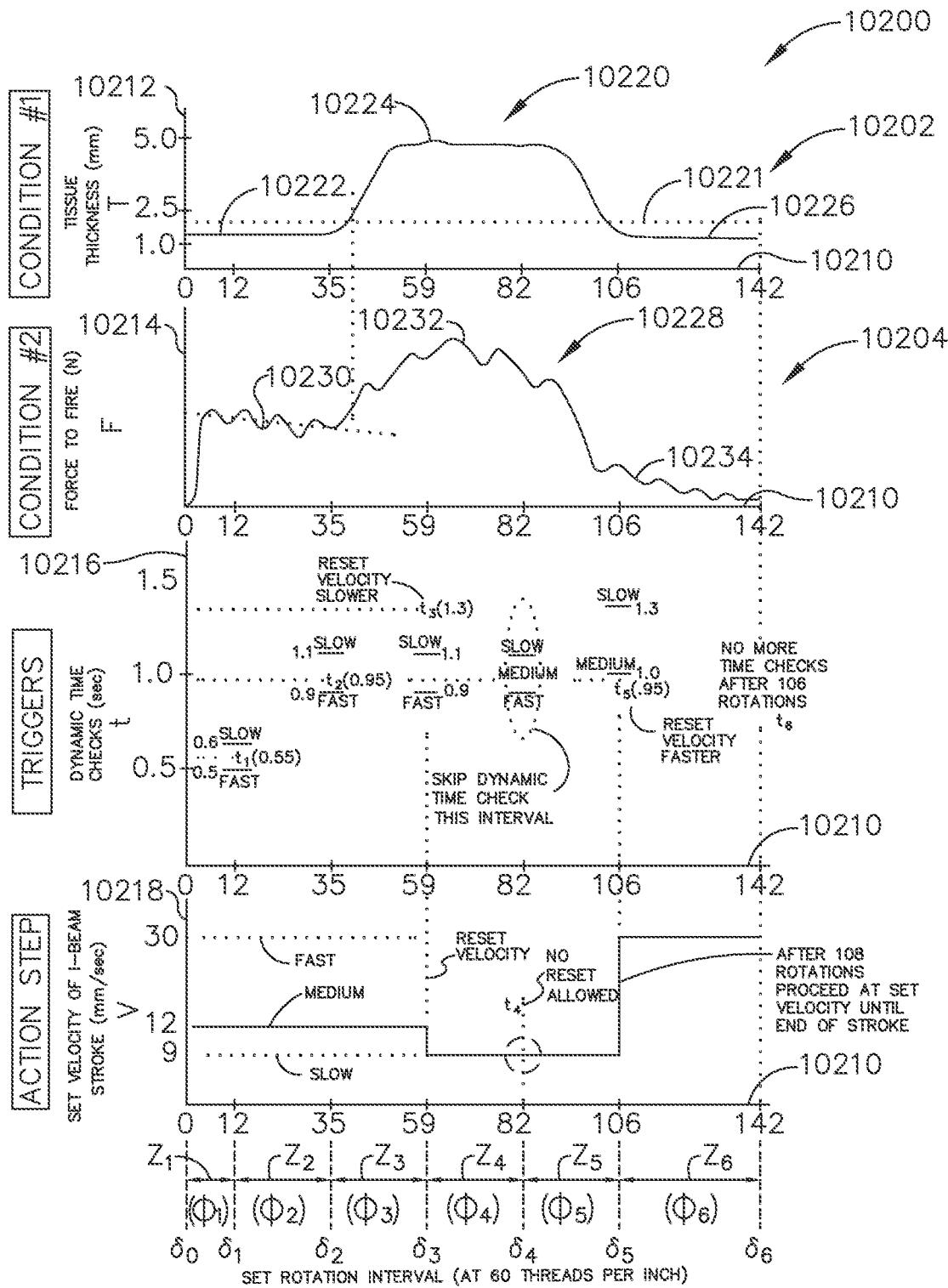

FIG. 40 is a graphical depiction comparing tissue thickness as a function of set rotation interval of I-beam stroke (top graph), force to fire as a function of set rotation interval of I-beam stroke (second graph from the top), dynamic time checks as a function of set rotation interval of I-beam stroke (third graph from the top), and set velocity of I-beam as a function of set rotation interval of I-beam stroke (bottom graph) according to one aspect of this disclosure.

Figure 41:
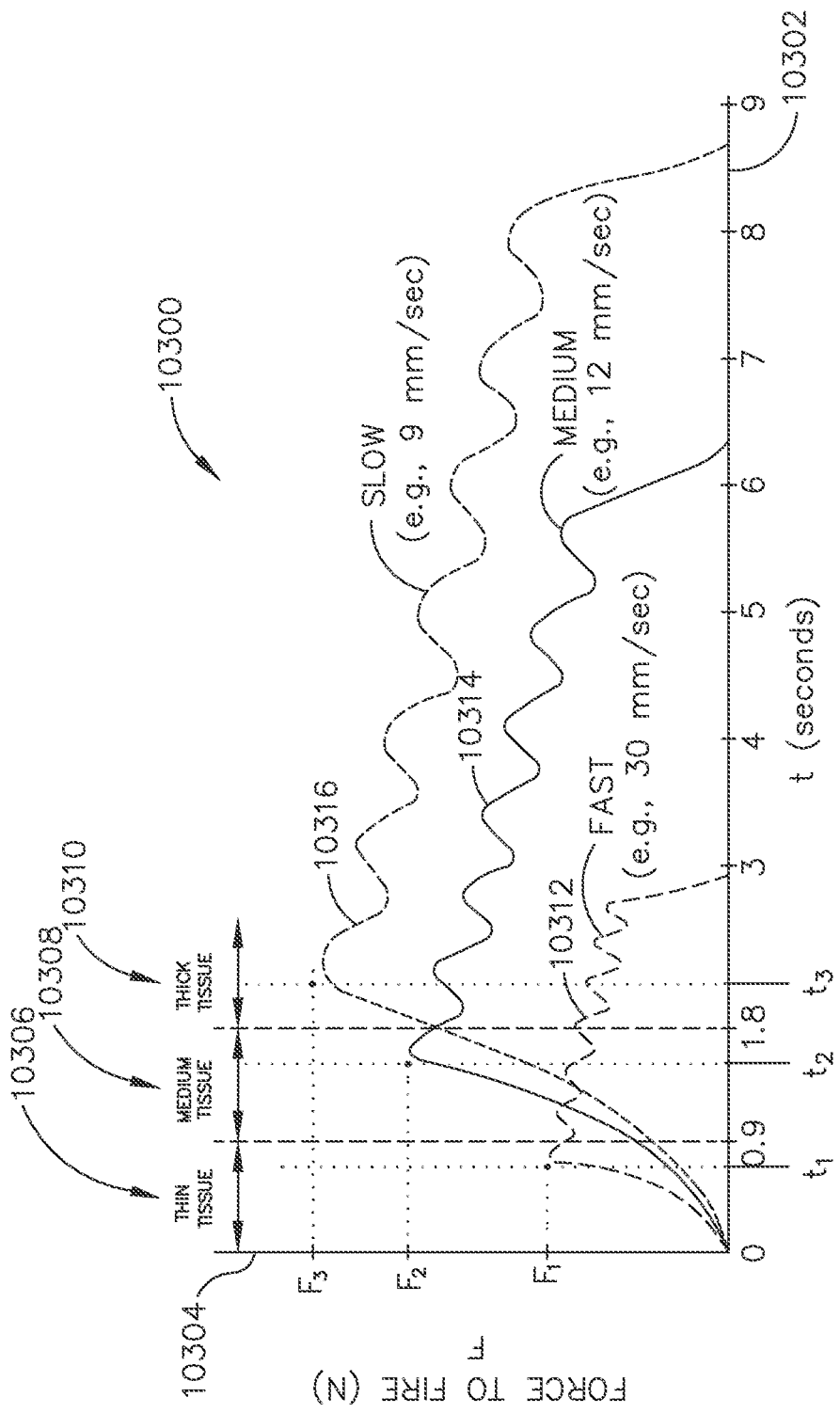

FIG. 41 is a graphical depiction of force to fire as a function of time comparing slow, medium and fast I-beam displacement velocities according to one aspect of this disclosure.

Figure 42:
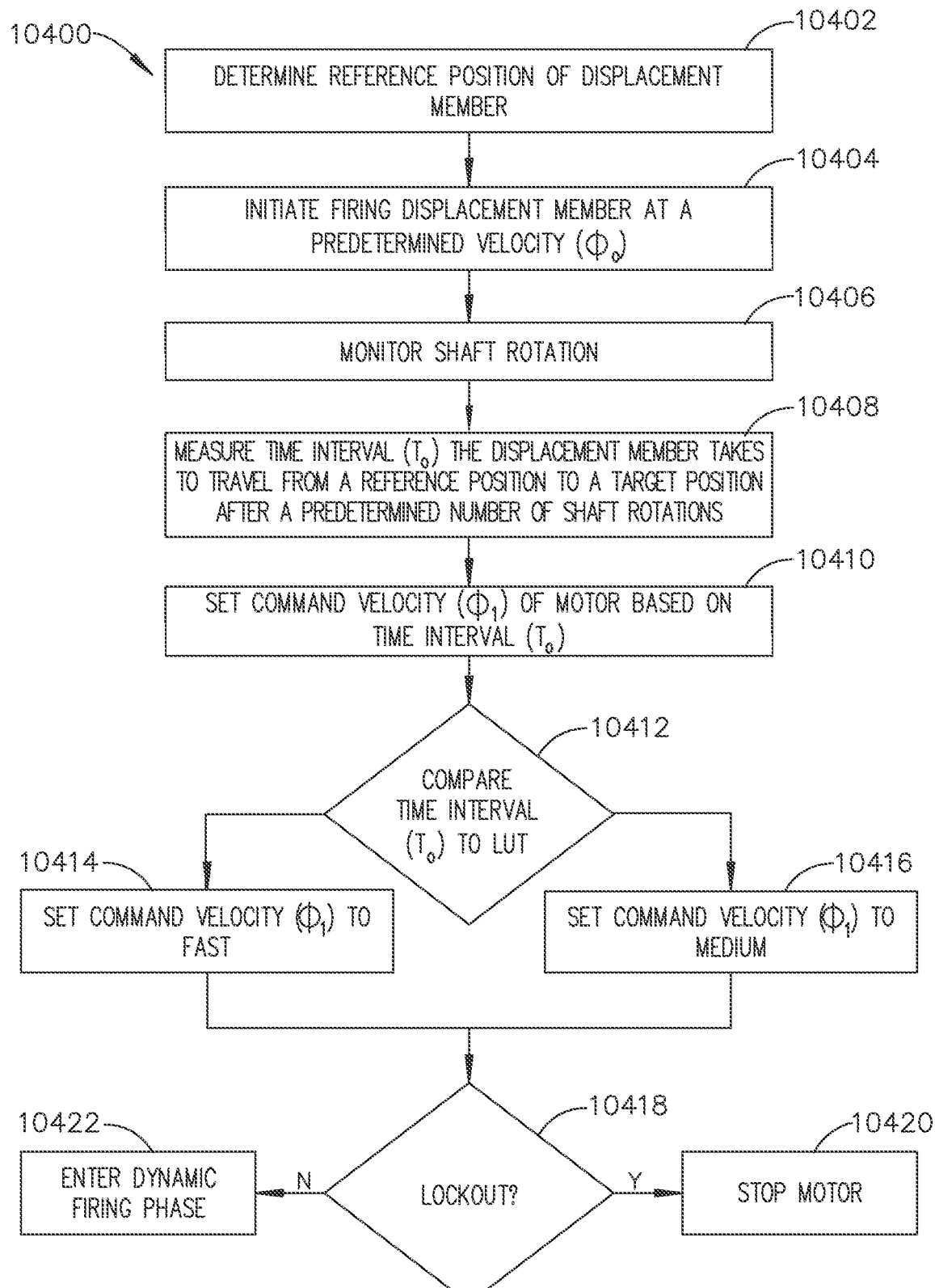

FIG. 42 is a logic flow diagram of a process depicting a control program or logic configuration for controlling command velocity in an initial firing stage according to one aspect of this disclosure.

Figure 43:
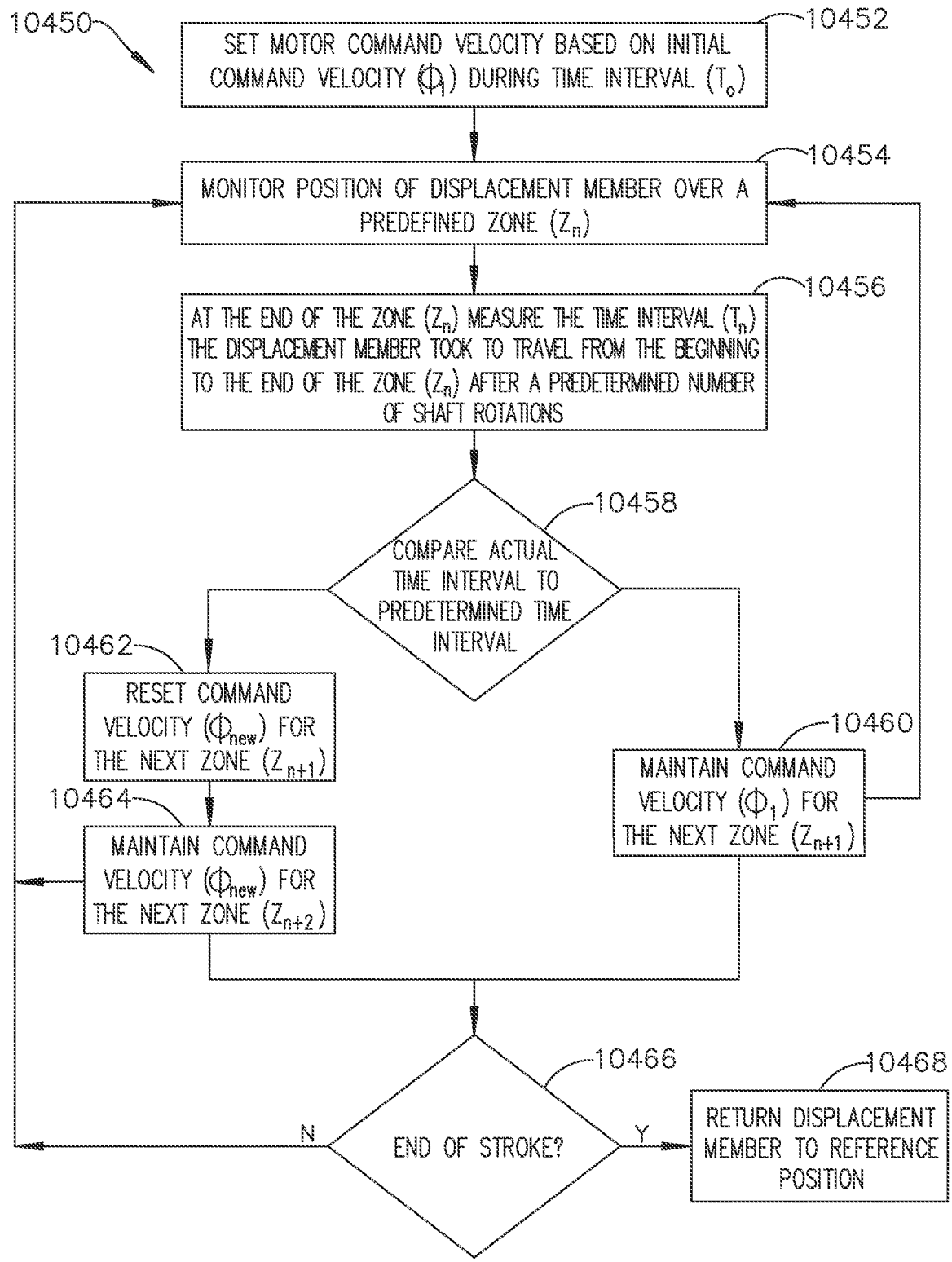

FIG. 43 is a logic flow diagram of a process depicting a control program or logic configuration for controlling command velocity in a dynamic firing stage according to one aspect of this disclosure.

Figure 44:
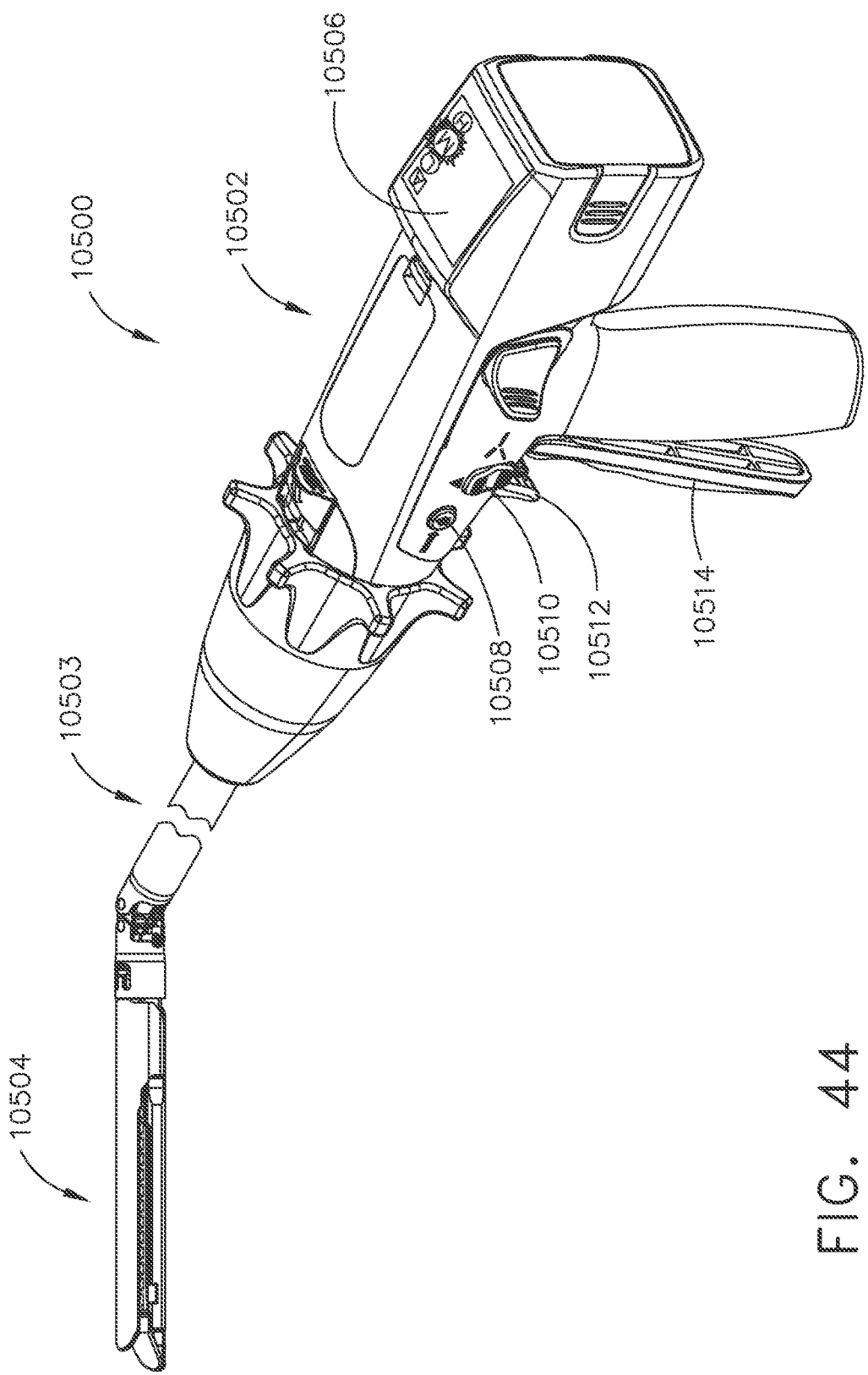

FIG. 44 is a perspective view of a surgical instrument according to one aspect of this disclosure.

Figure 45:
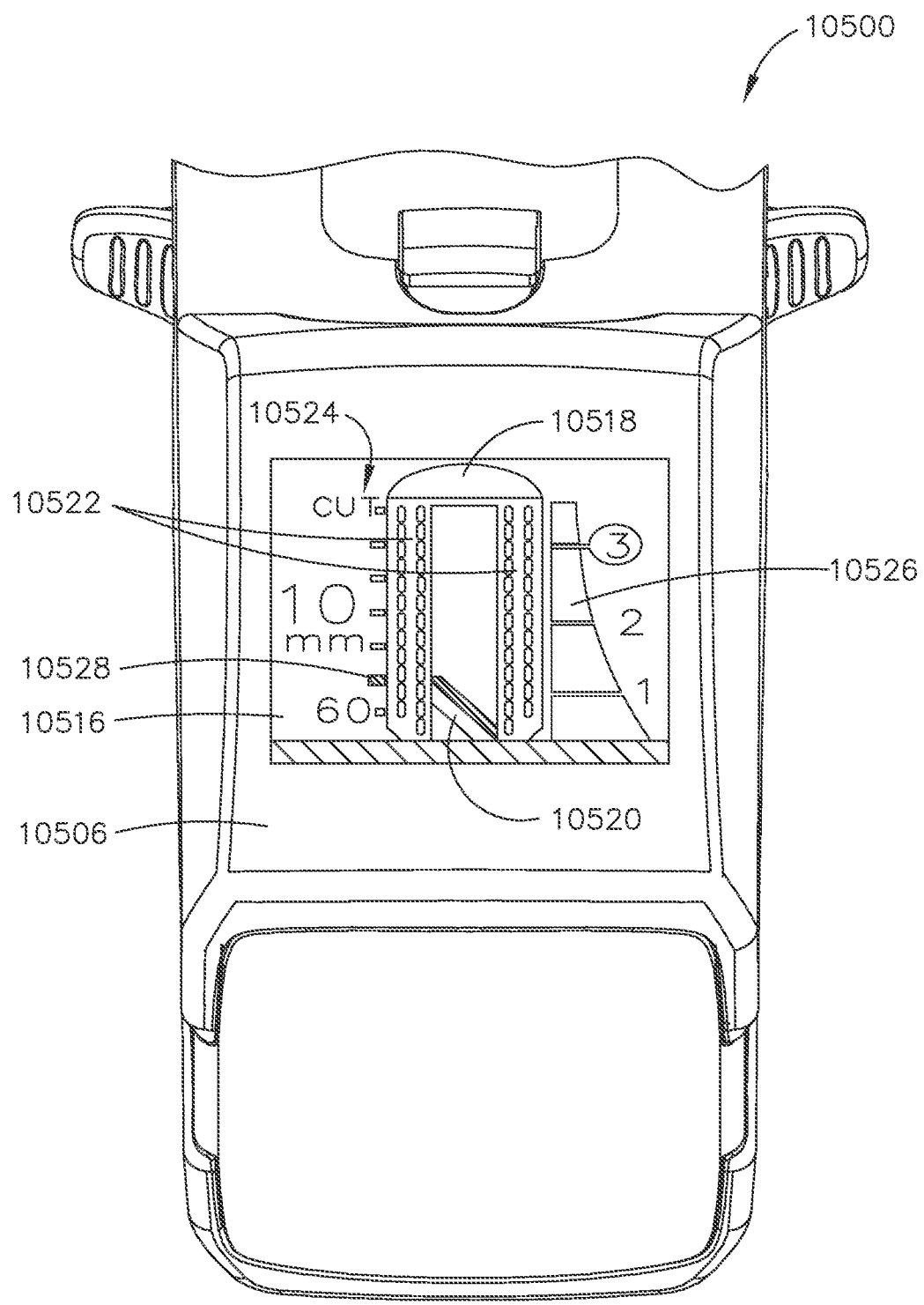

FIG. 45 is a detail view of a display portion of the surgical instrument shown in FIG. 44 according to one aspect of this disclosure.

Figure 46:
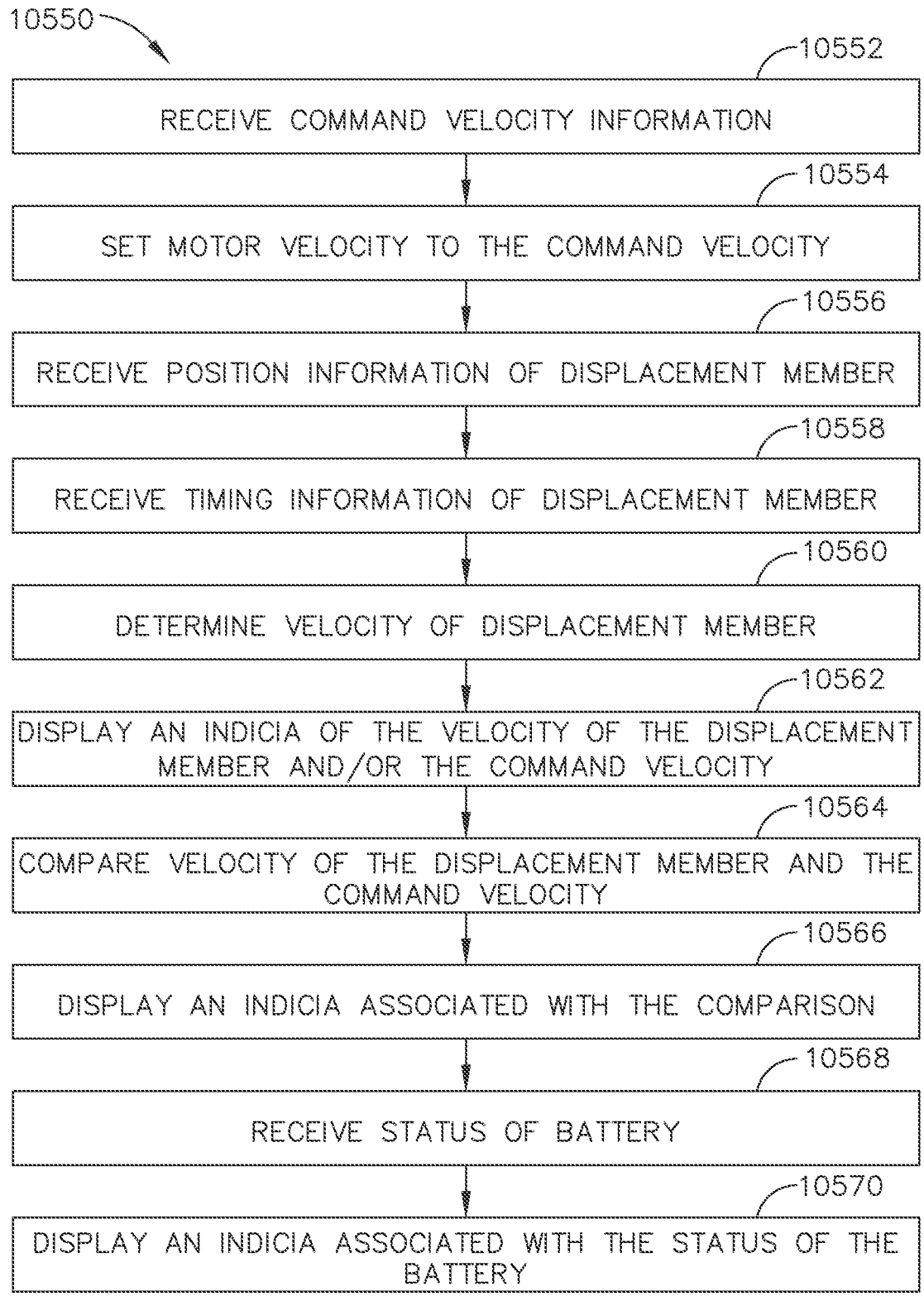

FIG. 46 is a logic flow diagram of a process depicting a control program or logic configuration for controlling a display according to one aspect of this disclosure.

FIG. 47 is a display depicting a velocity feedback screen according to one aspect of this disclosure.

FIG. 48 is a display depicting a velocity feedback screen according to one aspect of this disclosure.

FIG. 49 is a display depicting a velocity feedback screen indicative of an automatic mode according to one aspect of this disclosure.

FIG. 50 is a display depicting a velocity feedback screen indicative of an automatic mode according to one aspect of this disclosure.

FIG. 51 is a display depicting a velocity feedback screen indicative of an automatic mode according to one aspect of this disclosure.

FIG. 52 is a display depicting a velocity feedback screen indicative of an automatic mode according to one aspect of this disclosure.

FIG. 53 is a display depicting a velocity feedback screen indicative of a manual mode according to one aspect of this disclosure.

FIG. 54 is a display depicting a velocity feedback screen indicative of a manual mode according to one aspect of this disclosure.

FIG. 55 is a display depicting a velocity feedback screen indicative of an automatic mode according to one aspect of this disclosure.

FIG. 56 is a display depicting a velocity feedback screen according to one aspect of this disclosure.

FIG. 57 is a display depicting a velocity feedback screen according to one aspect of this disclosure.

FIG. 58 is a display depicting a velocity feedback screen according to one aspect of this disclosure.

FIG. 59 is a display depicting a velocity feedback screen according to one aspect of this disclosure.

FIG. 60 is a display depicting a velocity feedback screen according to one aspect of this disclosure.

FIG. 61 is a display depicting a velocity feedback screen according to one aspect of this disclosure.

FIG. 62 is a display depicting a velocity feedback screen according to one aspect of this disclosure.

FIG. 63 is a display depicting a velocity feedback screen according to one aspect of this disclosure.

FIG. 64 is a display depicting a velocity feedback screen according to one aspect of this disclosure.

FIG. 65 is a display depicting a velocity feedback screen according to one aspect of this disclosure.

FIG. 66 is a display depicting a velocity feedback screen according to one aspect of this disclosure.

FIG. 67 is a display depicting a velocity feedback screen according to one aspect of this disclosure.

FIG. 68 is a display depicting a velocity feedback screen according to one aspect of this disclosure.

FIG. 69 is a display depicting a velocity feedback screen according to one aspect of this disclosure.

FIG. 70 is a display depicting a velocity feedback screen according to one aspect of this disclosure.

FIG. 71 is a display depicting a velocity feedback screen according to one aspect of this disclosure.

FIG. 72 is a display depicting a velocity feedback screen according to one aspect of this disclosure.

FIG. 73 is a display depicting a velocity feedback screen according to one aspect of this disclosure.

FIG. 74 is a display depicting a velocity feedback screen indicative of a command velocity and an actual velocity according to one aspect of this disclosure.

FIG. 75 is a display depicting a velocity feedback screen indicative of a command velocity and an actual velocity according to one aspect of this disclosure.

FIG. 76 is a display depicting a velocity feedback screen indicative of a command velocity and an actual velocity according to one aspect of this disclosure.

FIG. 77 is a display depicting a velocity feedback screen according to one aspect of this disclosure.

FIG. 78 is a display depicting a velocity feedback screen according to one aspect of this disclosure.

FIG. 79 is a display depicting a velocity feedback screen according to one aspect of this disclosure.

FIG. 80 is a display depicting a velocity feedback screen according to one aspect of this disclosure.

FIG. 81 is a display depicting a temperature feedback screen according to one aspect of this disclosure.

Figure 82:
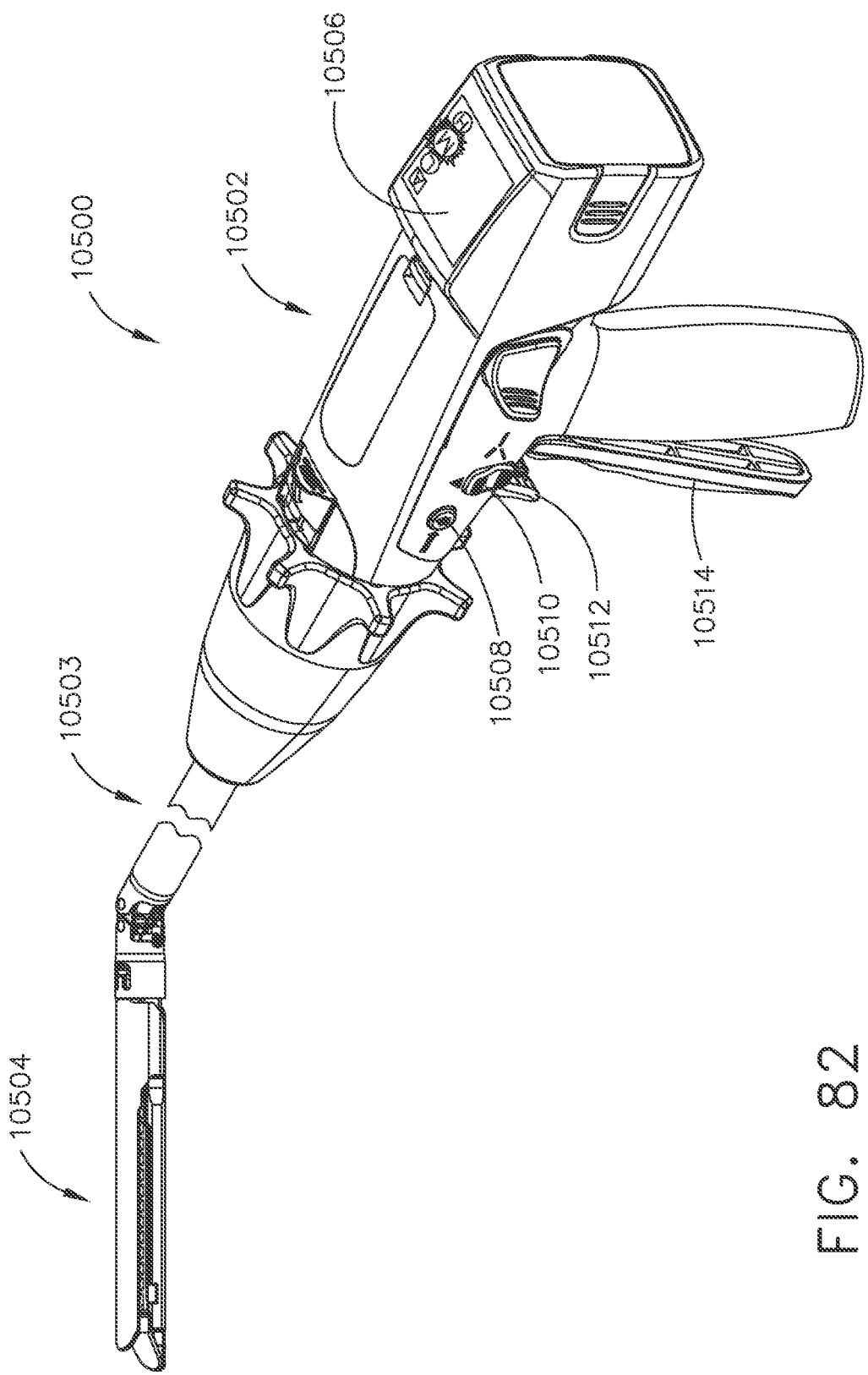

FIG. 82 is a perspective view of a surgical instrument according to one aspect of this disclosure.

Figure 83:
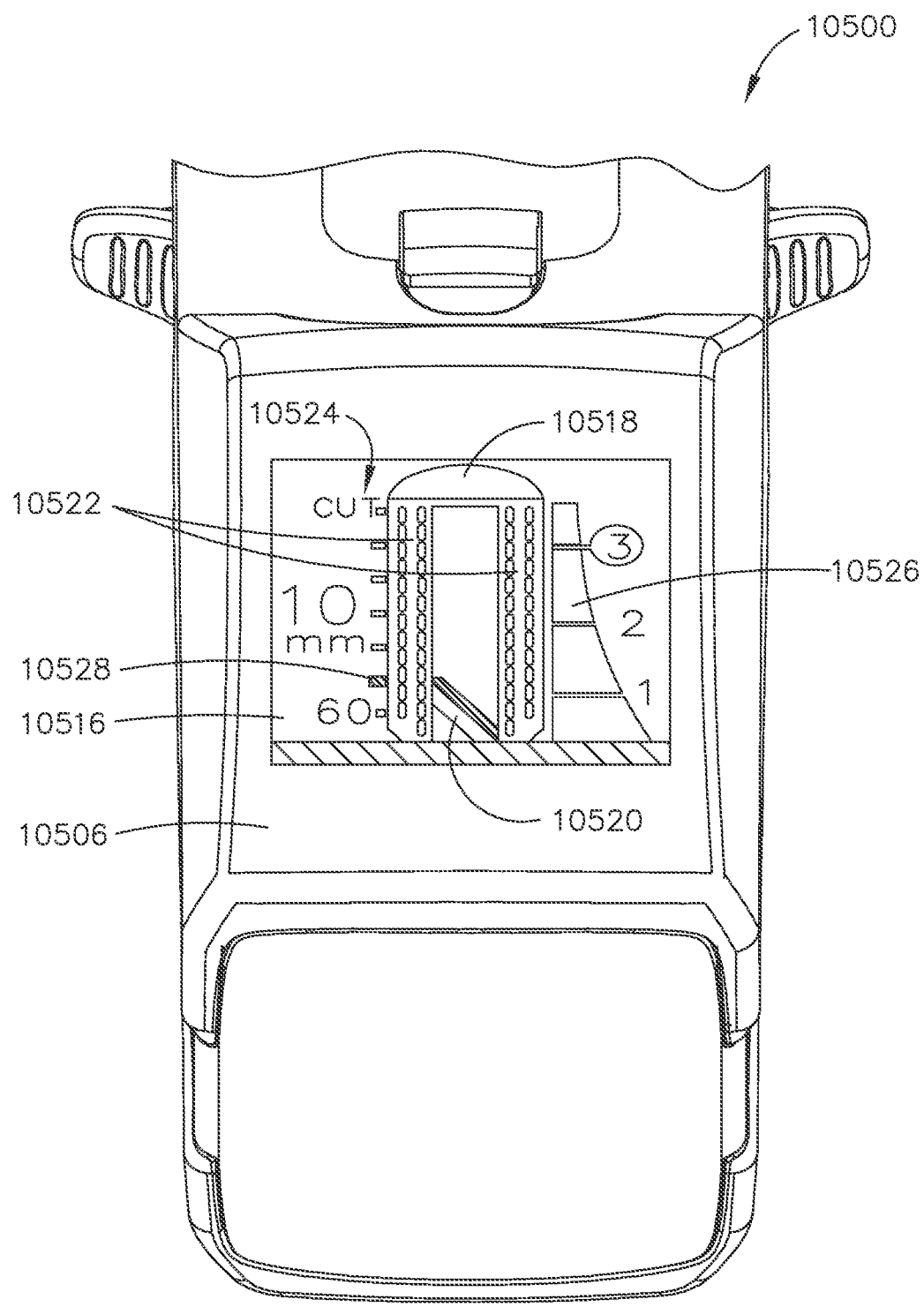

FIG. 83 is a detail view of a display portion of the surgical instrument shown in FIG. 82 according to one aspect of this disclosure.

Figure 84:
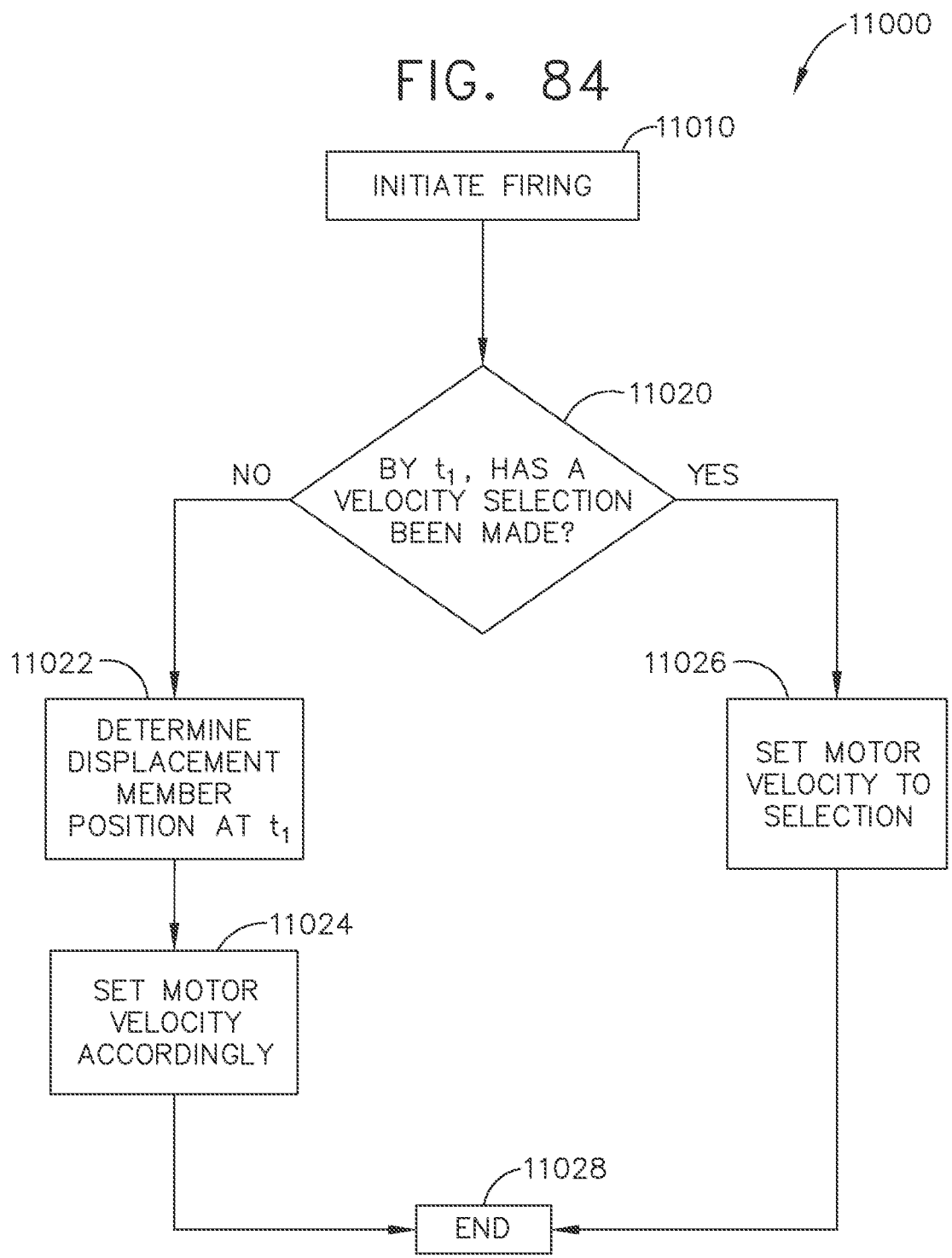

FIG. 84 is a logic flow diagram of a process depicting a control program or logic configuration for controlling a display according to one aspect of this disclosure.

FIG. 85 is a display depicting a velocity feedback screen according to one aspect of this disclosure.

FIG. 86 is a display depicting a velocity feedback screen according to one aspect of this disclosure.

FIG. 87 is a switch located on the housing of the surgical instrument shown in FIG. 82.

Figure 88:
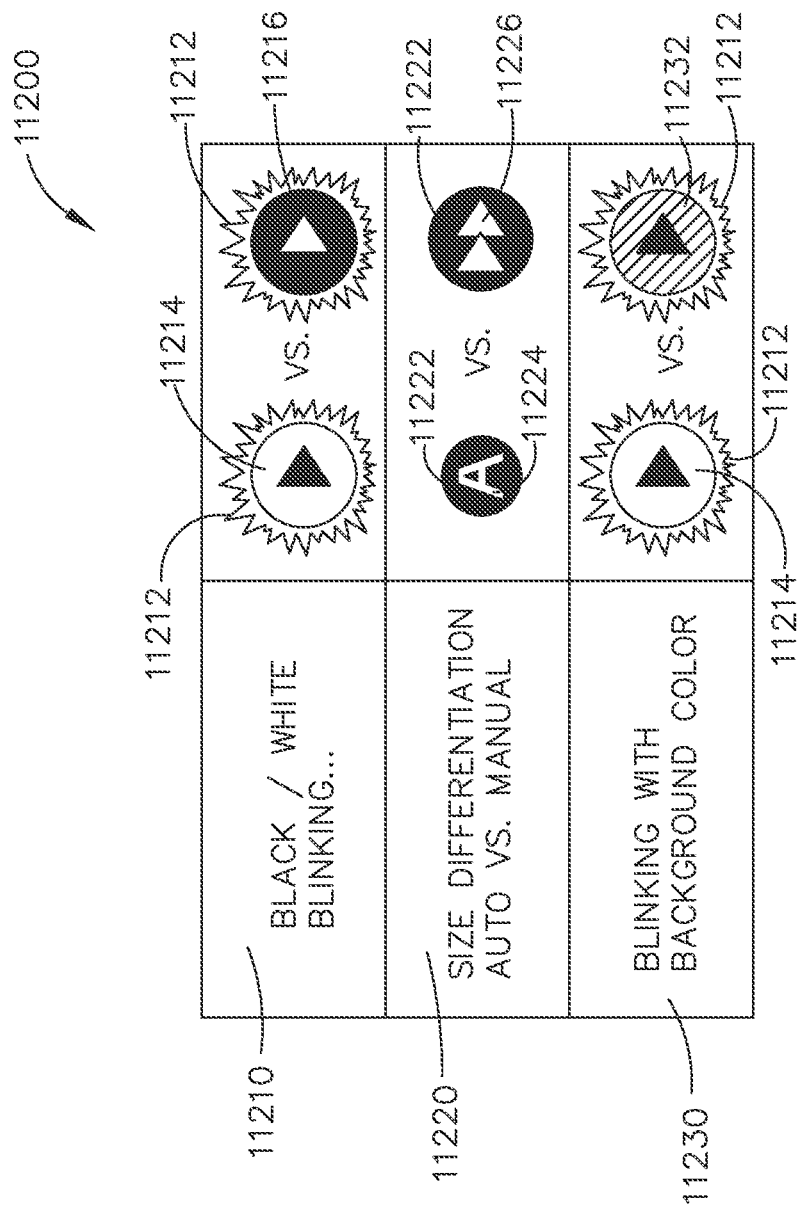

FIG. 88 is a chart representing various manners of how the display highlights selection menu options.

Figure 89:
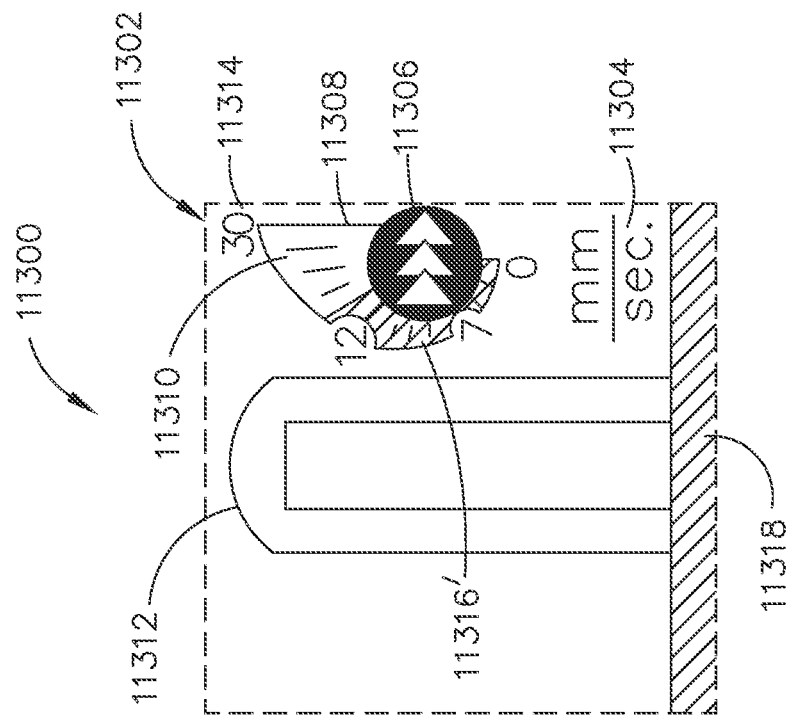

FIG. 89 is a display depicting a velocity feedback screen indicative of a manual fast mode according to one aspect of this disclosure.

Figure 90:
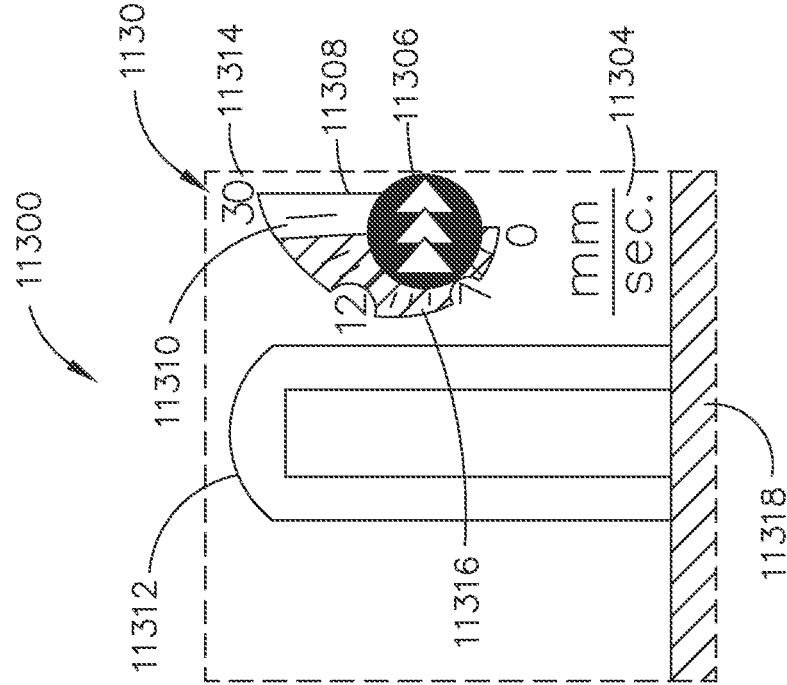

FIG. 90 is a display depicting a velocity feedback screen indicative of a manual fast mode according to one aspect of this disclosure.

Figure 91:
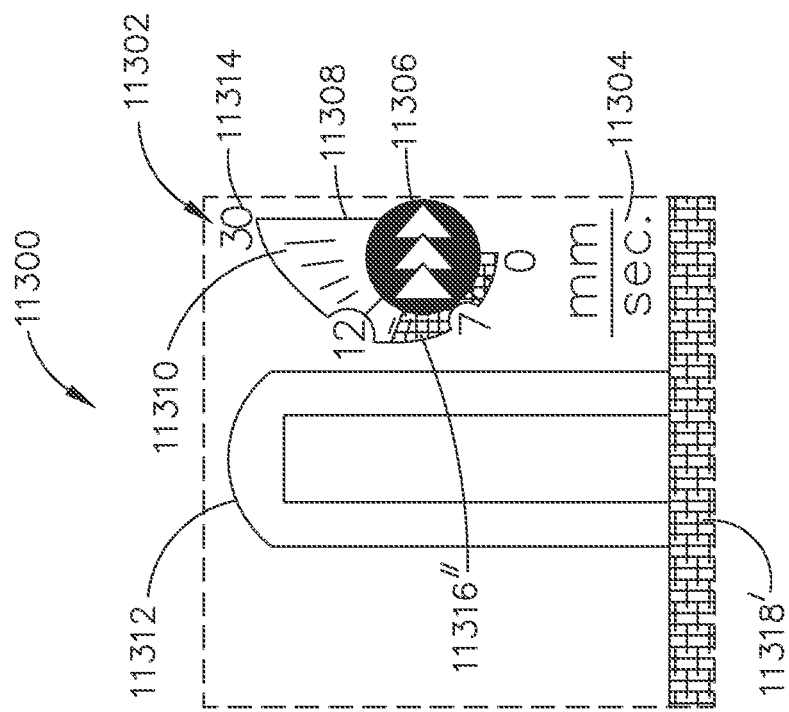

FIG. 91 is a display depicting a velocity feedback screen indicative of a manual fast mode according to one aspect of this disclosure.

Figure 92:
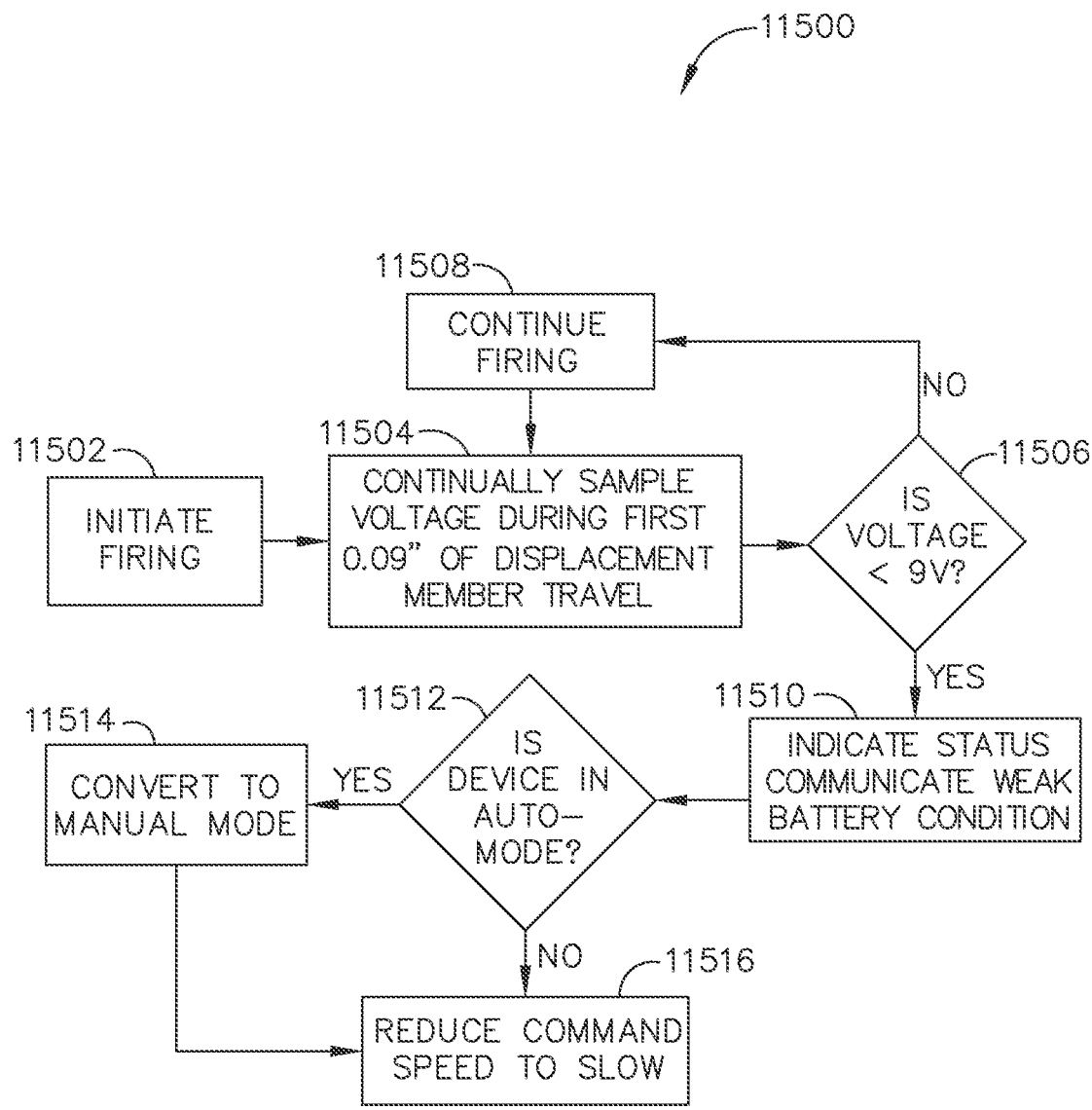

FIG. 92 is a logic flow diagram of a process depicting a control program or logic configuration for controlling motor velocity based on battery condition according to one aspect of this disclosure.

Figure 93:
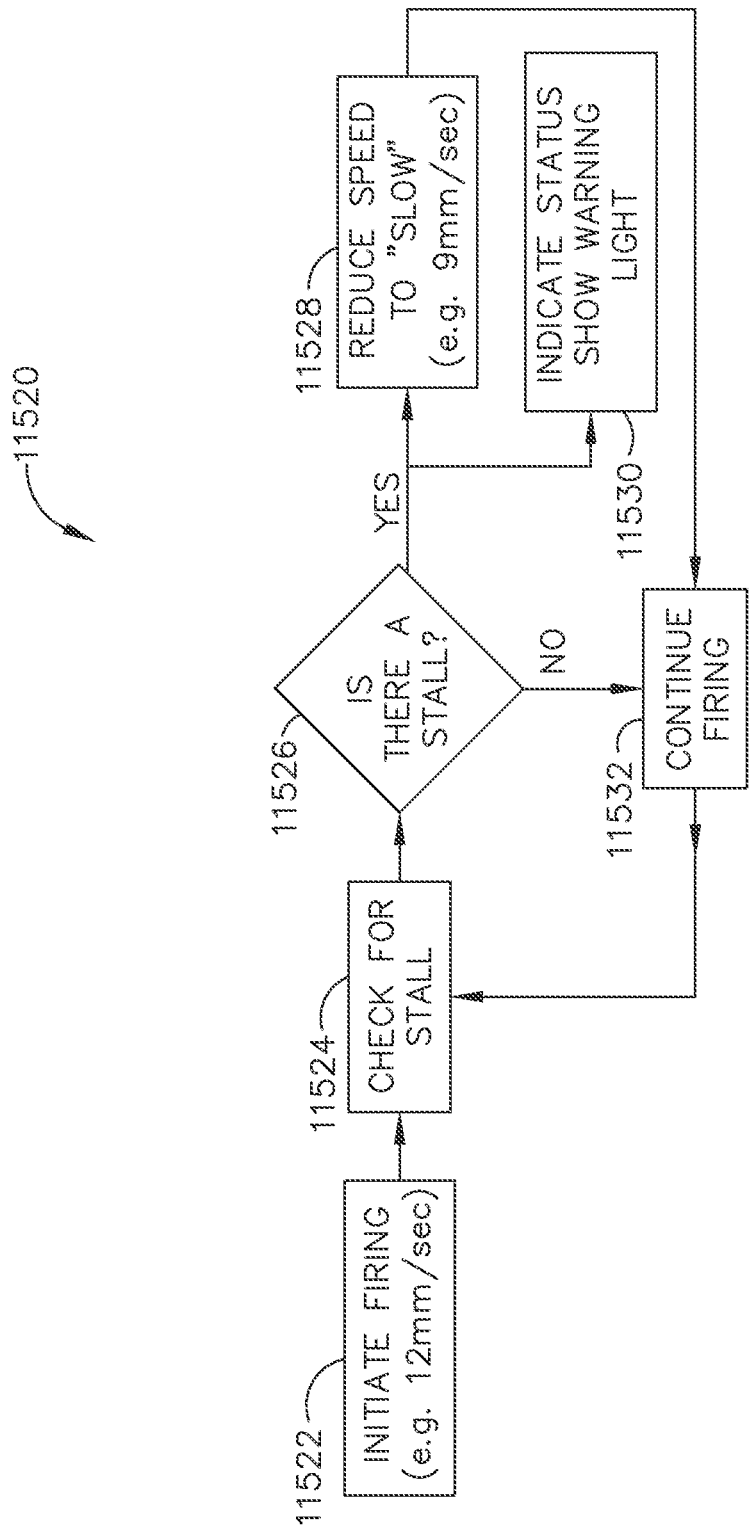

FIG. 93 is a logic flow diagram of a process depicting a control program or logic configuration for controlling motor velocity based on stalled condition during a normal firing cycle according to one aspect of this disclosure.

Figure 94:
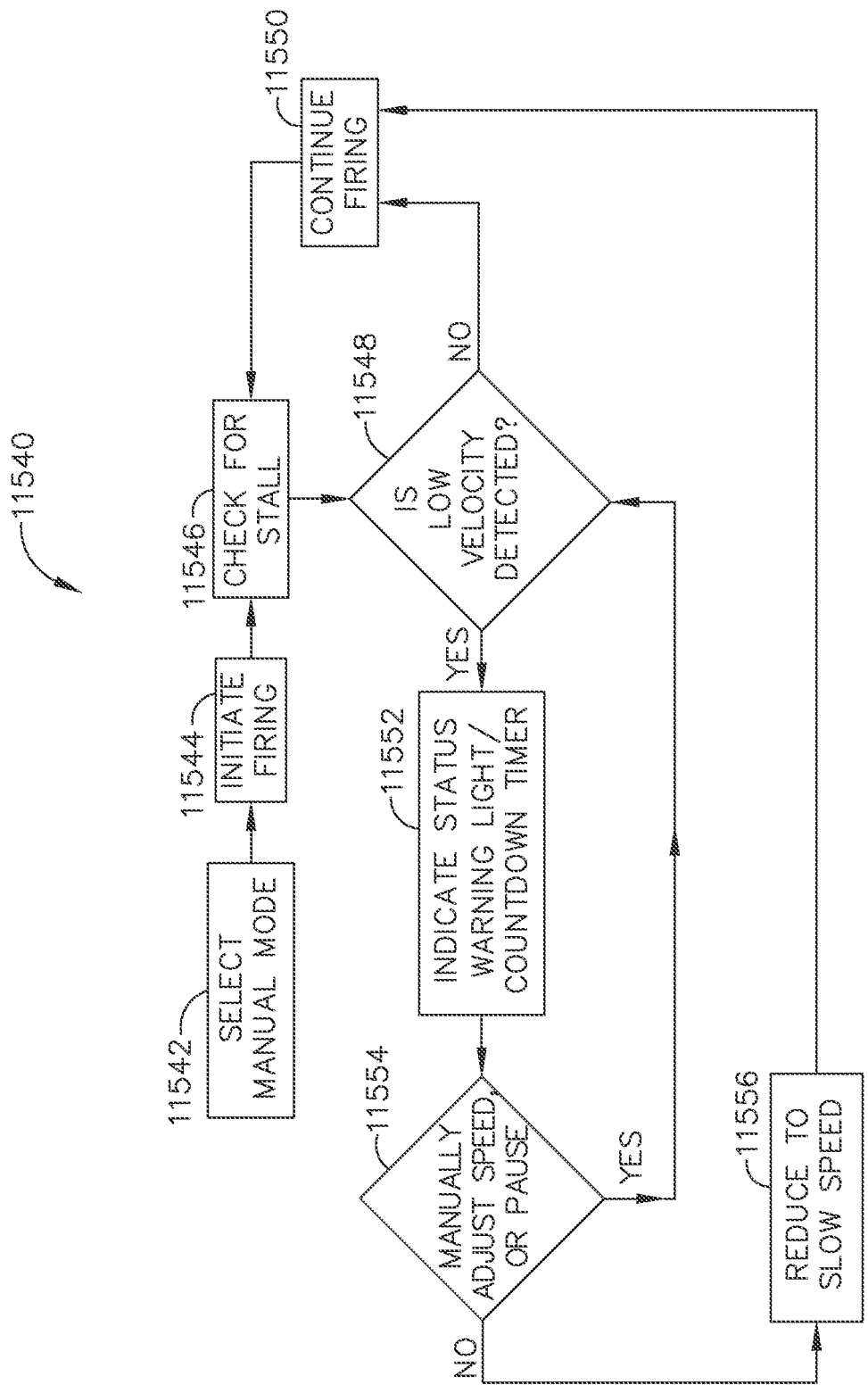

FIG. 94 is a logic flow diagram of a process depicting a control program or logic configuration for controlling motor velocity while in manual mode according to one aspect of this disclosure.

Figure 95:
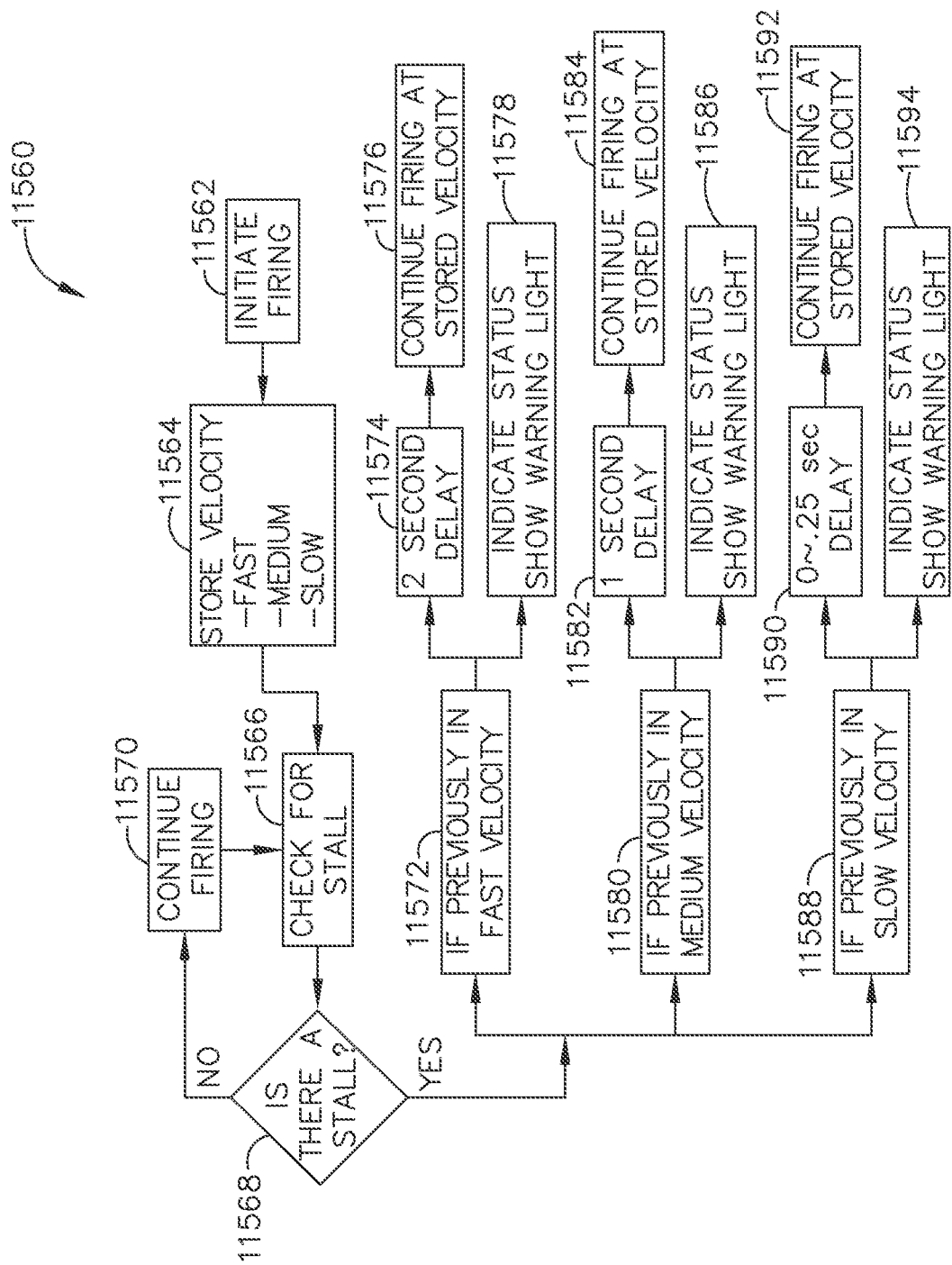

FIG. 95 is a logic flow diagram of a process depicting a control program or logic configuration for controlling motor velocity based on stalled condition during a normal firing cycle and implementing a forced pause in the firing cycle according to one aspect of this disclosure.

Figure 96:
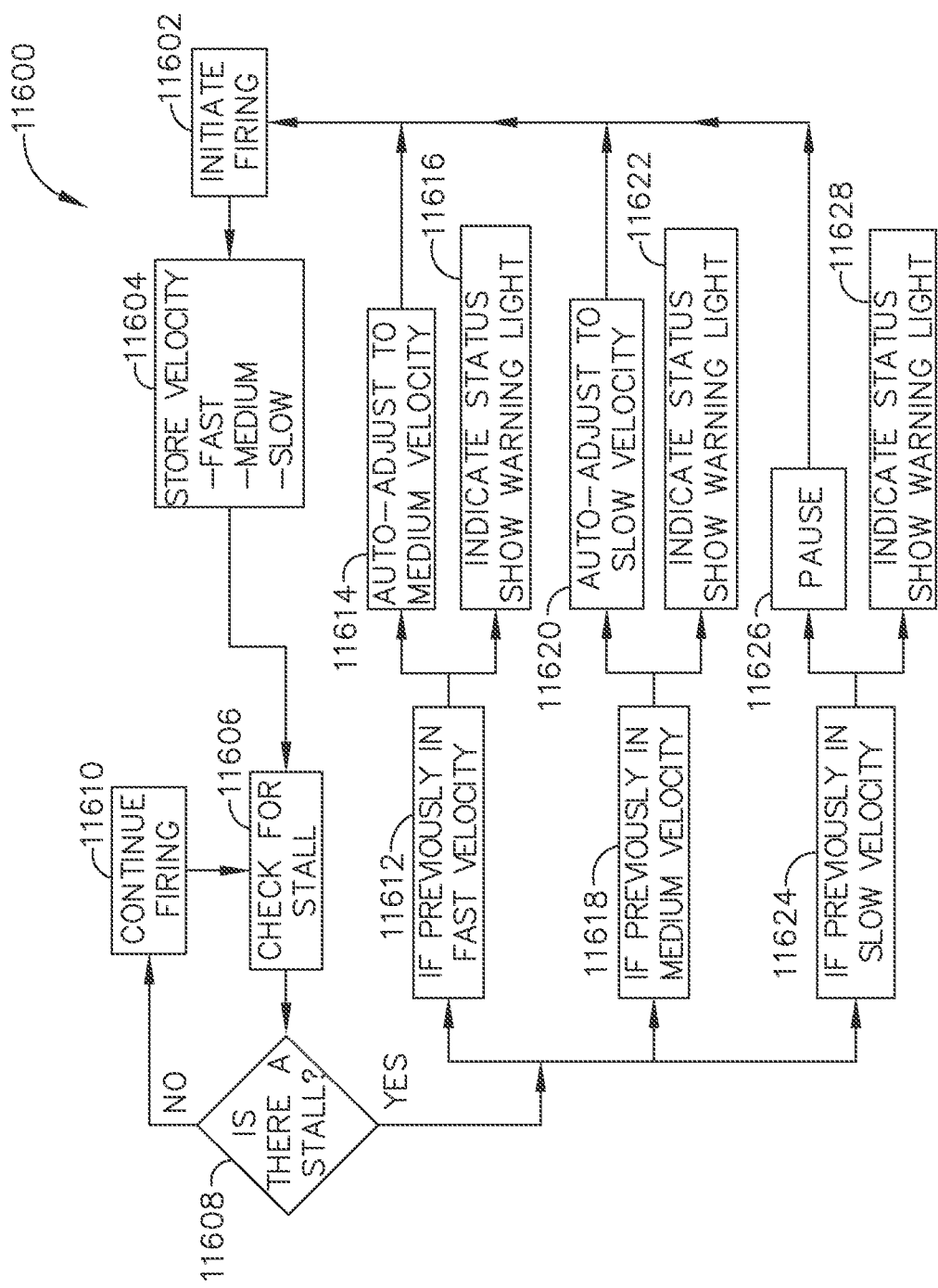

FIG. 96 is a logic flow diagram of a process depicting a control program or logic configuration for controlling motor velocity based on stalled condition during a normal firing and reducing the velocity one level once the firing cycle is restarted according to one aspect of this disclosure.

Figure 97:
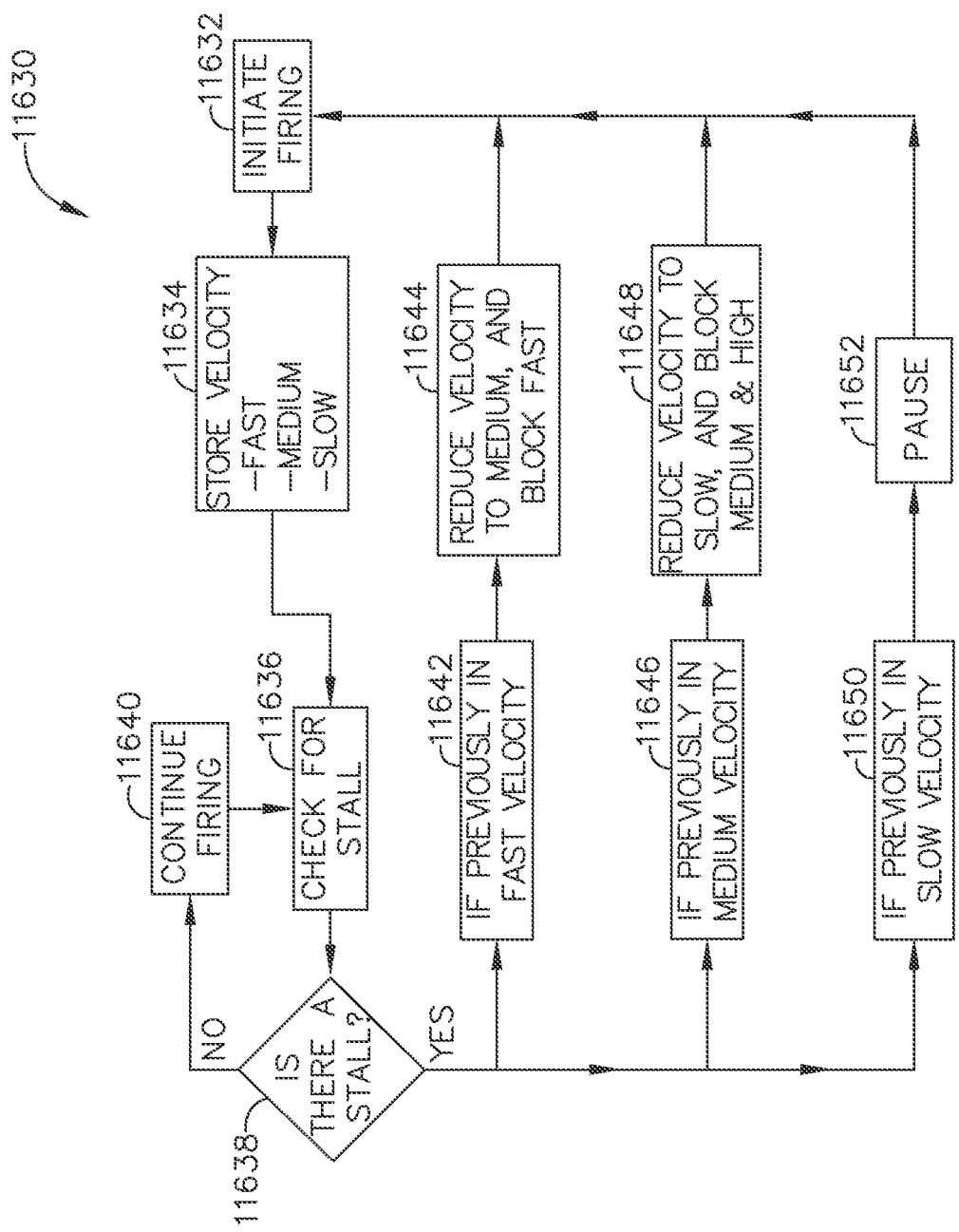

FIG. 97 is a logic flow diagram of a process depicting a control program or logic configuration for controlling motor velocity based on stalled condition during a normal firing cycle in manual mode and reducing velocity one level once the firing cycle is restarted according to one aspect of this disclosure.

Figure 98:
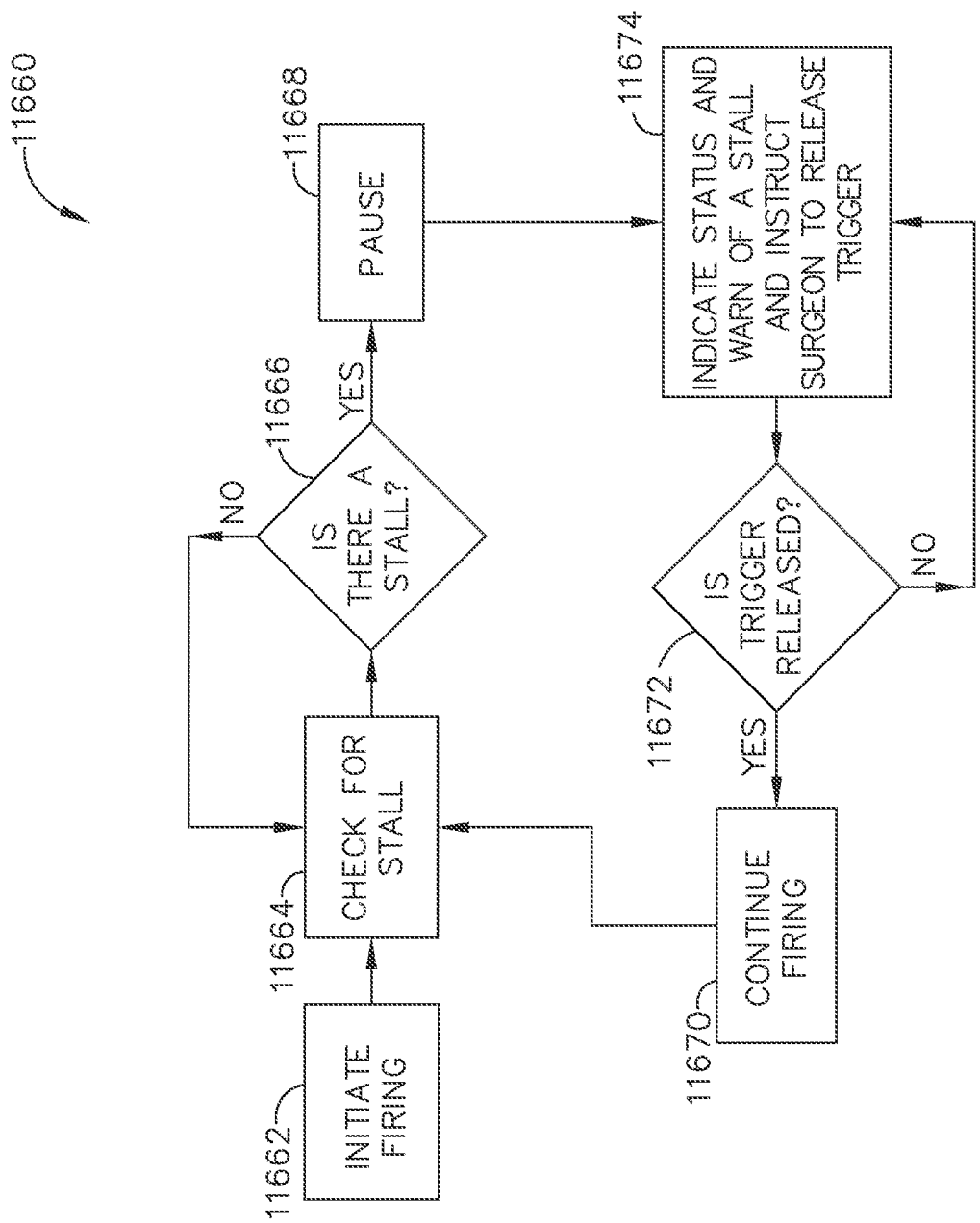

FIG. 98 is a logic flow diagram of a process depicting a control program or logic configuration for controlling motor velocity based on stalled condition during a normal firing cycle and pausing the firing cycle until the user releases the firing trigger according to one aspect of this disclosure.

Figure 99:
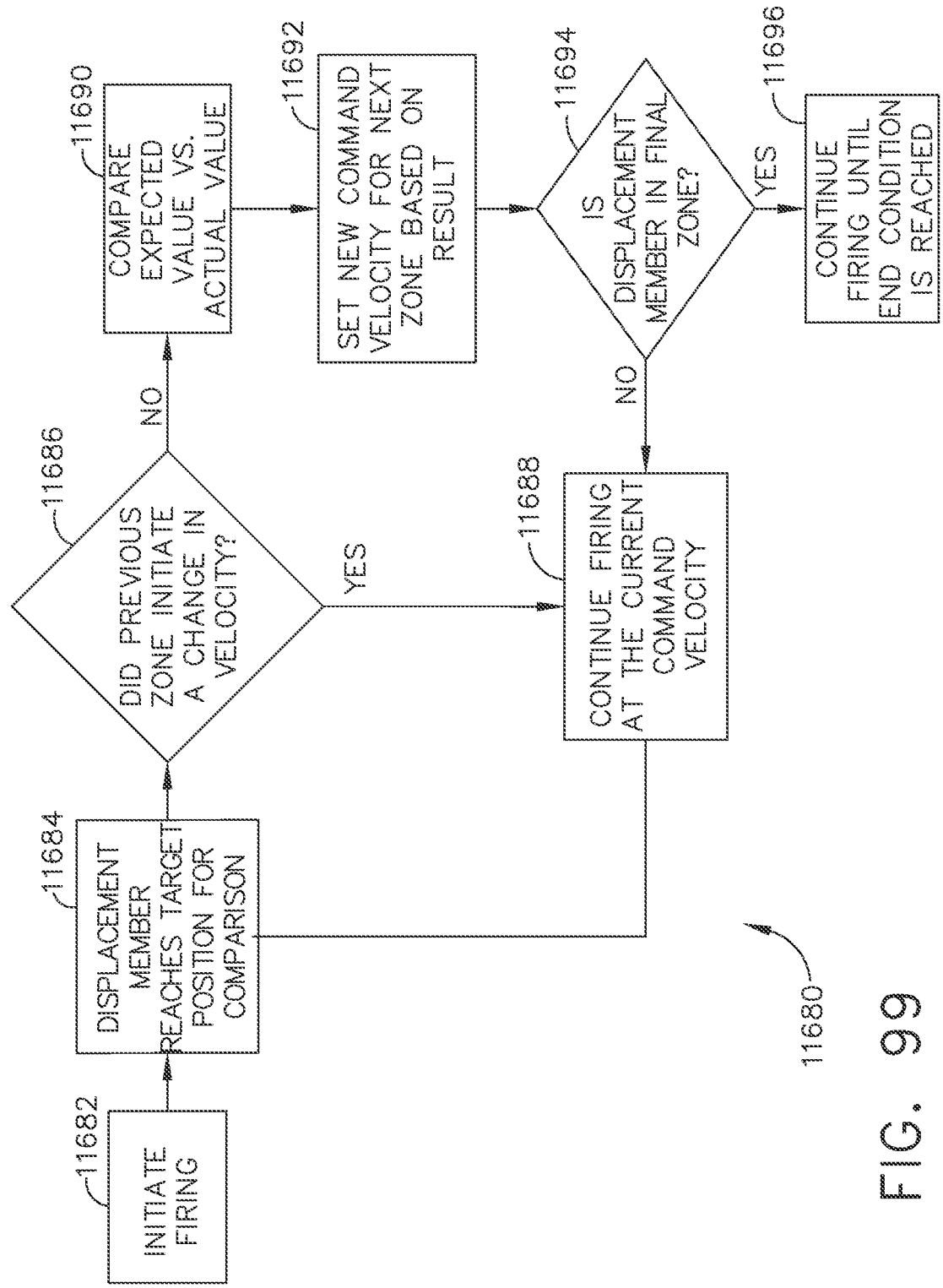

FIG. 99 is a logic flow diagram of a process depicting a control program or logic configuration for controlling motor velocity during transition between velocities according to one aspect of this disclosure.

Figure 100:
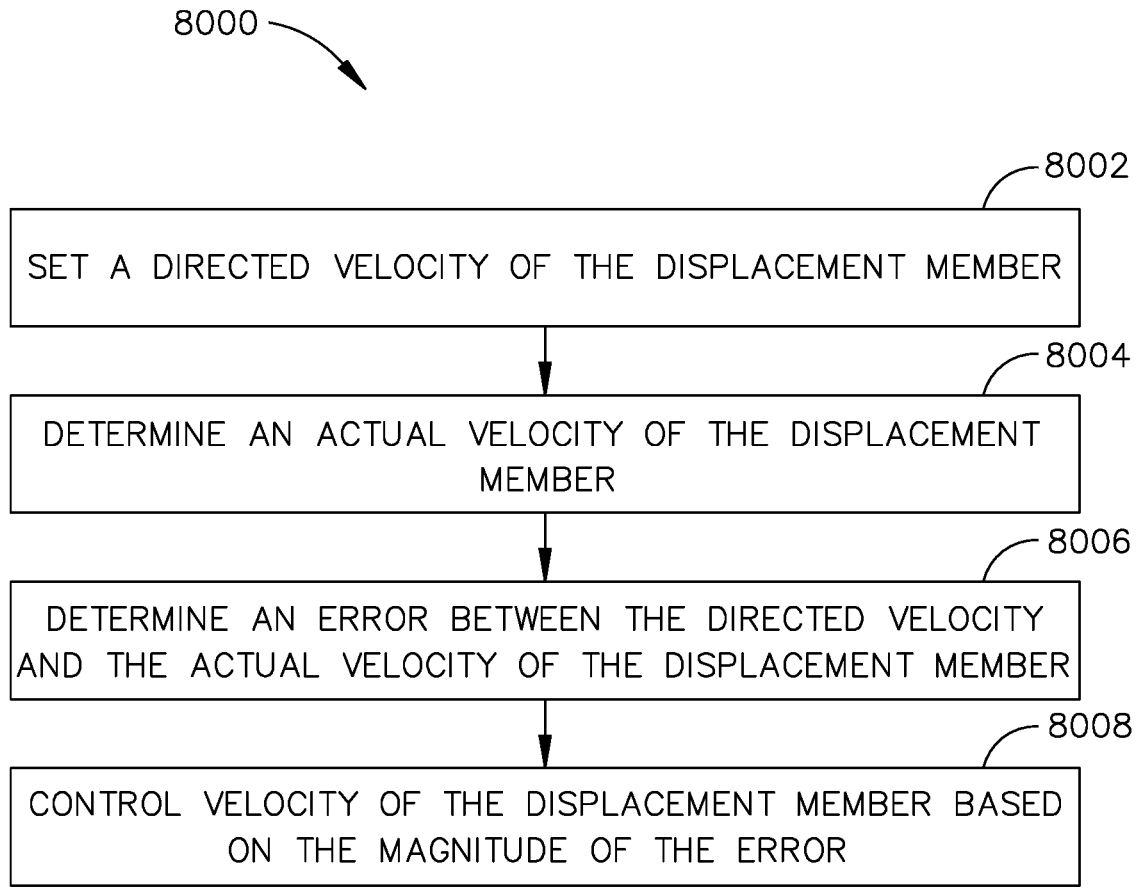

FIG. 100 is a logic flow diagram depicting a process of a control program or a logic configuration for adjusting the velocity of a displacement member based on the magnitude of one or more error terms based on the difference between an actual velocity of the displacement member and a command or directed velocity of the displacement member over a specified increment of time or distance according to one aspect of this disclosure.

DESCRIPTION

Applicant of the present application owns the following patent applications filed on Jun. 20, 2017 and which are each herein incorporated by reference in their respective entireties:

U.S. patent application Ser. No. 15/627,998, titled CONTROL OF MOTOR VELOCITY OF A SURGICAL STAPLING AND CUTTING INSTRUMENT BASED ON ANGLE OF ARTICULATION, by inventors Frederick E. Shelton, IV et al., filed Jun. 20, 2017, now U.S. Pat. No. 10,390,841.

U.S. patent application Ser. No. 15/628,019, titled SURGICAL INSTRUMENT WITH VARIABLE DURATION TRIGGER ARRANGEMENT, by inventors Frederick E. Shelton, IV et al., filed Jun. 20, 2017, now U.S. Pat. No. 10,881,396.

U.S. patent application Ser. No. 15/628,036, titled SYSTEMS AND METHODS FOR CONTROLLING DISPLACEMENT MEMBER MOTION OF A SURGICAL STAPLING AND CUTTING INSTRUMENT, by inventors Frederick E. Shelton, IV et al., filed Jun. 20, 2017, now U.S. Pat. No. 11,090,046.

U.S. patent application Ser. No. 15/628,050, titled SYSTEMS AND METHODS FOR CONTROLLING MOTOR VELOCITY OF A SURGICAL STAPLING AND CUTTING INSTRUMENT ACCORDING TO ARTICULATION ANGLE OF END EFFECTOR, by inventors Frederick E. Shelton, IV et al., filed Jun. 20, 2017, now U.S. Pat. No. 11,653,914.

U.S. patent application Ser. No. 15/628,075, titled SYSTEMS AND METHODS FOR CONTROLLING MOTOR VELOCITY OF A SURGICAL STAPLING AND CUTTING INSTRUMENT, by inventors Frederick E. Shelton, IV et al., filed Jun. 20, 2017, now U.S. Pat. No. 10,624,633.

U.S. patent application Ser. No. 15/628,154, titled SURGICAL INSTRUMENT HAVING CONTROLLABLE ARTICULATION VELOCITY, by inventors Frederick E. Shelton, IV et al., filed Jun. 20, 2017, now U.S. Patent Application Publication No. 2018/0360456.

U.S. patent application Ser. No. 15/628,158, titled SYSTEMS AND METHODS FOR CONTROLLING VELOCITY OF A DISPLACEMENT MEMBER OF A SURGICAL STAPLING AND CUTTING INSTRUMENT, by inventors Frederick E. Shelton, IV et al., filed Jun. 20, 2017, now U.S. Pat. No. 10,888,321.

U.S. patent application Ser. No. 15/628,162, titled SYSTEMS AND METHODS FOR CONTROLLING DISPLACEMENT MEMBER VELOCITY FOR A SURGICAL INSTRUMENT, by inventors Frederick E. Shelton, IV et al., filed Jun. 20, 2017, now U.S. Pat. No. 10,646,220.

U.S. patent application Ser. No. 15/628,168, titled CONTROL OF MOTOR VELOCITY OF A SURGICAL STAPLING AND CUTTING INSTRUMENT BASED ON ANGLE OF ARTICULATION, by inventors Frederick E. Shelton, IV et al., filed Jun. 20, 2017, now U.S. Pat. No. 10,327,767.

U.S. patent application Ser. No. 15/628,175, titled TECHNIQUES FOR ADAPTIVE CONTROL OF MOTOR VELOCITY OF A SURGICAL STAPLING AND CUTTING INSTRUMENT, by inventors Frederick E. Shelton, IV et al., filed Jun. 20, 2017, now U.S. Pat. No. 10,881,399.

U.S. patent application Ser. No. 15/628,053, titled CLOSED LOOP FEEDBACK CONTROL OF MOTOR VELOCITY OF A SURGICAL STAPLING AND CUTTING INSTRUMENT BASED ON MAGNITUDE OF VELOCITY ERROR MEASUREMENTS, by inventors Raymond E. Parfett et al., filed Jun. 20, 2017, now U.S. Pat. No. 11,071,554.

U.S. patent application Ser. No. 15/628,060, titled CLOSED LOOP FEEDBACK CONTROL OF MOTOR VELOCITY OF A SURGICAL STAPLING AND CUTTING INSTRUMENT BASED ON MEASURED TIME OVER A SPECIFIED DISPLACEMENT DISTANCE, by inventors Jason L. Harris et al., filed Jun. 20, 2017, now U.S. Pat. No. 11,382,638.

U.S. patent application Ser. No. 15/628,067, titled CLOSED LOOP FEEDBACK CONTROL OF MOTOR VELOCITY OF A SURGICAL STAPLING AND CUTTING INSTRUMENT BASED ON MEASURED DISPLACEMENT DISTANCE TRAVELED OVER A SPECIFIED TIME INTERVAL, by inventors Frederick E. Shelton, IV et al., filed Jun. 20, 2017, now U.S. Pat. 11,517,325.

U.S. patent application Ser. No. 15/628,072, titled CLOSED LOOP FEEDBACK CONTROL OF MOTOR VELOCITY OF A SURGICAL STAPLING AND CUTTING INSTRUMENT BASED ON MEASURED TIME OVER A SPECIFIED NUMBER OF SHAFT ROTATIONS, by inventors Frederick E. Shelton, IV et al., filed Jun. 20, 2017, now U.S. Pat. No. 10,980,537.

U.S. patent application Ser. No. 15/628,029, titled SYSTEMS AND METHODS FOR CONTROLLING DISPLAYING MOTOR VELOCITY FOR A SURGICAL INSTRUMENT, by inventors Jason L. Harris et al., filed Jun. 20, 2017, now U.S. Pat. No. 10,368,864.

U.S. patent application Ser. No. 15/628,077, titled SYSTEMS AND METHODS FOR CONTROLLING MOTOR SPEED ACCORDING TO USER INPUT FOR A SURGICAL INSTRUMENT, by inventors Jason L. Harris et al., filed Jun. 20, 2017, now U.S. Pat. No. 10,779,820.

U.S. patent application Ser. No. 15/628,115, titled CLOSED LOOP FEEDBACK CONTROL OF MOTOR VELOCITY OF A SURGICAL STAPLING AND CUTTING INSTRUMENT BASED ON SYSTEM CONDITIONS, by inventors Frederick E. Shelton, IV et al., filed Jun. 20, 2017, now U.S. Pat. Application Publication No. 10,813,639.

U.S. Design patent application Ser. No. 29/608,238, titled GRAPHICAL USER INTERFACE FOR A DISPLAY OR PORTION THEREOF, by inventors Jason L. Harris et al., filed Jun. 20, 2017.

U.S. Design patent application Ser. No. 29/608,231, titled GRAPHICAL USER INTERFACE FOR A DISPLAY OR PORTION THEREOF, by inventors Jason L. Harris et al., filed Jun. 20, 2017.

U.S. Design patent application Ser. No. 29/608,246, titled GRAPHICAL USER INTERFACE FOR A DISPLAY OR PORTION THEREOF, by inventors Frederick E. Shelton, IV et al., filed Jun. 20, 2017.

Certain aspects are shown and described to provide an understanding of the structure, function, manufacture, and use of the disclosed devices and methods. Features shown or described in one example may be combined with features of other examples and modifications and variations are within the scope of this disclosure.

The terms "proximal" and "distal" are relative to a clinician manipulating the handle of the surgical instrument where "proximal" refers to the portion closer to the clinician and "distal" refers to the portion located further from the clinician. For expediency, spatial terms "vertical," "horizontal," "up," and "down" used with respect to the drawings are not intended to be limiting and/or absolute, because surgical instruments can used in many orientations and positions.

Example devices and methods are provided for performing laparoscopic and minimally invasive surgical procedures. Such devices and methods, however, can be used in other surgical procedures and applications including open surgical procedures, for example. The surgical instruments can be inserted into a through a natural orifice or through an incision or puncture hole formed in tissue. The working portions or end effector portions of the instruments can be inserted directly into the body or through an access device that has a working channel through which the end effector and elongated shaft of the surgical instrument can be advanced.

FIGS. 1-4 depict a motor-driven surgical instrument 10 for cutting and fastening that may or may not be reused. In the illustrated examples, the surgical instrument 10 includes a housing 12 that comprises a handle assembly 14 that is configured to be grasped, manipulated, and actuated by the clinician. The housing 12 is configured for operable attachment to an interchangeable shaft assembly 200 that has an end effector 300 operably coupled thereto that is configured to perform one or more surgical tasks or procedures. In accordance with the present disclosure, various forms of interchangeable shaft assemblies may be effectively employed in connection with robotically controlled surgical systems. The term "housing" may encompass a housing or similar portion of a robotic system that houses or otherwise operably supports at least one drive system configured to generate and apply at least one control motion that could be used to actuate interchangeable shaft assemblies. The term "frame" may refer to a portion of a handheld surgical instrument. The term "frame" also may represent a portion of a robotically controlled surgical instrument and/or a portion of the robotic system that may be used to operably control a surgical instrument. Interchangeable shaft assemblies may be employed with various robotic systems, instruments, components, and methods disclosed in U.S. Pat. No. 9,072,535, entitled SURGICAL STAPLING INSTRUMENTS WITH ROTATABLE STAPLE DEPLOYMENT ARRANGEMENTS, which is herein incorporated by reference in its entirety.

Figure 1:
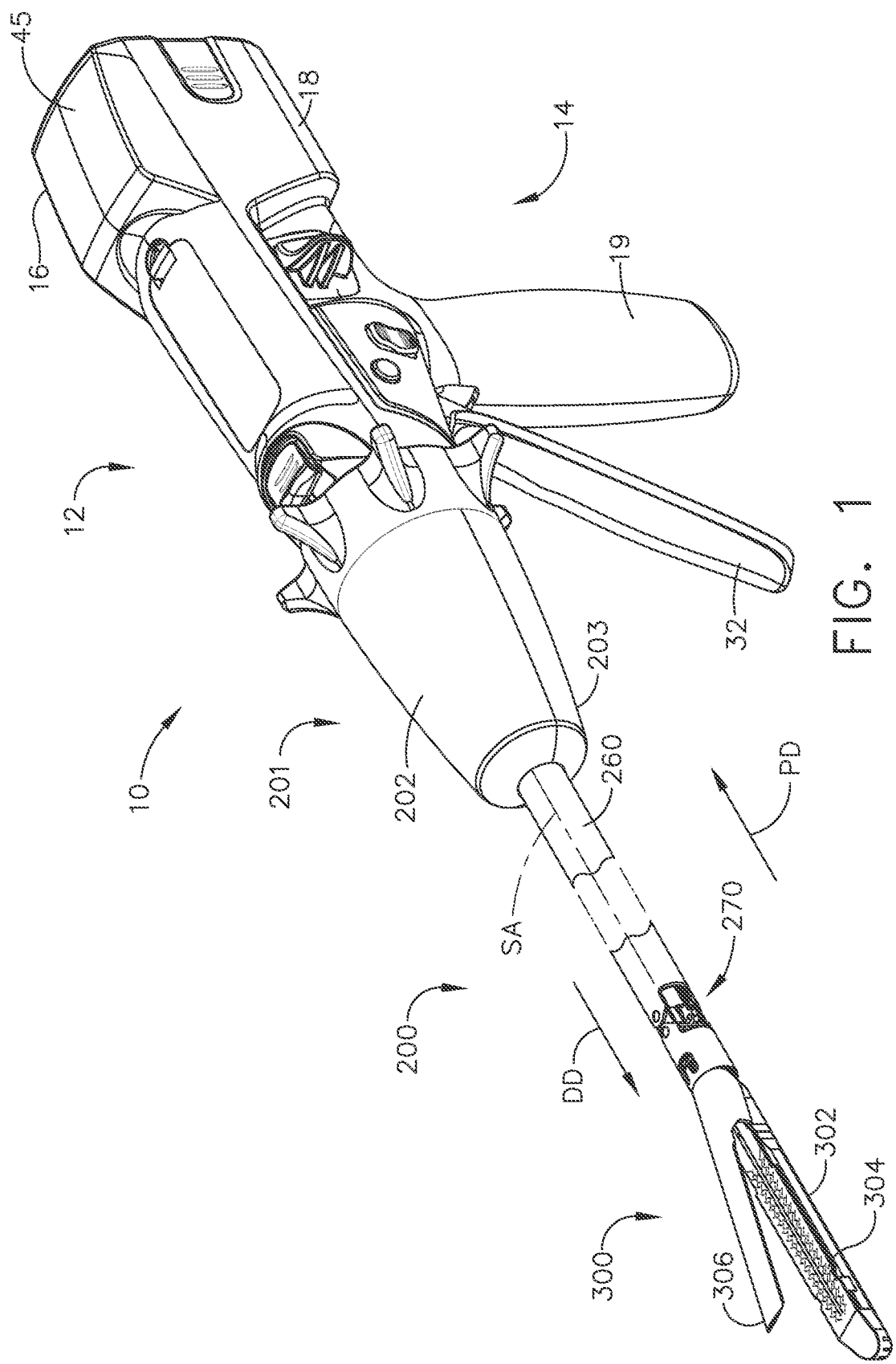
FIG. 1 is a perspective view of a surgical instrument that has an interchangeable shaft assembly operably coupled thereto according to one aspect of this disclosure.

FIG. 1 is a perspective view of a surgical instrument 10 that has an interchangeable shaft assembly 200 operably coupled thereto according to one aspect of this disclosure. The housing 12 includes an end effector 300 that comprises a surgical cutting and fastening device configured to operably support a surgical staple cartridge 304 therein. The housing 12 may be configured for use in connection with interchangeable shaft assemblies that include end effectors that are adapted to support different sizes and types of staple cartridges, have different shaft lengths, sizes, and types. The housing 12 may be employed with a variety of interchangeable shaft assemblies, including assemblies configured to apply other motions and forms of energy such as, radio frequency (RF) energy, ultrasonic energy, and/or motion to end effector arrangements adapted for use in connection with various surgical applications and procedures. The end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

The handle assembly 14 may comprise a pair of interconnectable handle housing segments 16, 18 interconnected by screws, snap features, adhesive, etc. The handle housing segments 16, 18 cooperate to form a pistol grip portion 19 that can be gripped and manipulated by the clinician. The handle assembly 14 operably supports a plurality of drive systems configured to generate and apply control motions to corresponding portions of the interchangeable shaft assembly that is operably attached thereto. A display may be provided below a cover 45.

Figure 2:
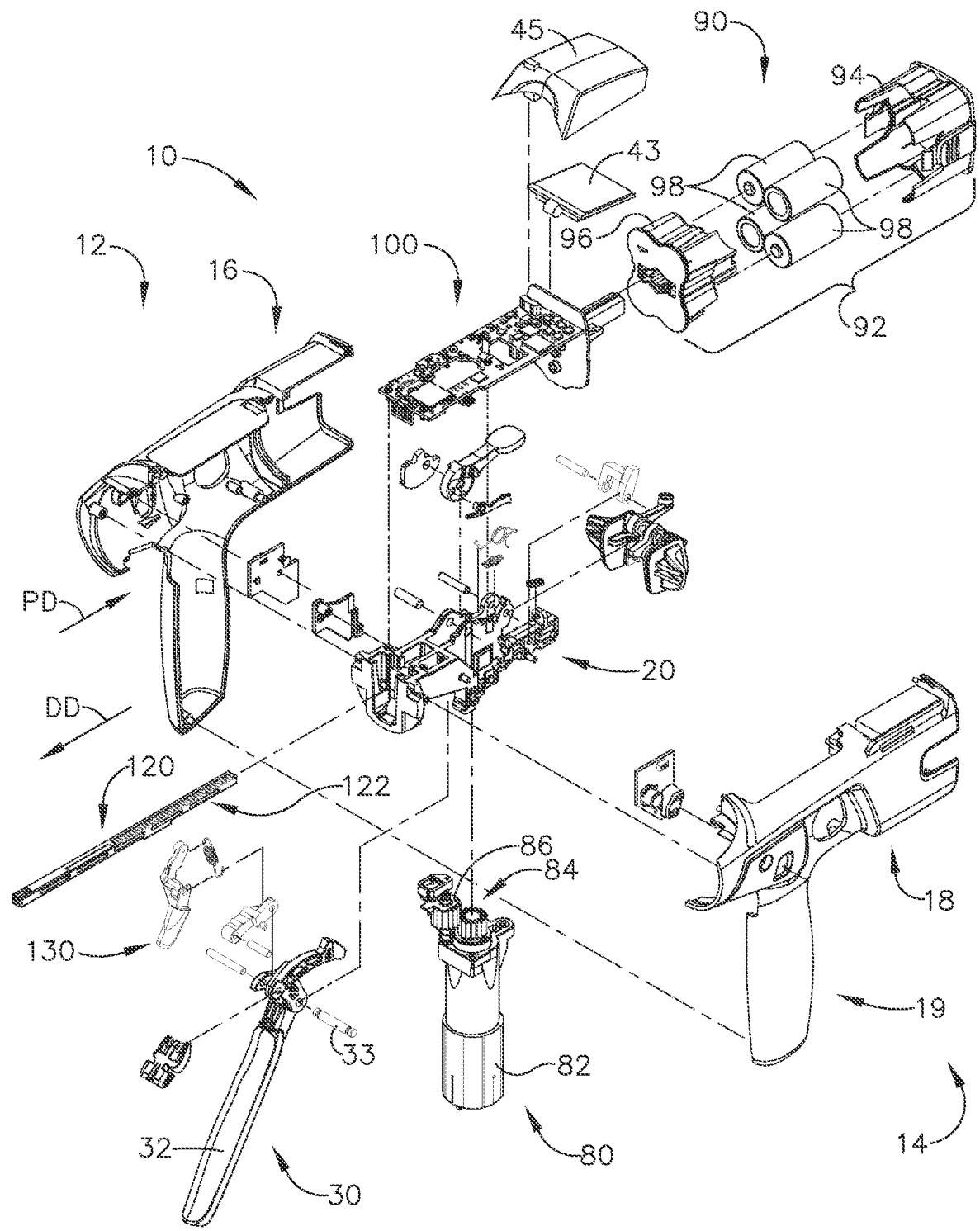
FIG. 2 is an exploded assembly view of a portion of the surgical instrument of FIG. 1 according to one aspect of this disclosure.

FIG. 2 is an exploded assembly view of a portion of the surgical instrument 10 of FIG. 1 according to one aspect of this disclosure. The handle assembly 14 may include a frame 20 that operably supports a plurality of drive systems. The frame 20 can operably support a "first" or closure drive system 30, which can apply closing and opening motions to the interchangeable shaft assembly 200. The closure drive system 30 may include an actuator such as a closure trigger 32 pivotally supported by the frame 20. The closure trigger 32 is pivotally coupled to the handle assembly 14 by a pivot pin 33 to enable the closure trigger 32 to be manipulated by a clinician. When the clinician grips the pistol grip portion 19 of the handle assembly 14, the closure trigger 32 can pivot from a starting or "unactuated" position to an "actuated" position and more particularly to a fully compressed or fully actuated position.

The handle assembly 14 and the frame 20 may operably support a firing drive system 80 configured to apply firing motions to corresponding portions of the interchangeable shaft assembly attached thereto. The firing drive system 80 may employ an electric motor 82 located in the pistol grip portion 19 of the handle assembly 14. The electric motor 82 may be a DC brushed motor having a maximum rotational speed of approximately 25,000 RPM, for example. In other arrangements, the motor may include a brushless motor, a cordless motor, a synchronous motor, a stepper motor, or any other suitable electric motor. The electric motor 82 may be powered by a power source 90 that may comprise a removable power pack 92. The removable power pack 92 may comprise a proximal housing portion 94 configured to attach to a distal housing portion 96. The proximal housing portion 94 and the distal housing portion 96 are configured to operably support a plurality of batteries 98 therein. Batteries 98 may each comprise, for example, a Lithium Ion (LI) or other suitable battery. The distal housing portion 96 is configured for removable operable attachment to a control circuit board 100, which is operably coupled to the electric motor 82. Several batteries 98 connected in series may power the surgical instrument 10. The power source 90 may be replaceable and/or rechargeable. A display 43, which is located below the cover 45, is electrically coupled to the control circuit board 100. The cover 45 may be removed to expose the display 43.

The electric motor 82 can include a rotatable shaft (not shown) that operably interfaces with a gear reducer assembly 84 mounted in meshing engagement with a with a set, or rack, of drive teeth 122 on a longitudinally movable drive member 120. The longitudinally movable drive member 120 has a rack of drive teeth 122 formed thereon for meshing engagement with a corresponding drive gear 86 of the gear reducer assembly 84.

In use, a voltage polarity provided by the power source 90 can operate the electric motor 82 in a clockwise direction wherein the voltage polarity applied to the electric motor by the battery can be reversed in order to operate the electric motor 82 in a counter-clockwise direction. When the electric motor 82 is rotated in one direction, the longitudinally movable drive member 120 will be axially driven in the distal direction "DD." When the electric motor 82 is driven in the opposite rotary direction, the longitudinally movable drive member 120 will be axially driven in a proximal direction "PD." The handle assembly 14 can include a switch that can be configured to reverse the polarity applied to the electric motor 82 by the power source 90. The handle assembly 14 may include a sensor configured to detect the position of the longitudinally movable drive member 120 and/or the direction in which the longitudinally movable drive member 120 is being moved.

Actuation of the electric motor 82 can be controlled by a firing trigger 130 that is pivotally supported on the handle assembly 14. The firing trigger 130 may be pivoted between an unactuated position and an actuated position.

Turning back to FIG. 1, the interchangeable shaft assembly 200 includes an end effector 300 comprising an elongated channel 302 configured to operably support a surgical staple cartridge 304 therein. The end effector 300 may include an anvil 306 that is pivotally supported relative to the elongated channel 302. The interchangeable shaft assembly 200 may include an articulation joint 270. Construction and operation of the end effector 300 and the articulation joint 270 are set forth in U.S. Patent Application Publication No. 2014/0263541, entitled ARTICULATABLE SURGICAL INSTRUMENT COMPRISING AN ARTICULATION LOCK, which is herein incorporated by reference in its entirety. The interchangeable shaft assembly 200 may include a proximal housing or nozzle 201 comprised of nozzle portions 202, 203. The interchangeable shaft assembly 200 may include a closure tube 260 extending along a shaft axis SA that can be utilized to close and/or open the anvil 306 of the end effector 300.

Turning back to FIG. 1, the closure tube 260 is translated distally (direction "DD") to close the anvil 306, for example, in response to the actuation of the closure trigger 32 in the manner described in the aforementioned reference U.S. Patent Application Publication No. 2014/0263541. The anvil 306 is opened by proximally translating the closure tube 260. In the anvil-open position, the closure tube 260 is moved to its proximal position.

Figure 3:
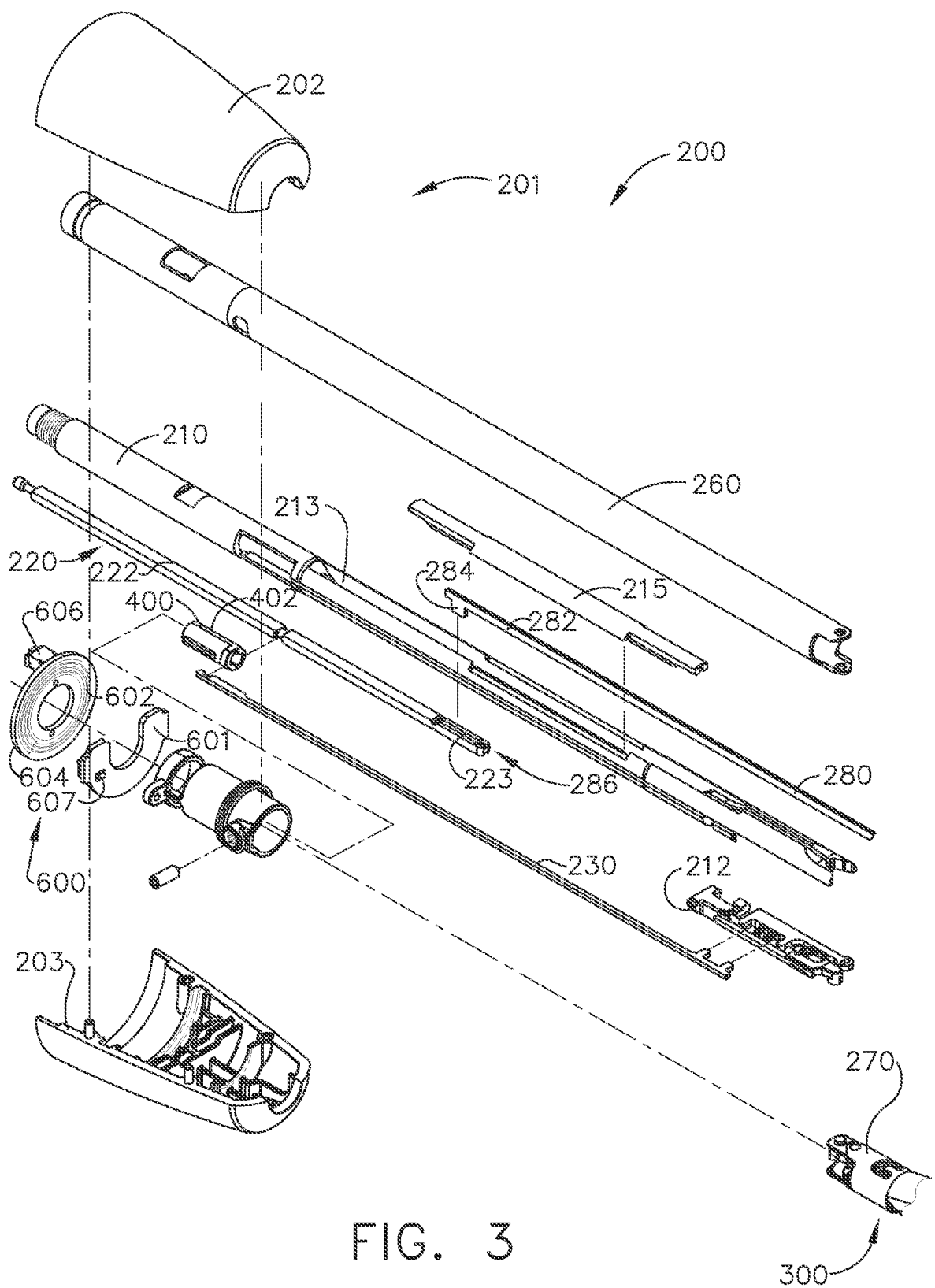
FIG. 3 is an exploded assembly view of portions of the interchangeable shaft assembly according to one aspect of this disclosure.

FIG. 3 is another exploded assembly view of portions of the interchangeable shaft assembly 200 according to one aspect of this disclosure. The interchangeable shaft assembly 200 may include a firing member 220 supported for axial travel within the spine 210. The firing member 220 includes an intermediate firing shaft 222 configured to attach to a distal cutting portion or knife bar 280. The firing member 220 may be referred to as a "second shaft" or a "second shaft assembly". The intermediate firing shaft 222 may include a longitudinal slot 223 in a distal end configured to receive a tab 284 on the proximal end 282 of the knife bar 280. The longitudinal slot 223 and the proximal end 282 may be configured to permit relative movement there between and can comprise a slip joint 286. The slip joint 286 can permit the intermediate firing shaft 222 of the firing member 220 to articulate the end effector 300 about the articulation joint 270 without moving, or at least substantially moving, the knife bar 280. Once the end effector 300 has been suitably oriented, the intermediate firing shaft 222 can be advanced distally until a proximal sidewall of the longitudinal slot 223 contacts the tab 284 to advance the knife bar 280 and fire the staple cartridge positioned within the channel 302. The spine 210 has an elongated opening or window 213 therein to facilitate assembly and insertion of the intermediate firing shaft 222 into the spine 210. Once the intermediate firing shaft 222 has been inserted therein, a top frame segment 215 may be engaged with the shaft frame 212 to enclose the intermediate firing shaft 222 and knife bar 280 therein. Operation of the firing member 220 may be found in U.S. Patent Application Publication No. 2014/0263541. A spine 210 can be configured to slidably support a firing member 220 and the closure tube 260 that extends around the spine 210. The spine 210 may slidably support an articulation driver 230.

The interchangeable shaft assembly 200 can include a clutch assembly 400 configured to selectively and releasably couple the articulation driver 230 to the firing member 220. The clutch assembly 400 includes a lock collar, or lock sleeve 402, positioned around the firing member 220 wherein the lock sleeve 402 can be rotated between an engaged position in which the lock sleeve 402 couples the articulation driver 230 to the firing member 220 and a disengaged position in which the articulation driver 230 is not operably coupled to the firing member 220. When the lock sleeve 402 is in the engaged position, distal movement of the firing member 220 can move the articulation driver 230 distally and, correspondingly, proximal movement of the firing member 220 can move the articulation driver 230 proximally. When the lock sleeve 402 is in the disengaged position, movement of the firing member 220 is not transmitted to the articulation driver 230 and, as a result, the firing member 220 can move independently of the articulation driver 230. The nozzle 201 may be employed to operably engage and disengage the articulation drive system with the firing drive system in the various manners described in U.S. Patent Application Publication No. 2014/0263541.

The interchangeable shaft assembly 200 can comprise a slip ring assembly 600 which can be configured to conduct electrical power to and/or from the end effector 300 and/or communicate signals to and/or from the end effector 300, for example. The slip ring assembly 600 can comprise a proximal connector flange 604 and a distal connector flange 601 positioned within a slot defined in the nozzle portions 202, 203. The proximal connector flange 604 can comprise a first face and the distal connector flange 601 can comprise a second face positioned adjacent to and movable relative to the first face. The distal connector flange 601 can rotate relative to the proximal connector flange 604 about the shaft axis SA-SA (FIG. 1). The proximal connector flange 604 can comprise a plurality of concentric, or at least substantially concentric, conductors 602 defined in the first face thereof. A connector 607 can be mounted on the proximal side of the distal connector flange 601 and may have a plurality of contacts wherein each contact corresponds to and is in electrical contact with one of the conductors 602. Such an arrangement permits relative rotation between the proximal connector flange 604 and the distal connector flange 601 while maintaining electrical contact there between. The proximal connector flange 604 can include an electrical connector 606 that can place the conductors 602 in signal communication with a shaft circuit board, for example. In at least one instance, a wiring harness comprising a plurality of conductors can extend between the electrical connector 606 and the shaft circuit board. The electrical connector 606 may extend proximally through a connector opening defined in the chassis mounting flange. U.S. Patent Application Publication No. 2014/0263551, entitled STAPLE CARTRIDGE TISSUE THICKNESS SENSOR SYSTEM, is incorporated herein by reference in its entirety. U.S. Patent Application Publication No. 2014/0263552, entitled STAPLE CARTRIDGE TISSUE THICKNESS SENSOR SYSTEM, is incorporated by reference in its entirety. Further details regarding slip ring assembly 600 may be found in U.S. Patent Application Publication No. 2014/0263541.

The interchangeable shaft assembly 200 can include a proximal portion fixably mounted to the handle assembly 14 and a distal portion that is rotatable about a longitudinal axis. The rotatable distal shaft portion can be rotated relative to the proximal portion about the slip ring assembly 600. The distal connector flange 601 of the slip ring assembly 600 can be positioned within the rotatable distal shaft portion.

Figure 4:
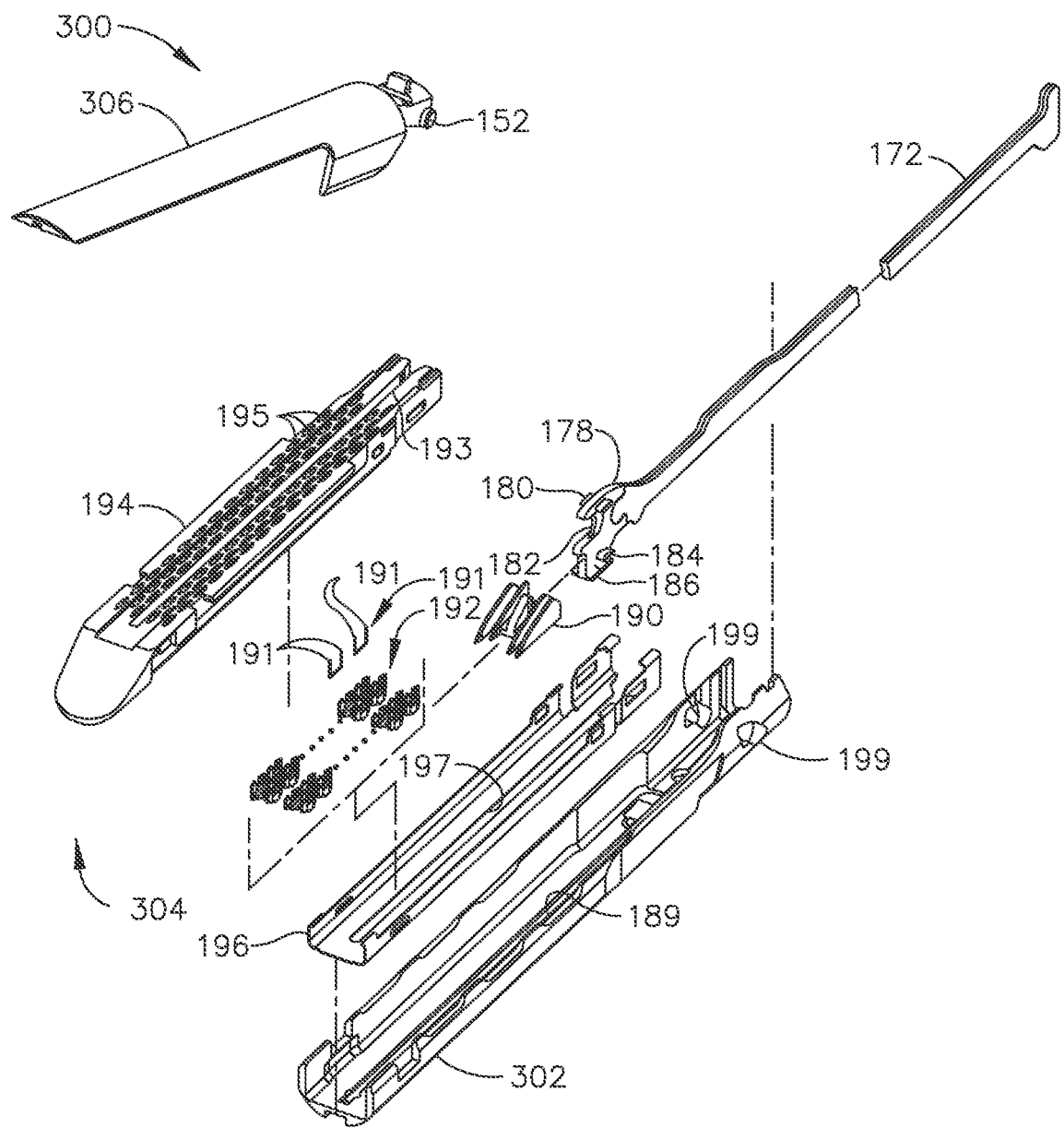
FIG. 4 is an exploded view of an end effector of the surgical instrument of FIG. 1 according to one aspect of this disclosure.

FIG. 4 is an exploded view of one aspect of an end effector 300 of the surgical instrument 10 of FIG. 1 according to one aspect of this disclosure. The end effector 300 may include the anvil 306 and the surgical staple cartridge 304. The anvil 306 may be coupled to an elongated channel 302. Apertures 199 can be defined in the elongated channel 302 to receive pins 152 extending from the anvil 306 to allow the anvil 306 to pivot from an open position to a closed position relative to the elongated channel 302 and surgical staple cartridge 304. A firing bar 172 is configured to longitudinally translate into the end effector 300. The firing bar 172 may be constructed from one solid section, or may include a laminate material comprising a stack of steel plates. The firing bar 172 comprises an I-beam 178 and a cutting edge 182 at a distal end thereof. A distally projecting end of the firing bar 172 can be attached to the I-beam 178 to assist in spacing the anvil 306 from a surgical staple cartridge 304 positioned in the elongated channel 302 when the anvil 306 is in a closed position. The I-beam 178 may include a sharpened cutting edge 182 to sever tissue as the I-beam 178 is advanced distally by the firing bar 172. In operation, the I-beam 178 may, or fire, the surgical staple cartridge 304. The surgical staple cartridge 304 can include a molded cartridge body 194 that holds a plurality of staples 191 resting upon staple drivers 192 within respective upwardly open staple cavities 195. A wedge sled 190 is driven distally by the I-beam 178, sliding upon a cartridge tray 196 of the surgical staple cartridge 304. The wedge sled 190 upwardly cams the staple drivers 192 to force out the staples 191 into deforming contact with the anvil 306 while the cutting edge 182 of the I-beam 178 severs clamped tissue.

The I-beam 178 can include upper pins 180 that engage the anvil 306 during firing. The I-beam 178 may include middle pins 184 and a bottom foot 186 to engage portions of the cartridge body 194, cartridge tray 196, and elongated channel 302. When a surgical staple cartridge 304 is positioned within the elongated channel 302, a slot 193 defined in the cartridge body 194 can be aligned with a longitudinal slot 197 defined in the cartridge tray 196 and a slot 189 defined in the elongated channel 302. In use, the I-beam 178 can slide through the aligned longitudinal slots 193, 197, and 189 wherein, as indicated in FIG. 4, the bottom foot 186 of the I-beam 178 can engage a groove running along the bottom surface of elongated channel 302 along the length of slot 189, the middle pins 184 can engage the top surfaces of cartridge tray 196 along the length of longitudinal slot 197, and the upper pins 180 can engage the anvil 306. The I-beam 178 can space, or limit the relative movement between, the anvil 306 and the surgical staple cartridge 304 as the firing bar 172 is advanced distally to fire the staples from the surgical staple cartridge 304 and/or incise the tissue captured between the anvil 306 and the surgical staple cartridge 304. The firing bar 172 and the I-beam 178 can be retracted proximally allowing the anvil 306 to be opened to release the two stapled and severed tissue portions.

Figure 5A:
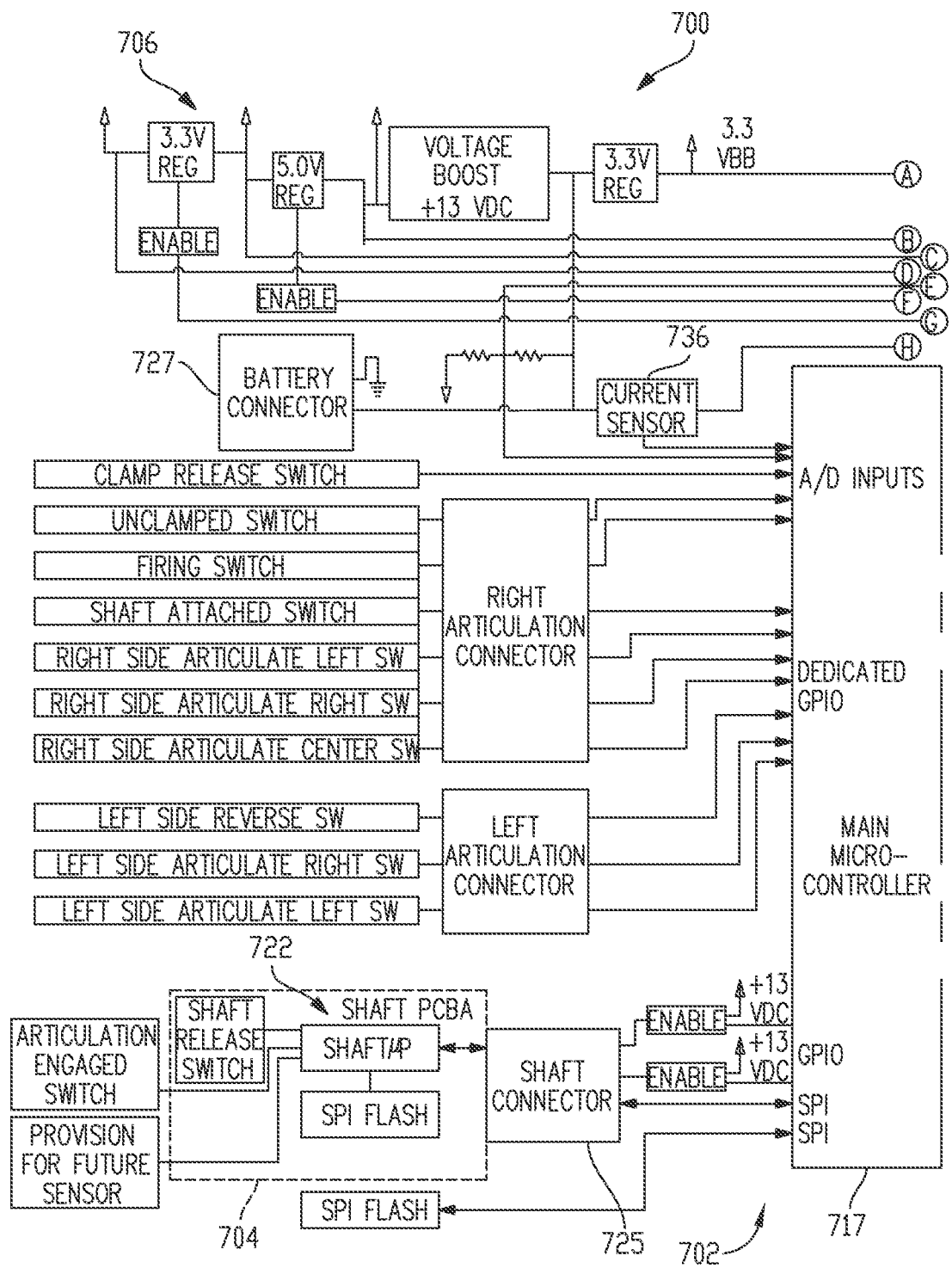
FIGS. 5A-5B is a block diagram of a control circuit of the surgical instrument of FIG. 1 spanning two drawing sheets according to one aspect of this disclosure.
Figure 5B:
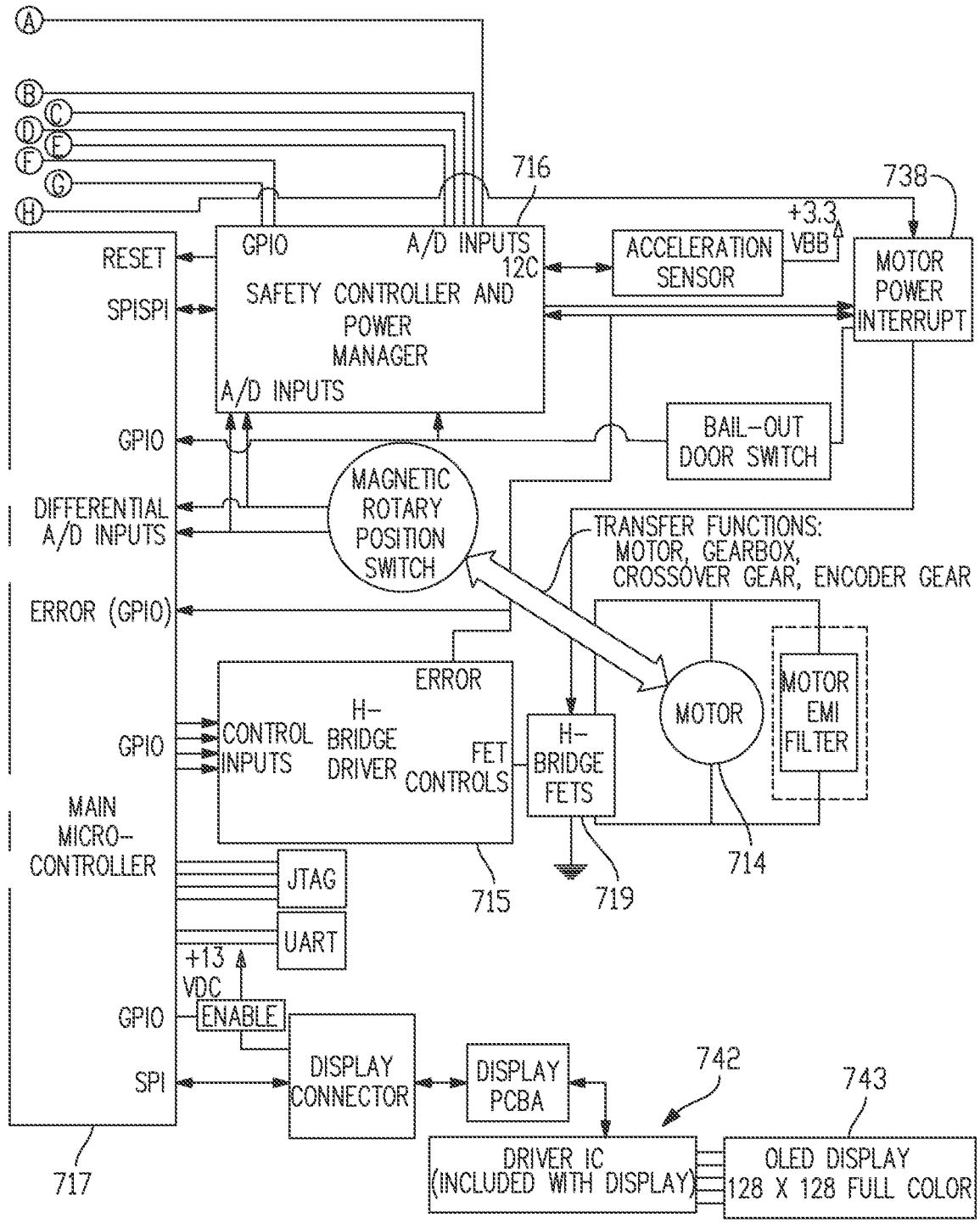

FIGS. 5A-5B is a block diagram of a control circuit 700 of the surgical instrument 10 of FIG. 1 spanning two drawing sheets according to one aspect of this disclosure. Referring primarily to FIGS. 5A-5B, a handle assembly 702 may include a motor 714 which can be controlled by a motor driver 715 and can be employed by the firing system of the surgical instrument 10. In various forms, the motor 714 may be a DC brushed driving motor having a maximum rotational speed of approximately 25,000 RPM. In other arrangements, the motor 714 may include a brushless motor, a cordless motor, a synchronous motor, a stepper motor, or any other suitable electric motor. The motor driver 715 may comprise an H-Bridge driver comprising field-effect transistors (FETs) 719, for example. The motor 714 can be powered by the power assembly 706 releasably mounted to the handle assembly 200 for supplying control power to the surgical instrument 10. The power assembly 706 may comprise a battery which may include a number of battery cells connected in series that can be used as the power source to power the surgical instrument 10. In certain circumstances, the battery cells of the power assembly 706 may be replaceable and/or rechargeable. In at least one example, the battery cells can be Lithium-Ion batteries which can be separably couplable to the power assembly 706.

The shaft assembly 704 may include a shaft assembly controller 722 which can communicate with a safety controller and power management controller 716 through an interface while the shaft assembly 704 and the power assembly 706 are coupled to the handle assembly 702. For example, the interface may comprise a first interface portion 725 which may include one or more electric connectors for coupling engagement with corresponding shaft assembly electric connectors and a second interface portion 727 which may include one or more electric connectors for coupling engagement with corresponding power assembly electric connectors to permit electrical communication between the shaft assembly controller 722 and the power management controller 716 while the shaft assembly 704 and the power assembly 706 are coupled to the handle assembly 702. One or more communication signals can be transmitted through the interface to communicate one or more of the power requirements of the attached interchangeable shaft assembly 704 to the power management controller 716. In response, the power management controller may modulate the power output of the battery of the power assembly 706, as described below in greater detail, in accordance with the power requirements of the attached shaft assembly 704. The connectors may comprise switches which can be activated after mechanical coupling engagement of the handle assembly 702 to the shaft assembly 704 and/or to the power assembly 706 to allow electrical communication between the shaft assembly controller 722 and the power management controller 716.

The interface can facilitate transmission of the one or more communication signals between the power management controller 716 and the shaft assembly controller 722 by routing such communication signals through a main controller 717 residing in the handle assembly 702, for example. In other circumstances, the interface can facilitate a direct line of communication between the power management controller 716 and the shaft assembly controller 722 through the handle assembly 702 while the shaft assembly 704 and the power assembly 706 are coupled to the handle assembly 702.

The main controller 717 may be any single core or multicore processor such as those known under the trade name ARM Cortex by Texas Instruments. In one aspect, the main controller 717 may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

The safety controller may be a safety controller platform comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The power assembly 706 may include a power management circuit which may comprise the power management controller 716, a power modulator 738, and a current sense circuit 736. The power management circuit can be configured to modulate power output of the battery based on the power requirements of the shaft assembly 704 while the shaft assembly 704 and the power assembly 706 are coupled to the handle assembly 702. The power management controller 716 can be programmed to control the power modulator 738 of the power output of the power assembly 706 and the current sense circuit 736 can be employed to monitor power output of the power assembly 706 to provide feedback to the power management controller 716 about the power output of the battery so that the power management controller 716 may adjust the power output of the power assembly 706 to maintain a desired output. The power management controller 716 and/or the shaft assembly controller 722 each may comprise one or more processors and/or memory units which may store a number of software modules.

The surgical instrument 10 (FIGS. 1-4) may comprise an output device 742 which may include devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 742 may comprise a display 743 which may be included in the handle assembly 702. The shaft assembly controller 722 and/or the power management controller 716 can provide feedback to a user of the surgical instrument 10 through the output device 742. The interface can be configured to connect the shaft assembly controller 722 and/or the power management controller 716 to the output device 742. The output device 742 can instead be integrated with the power assembly 706. In such circumstances, communication between the output device 742 and the shaft assembly controller 722 may be accomplished through the interface while the shaft assembly 704 is coupled to the handle assembly 702.

The control circuit 700 comprises circuit segments configured to control operations of the powered surgical instrument 10. A safety controller segment (Segment 1) comprises a safety controller and the main controller 717 segment (Segment 2). The safety controller and/or the main controller 717 are configured to interact with one or more additional circuit segments such as an acceleration segment, a display segment, a shaft segment, an encoder segment, a motor segment, and a power segment. Each of the circuit segments may be coupled to the safety controller and/or the main controller 717. The main controller 717 is also coupled to a flash memory. The main controller 717 also comprises a serial communication interface. The main controller 717 comprises a plurality of inputs coupled to, for example, one or more circuit segments, a battery, and/or a plurality of switches. The segmented circuit may be implemented by any suitable circuit, such as, for example, a printed circuit board assembly (PCBA) within the powered surgical instrument 10. It should be understood that the term processor as used herein includes any microprocessor, processors, controller, controllers, or other basic computing device that incorporates the functions of a computer's central processing unit (CPU) on an integrated circuit or at most a few integrated circuits. The main controller 717 is a multipurpose, programmable device that accepts digital data as input, processes it according to instructions stored in its memory, and provides results as output. It is an example of sequential digital logic, as it has internal memory. The control circuit 700 can be configured to implement one or more of the processes described herein.

The acceleration segment (Segment 3) comprises an accelerometer. The accelerometer is configured to detect movement or acceleration of the powered surgical instrument 10. Input from the accelerometer may be used to transition to and from a sleep mode, identify an orientation of the powered surgical instrument, and/or identify when the surgical instrument has been dropped. In some examples, the acceleration segment is coupled to the safety controller and/or the main controller 717.

The display segment (Segment 4) comprises a display connector coupled to the main controller 717. The display connector couples the main controller 717 to a display through one or more integrated circuit drivers of the display. The integrated circuit drivers of the display may be integrated with the display and/or may be located separately from the display. The display may comprise any suitable display, such as, for example, an organic light-emitting diode (OLED) display, a liquid-crystal display (LCD), and/or any other suitable display. In some examples, the display segment is coupled to the safety controller.

The shaft segment (Segment 5) comprises controls for an interchangeable shaft assembly 200 (FIGS. 1 and 3) coupled to the surgical instrument 10 (FIGS. 1-4) and/or one or more controls for an end effector 300 coupled to the interchangeable shaft assembly 200. The shaft segment comprises a shaft connector configured to couple the main controller 717 to a shaft PCBA. The shaft PCBA comprises a low-power microcontroller with a ferroelectric random access memory (FRAM), an articulation switch, a shaft release Hall effect switch, and a shaft PCBA EEPROM. The shaft PCBA EEPROM comprises one or more parameters, routines, and/or programs specific to the interchangeable shaft assembly 200 and/or the shaft PCBA. The shaft PCBA may be coupled to the interchangeable shaft assembly 200 and/or integral with the surgical instrument 10. In some examples, the shaft segment comprises a second shaft EEPROM. The second shaft EEPROM comprises a plurality of algorithms, routines, parameters, and/or other data corresponding to one or more shaft assemblies 200 and/or end effectors 300 that may be interfaced with the powered surgical instrument 10.

The position encoder segment (Segment 6) comprises one or more magnetic angle rotary position encoders. The one or more magnetic angle rotary position encoders are configured to identify the rotational position of the motor 714, an interchangeable shaft assembly 200 (FIGS. 1 and 3), and/or an end effector 300 of the surgical instrument 10 (FIGS. 1-4). In some examples, the magnetic angle rotary position encoders may be coupled to the safety controller and/or the main controller 717.

The motor circuit segment (Segment 7) comprises a motor 714 configured to control movements of the powered surgical instrument 10 (FIGS. 1-4). The motor 714 is coupled to the main microcontroller processor 717 by an H-bridge driver comprising one or more H-bridge field-effect transistors (FETs) and a motor controller. The H-bridge driver is also coupled to the safety controller. A motor current sensor is coupled in series with the motor to measure the current draw of the motor. The motor current sensor is in signal communication with the main controller 717 and/or the safety controller. In some examples, the motor 714 is coupled to a motor electromagnetic interference (EMI) filter.

The motor controller controls a first motor flag and a second motor flag to indicate the status and position of the motor 714 to the main controller 717. The main controller 717 provides a pulse-width modulation (PWM) high signal, a PWM low signal, a direction signal, a synchronize signal, and a motor reset signal to the motor controller through a buffer. The power segment is configured to provide a segment voltage to each of the circuit segments.

The power segment (Segment 8) comprises a battery coupled to the safety controller, the main controller 717, and additional circuit segments. The battery is coupled to the segmented circuit by a battery connector and a current sensor. The current sensor is configured to measure the total current draw of the segmented circuit. In some examples, one or more voltage converters are configured to provide predetermined voltage values to one or more circuit segments. For example, in some examples, the segmented circuit may comprise 3.3V voltage converters and/or 5V voltage converters. A boost converter is configured to provide a boost voltage up to a predetermined amount, such as, for example, up to 13V. The boost converter is configured to provide additional voltage and/or current during power intensive operations and prevent brownout or low-power conditions.

A plurality of switches are coupled to the safety controller and/or the main controller 717. The switches may be configured to control operations of the surgical instrument 10 (FIGS. 1-4), of the segmented circuit, and/or indicate a status of the surgical instrument 10. A bail-out door switch and Hall effect switch for bailout are configured to indicate the status of a bail-out door. A plurality of articulation switches, such as, for example, a left side articulation left switch, a left side articulation right switch, a left side articulation center switch, a right side articulation left switch, a right side articulation right switch, and a right side articulation center switch are configured to control articulation of an interchangeable shaft assembly 200 (FIGS. 1 and 3) and/or the end effector 300 (FIGS. 1 and 4). A left side reverse switch and a right side reverse switch are coupled to the main controller 717. The left side switches comprising the left side articulation left switch, the left side articulation right switch, the left side articulation center switch, and the left side reverse switch are coupled to the main controller 717 by a left flex connector. The right side switches comprising the right side articulation left switch, the right side articulation right switch, the right side articulation center switch, and the right side reverse switch are coupled to the main controller 717 by a right flex connector. A firing switch, a clamp release switch, and a shaft engaged switch are coupled to the main controller 717.

Any suitable mechanical, electromechanical, or solid state switches may be employed to implement the plurality of switches, in any combination. For example, the switches may be limit switches operated by the motion of components associated with the surgical instrument 10 (FIGS. 1-4) or the presence of an object. Such switches may be employed to control various functions associated with the surgical instrument 10. A limit switch is an electromechanical device that consists of an actuator mechanically linked to a set of contacts. When an object comes into contact with the actuator, the device operates the contacts to make or break an electrical connection. Limit switches are used in a variety of applications and environments because of their ruggedness, ease of installation, and reliability of operation. They can determine the presence or absence, passing, positioning, and end of travel of an object. In other implementations, the switches may be solid state switches that operate under the influence of a magnetic field such as Hall-effect devices, magneto-resistive (MR) devices, giant magneto-resistive (GMR) devices, magnetometers, among others. In other implementations, the switches may be solid state switches that operate under the influence of light, such as optical sensors, infrared sensors, ultraviolet sensors, among others. Still, the switches may be solid state devices such as transistors (e.g., FET, Junction-FET, metal-oxide semiconductor-FET (MOSFET), bipolar, and the like). Other switches may include wireless switches, ultrasonic switches, accelerometers, inertial sensors, among others.

Figure 6:
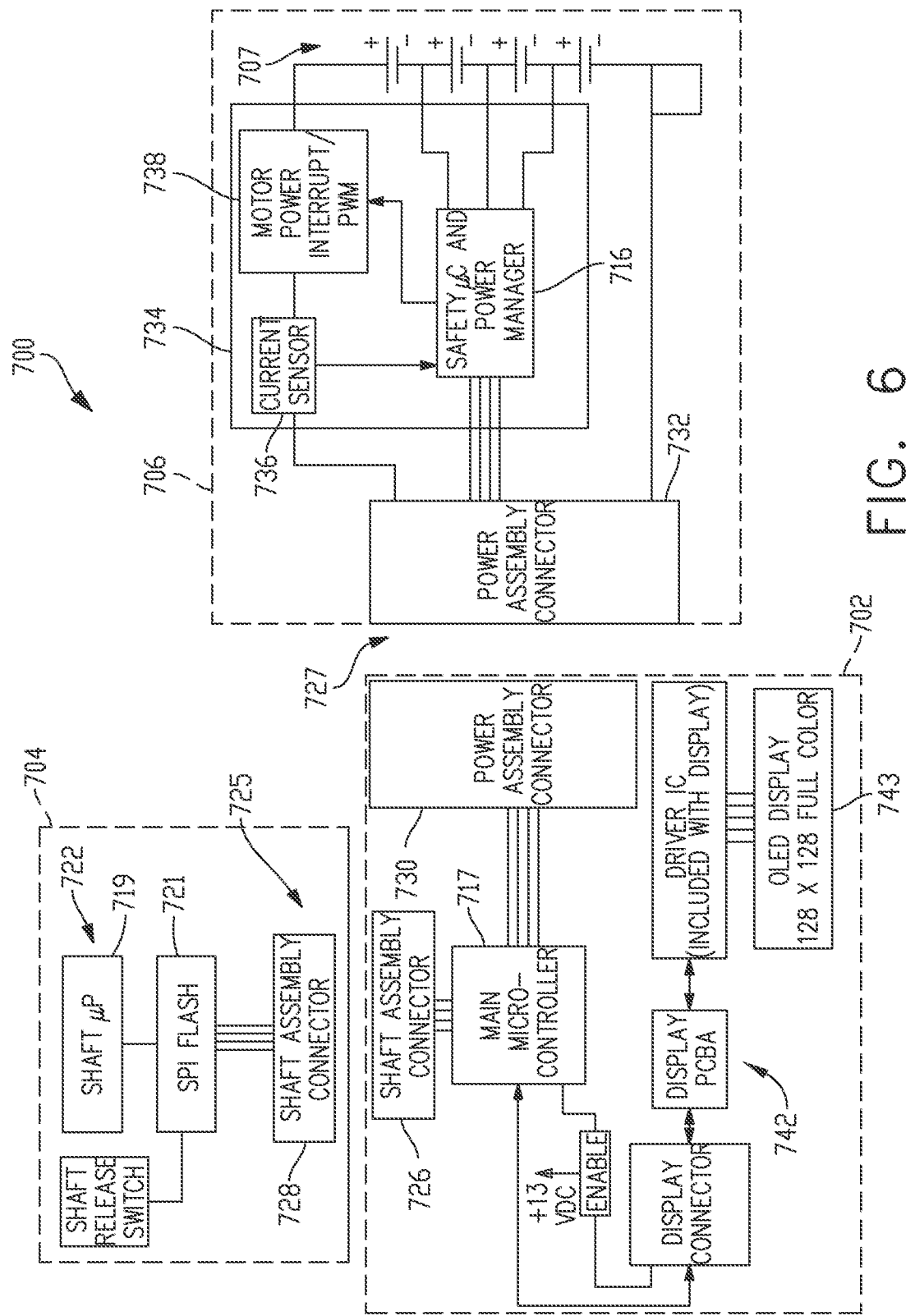
FIG. 6 is a block diagram of the control circuit of the surgical instrument of FIG. 1 illustrating interfaces between the handle assembly, the power assembly, and the handle assembly and the interchangeable shaft assembly according to one aspect of this disclosure.

FIG. 6 is another block diagram of the control circuit 700 of the surgical instrument of FIG. 1 illustrating interfaces between the handle assembly 702 and the power assembly 706 and between the handle assembly 702 and the interchangeable shaft assembly 704 according to one aspect of this disclosure. The handle assembly 702 may comprise a main controller 717, a shaft assembly connector 726 and a power assembly connector 730. The power assembly 706 may include a power assembly connector 732, a power management circuit 734 that may comprise the power management controller 716, a power modulator 738, and a current sense circuit 736. The shaft assembly connectors 730, 732 form an interface 727. The power management circuit 734 can be configured to modulate power output of the battery 707 based on the power requirements of the interchangeable shaft assembly 704 while the interchangeable shaft assembly 704 and the power assembly 706 are coupled to the handle assembly 702. The power management controller 716 can be programmed to control the power modulator 738 of the power output of the power assembly 706 and the current sense circuit 736 can be employed to monitor power output of the power assembly 706 to provide feedback to the power management controller 716 about the power output of the battery 707 so that the power management controller 716 may adjust the power output of the power assembly 706 to maintain a desired output. The shaft assembly 704 comprises a shaft processor 719 coupled to a non-volatile memory 721 and shaft assembly connector 728 to electrically couple the shaft assembly 704 to the handle assembly 702. The shaft assembly connectors 726, 728 form interface 725. The main controller 717, the shaft processor 719, and/or the power management controller 716 can be configured to implement one or more of the processes described herein.

The surgical instrument 10 (FIGS. 1-4) may comprise an output device 742 to a sensory feedback to a user. Such devices may comprise visual feedback devices (e.g., an LCD display screen, LED indicators), audio feedback devices (e.g., a speaker, a buzzer), or tactile feedback devices (e.g., haptic actuators). In certain circumstances, the output device 742 may comprise a display 743 that may be included in the handle assembly 702. The shaft assembly controller 722 and/or the power management controller 716 can provide feedback to a user of the surgical instrument 10 through the output device 742. The interface 727 can be configured to connect the shaft assembly controller 722 and/or the power management controller 716 to the output device 742. The output device 742 can be integrated with the power assembly 706. Communication between the output device 742 and the shaft assembly controller 722 may be accomplished through the interface 725 while the interchangeable shaft assembly 704 is coupled to the handle assembly 702. Having described a control circuit 700 (FIGS. 5A-5B and 6) for controlling the operation of the surgical instrument 10 (FIGS. 1-4), the disclosure now turns to various configurations of the surgical instrument 10 (FIGS. 1-4) and control circuit 700.

Figure 7:
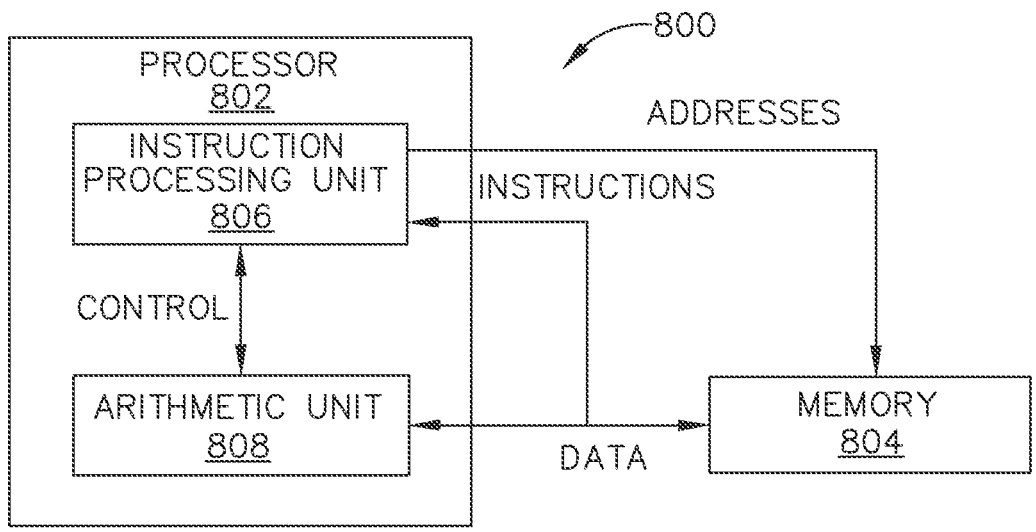
FIG. 7 illustrates a control circuit configured to control aspects of the surgical instrument of FIG. 1 according to one aspect of this disclosure.

FIG. 7 illustrates a control circuit 800 configured to control aspects of the surgical instrument 10 (FIGS. 1-4) according to one aspect of this disclosure. The control circuit 800 can be configured to implement various processes described herein. The control circuit 800 may comprise a controller comprising one or more processors 802 (e.g., microprocessor, microcontroller) coupled to at least one memory circuit 804. The memory circuit 804 stores machine executable instructions that when executed by the processor 802, cause the processor 802 to execute machine instructions to implement various processes described herein. The processor 802 may be any one of a number of single or multi-core processors known in the art. The memory circuit 804 may comprise volatile and non-volatile storage media. The processor 802 may include an instruction processing unit 806 and an arithmetic unit 808. The instruction processing unit may be configured to receive instructions from the memory circuit 804.

Figure 8:
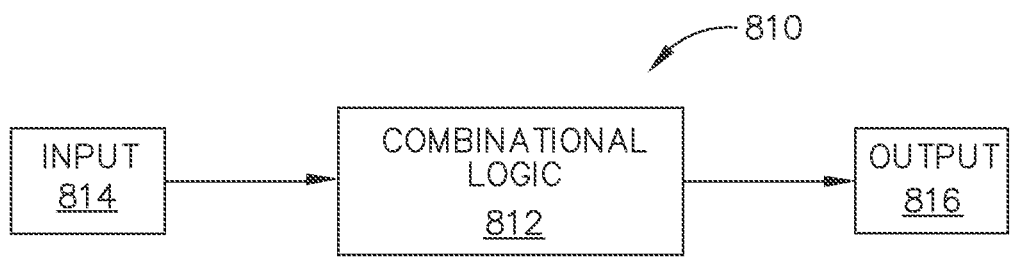
FIG. 8 illustrates a combinational logic circuit configured to control aspects of the surgical instrument of FIG. 1 according to one aspect of this disclosure.

FIG. 8 illustrates a combinational logic circuit 810 configured to control aspects of the surgical instrument 10 (FIGS. 1-4) according to one aspect of this disclosure. The combinational logic circuit 810 can be configured to implement various processes described herein. The circuit 810 may comprise a finite state machine comprising a combinational logic circuit 812 configured to receive data associated with the surgical instrument 10 at an input 814, process the data by the combinational logic 812, and provide an output 816.

Figure 9:
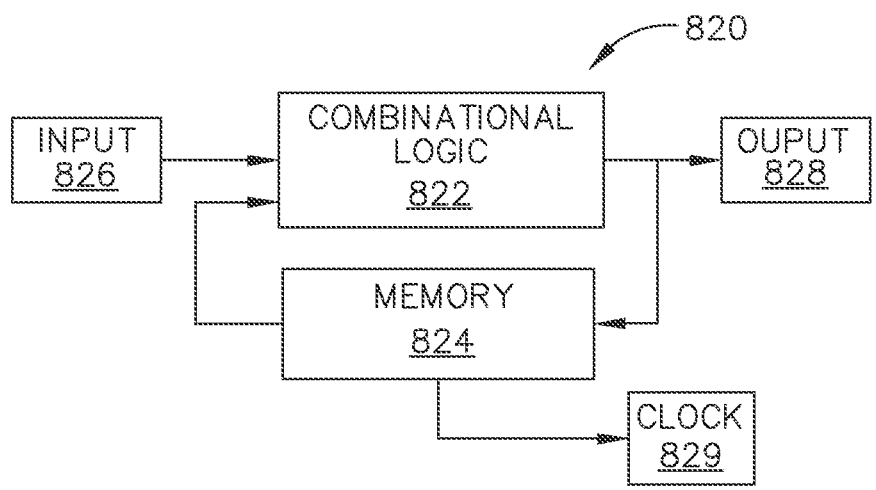
FIG. 9 illustrates a sequential logic circuit configured to control aspects of the surgical instrument of FIG. 1 according to one aspect of this disclosure.

FIG. 9 illustrates a sequential logic circuit 820 configured to control aspects of the surgical instrument 10 (FIGS. 1-4) according to one aspect of this disclosure. The sequential logic circuit 820 or the combinational logic circuit 822 can be configured to implement various processes described herein. The circuit 820 may comprise a finite state machine. The sequential logic circuit 820 may comprise a combinational logic circuit 822, at least one memory circuit 824, and a clock 829, for example. The at least one memory circuit 820 can store a current state of the finite state machine. In certain instances, the sequential logic circuit 820 may be synchronous or asynchronous. The combinational logic circuit 822 is configured to receive data associated with the surgical instrument 10 an input 826, process the data by the combinational logic circuit 822, and provide an output 828. In other aspects, the circuit may comprise a combination of the processor 802 and the finite state machine to implement various processes herein. In other aspects, the finite state machine may comprise a combination of the combinational logic circuit 810 and the sequential logic circuit 820.

Aspects may be implemented as an article of manufacture. The article of manufacture may include a computer readable storage medium arranged to store logic, instructions, and/or data for performing various operations of one or more aspects. For example, the article of manufacture may comprise a magnetic disk, optical disk, flash memory, or firmware containing computer program instructions suitable for execution by a general purpose processor or application specific processor.

Figure 10:
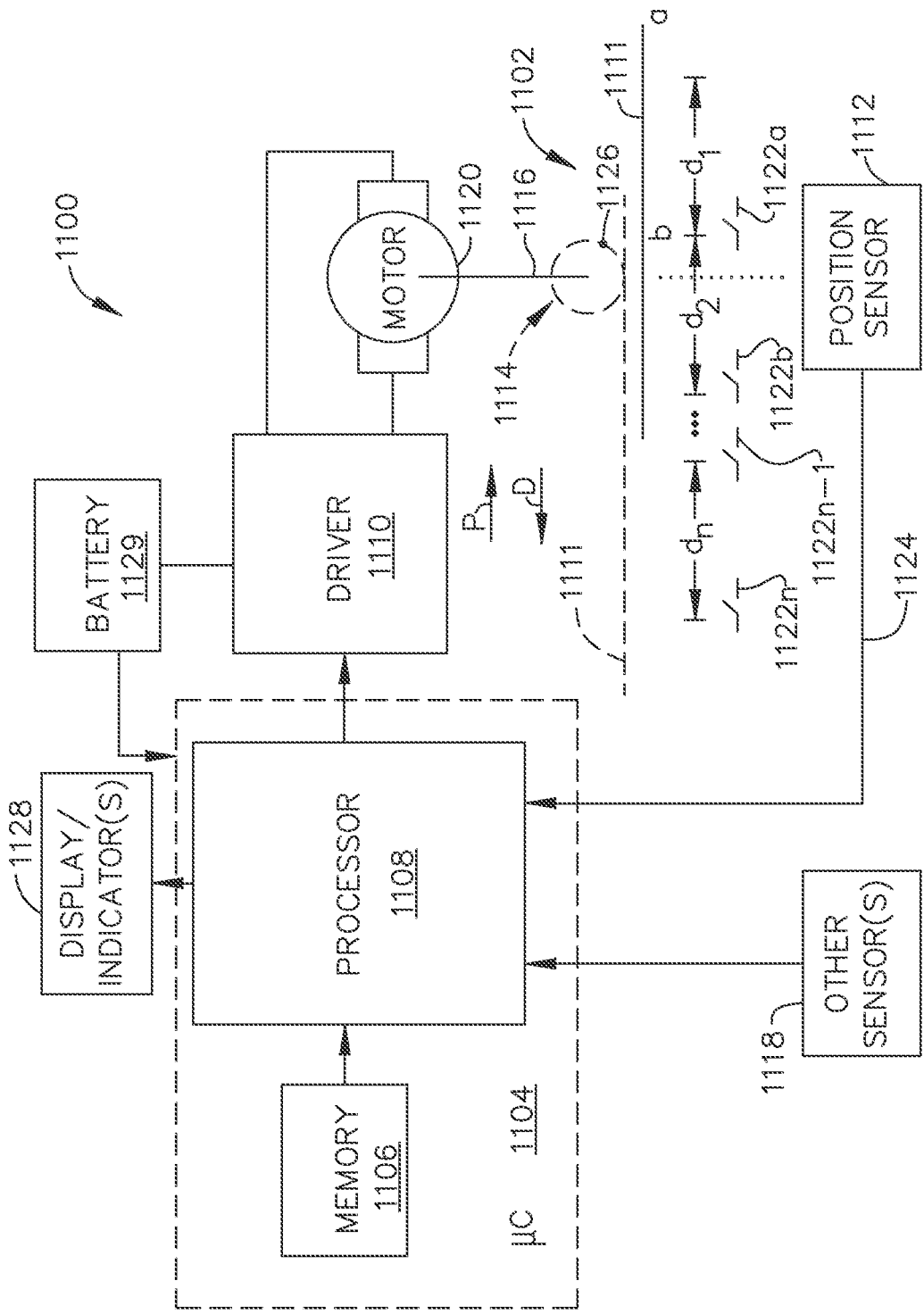
FIG. 10 is a diagram of an absolute positioning system of the surgical instrument of FIG. 1 where the absolute positioning system comprises a controlled motor drive circuit arrangement comprising a sensor arrangement according to one aspect of this disclosure.

FIG. 10 is a diagram of an absolute positioning system 1100 of the surgical instrument 10 (FIGS. 1-4) where the absolute positioning system 1100 comprises a controlled motor drive circuit arrangement comprising a sensor arrangement 1102 according to one aspect of this disclosure. The sensor arrangement 1102 for an absolute positioning system 1100 provides a unique position signal corresponding to the location of a displacement member 1111. Turning briefly to FIGS. 2-4, in one aspect the displacement member 1111 represents the longitudinally movable drive member 120 (FIG. 2) comprising a rack of drive teeth 122 for meshing engagement with a corresponding drive gear 86 of the gear reducer assembly 84. In other aspects, the displacement member 1111 represents the firing member 220 (FIG. 3), which could be adapted and configured to include a rack of drive teeth. In yet another aspect, the displacement member 1111 represents the firing bar 172 (FIG. 4) or the I-beam 178 (FIG. 4), each of which can be adapted and configured to include a rack of drive teeth. Accordingly, as used herein, the term displacement member is used generically to refer to any movable member of the surgical instrument 10 such as the drive member 120, the firing member 220, the firing bar 172, the I-beam 178, or any element that can be displaced. In one aspect, the longitudinally movable drive member 120 is coupled to the firing member 220, the firing bar 172, and the I-beam 178. Accordingly, the absolute positioning system 1100 can, in effect, track the displacement of the I-beam 178 by tracking the displacement of the longitudinally movable drive member 120. In various other aspects, the displacement member 1111 may be coupled to any sensor suitable for measuring displacement. Thus, the longitudinally movable drive member 120, the firing member 220, the firing bar 172, or the I-beam 178, or combinations, may be coupled to any suitable displacement sensor. Displacement sensors may include contact or non-contact displacement sensors. Displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable linearly arranged Hall effect sensors, an optical sensing system comprising a movable light source and a series of linearly arranged photo diodes or photo detectors, or an optical sensing system comprising a fixed light source and a series of movable linearly arranged photo diodes or photo detectors, or any combination thereof.

An electric motor 1120 can include a rotatable shaft 1116 that operably interfaces with a gear assembly 1114 that is mounted in meshing engagement with a set, or rack, of drive teeth on the displacement member 1111. A sensor element 1126 may be operably coupled to a gear assembly 1114 such that a single revolution of the sensor element 1126 corresponds to some linear longitudinal translation of the displacement member 1111. An arrangement of gearing and sensors 1118 can be connected to the linear actuator via a rack and pinion arrangement or a rotary actuator via a spur gear or other connection. A power source 1129 supplies power to the absolute positioning system 1100 and an output indicator 1128 may display the output of the absolute positioning system 1100. In FIG. 2, the displacement member 1111 represents the longitudinally movable drive member 120 comprising a rack of drive teeth 122 formed thereon for meshing engagement with a corresponding drive gear 86 of the gear reducer assembly 84. The displacement member 1111 represents the longitudinally movable firing member 220, firing bar 172, I-beam 178, or combinations thereof.

A single revolution of the sensor element 1126 associated with the position sensor 1112 is equivalent to a longitudinal displacement d1 of the of the displacement member 1111, where d1 is the longitudinal distance that the displacement member 1111 moves from point "a" to point "b" after a single revolution of the sensor element 1126 coupled to the displacement member 1111. The sensor arrangement 1102 may be connected via a gear reduction that results in the position sensor 1112 completing one or more revolutions for the full stroke of the displacement member 1111. The position sensor 1112 may complete multiple revolutions for the full stroke of the displacement member 1111.

A series of switches 1122a-1122n, where n is an integer greater than one, may be employed alone or in combination with gear reduction to provide a unique position signal for more than one revolution of the position sensor 1112. The state of the switches 1122a-1122n are fed back to a controller 1104 that applies logic to determine a unique position signal corresponding to the longitudinal displacement d1+d2+ . . . dn of the displacement member 1111. The output 1124 of the position sensor 1112 is provided to the controller 1104. The position sensor 1112 of the sensor arrangement 1102 may comprise a magnetic sensor, an analog rotary sensor like a potentiometer, an array of analog Hall-effect elements, which output a unique combination of position signals or values.

The absolute positioning system 1100 provides an absolute position of the displacement member 1111 upon power up of the instrument without retracting or advancing the displacement member 1111 to a reset (zero or home) position as may be required with conventional rotary encoders that merely count the number of steps forwards or backwards that the motor 1120 has taken to infer the position of a device actuator, drive bar, knife, and the like.

The controller 1104 may be programmed to perform various functions such as precise control over the speed and position of the knife and articulation systems. In one aspect, the controller 1104 includes a processor 1108 and a memory 1106. The electric motor 1120 may be a brushed DC motor with a gearbox and mechanical links to an articulation or knife system. In one aspect, a motor driver 1110 may be an A3941 available from Allegro Microsystems, Inc. Other motor drivers may be readily substituted for use in the absolute positioning system 1100. A more detailed description of the absolute positioning system 1100 is described in U.S. patent application Ser. No. 15/130,590, entitled SYSTEMS AND METHODS FOR CONTROLLING A SURGICAL STAPLING AND CUTTING INSTRUMENT, filed on Apr. 15, 2016, the entire disclosure of which is herein incorporated by reference.

The controller 1104 may be programmed to provide precise control over the speed and position of the displacement member 1111 and articulation systems. The controller 1104 may be configured to compute a response in the software of the controller 1104. The computed response is compared to a measured response of the actual system to obtain an "observed" response, which is used for actual feedback decisions. The observed response is a favorable, tuned, value that balances the smooth, continuous nature of the simulated response with the measured response, which can detect outside influences on the system.

The absolute positioning system 1100 may comprise and/or be programmed to implement a feedback controller, such as a PID, state feedback, and adaptive controller. A power source 1129 converts the signal from the feedback controller into a physical input to the system, in this case voltage. Other examples include pulse width modulation (PWM) of the voltage, current, and force. Other sensor(s) 1118 may be provided to measure physical parameters of the physical system in addition to position measured by the position sensor 1112. In a digital signal processing system, absolute positioning system 1100 is coupled to a digital data acquisition system where the output of the absolute positioning system 1100 will have finite resolution and sampling frequency. The absolute positioning system 1100 may comprise a compare and combine circuit to combine a computed response with a measured response using algorithms such as weighted average and theoretical control loop that drives the computed response towards the measured response. The computed response of the physical system takes into account properties like mass, inertial, viscous friction, inductance resistance, etc., to predict what the states and outputs of the physical system will be by knowing the input. The controller 1104 may be a control circuit 700 (FIGS. 5A-5B).

The motor driver 1110 may be an A3941 available from Allegro Microsystems, Inc. The A3941 driver 1110 is a full-bridge controller for use with external N-channel power metal oxide semiconductor field effect transistors (MOSFETs) specifically designed for inductive loads, such as brush DC motors. The driver 1110 comprises a unique charge pump regulator provides full (>10 V) gate drive for battery voltages down to 7 V and allows the A3941 to operate with a reduced gate drive, down to 5.5 V. A bootstrap capacitor may be employed to provide the above-battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor adjustable dead time. Integrated diagnostics provide indication of undervoltage, overtemperature, and power bridge faults, and can be configured to protect the power MOSFETs under most short circuit conditions. Other motor drivers may be readily substituted for use in the absolute positioning system 1100.

Figure 11:
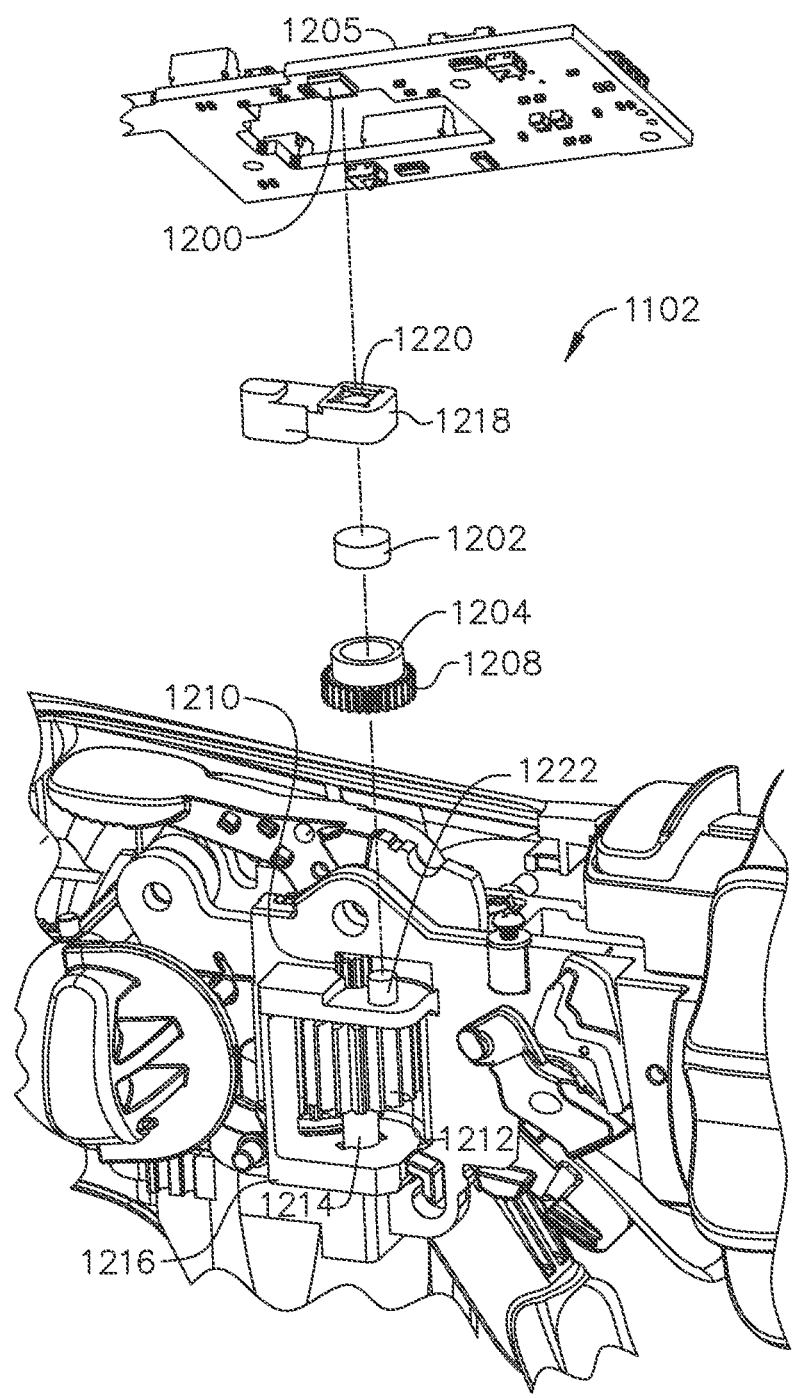
FIG. 11 is an exploded perspective view of the sensor arrangement for an absolute positioning system showing a control circuit board assembly and the relative alignment of the elements of the sensor arrangement according to one aspect of this disclosure.
Figure 12:
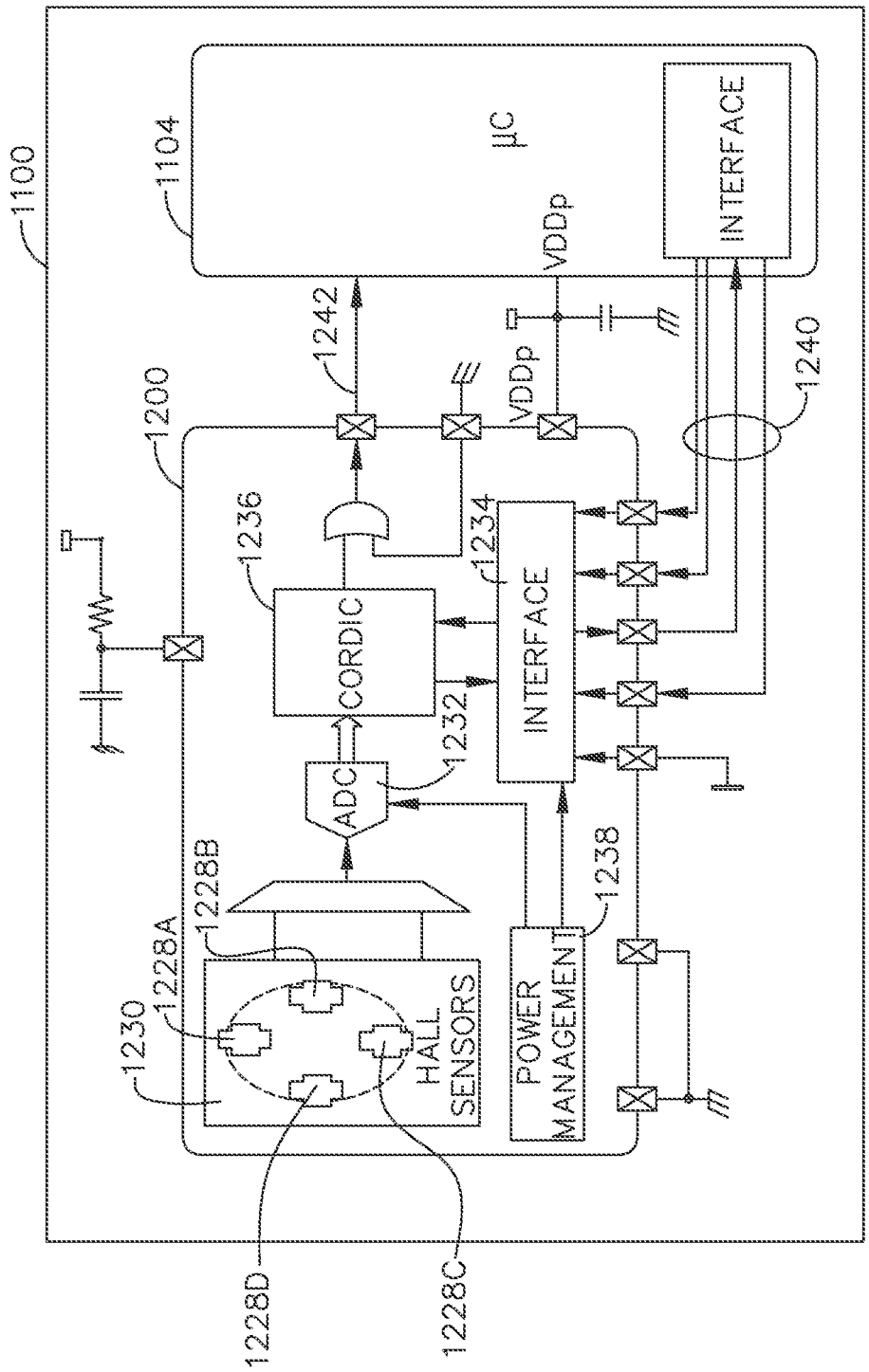
FIG. 12 is a diagram of a position sensor comprising a magnetic rotary absolute positioning system according to one aspect of this disclosure.

Having described a general architecture for implementing aspects of an absolute positioning system 1100 for a sensor arrangement 1102, the disclosure now turns to FIGS. 11 and 12 for a description of one aspect of a sensor arrangement 1102 for the absolute positioning system 1100. FIG. 11 is an exploded perspective view of the sensor arrangement 1102 for the absolute positioning system 1100 showing a circuit 1205 and the relative alignment of the elements of the sensor arrangement 1102, according to one aspect. The sensor arrangement 1102 for an absolute positioning system 1100 comprises a position sensor 1200, a magnet 1202 sensor element, a magnet holder 1204 that turns once every full stroke of the displacement member 1111, and a gear assembly 1206 to provide a gear reduction. With reference briefly to FIG. 2, the displacement member 1111 may represent the longitudinally movable drive member 120 comprising a rack of drive teeth 122 for meshing engagement with a corresponding drive gear 86 of the gear reducer assembly 84. Returning to FIG. 11, a structural element such as bracket 1216 is provided to support the gear assembly 1206, the magnet holder 1204, and the magnet 1202. The position sensor 1200 comprises magnetic sensing elements such as Hall elements and is placed in proximity to the magnet 1202. As the magnet 1202 rotates, the magnetic sensing elements of the position sensor 1200 determine the absolute angular position of the magnet 1202 over one revolution.

The sensor arrangement 1102 may comprises any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

A gear assembly comprises a first gear 1208 and a second gear 1210 in meshing engagement to provide a 3:1 gear ratio connection. A third gear 1212 rotates about a shaft 1214. The third gear 1212 is in meshing engagement with the displacement member 1111 (or 120 as shown in FIG. 2) and rotates in a first direction as the displacement member 1111 advances in a distal direction D and rotates in a second direction as the displacement member 1111 retracts in a proximal direction P. The second gear 1210 also rotates about the shaft 1214 and, therefore, rotation of the second gear 1210 about the shaft 1214 corresponds to the longitudinal translation of the displacement member 1111. Thus, one full stroke of the displacement member 1111 in either the distal or proximal directions D, P corresponds to three rotations of the second gear 1210 and a single rotation of the first gear 1208. Since the magnet holder 1204 is coupled to the first gear 1208, the magnet holder 1204 makes one full rotation with each full stroke of the displacement member 1111.

The position sensor 1200 is supported by a position sensor holder 1218 defining an aperture 1220 suitable to contain the position sensor 1200 in precise alignment with a magnet 1202 rotating below within the magnet holder 1204. The fixture is coupled to the bracket 1216 and to the circuit 1205 and remains stationary while the magnet 1202 rotates with the magnet holder 1204. A hub 1222 is provided to mate with the first gear 1208 and the magnet holder 1204. The second gear 1210 and third gear 1212 coupled to shaft 1214 also are shown.

Figure 15:
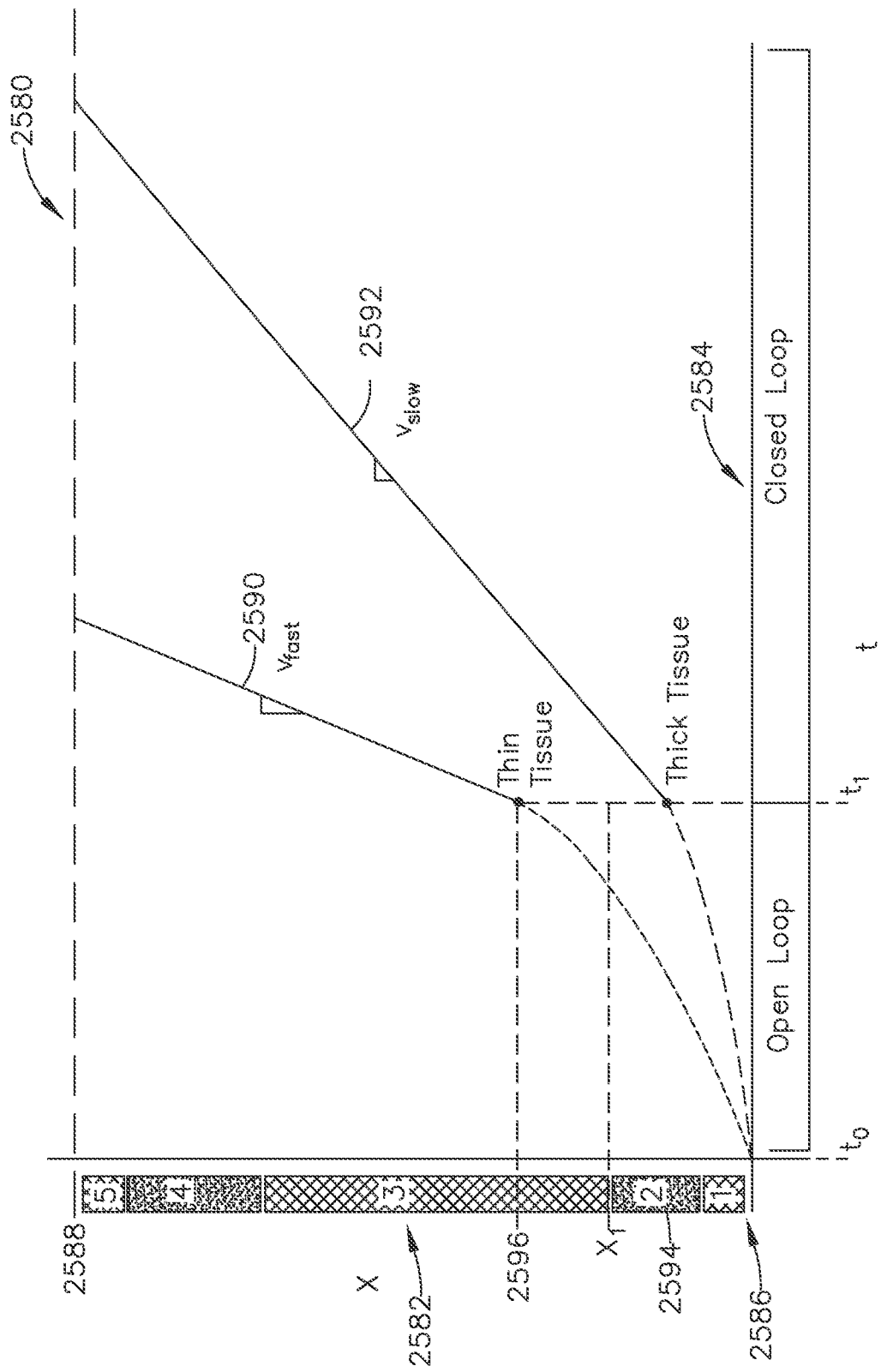
FIG. 15 illustrates a diagram plotting two example displacement member strokes executed according to one aspect of this disclosure.
Figure 16:
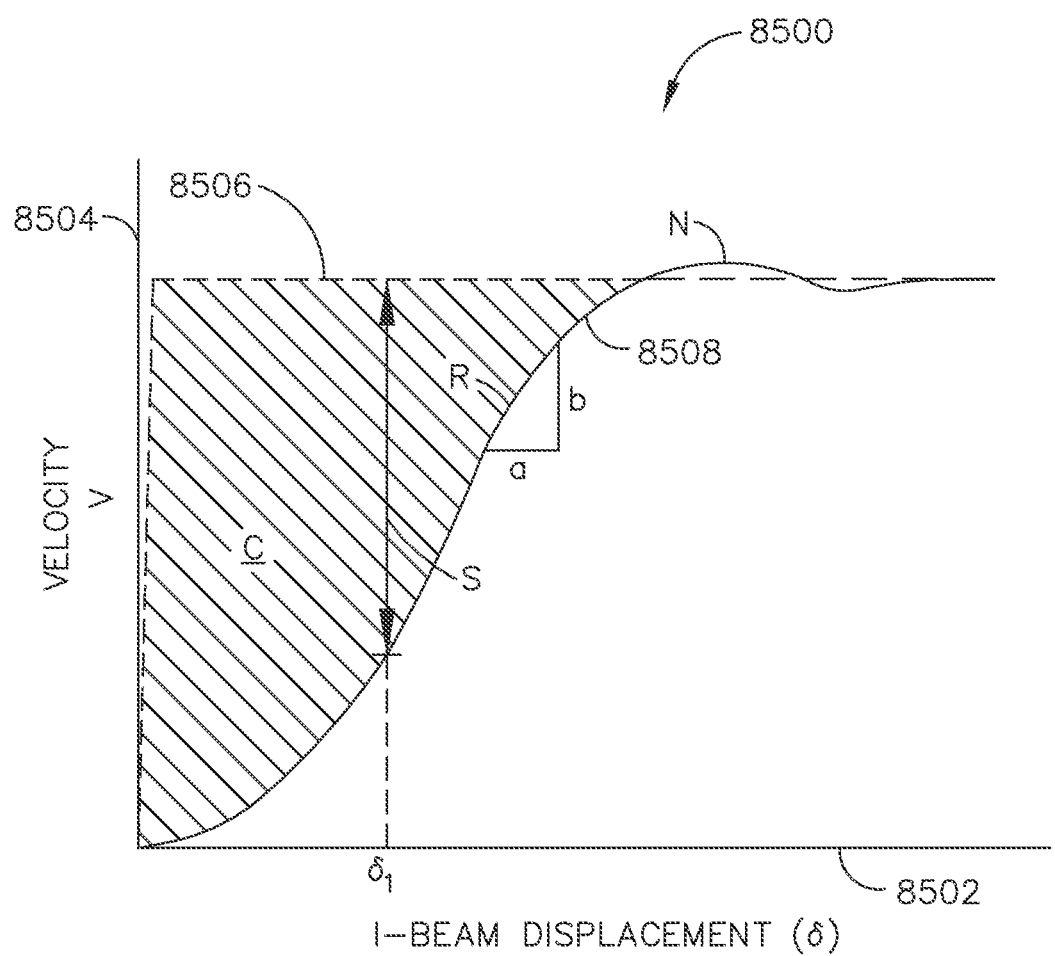
FIG. 16 is a graph depicting velocity (v) of a displacement member as a function of displacement (δ) of the displacement member according to one aspect of this disclosure.

FIG. 12 is a diagram of a position sensor 1200 for an absolute positioning system 1100 comprising a magnetic rotary absolute positioning system according to one aspect of this disclosure. The position sensor 1200 may be implemented as an AS5055EQFT single-chip magnetic rotary position sensor available from Austria Microsystems, AG. The position sensor 1200 is interfaced with the controller 1104 to provide an absolute positioning system 1100. The position sensor 1200 is a low-voltage and low-power component and includes four Hall-effect elements 1228A, 1228B, 1228C, 1228D in an area 1230 of the position sensor 1200 that is located above the magnet 1202 (FIGS. 15 and 16). A high-resolution ADC 1232 and a smart power management controller 1238 are also provided on the chip. A CORDIC processor 1236 (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface such as an SPI interface 1234 to the controller 1104. The position sensor 1200 provides 12 or 14 bits of resolution. The position sensor 1200 may be an AS5055 chip provided in a small QFN 16-pin 4×4×0.85 mm package.

The Hall-effect elements 1228A, 1228B, 1228C, 1228D are located directly above the rotating magnet 1202 (FIG. 11). The Hall-effect is a well-known effect and for expediency will not be described in detail herein, however, generally, the Hall-effect produces a voltage difference (the Hall voltage) across an electrical conductor transverse to an electric current in the conductor and a magnetic field perpendicular to the current. A Hall coefficient is defined as the ratio of the induced electric field to the product of the current density and the applied magnetic field. It is a characteristic of the material from which the conductor is made, since its value depends on the type, number, and properties of the charge carriers that constitute the current. In the AS5055 position sensor 1200, the Hall-effect elements 1228A, 1228B, 1228C, 1228D are capable producing a voltage signal that is indicative of the absolute position of the magnet 1202 in terms of the angle over a single revolution of the magnet 1202. This value of the angle, which is unique position signal, is calculated by the CORDIC processor 1236 is stored onboard the AS5055 position sensor 1200 in a register or memory. The value of the angle that is indicative of the position of the magnet 1202 over one revolution is provided to the controller 1104 in a variety of techniques, e.g., upon power up or upon request by the controller 1104.

The AS5055 position sensor 1200 requires only a few external components to operate when connected to the controller 1104. Six wires are needed for a simple application using a single power supply: two wires for power and four wires 1240 for the SPI interface 1234 with the controller 1104. A seventh connection can be added in order to send an interrupt to the controller 1104 to inform that a new valid angle can be read. Upon power-up, the AS5055 position sensor 1200 performs a full power-up sequence including one angle measurement. The completion of this cycle is indicated as an INT output 1242, and the angle value is stored in an internal register. Once this output is set, the AS5055 position sensor 1200 suspends to sleep mode. The controller 1104 can respond to the INT request at the INT output 1242 by reading the angle value from the AS5055 position sensor 1200 over the SPI interface 1234. Once the angle value is read by the controller 1104, the INT output 1242 is cleared again. Sending a "read angle" command by the SPI interface 1234 by the controller 1104 to the position sensor 1200 also automatically powers up the chip and starts another angle measurement. As soon as the controller 1104 has completed reading of the angle value, the INT output 1242 is cleared and a new result is stored in the angle register. The completion of the angle measurement is again indicated by setting the INT output 1242 and a corresponding flag in the status register.

Due to the measurement principle of the AS5055 position sensor 1200, only a single angle measurement is performed in very short time (~600 µs) after each power-up sequence. As soon as the measurement of one angle is completed, the AS5055 position sensor 1200 suspends to power-down state. An on-chip filtering of the angle value by digital averaging is not implemented, as this would require more than one angle measurement and, consequently, a longer power-up time that is not desired in low-power applications. The angle jitter can be reduced by averaging of several angle samples in the controller 1104. For example, an averaging of four samples reduces the jitter by 6 dB (50%).

Figure 13:
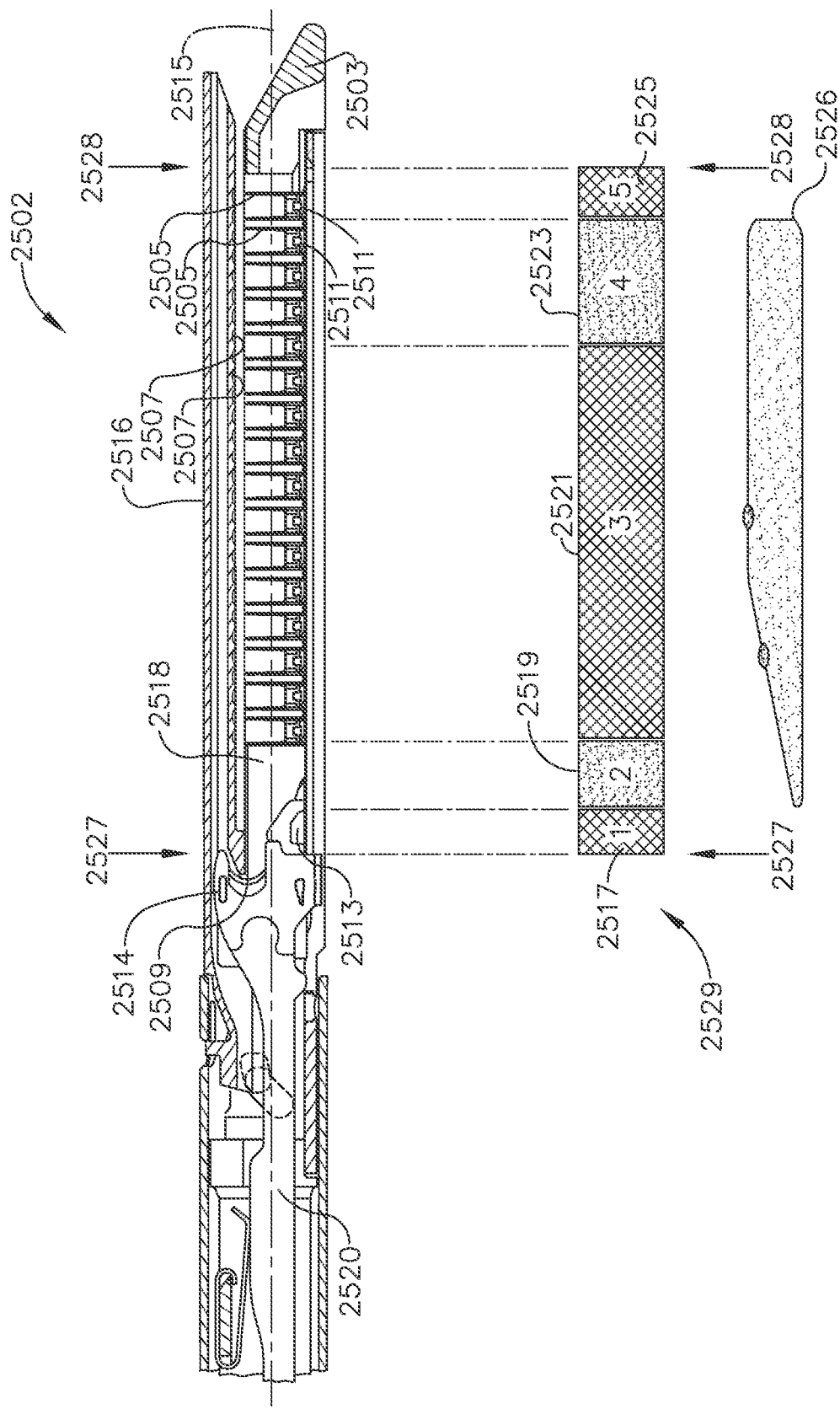
FIG. 13 is a section view of an end effector of the surgical instrument of FIG. 1 showing a firing member stroke relative to tissue grasped within the end effector according to one aspect of this disclosure.

FIG. 13 is a section view of an end effector 2502 of the surgical instrument 10 (FIGS. 1-4) showing an I-beam 2514 firing stroke relative to tissue 2526 grasped within the end effector 2502 according to one aspect of this disclosure. The end effector 2502 is configured to operate with the surgical instrument 10 shown in FIGS. 1-4. The end effector 2502 comprises an anvil 2516 and an elongated channel 2503 with a staple cartridge 2518 positioned in the elongated channel 2503. A firing bar 2520 is translatable distally and proximally along a longitudinal axis 2515 of the end effector 2502. When the end effector 2502 is not articulated, the end effector 2502 is in line with the shaft of the instrument. An I-beam 2514 comprising a cutting edge 2509 is illustrated at a distal portion of the firing bar 2520. A wedge sled 2513 is positioned in the staple cartridge 2518. As the I-beam 2514 translates distally, the cutting edge 2509 contacts and may cut tissue 2526 positioned between the anvil 2516 and the staple cartridge 2518. Also, the I-beam 2514 contacts the wedge sled 2513 and pushes it distally, causing the wedge sled 2513 to contact staple drivers 2511. The staple drivers 2511 may be driven up into staples 2505, causing the staples 2505 to advance through tissue and into pockets 2507 defined in the anvil 2516, which shape the staples 2505.

An example I-beam 2514 firing stroke is illustrated by a chart 2529 aligned with the end effector 2502. Example tissue 2526 is also shown aligned with the end effector 2502. The firing member stroke may comprise a stroke begin position 2527 and a stroke end position 2528. During an I-beam 2514 firing stroke, the I-beam 2514 may be advanced distally from the stroke begin position 2527 to the stroke end position 2528. The I-beam 2514 is shown at one example location of a stroke begin position 2527. The I-beam 2514 firing member stroke chart 2529 illustrates five firing member stroke regions 2517, 2519, 2521, 2523, 2525. In a first firing stroke region 2517, the I-beam 2514 may begin to advance distally. In the first firing stroke region 2517, the I-beam 2514 may contact the wedge sled 2513 and begin to move it distally. While in the first region, however, the cutting edge 2509 may not contact tissue and the wedge sled 2513 may not contact a staple driver 2511. After static friction is overcome, the force to drive the I-beam 2514 in the first region 2517 may be substantially constant.

In the second firing member stroke region 2519, the cutting edge 2509 may begin to contact and cut tissue 2526. Also, the wedge sled 2513 may begin to contact staple drivers 2511 to drive staples 2505. Force to drive the I-beam 2514 may begin to ramp up. As shown, tissue encountered initially may be compressed and/or thinner because of the way that the anvil 2516 pivots relative to the staple cartridge 2518. In the third firing member stroke region 2521, the cutting edge 2509 may continuously contact and cut tissue 2526 and the wedge sled 2513 may repeatedly contact staple drivers 2511. Force to drive the I-beam 2514 may plateau in the third region 2521. By the fourth firing stroke region 2523, force to drive the I-beam 2514 may begin to decline. For example, tissue in the portion of the end effector 2502 corresponding to the fourth firing region 2523 may be less compressed than tissue closer to the pivot point of the anvil 2516, requiring less force to cut. Also, the cutting edge 2509 and wedge sled 2513 may reach the end of the tissue 2526 while in the fourth region 2523. When the I-beam 2514 reaches the fifth region 2525, the tissue 2526 may be completely severed. The wedge sled 2513 may contact one or more staple drivers 2511 at or near the end of the tissue. Force to advance the I-beam 2514 through the fifth region 2525 may be reduced and, in some examples, may be similar to the force to drive the I-beam 2514 in the first region 2517. At the conclusion of the firing member stroke, the I-beam 2514 may reach the stroke end position 2528. The positioning of firing member stroke regions 2517, 2519, 2521, 2523, 2525 in FIG. 13 is just one example. In some examples, different regions may begin at different positions along the end effector longitudinal axis 2515, for example, based on the positioning of tissue between the anvil 2516 and the staple cartridge 2518.

As discussed above and with reference now to FIGS. 10-13, the electric motor 1122 positioned within the handle assembly of the surgical instrument 10 (FIGS. 1-4) can be utilized to advance and/or retract the firing system of the shaft assembly, including the I-beam 2514, relative to the end effector 2502 of the shaft assembly in order to staple and/or incise tissue captured within the end effector 2502.

The I-beam 2514 may be advanced or retracted at a desired speed, or within a range of desired speeds. The controller 1104 may be configured to control the speed of the I-beam 2514. The controller 1104 may be configured to predict the speed of the I-beam 2514 based on various parameters of the power supplied to the electric motor 1122, such as voltage and/or current, for example, and/or other operating parameters of the electric motor 1122 or external influences. The controller 1104 may be configured to predict the current speed of the I-beam 2514 based on the previous values of the current and/or voltage supplied to the electric motor 1122, and/or previous states of the system like velocity, acceleration, and/or position. The controller 1104 may be configured to sense the speed of the I-beam 2514 utilizing the absolute positioning sensor system described herein. The controller can be configured to compare the predicted speed of the I-beam 2514 and the sensed speed of the I-beam 2514 to determine whether the power to the electric motor 1122 should be increased in order to increase the speed of the I-beam 2514 and/or decreased in order to decrease the speed of the I-beam 2514. U.S. Pat. No. 8,210,411, entitled MOTOR-DRIVEN SURGICAL CUTTING INSTRUMENT, which is incorporated herein by reference in its entirety. U.S. Pat. No. 7,845,537, entitled SURGICAL INSTRUMENT HAVING RECORDING CAPABILITIES, which is incorporated herein by reference in its entirety.

Force acting on the I-beam 2514 may be determined using various techniques. The I-beam 2514 force may be determined by measuring the motor 2504 current, where the motor 2504 current is based on the load experienced by the I-beam 2514 as it advances distally. The I-beam 2514 force may be determined by positioning a strain gauge on the drive member 120 (FIG. 2), the firing member 220 (FIG. 2), I-beam 2514 (I-beam 178, FIG. 20), the firing bar 172 (FIG. 2), and/or on a proximal end of the cutting edge 2509. The I-beam 2514 force may be determined by monitoring the actual position of the I-beam 2514 moving at an expected velocity based on the current set velocity of the motor 2504 after a predetermined elapsed period $T_1$ and comparing the actual position of the I-beam 2514 relative to the expected position of the I-beam 2514 based on the current set velocity of the motor 2504 at the end of the period $T_1$. Thus, if the actual position of the I-beam 2514 is less than the expected position of the I-beam 2514, the force on the I-beam 2514 is greater than a nominal force. Conversely, if the actual position of the I-beam 2514 is greater than the expected position of the I-beam 2514, the force on the I-beam 2514 is less than the nominal force. The difference between the actual and expected positions of the I-beam 2514 is proportional to the deviation of the force on the I-beam 2514 from the nominal force. Such techniques are described in U.S. patent application Ser. No. 15/628,075, titled SYSTEMS AND METHODS FOR CONTROLLING MOTOR VELOCITY OF A SURGICAL STAPLING AND CUTTING INSTRUMENT, filed Jun. 20, 2017, which is incorporated herein by reference in its entirety.

Figure 14:
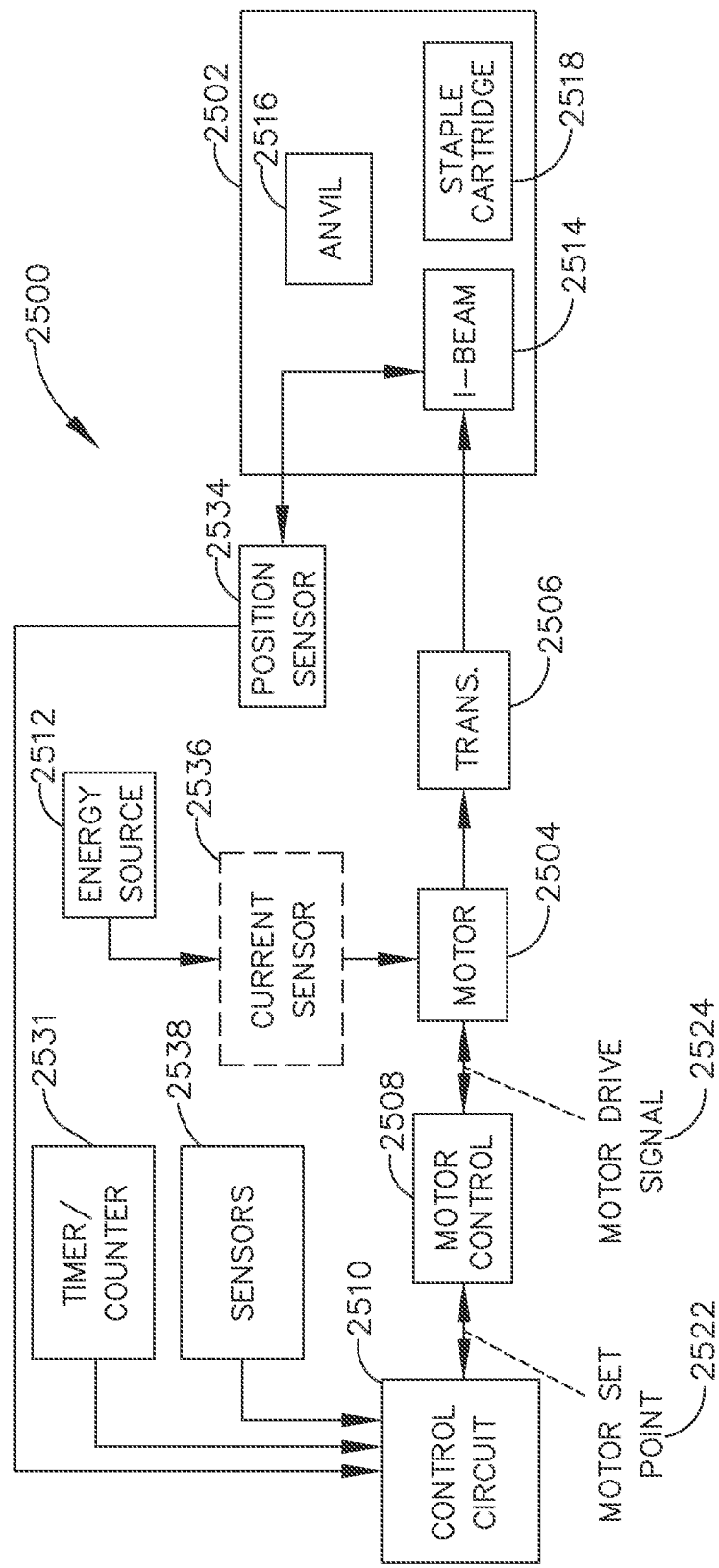
FIG. 14 illustrates a block diagram of a surgical instrument programmed to control distal translation of a displacement member according to one aspect of this disclosure.

FIG. 14 illustrates a block diagram of a surgical instrument 2500 programmed to control distal translation of a displacement member according to one aspect of this disclosure. In one aspect, the surgical instrument 2500 is programmed to control distal translation of a displacement member 1111 such as the I-beam 2514. The surgical instrument 2500 comprises an end effector 2502 that may comprise an anvil 2516, an I-beam 2514 (including a sharp cutting edge 2509), and a removable staple cartridge 2518. The end effector 2502, anvil 2516, I-beam 2514, and staple cartridge 2518 may be configured as described herein, for example, with respect to FIGS. 1-13.

The position, movement, displacement, and/or translation of a liner displacement member 1111, such as the I-beam 2514, can be measured by the absolute positioning system 1100, sensor arrangement 1102, and position sensor 1200 as shown in FIGS. 10-12 and represented as position sensor 2534 in FIG. 14. Because the I-beam 2514 is coupled to the longitudinally movable drive member 120, the position of the I-beam 2514 can be determined by measuring the position of the longitudinally movable drive member 120 employing the position sensor 2534. Accordingly, in the following description, the position, displacement, and/or translation of the I-beam 2514 can be achieved by the position sensor 2534 as described herein. A control circuit 2510, such as the control circuit 700 described in FIGS. 5A and 5B, may be programmed to control the translation of the displacement member 1111, such as the I-beam 2514, as described in connection with FIGS. 10-12. The control circuit 2510, in some examples, may comprise one or more microcontrollers, microprocessors, or other suitable processors for executing instructions that cause the processor or processors to control the displacement member, e.g., the I-beam 2514, in the manner described. In one aspect, a timer/counter circuit 2531 provides an output signal, such as elapsed time or a digital count, to the control circuit 2510 to correlate the position of the I-beam 2514 as determined by the position sensor 2534 with the output of the timer/counter circuit 2531 such that the control circuit 2510 can determine the position of the I-beam 2514 at a specific time (t) relative to a starting position. The timer/counter circuit 2531 may be configured to measure elapsed time, count external [evens,] events, or time external events.

The control circuit 2510 may generate a motor set point signal 2522. The motor set point signal 2522 may be provided to a motor controller 2508. The motor controller 2508 may comprise one or more circuits configured to provide a motor drive signal 2524 to the motor 2504 to drive the motor 2504 as described herein. In some examples, the motor 2504 may be a brushed DC electric motor, such as the motor 82, 714, 1120 shown in FIGS. 1, 5B, 10. For example, the velocity of the motor 2504 may be proportional to the motor drive signal 2524. In some examples, the motor 2504 may be a brushless direct current (DC) electric motor and the motor drive signal 2524 may comprise a pulse-width-modulated (PWM) signal provided to one or more stator windings of the motor 2504. Also, in some examples, the motor controller 2508 may be omitted and the control circuit 2510 may generate the motor drive signal 2524 directly.

The motor 2504 may receive power from an energy source 2512. The energy source 2512 may be or include a battery, a super capacitor, or any other suitable energy source 2512. The motor 2504 may be mechanically coupled to the I-beam 2514 via a transmission 2506. The transmission 2506 may include one or more gears or other linkage components to couple the motor 2504 to the I-beam 2514. A position sensor 2534 may sense a position of the I-beam 2514. The position sensor 2534 may be or include any type of sensor that is capable of generating position data that indicates a position of the I-beam 2514. In some examples, the position sensor 2534 may include an encoder configured to provide a series of pulses to the control circuit 2510 as the I-beam 2514 translates distally and proximally. The control circuit 2510 may track the pulses to determine the position of the I-beam 2514. Other suitable position sensor may be used, including, for example, a proximity sensor. Other types of position sensors may provide other signals indicating motion of the I-beam 2514. Also, in some examples, the position sensor 2534 may be omitted. Where the motor 2504 is a stepper motor, the control circuit 2510 may track the position of the I-beam 2514 by aggregating the number and direction of steps that the motor 2504 has been instructed to execute. The position sensor 2534 may be located in the end effector 2502 or at any other portion of the instrument.

The control circuit 2510 may be in communication with one or more sensors 2538. The sensors 2538 may be positioned on the end effector 2502 and adapted to operate with the surgical instrument 2500 to measure the various derived parameters such as gap distance versus time, tissue compression versus time, and anvil strain versus time. The sensors 2538 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 2502. The sensors 2538 may include one or more sensors.

The one or more sensors 2538 may comprise a strain gauge, such as a micro-strain gauge, configured to measure the magnitude of the strain in the anvil 2516 during a clamped condition. The strain gauge provides an electrical signal whose amplitude varies with the magnitude of the strain. The sensors 2538 may comprise a pressure sensor configured to detect a pressure generated by the presence of compressed tissue between the anvil 2516 and the staple cartridge 2518. The sensors 2538 may be configured to detect impedance of a tissue section located between the anvil 2516 and the staple cartridge 2518 that is indicative of the thickness and/or fullness of tissue located therebetween.

The sensors 2538 may be is configured to measure forces exerted on the anvil 2516 by the closure drive system 30. For example, one or more sensors 2538 can be at an interaction point between the closure tube 260 (FIG. 3) and the anvil 2516 to detect the closure forces applied by the closure tube 260 to the anvil 2516. The forces exerted on the anvil 2516 can be representative of the tissue compression experienced by the tissue section captured between the anvil 2516 and the staple cartridge 2518. The one or more sensors 2538 can be positioned at various interaction points along the closure drive system 30 (FIG. 2) to detect the closure forces applied to the anvil 2516 by the closure drive system 30. The one or more sensors 2538 may be sampled in real time during a clamping operation by a processor as described in FIGS. 5A-5B. The control circuit 2510 receives real-time sample measurements to provide analyze time based information and assess, in real time, closure forces applied to the anvil 2516.

A current sensor 2536 can be employed to measure the current drawn by the motor 2504. The force required to advance the I-beam 2514 corresponds to the current drawn by the motor 2504. The force is converted to a digital signal and provided to the control circuit 2510.

Using the physical properties of the instruments disclosed herein in connection with FIGS. 1-14, and with reference to FIG. 14, the control circuit 2510 can be configured to simulate the response of the actual system of the instrument in the software of the controller. A displacement member can be actuated to move an I-beam 2514 in the end effector 2502 at or near a target velocity. The surgical instrument 2500 can include a feedback controller, which can be one of any feedback controllers, including, but not limited to a PID, a State Feedback, LQR, and/or an Adaptive controller, for example. The surgical instrument 2500 can include a power source to convert the signal from the feedback controller into a physical input such as case voltage, pulse width modulated (PWM) voltage, frequency modulated voltage, current, torque, and/or force, for example.

The actual drive system of the surgical instrument 2500 is configured to drive the displacement member, cutting member, or I-beam 2514, by a brushed DC motor with gearbox and mechanical links to an articulation and/or knife system. Another example is the electric motor 2504 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 2504. The outside influence, such as drag, may cause the operation of the physical system to deviate from a desired operation of the physical system.

Before explaining aspects of the surgical instrument 2500 in detail, it should be noted that the example aspects are not limited in application or use to the details of construction and arrangement of parts illustrated in the accompanying drawings and description. The example aspects may be implemented or incorporated in other aspects, variations and modifications, and may be practiced or carried out in various ways. Further, unless otherwise indicated, the terms and expressions employed herein have been chosen for the purpose of describing the example aspects for the convenience of the reader and are not for the purpose of limitation thereof. Also, it will be appreciated that one or more of the following-described aspects, expressions of aspects and/or examples, can be combined with any one or more of the other following-described aspects, expressions of aspects and/or examples.

Various example aspects are directed to a surgical instrument 2500 comprising an end effector 2502 with motor-driven surgical stapling and cutting implements. For example, a motor 2504 may drive a displacement member distally and proximally along a longitudinal axis of the end effector 2502. The end effector 2502 may comprise a pivotable anvil 2516 and, when configured for use, a staple cartridge 2518 positioned opposite the anvil 2516. A clinician may grasp tissue between the anvil 2516 and the staple cartridge 2518, as described herein. When ready to use the instrument 2500, the clinician may provide a firing signal, for example by depressing a trigger of the instrument 2500. In response to the firing signal, the motor 2504 may drive the displacement member distally along the longitudinal axis of the end effector 2502 from a proximal stroke begin position to a stroke end position distal of the stroke begin position. As the displacement member translates distally, an I-beam 2514 with a cutting element positioned at a distal end, may cut the tissue between the staple cartridge 2518 and the anvil 2516.

In various examples, the surgical instrument 2500 may comprise a control circuit 2510 programmed to control the distal translation of the displacement member, such as the I-beam 2514, for example, based on one or more tissue conditions. The control circuit 2510 may be programmed to sense tissue conditions, such as thickness, either directly or indirectly, as described herein. The control circuit 2510 may be programmed to select a firing control program based on tissue conditions. A firing control program may describe the distal motion of the displacement member. Different firing control programs may be selected to better treat different tissue conditions. For example, when thicker tissue is present, the control circuit 2510 may be programmed to translate the displacement member at a lower velocity and/or with lower power. When thinner tissue is present, the control circuit 2510 may be programmed to translate the displacement member at a higher velocity and/or with higher power.

In some examples, the control circuit 2510 may initially operate the motor 2504 in an open-loop configuration for a first open-loop portion of a stroke of the displacement member. Based on a response of the instrument 2500 during the open-loop portion of the stroke, the control circuit 2510 may select a firing control program. The response of the instrument may include, a translation distance of the displacement member during the open-loop portion, a time elapsed during the open-loop portion, energy provided to the motor 2504 during the open-loop portion, a sum of pulse widths of a motor drive signal, etc. After the open-loop portion, the control circuit 2510 may implement the selected firing control program for a second portion of the displacement member stroke. For example, during the closed loop portion of the stroke, the control circuit 2510 may modulate the motor 2504 based on translation data describing a position of the displacement member in a closed-loop manner to translate the displacement member at a constant velocity.

FIG. 15 illustrates a diagram 2580 plotting two example displacement member strokes executed according to one aspect of this disclosure. The diagram 2580 comprises two axes. A horizontal axis 2584 indicates elapsed time. A vertical axis 2582 indicates the position of the I-beam 2514 between a stroke begin position 2586 and a stroke end position 2588. On the horizontal axis 2584, the control circuit 2510 may receive the firing signal and begin providing the initial motor setting at to. The open-loop portion of the displacement member stroke is an initial time period that may elapse between $t_0$ and $t_1$.

A first example 2592 shows a response of the surgical instrument 2500 when thick tissue is positioned between the anvil 2516 and the staple cartridge 2518. During the open-loop portion of the displacement member stroke, e.g., the initial time period between $t_0$ and $t_1$, the I-beam 2514 may traverse from the stroke begin position 2586 to position 2594. The control circuit 2510 may determine that position 2594 corresponds to a firing control program that advances the I-beam 2514 at a selected constant velocity (Vslow), indicated by the slope of the example 2592 after $t_1$ (e.g., in the closed loop portion). The control circuit 2510 may drive I-beam 2514 to the velocity Vslow by monitoring the position of I-beam 2514 and modulating the motor set point 2522 and/or motor drive signal 2524 to maintain Vslow. A second example 2590 shows a response of the surgical instrument 2500 when thin tissue is positioned between the anvil 2516 and the staple cartridge 2518.

During the initial time period (e.g., the open-loop period) between $t_0$ and $t_1$, the I-beam 2514 may traverse from the stroke begin position 2586 to position 2596. The control circuit may determine that position 2596 corresponds to a firing control program that advances the displacement member at a selected constant velocity (Vfast). Because the tissue in example 2590 is thinner than the tissue in example 2592, it may provide less resistance to the motion of the I-beam 2514. As a result, the I-beam 2514 may traverse a larger portion of the stroke during the initial time period. Also, in some examples, thinner tissue (e.g., a larger portion of the displacement member stroke traversed during the initial time period) may correspond to higher displacement member velocities after the initial time period.

Closed Loop Feedback Control of Motor Velocity of a Surgical Stapling and Cutting Instrument Based on Magnitude of Velocity Error Measurements During use of a motorized surgical stapling and cutting instrument it is possible that a velocity controlled system error may occur between the command velocity and the actual measured velocity of the cutting member or firing member. Therefore, it may be desirable to provide a closed loop feedback system that adjusts the velocity of the cutting member or firing member based on the magnitude of one or more error terms determined based on the difference between an actual speed and a command speed over a specified increment of time/distance.

FIGS. 16-22 illustrate various graphical representations and processes for determining the error between a directed velocity of a displacement member and the actual velocity of a displacement member and adjusting the directed velocity of the displacement member based on the error. In the aspects illustrated in FIGS. 16-22 the displacement member is the I-beam 2514. In other aspects, however, the displacement member may be the drive member 120 (FIG. 2), the firing member 220, 2509 (FIGS. 3, 13), the firing bar 172 (FIG. 4), the I-beam 178, 2514 (FIGS. 4, 13, 14) or any combination thereof.

Turning now to FIG. 16, there is a shown a graph 8500 depicting velocity (v) of a displacement member as a function of displacement (δ) of the displacement member according to one aspect of this disclosure. In the illustrated aspect, the displacement (δ) of the I-beam 2514 is shown along the horizontal axis 8502 and the velocity (v) of the I-beam 2514 is shown along the vertical axis 8504. It will be appreciate that the velocity of the motor 2504 may be shown along the vertical axis 8504 instead of the velocity of the I-beam 2514. The function shown in dashed line represents directed velocity 8506 of the I-beam 2514 and the function shown in solid line form represents actual velocity 8508 of the I-beam 2514. The directed velocity 8506 is based on a motor set point 2522 velocity applied to the motor control 2508 circuit by the control circuit 2510. In response, the motor control 2508 applies a corresponding motor drive signal 2524 having a predetermined duty cycle to the motor 2504 to set the velocity of the motor 2504 to achieve a directed velocity 8506 of the I-beam 2514, as shown in FIG. 14. The directed velocity 8506 also can be referred to as the command velocity. Based on the motor set point 2522 velocity, displacement of the I-beam 2514 is given by the directed velocity 8506. However, due to outside influences, the actual displacement of the I-beam 2514 is given by the actual velocity 8508. As can be ascertained from the graph 8500, a difference is evident between the directed velocity 8506 and the actual velocity 8508 of the I-beam 2514. The differences between the directed velocity 8506 and the actual velocity 8508 are referred to herein as the velocity error terms such as short term error (S), cumulative error (C), rate of change error (R), and number of overshoots error (N). The short term error S represents how far the actual velocity 8508 is from the directed velocity 8506 at a displacement of $\delta_1$. The cumulative error C, shown as the cross-hatched area over time (mm$^2$/sec), represents error deviation between actual velocity 8508 and directed velocity 8506 accumulated over time. The rate of change R, given by the slope b/a, represents the rate at which the actual velocity 8508 is approaching the directed velocity 8506. Finally, the number of overshoots N represents the number of times the actual velocity 8508 overshoots or undershoots the directed velocity 8506.

Figure 17:
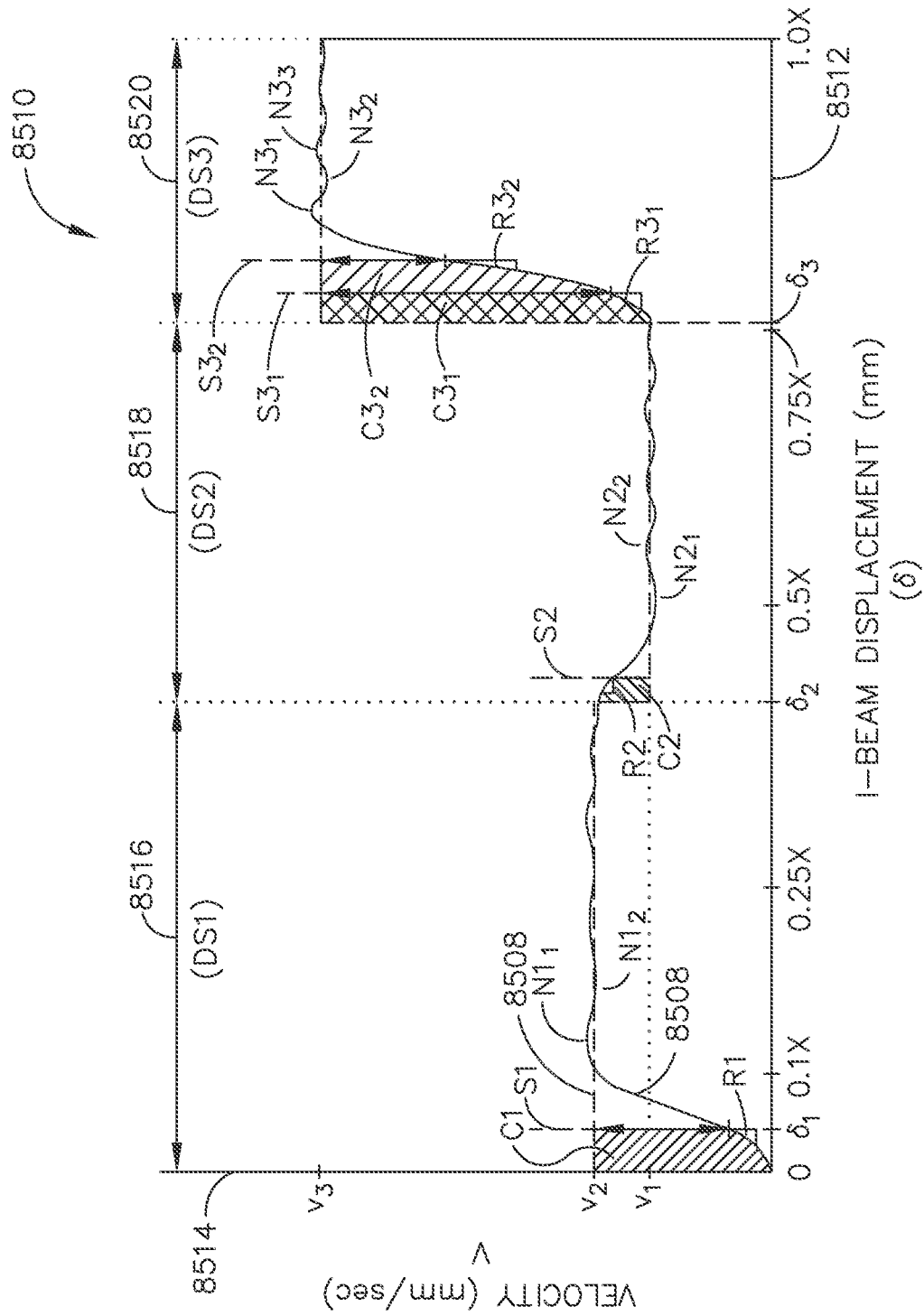
FIG. 17 is a graph depicting velocity (v) of a displacement member as a function of displacement (δ) of the displacement member according to one aspect of this disclosure.

FIG. 17 is a graph 8510 depicting velocity (v) of a displacement member as a function of displacement (δ) of the displacement member according to one aspect of this disclosure. In the illustrated aspect, the displacement (δ)

(mm) of the I-beam 2514 is shown along the horizontal axis 8512 and the velocity (v) (mm/sec) of the I-beam 2514 is shown along the vertical axis 8514. The horizontal axis 8512 is scaled to represent the displacement of the I-beam 2514 over a length X of the staple cartridge 2518, such as 10-60 mm staple cartridges, for example. In one aspect, for a 60 mm cartridge 2518 the I-beam 2514 displacement is 60 mm and the velocity of the I-beam 2514 varies from 0-30 mm/sec. The function shown in dashed line form represents directed velocity 8506 of the I-beam 2514 and the function shown in solid line form represents actual velocity 8508 of the I-beam 2514. As shown by the graph 8510, the I-beam 2514 displacement along the staple cartridge 2518 stroke is divided into three zones 8516, 8518, 8520. In the first zone 8516 (0 to $\delta_2$ mm), at the beginning of the stroke (0 mm), the control circuit 2510 sets the motor drive signal 2524 to a first duty cycle (DS1). In the second zone 8518 ($\delta_2$ mm to $\delta_3$ mm), the control circuit 2510 sets the motor drive signal 2524 to a second duty cycle (DS2). In the third zone 8520 ($\delta_3$ mm to end of stroke), the control circuit 2510 sets the motor drive signal 2524 to a third duty cycle (DS3). In accordance with this aspect, the directed velocity 8506 is adjusted based on the position of the I-beam 2514 during a firing stroke. Although, the graph 8510 shows a firing stroke divided into three zones 8516, 8518, 8520, it will be appreciated that the firing stroke may be divided into additional or fewer zones. The surgical instrument 2500 comprises a closed loop feedback system that adjusts or controls the duty cycle of the motor drive signal 2524 to adjust the velocity of the I-beam 2514 based on the magnitude of one or more of the error terms S, C, R, and N based on the difference between the directed velocity 8506 and the actual velocity 8508 over a specified increment of either time or distance as the I-beam 2514 traverses the staple cartridge 2518. In one aspect, the control system 2500 employs PID error control to control the velocity of the motor 2504 at discrete time/distance locations $\delta_n$ of the I-beam 2514 stroke and employs the PID errors to control constant velocity of the I-beam 2514 between the discrete time/displacement checks.

Referring to the first zone 8516, at the beginning of the stroke, the control circuit 2510 provides a motor set point 2522 to the motor control 2508, which applies a motor drive signal 2524 having a first duty cycle (DS1) to the motor 2504 to set the directed velocity 8506 of the I-beam 2514 to $V_2$. As the I-beam 2514 advances distally, the position sensor 2534 and the timer/counter 2531 circuit track the position and time, respectively, of the I-beam 2514 to determine the actual position and the actual velocity 8508 of the I-beam 2514. As the position of the I-beam 2514 approaches $\delta_1$, the actual velocity 8508 begins a positive transition towards the directed velocity 8506. As shown, the actual velocity 8508 lags the directed velocity 8506 by S1 and has lagged the directed velocity 8506 by a cumulative error C1 over a period of time. At $\delta_1$ the rate of change of the actual velocity 8508 is R1. As the I-beam 2514 advances distally towards $\delta_2$, the actual velocity 8508 overshoots $N1_1$, $N1_2 \ldots N1_n$ the directed velocity 8506 and eventually settles at the directed velocity 8506.

Turning now to the second zone 8518, at $\delta_2$ the control circuit 2510 provides a new motor set point 2522 to the motor control 2508, which applies a new motor drive signal 2524 having a second duty cycle (DS2) to the motor 2504 to decrease the directed velocity 8506 of the I-beam 2514 to $V_1$. At $\delta_2$ the actual velocity 8508 of the I-beam 2514 begins a negative transition to the lower directed velocity 8506. As the I-beam 2514 advances distally, the actual velocity 8508 lags the directed velocity 8506 by S2 and lags the directed velocity 8506 by a cumulative error C2 over a time period and the rate of change of the actual velocity 8508 is R2. As the I-beam 2514 advances distally towards $\delta_3$, the actual velocity 8508 undershoots $N2_1$, $N2_2 \ldots N2n$ the directed velocity 8506 and eventually settles at the directed velocity 8506.

Turning now to the third zone 8520, at $\delta_3$ the control circuit 2510 provides a new motor set point 2522 to the motor control 2508, which applies a new motor drive signal 2524 having a third duty cycle (DS3) to the motor 2504 to increase the directed velocity 8506 of the I-beam 2514 to $V_3$. At $\delta_3$ the actual velocity 8508 of the I-beam 2514 begins a positive transition to the higher directed velocity 8506. As the I-beam 2514 advances distally, the actual velocity 8508 lags the directed velocity 8506 by $S3_1$ and lags the directed velocity 8506 by a cumulative error $C3_1$ over a time period and the rate of change of the actual velocity 8508 is $R3_1$. As the I-beam 2514 advances distally, the actual velocity 8508 approaches the directed velocity 8506 at a rate of $R3_2$ decreasing the lag error to $S3_2$ and increasing the cumulative error by $C3_2$ over a time period. As the I-beam 2514 advances towards the end of stroke, the actual velocity 8508 overshoots $N3_1$, $N3_2$, $N3_3 \ldots N3n$ the directed velocity 8506 and eventually settles at the directed velocity 8506.

In another aspect, the control system of the surgical instrument 2500 employs PID control errors to control motor velocity based on the magnitude of the PID error terms S, C, R, N over the I-beam 2514 stroke. As the I-beam 2514 traverses the staple cartridge 2528 a change in directed velocity 8506 may be based on measured errors between the actual velocity 8508 and the directed velocity 8506. For example, in the velocity control system of the surgical instrument 2500, an error term is created between the directed velocity 8506 and the actual measured velocity 8508. The magnitude of these error terms can be used to set a new directed velocity 8506. The error terms of interest may include, for example, short term, steady state, and accumulated. Different error terms can be used in different zones 8516, 8518, 8520 (e.g., climbing the ramp, intermediate, final). Different error terms can be magnified differently based on their importance within the algorithm.

Figure 18:
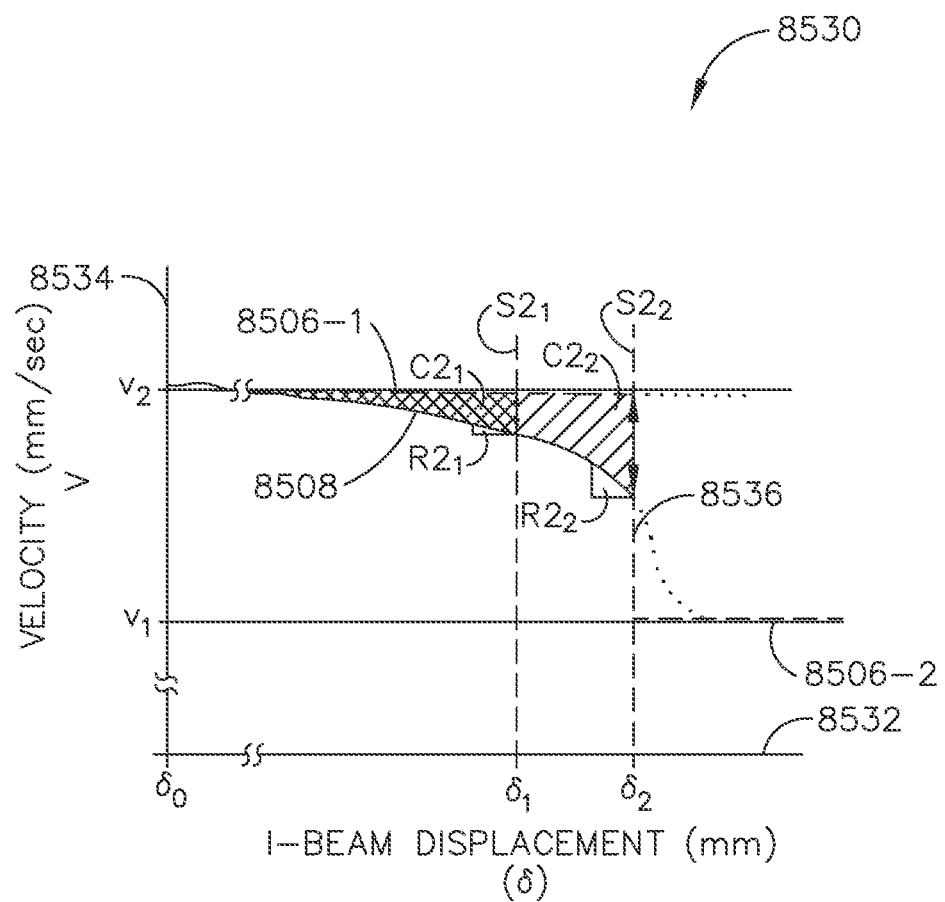
FIG. 18 is a graph of velocity (v) of a displacement member as a function of displacement (δ) of the displacement member depicting condition for threshold change of the directed velocity according to one aspect of this disclosure.

FIG. 18 is a graph 8530 of velocity (v) of a displacement member as a function of displacement ($\delta$) of the displacement member depicting condition for threshold change of the directed velocity 8506-1 according to one aspect of this disclosure. In the illustrated aspect, the displacement ($\delta$) (mm) of the I-beam 2514 is shown along the horizontal axis 8532 and velocity (v) (mm/sec) of the I-beam 2514 is shown along the vertical axis 8534. In accordance with FIG. 18, the velocity control system of the surgical instrument 2500 can be configured to measure the error between the directed velocity of the I-beam 2514 and the actual velocity 8508 of the I-beam 2514 and adjust the directed velocity 8506 based on the magnitude of the error. As shown in FIG. 18, at $\delta_0$ the directed velocity 8506-1 and the actual velocity 8508 are about the same. However, as the I-beam 2514 advances distally, due to outside tissue influences, the actual velocity deviates from the directed velocity 8506-1. The velocity control system of the surgical instrument 2500 measures the position and timing of the I-beam 2514 using the position sensor 2534 and the timer/counter 2531 to determine the position and the actual velocity 8508 of the I-beam 2514 and at each predetermined position, the velocity control system determines the error between the directed velocity of the I-beam 2514 and the actual velocity 8508 of the I-beam 2514 and compares the error to a threshold. For example, at $\delta_1$ the control circuit 2510 conducts a first error measurement and determines the lag $S2_1$ between the actual velocity 8508 and the directed velocity 8506-1, the accumulated error $C2_1$, and the rate of change $R2_1$. Based on the error measurements at $\delta_1$ the control circuit 2510 determines that the magnitude of the error is within the error threshold 8536 and maintains the current directed velocity 8506-1. At $\delta_2$ the control circuit 2510 conducts another error measurement and determines the lag $S2_2$ between the actual velocity 8508 and the directed velocity 8506-1, the accumulated error $C2_2$, and the rate of change $R2_2$. Based on the error measurements at $\delta_2$ the control circuit 2510 determines that the magnitude of the error exceeds the error threshold 8536 and lowers the directed velocity to a new directed velocity 8506-2. This process is repeated until the measured error falls with the threshold 8536 and the directed velocity may be adjusted back to the original directed velocity 8506-1 or to a new directed velocity 8506-$n$. It will be appreciated that multiple error thresholds may be employed at different I-beam 2514 displacement positions during the firing stroke.

In one aspect, the velocity error between the actual velocity 8508 and the directed velocity 8506 of the displacement member (e.g., I-beam 2514) $V_{DM}$ can be represented by Eq. 1:

$$V_{DM} = A \cdot S + B \cdot \sum C + D \cdot \frac{\Delta R}{\Delta t} \qquad \text{Eq. 1}$$

Where A, B, and D are coefficients and S is the short term error, C is the cumulative error, and R is the rate of change error. With reference to FIG. 18, if the sum of the errors is less than the error threshold Z as represented by Eq. 2:

$$S2_1 + C2_1 + R2_1 < Z \qquad \text{Eq. 2}$$

The control circuit 2510 determines that the error is within the threshold Z and does not in the directed velocity 8506. Accordingly, the directed velocity 8506-1 is maintained until the next predetermined position of the I-beam 2514. If the sum of the errors is greater than the error threshold Z as represented by Eq. 3:

$$S2_2 + C2_2 + R2_2 > Z \qquad \text{Eq. 3}$$

The control circuit 2510 determines that the error is outside the threshold Z and adjusts the directed velocity 8506 to a lower directed velocity 8506-2.

Figure 19:
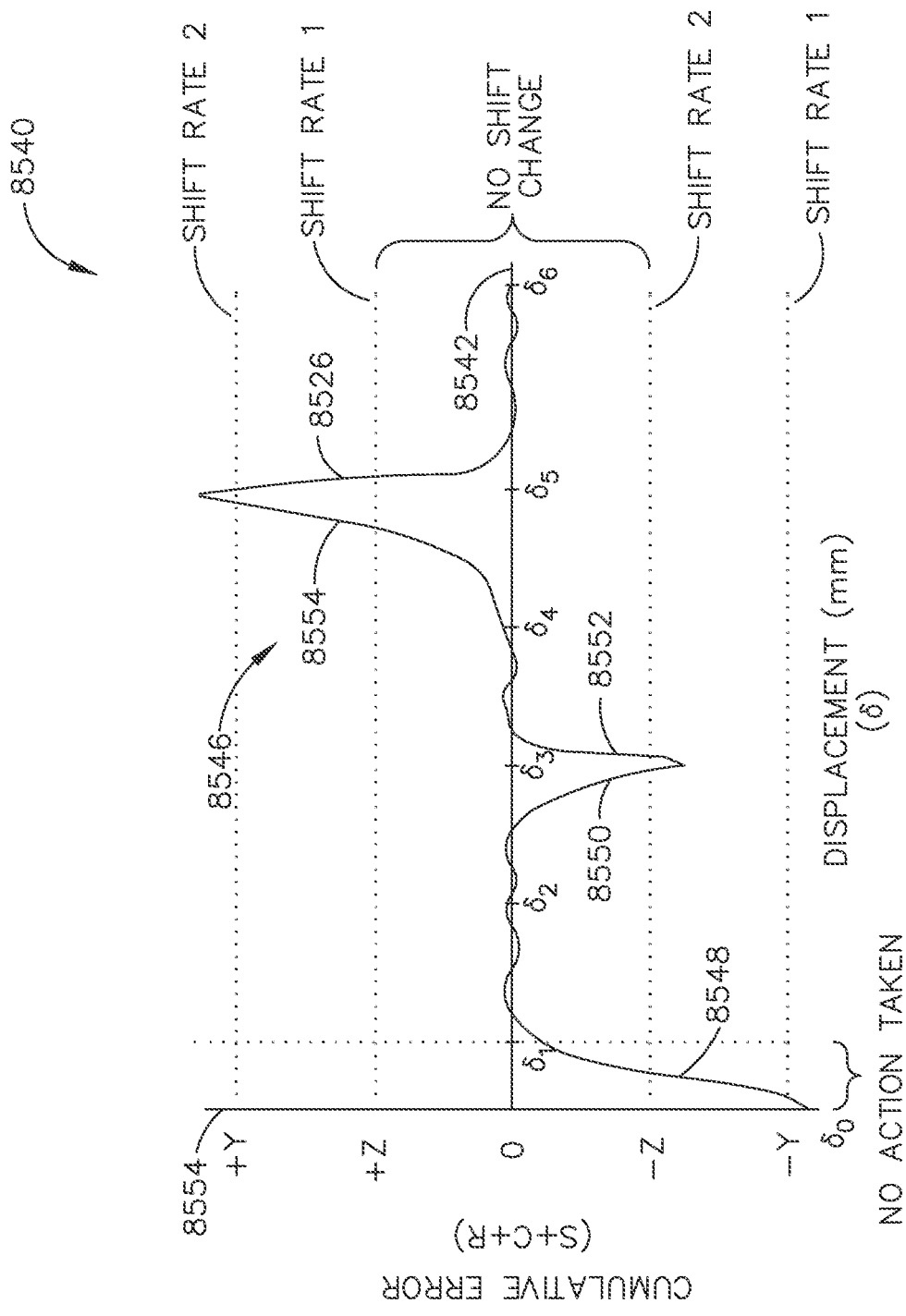
FIG. 19 is a graph that illustrates the conditions for changing the directed velocity 8506 of a displacement member according to one aspect of this disclosure.

FIG. 19 is a graph 8540 that illustrates the conditions for changing the directed velocity 8506 of a displacement member according to one aspect of this disclosure. In the illustrated aspect, the displacement of the I-beam 2514 is shown along the horizontal axis 8541 and the cumulative error (S+C+R) is shown along the vertical axis 8544. An error curve 8546 represents the change in the cumulative error as a function of I-beam 2514 displacement. Marked along the vertical axis 8544 are various error thresholds −Y, −Z, 0, +Z, +Y. As the error curve 8546 traverses the various error thresholds −Y, −Z, 0, +Z, +Y, the control circuit 2510 of the velocity control system of the surgical instrument 2500 shifts to a new directed velocity at a different rate or does not shift and maintains the current directed velocity. A cumulative error of 0 along the horizontal axis 8542 represents the condition where there is no difference between the directed velocity and the actual velocity of the I-beam 2514. When the cumulative error is within the ±Z error thresholds, the control circuit 2510 of the velocity control system makes no adjustments to the directed velocity. If the cumulative error is between the Z and Y thresholds or between the −Z and −Y thresholds, the control circuit 2510 of the velocity control system shifts to a new directed velocity at a first shift rate indicate din the graph 8540 as Shift Rate 1. If the cumulative error exceeds the ±Y error thresholds, the control circuit 2510 shifts to a new directed velocity at a second shift rate indicated in the graph 8540 as Shift Rate 2, where Shift Rate 2 is greater than Shift Rate 1, for example.

Still with reference to the graph 8540 in FIG. 19, the control circuit 2510 of the velocity control system of the surgical instrument 2500 takes no action during an initial displacement of the I-beam 2514 between $\delta_0$ and $\delta_1$. Accordingly, during the initial displacement ($\delta_1 - \delta_0$), the cumulative error 8548 returns to zero as the actual velocity approaches the directed velocity and remains around zero until $\delta_2$. After $\delta_2$ the cumulative error 8550 deviates from zero until it exceeds the −Z threshold at $\delta_3$. Upon exceeding the −Z threshold, the control circuit 2510 adjusts the velocity of the I-beam 2514 to a new directed velocity at Shift Rate 1. The cumulative error 8552 eventually returns to zero and remains around zero until $\delta_4$. Between $\delta_4$ and $\delta_5$ the cumulative error 8554 deviates from zero and exceeds the +Y error threshold and at $\delta_5$ the control circuit 2510 adjusts the velocity of the I-beam 2514 to a new directed velocity at Shift Rate 2, which is greater the Shift Rate 1. Upon adjusting the directed velocity of Shift Rate 2, the cumulative error 8556 returns to zero. Different error terms (S, C, R) can be magnified differently based on their importance with an algorithm and different error terms (S, C, R) can be employed in different zones, e.g., zones 8516, 8518, 8520 in FIG. 17, (e.g., climbing the ramp, intermediate, final).

Figure 20:
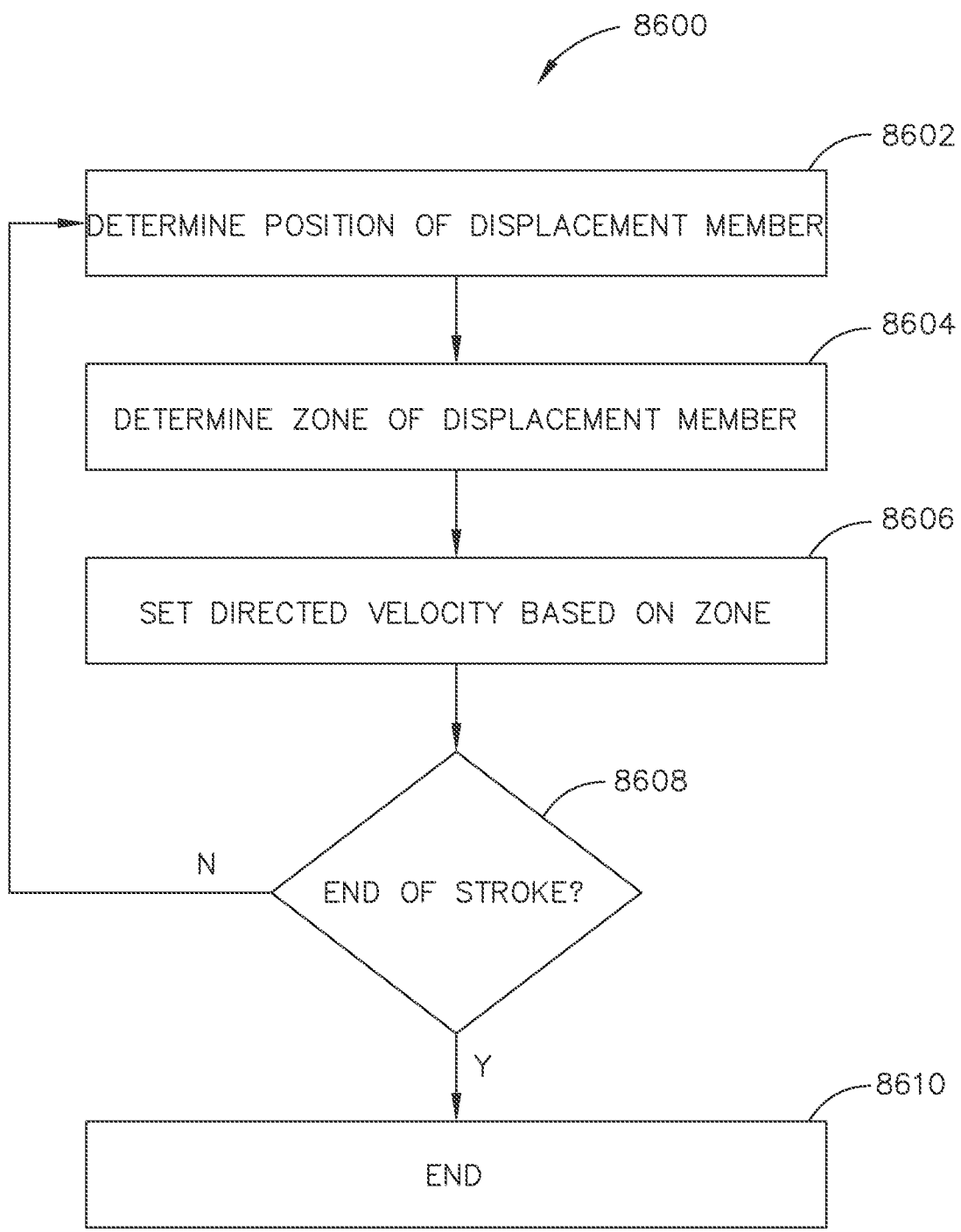
FIG. 20 is a logic flow diagram of a process depicting a control program or a logic configuration for controlling velocity of a displacement member based on the measured error between the directed velocity of a displacement member and the actual velocity of the displacement member according to one aspect of this disclosure.

FIG. 20 is a logic flow diagram of a process 8600 depicting a control program or a logic configuration for controlling velocity of a displacement member based on the position of a displacement member and the actual velocity of the displacement member according to one aspect of this disclosure. With reference also to the velocity control system of the surgical instrument 2500 shown in FIG. 14, the control circuit 2510 determines 8602 the position of a displacement member such as the I-beam 2514 utilizing the position sensor 2534 and the timer/counter 2531 circuits. The control circuit 2510 compares the position of the displacement member to one of a plurality of zones 8516, 8518, 8520 as discussed in connection with FIG. 17. The zones 8516, 8518, 8520 may be stored in memory. The control circuit 2510 determines 8604 in which zone 8516, 8518, 8520 the displacement member is located in based on the position of the displacement member previously determined 8602. The control circuit 2510 then sets 8606 the motor set point 2522 velocity and the motor control 2508 sets the motor drive signal 2524 to set the motor 254 velocity to achieve the desired directed velocity of the displacement member based on the zone. In one aspect, the motor control 2508 sets the motor drive signal 2524 to a duty cycle based on which zone 8516, 8518, 8520 the displacement member is located. The control circuit 2510 determines 8608 if the displacement member is at the end of stroke. If the displacement member is not at the end of stroke, the process 8600 continues along the N branch and determines 8602 a new position of the displacement member. The process 8600 continues until the displacement member reaches the end of stroke and proceeds along the YES branch and ends 8610.

Figure 21:
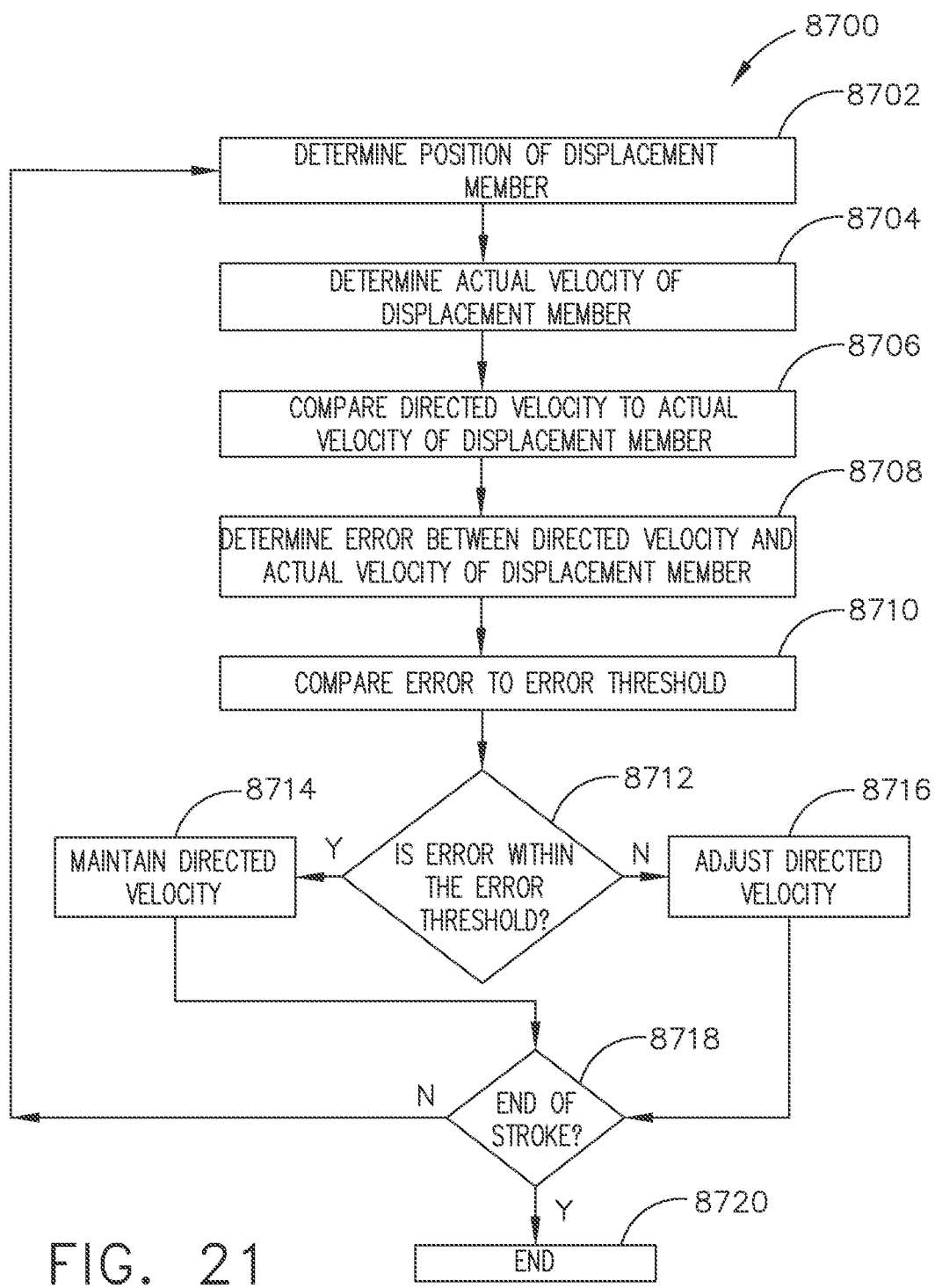
FIG. 21 is a logic flow diagram of a process depicting a control program or a logic configuration for controlling velocity of a displacement member based on the measured error between the directed velocity of a displacement member and the actual velocity of the displacement member according to one aspect of this disclosure.

FIG. 21 is a logic flow diagram of a process 8600 depicting a control program or a logic configuration for controlling velocity of a displacement member based on the measured error between the directed velocity of a displacement member and the actual velocity of the displacement member according to one aspect of this disclosure. With reference also to the velocity control system of the surgical instrument 2500 shown in FIG. 14, the control circuit 2510 determines 8702 the position of a displacement member such as the I-beam 2514 utilizing the position sensor 2534 and the timer/counter 2531 circuits. The control circuit 2510 then determines 8704 the actual velocity of the displacement member based on the position information received from the position sensor 2534 and the timer/counter 2531 circuits. Upon determining 8704 the actual velocity of the displacement member, the control circuit 2510 compares 8706 the directed velocity of the displacement member to the actual velocity of the displacement member. Based on the comparison 8706, the control circuit 2510 determines 8708 the error between the directed velocity of the displacement member to the actual velocity of the displacement member and compares 8710 the error to an error threshold.

The error may be calculated based on Eq. 1 above. The control circuit 2510 determines 8712 if the error is within the error threshold. If the error is within the error threshold (Eq. 2), the process 8700 continues along the YES branch and maintains 8714 the directed velocity at its present value. The control circuit 2510 then determines 8718 if the displacement member is at the end stroke. If the displacement member is at the end of stroke, the process 8700 continues along the YES branch and ends 8720. If the displacement member is not at the end of stroke, the process 8700 continues along the NO branch and determines 8702 the new position of the displacement member. The process 8700 continues until the displacement member reaches the end of stroke.

If the error exceeds the error threshold (Eq. 3), the process 8700 continues along the NO branch and adjusts the directed 8716 the directed velocity to a new value. The new directed velocity may be higher or lower than the current directed velocity of the displacement member. The control circuit 2510 then determines 8718 if the displacement member is at the end stroke. If the displacement member is at the end of stroke, the process 8700 continues along the YES branch and ends 8720. If the displacement member is not at the end of stroke, the process 8700 continues along the NO branch and determines 8702 the new position of the displacement member. The process 8700 continues until the displacement member reaches the end of stroke.

Figure 22:
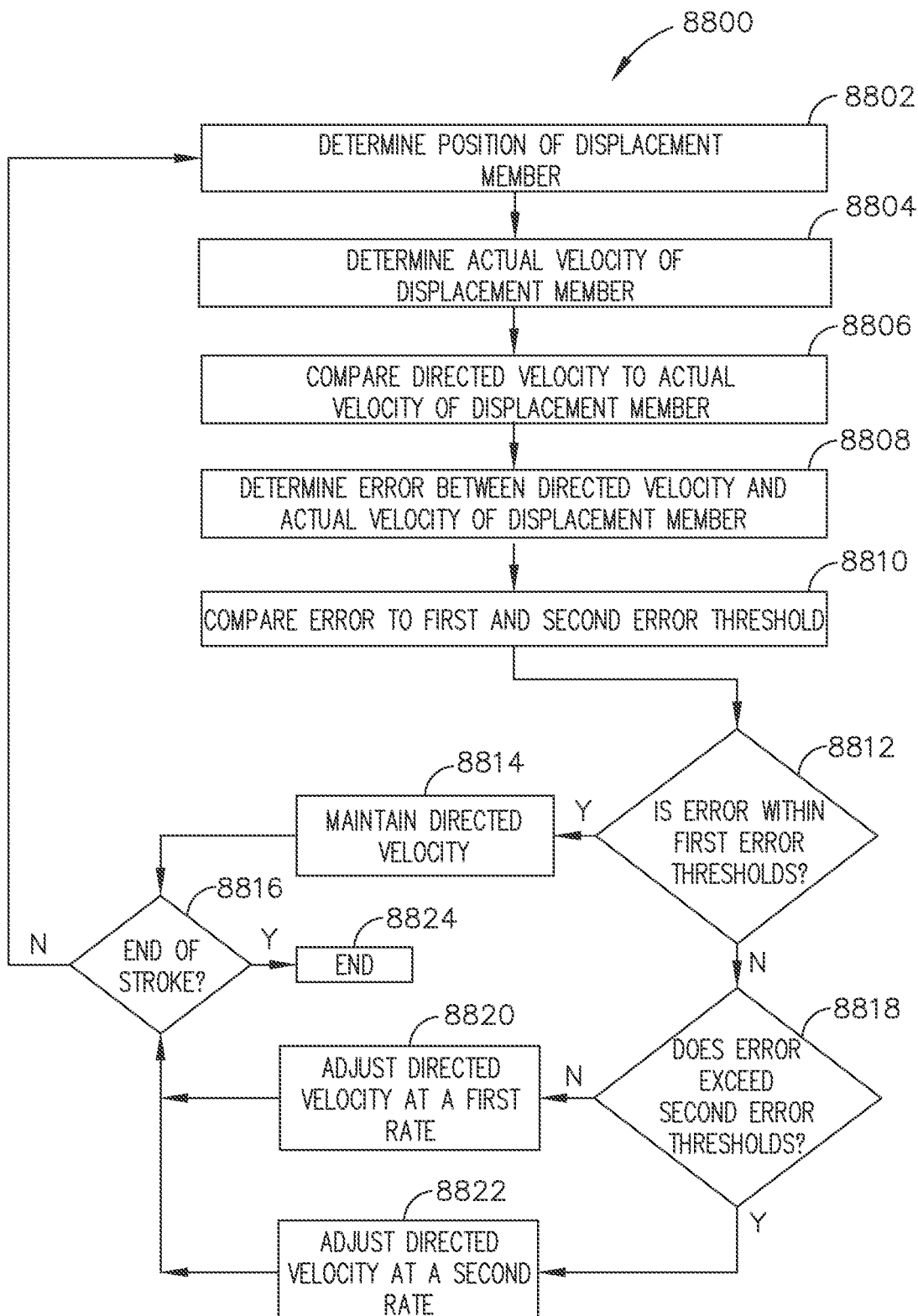
FIG. 22 is a logic flow diagram of a process depicting a control program of logic configuration for controlling velocity of a displacement member based on the measured error between the directed velocity of a displacement member and the actual velocity of the displacement member according to one aspect of this disclosure.

FIG. 22 is a logic flow diagram of a process 8700 depicting a control program of logic configuration for controlling velocity of a displacement member based on the measured error between the directed velocity of a displacement member and the actual velocity of the displacement member according to one aspect of this disclosure. With reference also to the velocity control system of the surgical instrument 2500 shown in FIG. 14, the control circuit 2510 determines 8802 the position of a displacement member such as the I-beam 2514 utilizing the position sensor 2534 and the timer/counter 2531 circuits. The control circuit 2510 then determines 8804 the actual velocity of the displacement member based on the position information received from the position sensor 2534 and the timer/counter 2531 circuits. Upon determining 8804 the actual velocity of the displacement member, the control circuit 2510 compares 8806 the directed velocity of the displacement member to the actual velocity of the displacement member. Based on the comparison 8806, the control circuit 2510 determines 8808 the error between the directed velocity of the displacement member to the actual velocity of the displacement member and compares 8810 the error to multiple error thresholds.

For example, in the illustrated example, the error is compared to two error thresholds as described in connection with FIG. 19.

The control circuit 2510 determines 8812 if the error is within the first error thresholds ($\pm Z$) as described in FIG. 19. If the error is within the first error thresholds ($\pm Z$), the process continues along the YES branch and the control circuit 2510 maintains 8814 the directed velocity without any shift changes. The control circuit 2510 determines 8816 if the displacement member is at the end of stroke. If the displacement member is at the end of stroke the process 8800 continues along the YES branch and ends 8824. If the displacement member is not at the end of stroke, the process 8800 continues along the NO branch and the control circuit 2510 determines 8802 the new position of the displacement member and the process 8800 continues until the displacement member reaches the end of stroke.

If the error is outside the first error thresholds ($\pm Z$) the process 8800 continues along the NO branch and the control circuit 2510 determines 8818 if the error exceeds the second error thresholds ($\pm Y$). If the error does not exceed the second error thresholds, the control circuit 2510 determines that the error is between $-Z$ and $-Y$ or between $+Z$ and $+Y$ error thresholds and proceeds along the NO branch and the control circuit 2510 adjusts 8820 the directed velocity at a first rate of change. The control circuit 2510 determines 8816 end of stroke and proceeds to determine 8802 the new position of the displacement member. The process 8800 continues until the displacement member reaches the end of stroke. If the error exceeds the second error thresholds, the control circuit 2510 determines that the error exceeds the second error thresholds ($\pm Y$) and proceeds along the YES branch and the control circuit 2510 adjusts 8822 the directed velocity at a second rate of change, which is higher than the first rate change. In one aspect, the second rate of change is twice the first rate of change. It will be appreciated that the second rate of change may be greater than or less than the first rate of change. The control circuit 2510 determines 8816 end of stroke and proceeds to determine 8802 the new position of the displacement member. The process 8800 continues until the displacement member reaches the end of stroke. It will be appreciated that additional error thresholds and corresponding rates of change may be implemented.

Various aspects of the subject matter described herein are set out in the following numbered examples:

Example 1. A surgical instrument, comprising: a displacement member configured to translate within the surgical instrument over a plurality of predefined zones; a motor coupled to the displacement member to translate the displacement member; a control circuit coupled to the motor; a position sensor coupled to the control circuit, the position sensor configured to measure the position of the displacement member; and a timer circuit coupled to the control circuit, the timer/counter circuit configured to measure elapsed time; wherein the control circuit is configured to: determine a position of the displacement member; determine a zone in which the displacement member is located; and set a directed velocity of the displacement member based on the zone in which the displacement member is located.

Example 2. The surgical instrument of Example 1, wherein the control circuit is configured to: receive the position of the displacement member from the position sensor; receive elapsed time from the timer circuit; and set duty cycle of the motor based on the zone in which the displacement member is located.

Example 3. The surgical instrument of Example 2, wherein the control circuit is configured to determine an actual velocity of the displacement member.

Example 4. The surgical instrument of Example 3, wherein the control circuit is configured to determine an error between the directed velocity of the displacement member and the actual velocity of the displacement member.

Example 5. The surgical instrument of Example 4, wherein the control circuit is configured to set a new directed velocity of the displacement member based on the error.

Example 6. The surgical instrument of Example 4, wherein the error is based on at least one of a short term error (S), cumulative error (C), rate of change error (R), and number of overshoots error (N).

Example 7. The surgical instrument of Example 1 through Example 6, comprising an end effector, wherein the displacement member is configured to translate within the end effector.

Example 8. A surgical instrument, comprising: a displacement member configured to translate within the surgical instrument; a motor coupled to the displacement member to translate the displacement member; a control circuit coupled to the motor; a position sensor coupled to the control circuit, the position sensor configured to measure the position of the displacement member; and a timer circuit coupled to the control circuit, the timer/counter circuit configured to measure elapsed time; wherein the control circuit is configured to: set a directed velocity of the displacement member; determine a position of the displacement member; determine actual velocity of the displacement member; compare directed velocity of the displacement member to the actual velocity of the displacement member; determine error between the displacement member to the actual velocity of the displacement member; and adjust the directed velocity of the displacement member based on the error.

Example 9. The surgical instrument of Example 8, wherein the control circuit is configured to compare the error to an error threshold.

Example 10. The surgical instrument of Example 9, wherein the control circuit is configured to maintain the directed velocity of the displacement member when the error is within the error threshold.

Example 11. The surgical instrument of Example 9 through Example 10, wherein the control circuit is configured to adjust the directed velocity of the displacement member to change the directed velocity when the error exceeds the error threshold.

Example 12. The surgical instrument of Example 8 through Example 11, wherein the actual velocity of the displacement member is given by the following expression: $V_{DM}=A \cdot S+B \cdot \Sigma C+D \cdot \Delta R/\Delta t$ where A, B, and D are coefficients and S is a short term error, C is a cumulative error, and R is a rate of change error.

Example 13. The surgical instrument of Example 8 through Example 12, comprising an end effector, wherein the displacement member is configured to translate within the end effector.

Example 14. A surgical instrument, comprising: a displacement member configured to translate within the surgical instrument; a motor coupled to the displacement member to translate the displacement member; a control circuit coupled to the motor; a position sensor coupled to the control circuit, the position sensor configured to measure the position of the displacement member; and a timer circuit coupled to the control circuit, the timer/counter circuit configured to measure elapsed time; wherein the control circuit is configured to: set a directed velocity of the displacement member; determine a position of the displacement member; determine actual velocity of the displacement member; compare directed velocity of the displacement member to the actual velocity of the displacement member; determine error between the displacement member to the actual velocity of the displacement member; and adjust the directed velocity of the displacement member at a rate of change based on the error.

Example 15. The surgical instrument of Example 14, wherein the control circuit is configured to compare the error to multiple error thresholds.

Example 16. The surgical instrument of Example 15, wherein the control circuit is configured to adjust the directed velocity of the displacement member at multiple rates of change based on the error.

Example 17. The surgical instrument of Example 15 through Example 16, wherein the control circuit is configured to: compare the error to a first error threshold; and maintain the directed velocity when the error is within the first error threshold.

Example 18. The surgical instrument of Example 17, wherein the control circuit is configured to: compare the error to a second error threshold; adjust the directed velocity at a first rate of change when the error exceeds the first error threshold and is within the second error threshold.

Example 19. The surgical instrument of Example 17 through Example 18, wherein the control circuit is configured to: compare the error to a second error threshold; adjust the directed velocity at a second rate of change when the error exceeds both the first error threshold and the second error threshold.

Example 20. The surgical instrument of Example 14 through Example 19, wherein the error is based on at least one of a short term error (S), cumulative error (C), rate of change error (R), and number of overshoots error (N).

Closed Loop Feedback Control of Motor Velocity of a Surgical Stapling and Cutting Instrument Based on Measured Time Over a Specified Displacement Distance During use of a motorized surgical stapling and cutting instrument it is possible that the velocity of the cutting member or the firing member may need to be measured and adjusted to compensate for tissue conditions. In thick tissue the velocity may be decreased to lower the force to fire experienced by the cutting member or firing member if the force to fire experienced by the cutting member or firing member is greater than a threshold force. In thin tissue the velocity may be increased if the force to fire experienced by the cutting member or firing member is less than a threshold. Therefore, it may be desirable to provide a closed loop feedback system that measures and adjusts the velocity of the cutting member or the firing member based on a measurement of time over a specified distance. It may be desirable to measure the velocity of the cutting member by measuring time at fixed set displacement intervals.

Figure 23A:
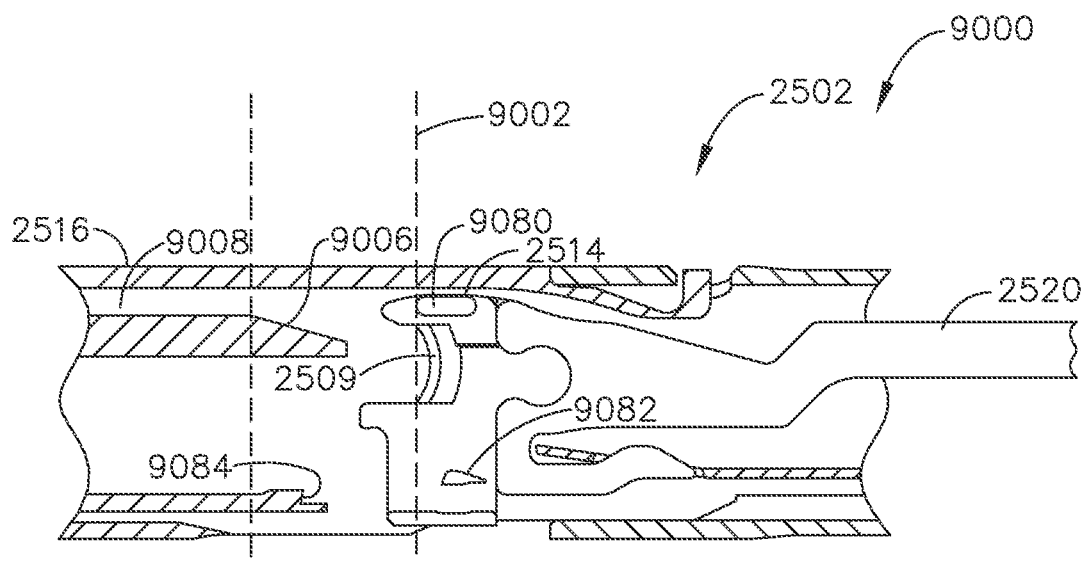
FIG. 23A illustrates an end effector comprising a firing member coupled to an I-beam comprising a cutting edge according to one aspect of this disclosure.
Figure 23B:
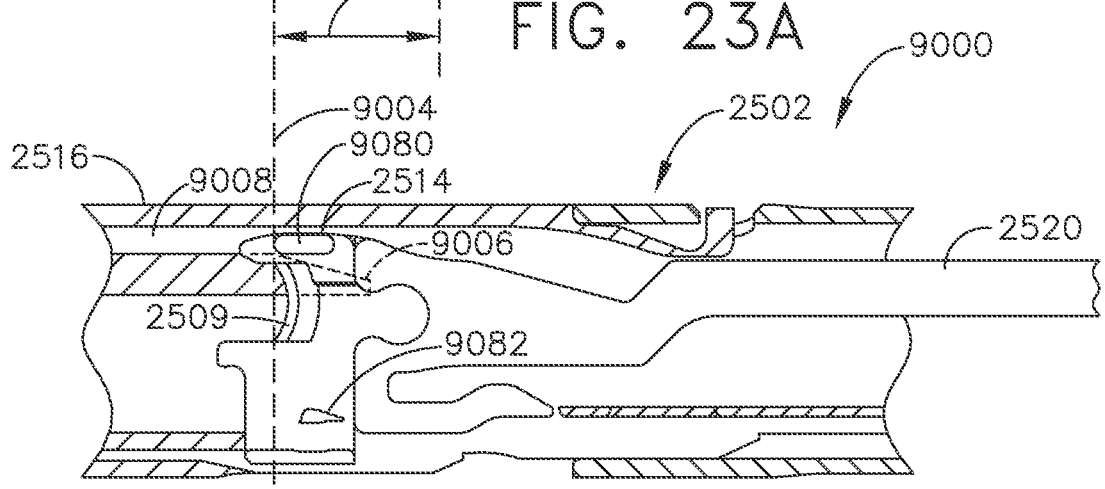
FIG. 23B illustrates an end effector where the I-beam is located in a target position at the top of a ramp with the top pin engaged in the T-slot according to one aspect of this disclosure.

The disclosure now turns to a closed loop feedback system to provide velocity control of a displacement member. The closed loop feedback system adjusts the velocity of the displacement member based on a measurement of actual time over a specified distance or displacement interval of the displacement member. In one aspect, the closed loop feedback system comprises two phases. A start phase defined as the start of a firing stroke followed by a dynamic firing phase while the I-beam 2514 advances distally during the firing stroke. FIGS. 23A and 23B show the I-beam 2514 positioned at the start phase of the firing stroke. FIG. 23A illustrates an end effector 2502 comprising a firing member 2520 coupled to an I-beam 2514 comprising a cutting edge 2509. The anvil 2516 is in the closed position and the I-beam 2514 is located in a proximal or parked position 9002 at the bottom of the closure ramp 9006. The parked position 9002 is the position of the I-beam 2514 prior to traveling up the anvil 2516 closure ramp 9006 to the top of the ramp 9006 to the T-slot 9008. A top pin 9080 is configured to engage a T-slot 9008 and a lockout pin 9082 is configured to engage a latch feature 9084.

In FIG. 23B the I-beam 2514 is located in a target position 9004 at the top of the ramp 9006 with the top pin 2580 engaged in the T-slot 9008. As shown in FIGS. 23A-23B, in traveling from the parked position 9002 to the target position 9004, the I-beam 2514 travels a distance indicated as $X_o$ in the horizontal distal direction. During the start phase, the velocity of the I-beam 2514 is set to a predetermined initial velocity $V_o$. A control circuit 2510 measures the actual time $t_o$ that it takes the I-beam 2514 to travel up the ramp 9006 from the parked position 9002 to the target position 9004 at the initial velocity $V_o$. In one aspect, the horizontal distance is 4.1 mm and the initial velocity $V_o$ is 12 mm/sec. As described in more detail below, the actual time $t_o$ is used to set the command velocity of the I-beam 2514 to slow, medium, or fast in the subsequent staple cartridge zone Z as the I-beam 2514 advances distally. The number of zones may depend on the length/size of the staple cartridge (e.g., 35 mm, 40 mm, 45 mm, 50 mm, 55 mm, 60 mm, >60 mm). The command velocity or set velocity is the velocity of the motor 2504 that is applied to the motor 2504 by the control circuit 2510 and motor control 2508 in order effect a desired velocity of the I-beam 2514. The actual velocity of the I-beam 2514 is determined by the control circuit 2510 by measuring the actual time $t_o$ with the timer/counter 2531 circuit that it takes the I-beam 2514 to traverse a specified or fixed distance provided by the position sensor 2534. In accordance with one aspect of the present disclosure, the closed loop feedback control system of the surgical instrument measures the actual time $t_n$ it takes the I-beam 2514, or a displacement member, to travel a predetermined fixed distance or displacement interval $X_n$. A predetermined fixed distance or displacement interval $X_n$ is defined for each zone (e.g., $Z_1, Z_2, Z_3 \ldots Z_n$).

With reference now to FIGS. 14-15 and 23A-24, at the start phase, e.g., at the beginning of a firing stroke, the control circuit 2510 is configured to initiate firing the displacement member, such as the I-beam 2514, at a predetermined velocity $V_o$ (e.g., 12 mm/s). During the start phase, the control circuit 2510 is configured to monitor the position of the I-beam 2514 and measure the time $t_o$ (sec) it takes for the I-beam 2514 to travel from the I-beam 2514 parked position 9002 to the I-beam 2514 target position 9004, either to the top of the anvil 2516 closure ramp 9006, or at the end of a low power mode of operation. Time $t_o$ in the initial zone 9010 is used by the control circuit 2510 to determine the firing velocity of the I-beam 2514 through the first zone $Z_1$. For example, in one aspect, if time $t_o$ is <0.9 sec the velocity $V_1$ may be set to fast and if time $t_o \geq 0.9$ sec the velocity may be set to medium. Faster or slower times may be selected based on the length of the staple cartridge 2518. The actual time $t_1$-$t_5$ that it takes the I-beam 2514 to traverse a corresponding zone $Z_1$ to $Z_5$ is measured at a corresponding set displacement $\delta_1$-$\delta_5$ and is compared to a corresponding reference time period $T_1$-$T_5$. In various aspects, if a lockout condition is encountered, the motor 2504 will stall before the I-beam 2514 reaches the target position 9004. When this condition occurs, the surgical instrument display indicates the instrument status and may issue a stall warning. The display also may indicate a speed selection.

Figure 24:
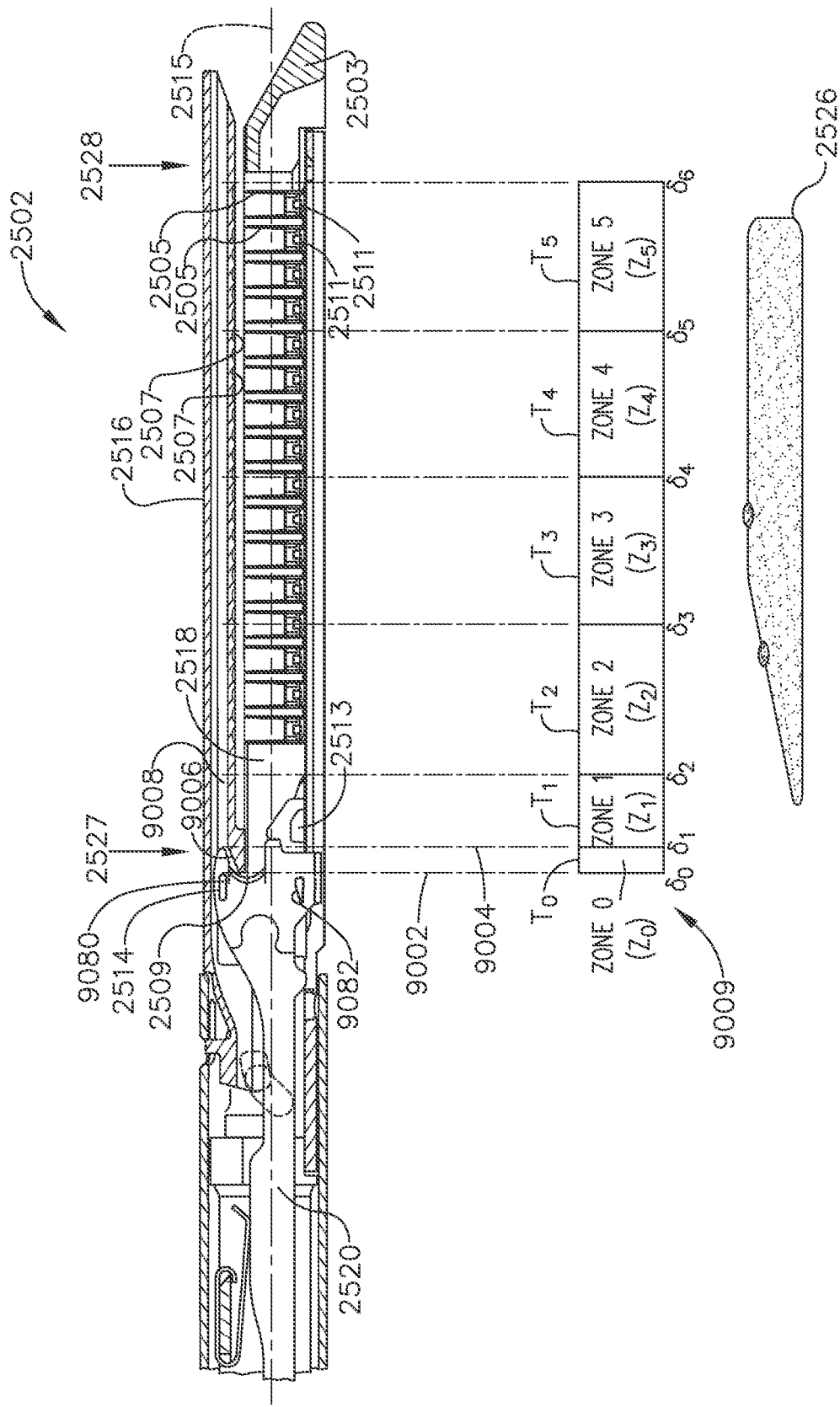
FIG. 24 illustrates the I-beam firing stroke is illustrated by a chart aligned with the end effector according to one aspect of this disclosure.

During the dynamic firing phase, the surgical instrument enters the dynamic firing phase, where the control circuit 2510 is configured to monitor the displacement interval $\delta_n$ of the I-beam 2514 and measure the time $t_n$ that it takes the I-beam 2514 to travel from the beginning of a zone to the end of a zone (e.g., a total distance of 5 mm or 10 mm). In FIG. 24, the reference time $T_1$ is the time taken by the I-beam 2514 to travel from the beginning of zone $Z_1$ to the end of zone $Z_1$ at a set velocity $V_1$. Likewise, the reference time $T_2$ is the time it takes the I-beam 2514 to travel from the beginning of zone $Z_2$ to the end of zone $Z_2$ at a set velocity $V_2$, and so on. Table 1 shows zones that may be defined for staple cartridges 2518 of various sizes.

TABLE 1

Defined Zones For Staple Cartridges Of Various Sizes

| Staple Cartridge | $Z_1$ | $Z_2$ | $Z_3$ | $Z_4$ | $Z_5$ | $Z_6$ |
|---|---|---|---|---|---|---|
| 35 mm | 0-5 mm | 5-15 mm | 15-25 mm | >25 mm | N/A | N/A |
| 40-45 mm | 0-5 mm | 5-15 mm | 15-25 mm | 25-35 mm | >35 mm | N/A |
| 55-60 mm | 0-5 mm | 5-15 mm | 15-25 mm | 25-35 mm | 35-45 mm | >45 mm |

FIG. 24 illustrates the I-beam 2514 firing stroke is illustrated by a chart 9009 aligned with the end effector 2502 according to one aspect of this disclosure. As shown, the initial zone ($Z_o$), or base zone, is defined as the distance traveled by the I-beam 2514 from the parked position 9002 to the target position 9004. The measured time $T_o$ is the time it takes the I-beam 2514 to travel up the closure ramp 9006 to the target position 9004 at an initial set velocity $V_o$. The measured times $T_1$-$T_5$ are reference periods of time for traversing the corresponding zones $Z_1$-$Z_5$, respectively. The displacement of the I-beam 2514 in zone $Z_o$ is $X_o$. The period $T_o$, the time it takes for the I-beam 2514 to travel over a distance $X_o$, is used to set the command velocity in the subsequent zone $Z_1$.

For staple cartridges 2518 over 60 mm, the pattern continues, but the last 10-15 mm continues at a command or indicated velocity of the previous zone pending other interventions for end of stroke, among others. At the end of each zone, the actual time $t_n$ it took the I-beam 2514 to pass through the zone is compared to the values in other tables (e.g., Tables 2-5 below) to determine how to set the command velocity for the next zone. The command velocity is updated for the next zone and the process continues. Whenever the command velocity is updated, the next zone will not be evaluated. The end of stroke is handled in accordance with a predetermined protocol/algorithm of the surgical instrument including limit switches, controlled deceleration, etc. At the end of stroke, the I-beam 2514 is returned to the initial I-beam park position 9002 at the fast speed. End of return stroke (returning to the parked position 9002) is handled in accordance with the protocol/algorithm of the surgical instrument. Other zones may be defined without limitation.

TABLE 2

Time To Travel Through Zones At Specified Command Velocity For Various Dynamic Firing Zones

| Dynamic Firing Zone (mm) | Time (sec) to Travel Through Zone at Specified Command Velocity | | |
|---|---|---|---|
| | Fast | Medium | Slow |
| First Zone ($X_1$ mm long) | $t < t_1$ | $t_1 < t < t_2$ | $t > t_2$ |
| Intermediate Zones ($X_2$ mm long) | $t < t_3$ | $t_3 < t < t_4$ | $t > t_4$ |
| Last Measured Zone ($X_3$ mm long) | $t < t_5$ | $t_5 < t < t_6$ | $t > t_6$ |

TABLE 3

Non-limiting Examples Of Time To Travel Through Zones At Specified Command Velocity For Various Dynamic Firing Zones

| Dynamic Firing Zone (mm) | Time (sec) to Travel Through Zone at Specified Command Velocity | | |
|---|---|---|---|
| | Fast | Medium | Slow |
| First Zone (5 mm long) | $t < 0.5$ | $0.5 < t < 0.6$ | $t > 0.6$ |
| Intermediate Zones (10 mm long) | $t < 0.9$ | $0.9 < t < 1.1$ | $t > 1.1$ |
| Last Measured Zone (10 mm long) | $t < 1.0$ | $1.0 < t < 1.3$ | $t > 1.3$ |

TABLE 4

Algorithm To Set Velocity Based On Time To Travel Up Ramp

| Algorithm | $t_a$ (sec) | $t_b$ (sec) |
|---|---|---|
| If time t (sec) for I-beam to travel up ramp is . . . | $t_1 < t < t_2$ | $t > t_2$ to $t_3$ |
| Then initial velocity V of I-beam in T-slot is . . . | $V_1$ (mm/sec) | $V_2$ (mm/sec) |
| And automatic velocity is set at . . . | FAST | MEDIUM |

TABLE 5

Non-limiting Example Of Algorithm To Set Velocity Based On Time To Travel Up Ramp

| Algorithm | $t_a$ (sec) | $t_b$ (sec) |
|---|---|---|
| If time t (sec) for I-beam to travel up ramp is . . . | $0.0 < t < 0.9$ | $t > 0.9$ to $1.8$ |
| Then initial velocity of I-beam in T-slot is . . . | 30 mm/sec | 12 mm/sec |
| And automatic velocity is set at . . . | FAST | MEDIUM |

In one aspect, Tables 1-5 may be stored in memory of the surgical instrument. The Tables 1-5 may be stored in memory in the form of a look-up table (LUT) such that the control circuit 2510 can retrieve the values and control the command velocity of the I-beam 2514 in each zone based on the values stored in the LUT.

Figure 25:
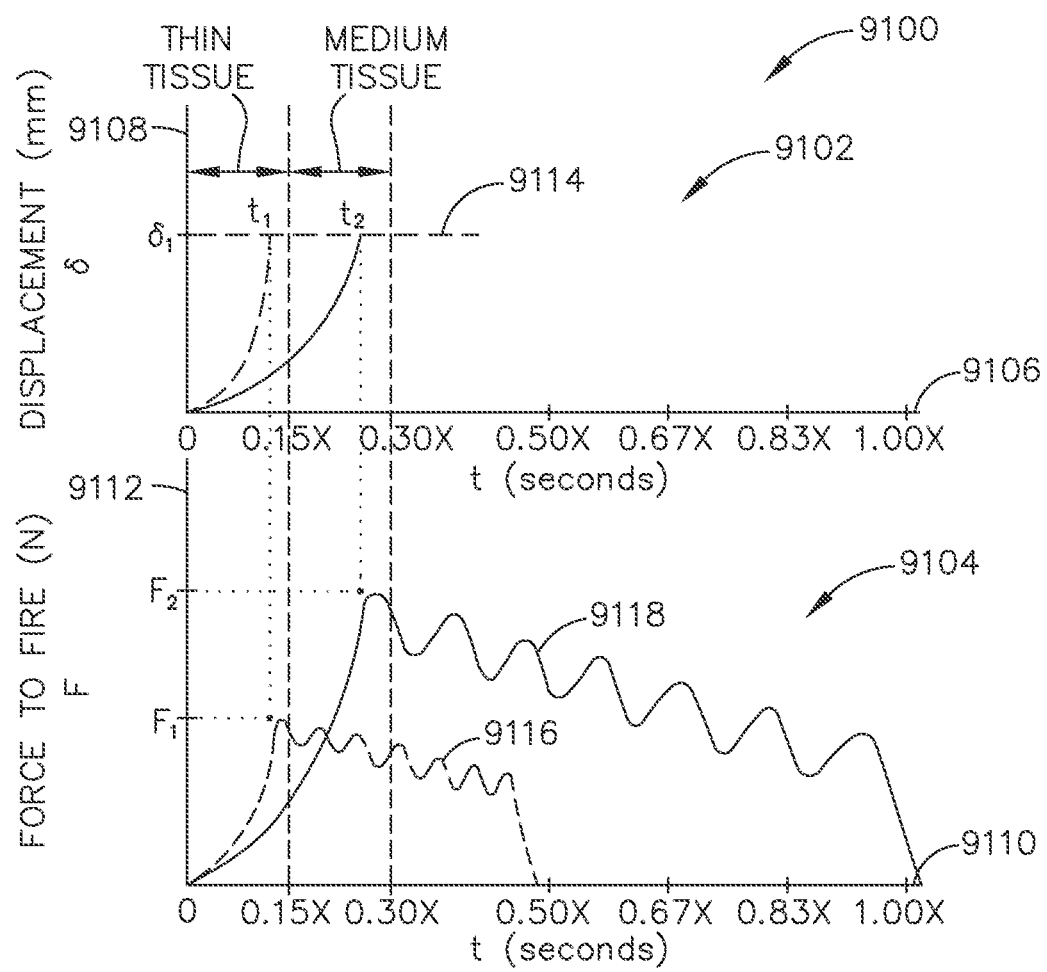
FIG. 25 is a graphical depiction comparing I-beam stroke displacement as a function of time (top graph) and expected force-to-fire as a function of time (bottom graph) according to one aspect of this disclosure.

FIG. 25 is a graphical depiction 9100 comparing the I-beam 2514 stroke displacement interval $\delta_n$ as a function of time 9102 (top graph) and expected force-to-fire the I-beam 2514 as a function of time 9104 (bottom graph) according to one aspect of this disclosure. Referring to the top graph 9102, the horizontal axis 9106 represents time (t) in seconds (sec) from 0-1.00X, where X is a scaling factor. For example, in one aspect, X=6 and the horizontal axis 9106 represents time from 0-6 sec. The vertical axis 9108 represents displacement ($\delta$) of the I-beam 2514 in millimeters (mm). The displacement interval 51 represents the I-beam 2615 stroke 9114 or displacement at the top of the ramp 9006 (FIGS. 23A, 23B) for thin tissue and medium thick tissue. The time for the I-beam 2514 to reach the top of ramp stroke 9114 for thin tissue is $t_1$ and the time for the I-beam 2514 to reach the top of ramp stroke 9114 for medium thick tissue is $t_2$. As shown, $t_1 < t_2$, such that it takes less time for the I-beam 2514 to reach the top of the ramp stroke 9114 for thin tissue as it takes for medium or thick tissue. In one example, the top of ramp stroke 9114 displacement interval 51 is about 4.1 mm (01.60 inches) and the time $t_1$ is less than 0.9 sec ($t_1 < 0.9$ sec) and the time $t_2$ is greater than 0.9 sec but less than 1.8 sec ($0.9 < t_2 < 1.8$ sec). Accordingly, with reference also to Table 5, the velocity to reach the top of ramp stroke 9114 is fast for thin tissue and medium for medium thick tissue.

Turning now to the bottom graph 9104, the horizontal axis 9110 represents time (t) in seconds (sec) and has the same scale as the horizontal axis 9106 of the top graph 9102. The vertical axis 9112, however, represents expected force to fire (F) the I-beam 2514 in newtons (N) for thin tissue force to fire graph 9116 and medium thick tissue force to fire graph 9118. The thin tissue force to fire graph 9116 is lower than medium thick tissue force to fire graph 9118. The peak force $F_1$ for the thin tissue force to fire graph 9116 is lower than the peak force $F_2$ for the medium thick tissue to fire graph 9118. Also, with reference to the top and bottom graphs 9102, 9104, the initial velocity of the I-beam 2514 in zone $Z_o$ can be determined based on estimated tissue thickness. As shown by the thin tissue force to fire graph 9116, the I-beam 2514 reaches the peak force $F_1$ top of ramp stroke 9114 at a fast initial velocity (e.g., 30 mm/sec) and as shown by the medium thick tissue force to fire graph 9118, the I-beam 2514 reaches the peak force $F_2$ top of ramp stroke 9114 at a medium initial velocity (e.g., 12 mm/sec). Once the initial velocity in zone $Z_o$ is determined, the control circuit 2510 can set the estimated velocity of the I-beam 2514 in zone $Z_1$, and so on.

FIG. 26 is a graphical depiction 9200 comparing tissue thickness as a function of set displacement interval of I-beam stroke 9202 (top graph), force to fire as a function of set displacement interval of I-beam stroke 9204 (second graph from the top), dynamic time checks as a function of set displacement interval of I-beam stroke 9206 (third graph from the top), and set velocity of I-beam as a function of set displacement interval of I-beam stroke 9208 (bottom graph) according to one aspect of this disclosure. The horizontal axis 9210 for each of the graphs 9202, 9204, 9206, 9208 represents set displacement interval of an I-beam 2514 stroke for a 60 mm staple cartridge, for example. With reference also to Table 1, the horizontal axis 9210 has been marked to identify the defined zones $Z_1$-$Z_6$ for a 60 mm staple cartridge. As indicated in Table 1, the defined zones may be marked for staple cartridges of various sizes. With reference also to FIG. 14, in accordance with the present disclosure, the control circuit 2510 samples or measures the elapsed time from the timer/counter circuit 2531 at set I-beam 2514, or other displacement member, displacement intervals along the staple cartridge 2518 during the firing stroke. At set displacement intervals $\delta_n$ received from the position sensor 2534, the control circuit 2510 samples or measures the elapsed time $t_n$ it took the I-beam 2514 to travel the fixed displacement intervals $\delta_n$. In this manner, the control circuit 2510 can determine the actual velocity of the I-beam 2514 and compare the actual velocity to the estimated velocity and make any necessary adjustments to the motor 2504 velocity.

The tissue thickness graph 9202 shows a tissue thickness profile 9220 along the staple cartridge 2518 and an indicated thickness 9221 as shown by the horizontal dashed line. The force to fire graph 9204 shows the force to fire profile 9228 along the staple cartridge 2518. The force to fire 9230 remains relatively constant while the tissue thickness 9222 remains below the indicated thickness 9221 as the I-beam 2514 traverse zones $Z_1$ and $Z_2$. As the I-beam 2514 enters zone $Z_3$, the tissue thickness 9224 increases and the force to fire also increase while the I-beam 2514 traverses the thicker tissue in zones $Z_3$, $Z_4$, and $Z_5$. As the I-beam 2514 exits zone $Z_5$ and enters zone $Z_6$, the tissue thickness 9226 decrease and the force to fire 9234 also decreases.

With reference now to FIGS. 14, 24-26 and Tables 2-3, the velocity $V_1$ in zone $Z_1$ is set to the command velocity $V_o$ determined by the control circuit 2510 in zone $Z_o$, which is based on the time it takes the I-beam 2514 to travel to the top of the ramp 9006 in zone $Z_o$ as discussed in reference to FIGS. 23A, 23B, and 25. Turning also to the graphs 9206, 9208 in FIG. 26, the initial set velocity $V_o$ was set to Medium and thus the set velocity $V_1$ in zone $Z_1$ is set to Medium such that $V_1=V_o$.

At set displacement position $\delta_1$ (e.g., 5 mm for a 60 mm staple cartridge), as the I-beam 2514 exits zone $Z_1$ and enters zone $Z_2$, the control circuit 2510 measures the actual time $t_1$ that it takes the I-beam 2514 to traverse the set displacement interval $X_1$ (5 mm long) and determines the actual velocity of the I-beam 2514. With reference to graphs 9206 and 9208 in FIG. 26, at set displacement position $\delta_1$, the actual time $t_1$ it takes the I-beam 2514 to travel the set displacement interval $X_1$ is $t_1=0.55$ sec. According to Table 3, an actual travel time $t_1=0.55$ sec in zone $Z_1$ requires the command or set velocity $V_2$ in zone $Z_2$ to be set to Medium. Accordingly, the control circuit 2510 does not reset the command velocity for zone $Z_2$ and maintains it at Medium.

At set displacement position $\delta_2$ (e.g., 15 mm for a 60 mm staple cartridge), as the I-beam 2514 exits zone $Z_2$ and enters zone $Z_3$, the control circuit 2510 measures the actual time $t_2$ it takes the I-beam 2514 to traverse the set displacement interval $X_2$ (10 mm long) and determines the actual velocity of the I-beam 2514. With reference to graphs 9606 and 9608 in FIG. 26, at set displacement position $\delta_2$, the actual time $t_2$ it takes the I-beam 2514 to travel the set displacement interval $X_2$ is $t_2=0.95$ sec. According to Table 3, an actual travel time $t_2=0.95$ sec in zone $Z_2$ requires the command or set velocity $V_3$ in zone $Z_3$ to be set to Medium. Accordingly, the control circuit 2510 does not reset the command velocity for zone $Z_3$ and maintains it at Medium.

At set displacement position $\delta_3$ (e.g., 25 mm for a 60 mm staple cartridge), as the I-beam 2514 exits zone $Z_3$ and enters zone $Z_4$, the control circuit 2510 measures the actual time $t_3$ it takes the I-beam 2514 to traverse the set displacement interval $X_3$ (10 mm long) and determines the actual velocity of the I-beam 2514. With reference to graphs 9606 and 9608 in FIG. 26, at set displacement position $\delta_3$, the actual time $t_3$ it takes the I-beam 2514 to travel the set displacement interval $X_3$ is $t_3=1.30$ sec. According to Table 3, an actual travel time $t_3=1.30$ sec in zone $Z_3$ requires the command or set velocity $V_4$ in zone $Z_4$ to be set to Slow. This is because the actual travel time of 1.3 sec is greater than 1.10 sec and is outside the previous range. Accordingly, the control circuit 2510 determines that the actual I-beam 2514 velocity in zone $Z_3$ was slower than expected due to external influences such as thicker tissue than expected as shown in tissue region 9224 in graph 9202. Accordingly, the control circuit 2510 resets the command velocity $V_4$ in zone $Z_4$ from Medium to Slow.

In one aspect, the control circuit 2510 may be configured to disable velocity reset in a zone following a zone in which the velocity was reset. Stated otherwise, whenever the velocity is updated in a present zone the subsequent zone will not be evaluated. Since the velocity was updated in zone $Z_4$, the time it takes the I-beam 2514 to traverse zone $Z_4$ will not be measured at the end of zone $Z_4$ at the set displacement distance $\delta_4$ (e.g., 35 mm for a 60 mm staple cartridge). Accordingly, the velocity in zone $Z_5$ will remain the same as the velocity in zone $Z_4$ and dynamic time measurements resume at set displacement position $\delta_5$ (e.g., 45 mm for a 60 mm staple cartridge).

At set displacement position $\delta_5$ (e.g., 45 mm for a 60 mm staple cartridge) as the I-beam 2514 exits zone $Z_5$ and enters zone $Z_6$, the control circuit 2510 measures the actual time $t_5$ it takes the I-beam 2514 to traverse the set displacement interval $X_5$ (10 mm long) and determines the actual velocity of the I-beam 2514. With reference to graphs 9606 and 9608 in FIG. 26, at set displacement position $\delta_5$, the actual time $t_5$ it takes the I-beam 2514 to traverse the set displacement interval $X_5$ is $t_5=0.95$ sec. According to Table 3, an actual travel time of $t_5=0.95$ sec in zone $Z_5$ requires the command or set velocity $V_6$ in zone $Z_6$ to be set to High. This is because the actual travel time of 0.95 sec is less than 1.00 sec is outside the previous range. Accordingly, the control circuit 2510 determines that the actual velocity of the I-beam 2514 in zone $Z_5$ was faster than expected due to external influences such as thinner tissue than expected as shown in tissue region 9626 in graph 9602. Accordingly, the control circuit 2510 resets the command velocity $V_6$ in zone $Z_6$ from Slow to High.

FIG. 27 is a graphical depiction 9300 of force to fire as a function of time comparing slow, medium and fast I-beam 2514 displacement velocities according to one aspect of this disclosure. The horizontal axis 9302 represents time t (sec) that it takes an I-beam to traverse a staple cartridge. The vertical axis 9304 represents force to fire F (N). The graphical depiction shows three separate force to fire curves versus time. A first force to fire curve 9312 represents an I-beam 2514 (FIG. 14) traversing through thin tissue 9306 at a fast velocity and reaching a maximum force to fire $F_1$ at the top of the ramp 9006 (FIG. 23B) at $t_1$. In one example, a fast traverse velocity for the I-beam 2514 is ~30 mm/sec. A second force to fire curve 9314 represents an I-beam 2514 traversing through medium tissue 9308 at a medium velocity and reaching a maximum force to fire $F_2$ at the top of the ramp 9006 at $t_2$, which is greater than $t_1$. In one example, a medium traverse velocity for the I-beam 2514 is ~12 mm/sec. A third force to fire curve 9316 represents an I-beam 2514 traversing through thick tissue 9310 at a slow velocity and reaching a maximum force to fire $F_3$ at the top of the ramp 9006 at $t_3$, which is greater than $t_2$. In one example, a slow traverse velocity for the I-beam 2514 is ~9 mm/sec.

FIG. 28 is a logic flow diagram of a process 9400 depicting a control program or logic configuration for controlling command velocity in an initial firing stage according to one aspect of this disclosure. With reference also to FIGS. 14 and 23A-27, the control circuit 2510 determines 9402 the reference position of the displacement member, such as the I-beam 2514, for example, based on position information provided by the position sensor 2534. In the I-beam 2514 example, the reference position is the proximal or parked position 9002 at the bottom of the closure ramp 9006 as shown in FIG. 23B. Once the reference position is determined 9402, the control circuit 2510 and motor control 2508 set the command velocity of the motor 2504 to a predetermined command velocity $V_o$ and initiates 9404 firing the displacement member (e.g., I-beam 2514) at the predetermined command velocity $V_o$ for the initial or base zone $Z_o$. In one example, the initial predetermined command velocity $V_o$ is ~12 mm/sec, however, other initial predetermined command velocity $V_o$ may be employed. The control circuit 2510 monitors 9406 the position of the displacement member with position information received from the position sensor 2534 until the I-beam 2514 reaches a target position at the top of the ramp 9006 as shown in FIG. 23B. The predetermined displacement period $T_o$ is the expected displacement period of the displacement member traveling at the current set command velocity $V_o$. The deviation between actual displacement period $T_n$ and the predetermined displacement period $T_o$ is due at least in part to external influences acting on the displacement member such as tissue thickness acting on the cutting edge 2509 of the I-beam 2514.

With timing information received from the timer/counter circuit 2531 and position information received from the position sensor 2534, the control circuit 2510 measures 9408 the time $t_o$ it takes the displacement member to travel from the reference position 9002 to the target position 9004. The control circuit 210 sets 9410 the command velocity $V_1$ for the first zone $Z_1$ based on the measured time $t_o$. As indicated in Table 1, various defined zones may be defined for staple cartridges of various sizes. Other zones, however, may be defined. The control circuit 2510 sets 9410 the command velocity $V_1$ for the first zone $Z_1$ by comparing 9412 the measured time $t_o$ to values stored in memory, such as, for example, stored in a lookup table (LUT). In one example, as indicated in Table 4 generally and in Table 5 by way of specific example, if the time $t_o$ it takes the I-beam 2514 to travel up the ramp 9006 from the reference positon 9002 to the target position 9004 is between 0.0 and 0.9 sec (0.0 sec<$t_o$<0.9 sec), then the command velocity for the first zone $Z_1$ is set 9414 to FAST (e.g., 30 mm/sec). Otherwise, if the time $t_o$ (sec) for the I-beam 2514 to travel up the ramp 9006 from the reference positon 9002 to the target position 9004 is greater than 0.9 sec to 1.8 sec ($t_o$>0.9 sec to 1.8 sec), then the command velocity for the first zone $Z_1$ is set 9416 to MEDIUM (e.g., 12 mm/sec). Subsequently, the control circuit 2510 checks 9418 for lockout and stops 9420 the motor 2504 if there is a lockout condition. Otherwise, the control circuit enters 9422 the dynamic firing phase as described below in reference to process 9450 in FIG. 29.

FIG. 29 is a logic flow diagram of a process 9450 depicting a control program or logic configuration for controlling command velocity in a dynamic firing stage according to one aspect of this disclosure. With reference also to FIGS. 14 and 23A-27, the control circuit 2510 sets 9452 the initial command velocity of the motor 2504 for the first zone $Z_1$ based on the initial time $t_o$, as described in reference to the process 9400 in FIG. 28. As the displacement member traverses the staple cartridge 2518, the control circuit 2510 receives the position of the displacement member from the position sensor 2534 and timing information from the timer/counter 2531 circuit and monitors 9454 the position of the displacement member over the predefined zone $Z_n$. At the end of the zone $Z_n$, the control circuit 2510 measures 9456 the actual time $t_n$ the displacement member took to travel from the beginning of the zone $Z_n$ to the end of the zone $Z_n$ and compares 9458 the actual time $t_n$ to a predetermined time for a particular zone as shown generally in Table 2 and by way of specific example in Table 3. The predetermined displacement period $T_n$ is the expected displacement period of the displacement member traveling at the current set command velocity $V_n$. The deviation between actual displacement period $t_n$ and the predetermined displacement period $T_n$ is due at least in part to external influences acting on the displacement member such as tissue thickness acting on the cutting edge 2509 of the I-beam 2514.

For example, with reference to Table 3 the time to travel through a zone at specified command velocity is provided for various dynamic firing zones. For example, if the dynamic firing zone is the zone $Z_1$ (5 mm long) and $t_n$<0.5 sec, the command velocity for the next zone $Z_2$ is set to FAST; if 0.5<$t_n$<0.6 sec, the command velocity for the next zone $Z_2$ is set to MEDIUM; and if $t_n$>0.6 sec, the command velocity for the next zone $Z_2$ is set to SLOW.

If, however, the dynamic firing zone is an intermediate zone $Z_2$-$Z_5$ (10 mm long), for example, located between the first zone $Z_1$ and the last zone $Z_6$ and if $t_n$<0.9 sec, the command velocity for the next zone $Z_2$ is set to FAST; if 0.9<$t_n$<1.1 sec, the command velocity for the next zone $Z_3$-$Z_5$ is set to MEDIUM; and if $t_n$>1.1 sec, the command velocity for the next zone $Z_3$-$Z_5$ is set to SLOW.

Finally, if the dynamic firing zone is the last measured zone $Z_5$ (10 mm long) and $t_n$<1.0 sec, the command velocity for the final zone $Z_6$ is set to FAST; if 1.0<$t_n$<1.3 sec, the command velocity for the final zone $Z_6$ is set to MEDIUM; and if $t_n$>1.3 sec, the command velocity for the final zone $Z_6$ is set to SLOW. Other parameters may be employed not only to define the dynamic firing zones but also to define the time to travel through a zone at specified command velocity for various dynamic firing zones.

Based on the results of the comparison 9458 algorithm, the control circuit 2510 will continue the process 9450. For example, if the results of the comparison 9458 indicate that the actual velocity (FAST, MEDIUM, SLOW) in the previous zone $Z_n$ is the same as the previous command velocity $V_1$ (FAST, MEDIUM, SLOW), the control circuit 2510 maintains 9460 the command velocity $V_1$ for the next zone $Z_{n+1}$ the same as the as the previous command velocity $V_1$. The process 9450 continues to monitor 9454 the position of the displacement member over the next predefined zone $Z_{n+1}$. At the end of the next zone $Z_{n+1}$, the control circuit 2510 measures 9456 the time $t_{n+1}$ the displacement member took to travel from the beginning of the next zone $Z_{n+1}$ to the end of the next zone $Z_{n1}$ and compares 9458 the actual time $t_{n+1}$ to a predetermined time for a particular zone as shown generally in Table 2 and by way of specific example in Table 3. If there are no changes required to the command velocity, the process 9450 until the displacement member, e.g., the I-beam 2514, reaches the end of stroke 9466 and returns 9468 the displacement member to the reference position 9002.

If the results of the comparison 9458 indicate that the actual velocity (FAST, MEDIUM, SLOW) in the previous zone $Z_n$ is different as the previous command velocity $V_1$ (FAST, MEDIUM, SLOW), the control circuit 2510 resets 9462 or updates the command velocity to $V_{new}$ for the next zone $Z_{n+1}$ according to the algorithm summarized in Tables 2 and 3. If the command velocity is reset 9462 or updated, the control circuit 2510 maintains 9464 the command velocity $V_{new}$ for an additional zone $Z_{n+2}$. In other words, at the end of the next zone $Z_{n+1}$, the control circuit 2510 does not evaluate or measure the time. The process 9450 continues to monitor 9454 the position of the displacement member over the next predefined zone $Z_{n+1}$ until the displacement member, e.g., the I-beam 2514, reaches the end of stroke 9466 and returns 9468 the displacement member to the reference position 9002.

Various aspects of the subject matter described herein are set out in the following numbered examples:

Example 1. A surgical instrument, comprising: a displacement member configured to translate within the surgical instrument over a plurality of predefined zones; a motor coupled to the displacement member to translate the displacement member; a control circuit coupled to the motor; a position sensor coupled to the control circuit, the position sensor configured to monitor the position of the displacement member; a timer circuit coupled to the control circuit, the timer/counter circuit configured to measure elapsed time; wherein the control circuit is configured to: receive, from the position sensor, a position of the displacement member in a current zone defined by a set displacement interval; measure time at a set position of the displacement interval, wherein the measured time is defined as the time taken by the displacement member to traverse the displacement interval; and set a command velocity of the displacement member for a subsequent zone based on the measured time in the current predefined zone.

Example 2. The surgical instrument of Example 1, wherein the control circuit is configured to: determine the set displacement interval in which the displacement member is located, wherein the set displacement interval is defined by a beginning position and an ending position; and measure the time when the displacement member reaches the ending position of the displacement interval.

Example 3. The surgical instrument of Example 1 through Example 2, wherein the control circuit is configured to: compare the measured time to a predetermined time stored in a memory coupled to the control circuit; and determine whether to adjust or maintain the command velocity based on the comparison.

Example 4. The surgical instrument of Example 3, wherein the control circuit is configured to maintain the command velocity for the subsequent zone the same as the command velocity of the current zone when the measured time is within a range of predetermined times.

Example 5. The surgical instrument of Example 3 through Example 4, wherein the control circuit is configured to set the command velocity for the subsequent zone different from the command velocity of the current zone when the measured time is outside a range of predetermined times.

Example 6. The surgical instrument of Example 5, wherein the control circuit is configured to skip a time measurement for a subsequent zone when the command velocity is adjusted.

Example 7. The surgical instrument of Example 1 through Example 6, wherein multiple zones are defined for a staple cartridge configured to operate with the surgical instrument.

Example 8. The surgical instrument of Example 7, wherein at least two zones have a different length.

Example 9. A surgical instrument, comprising: a displacement member configured to translate within the surgical instrument over a plurality of predefined zones; a motor coupled to the displacement member to translate the displacement member; a control circuit coupled to the motor; a position sensor coupled to the control circuit, the position sensor configured to monitor the position of the displacement member; a timer circuit coupled to the control circuit, the timer/counter circuit configured to measure elapsed time; wherein the control circuit is configured to: receive, from the position sensor, a position of the displacement member in a current zone defined by a predetermined displacement interval; measure time as the displacement member moves from a parked position to a target position; and set a command velocity of the displacement member for a first dynamic zone based on the measured time.

Example 10. The surgical instrument of Example 9, wherein the control circuit is configured to compare the measured time to a predetermined time stored in a memory coupled to the control circuit.

Example 11. The surgical instrument of Example 10, wherein the control circuit is configured to set the command velocity for the initial zone to a first velocity when the measured time is within a first range of times and set the command velocity for the initial zone to a second velocity when the measured time is within a second range of times.

Example 12. The surgical instrument of Example 9 through Example 11, wherein the control circuit is configured to determine a lockout condition and stop the motor.

Example 13. A method of controlling motor velocity in a surgical instrument, the surgical instrument comprising a displacement member configured to translate within the surgical instrument over a plurality of predefined zones, a motor coupled to the displacement member to translate the displacement member, a control circuit coupled to the motor, a position sensor coupled to the control circuit, the position sensor configured to monitor the position of the displacement member, a timer circuit coupled to the control circuit, the timer/counter circuit configured to measure elapsed time, the method comprising: receiving, from a position sensor, a position of a displacement member within a current zone defined by a set displacement interval; measuring, by a timer circuit, a time at a set position of the displacement member, wherein the time is defined by the time taken by the displacement member to traverse the displacement interval; and setting, by the control circuit, a command velocity of the displacement member for a subsequent zone based on the measured time in the current zone.

Example 14. The method of Example 13, further comprising: determining, by the control circuit and the timer circuit, the set displacement interval in which the displacement member is located, wherein the set displacement interval is defined by a beginning position and an ending position; and measuring, by the control circuit, the time when the displacement member reaches the ending position of the displacement interval.

Example 15. The method of Example 13 through Example 14, further comprising: comparing, by the control circuit, the measured time to a predetermined time stored in a memory coupled to the control circuit; and determining, by the control circuit, whether to adjust or maintain the command velocity based on the comparison.

Example 16. The method of Example 15, further comprising maintaining, by the control circuit, the command velocity for the subsequent zone the same as the command velocity of the current zone when the measured time is within a range of predetermined times.

Example 17. The method of Example 15 through Example 16, further comprising setting, by the control circuit, the command velocity for the subsequent zone different from the command velocity of the current zone when the measured time is outside a range of predetermined times.

Example 18. The method of Example 17, further comprising skipping, by the control circuit, a time measurement for a subsequent zone when the command velocity is adjusted.

Example 19. The method of Example 13 through Example 18, further comprising defining, by the control circuit, multiple zones are defined for a staple cartridge configured to operate with the surgical instrument.

Example 20. The method of Example 19, further comprising defining, by the control circuit, at least two zones having a different length.

Closed Loop Feedback Control of Motor Velocity of a Surgical Stapling and Cutting Instrument Based on Measured Displacement Distance Traveled Over a Specified Time Interval During use of a motorized surgical stapling and cutting instrument it is possible that the velocity of the cutting member or the firing member may need to be measured and adjusted to compensate for tissue conditions. In thick tissue the velocity may be decreased to lower the force to fire experienced by the cutting member or firing member if the force to fire experienced by the cutting member or firing member is greater than a threshold force. In thin tissue the velocity may be increased if the force to fire experienced by the cutting member or firing member is less than a threshold. Therefore, it may be desirable to provide a closed loop feedback system that measures and adjusts the velocity of the cutting member or firing member based on a measurement of distance traveled over a specified time increment. It may be desirable to measure the velocity of the cutting member or firing member by measuring distance at fixed set time intervals.

The disclosure now turns to a closed loop feedback system to provide velocity control of a displacement member. The closed loop feedback system adjusts the velocity of the displacement member based on a measurement of time over a specified distance or displacement of the displacement member. In one aspect, the closed loop feedback system comprises two phases. A start phase defined as the start of a firing stroke followed by a dynamic firing phase as the I-beam 2514 advances distally during the firing stroke. FIGS. 30A and 30B show the I-beam 2514 positioned at the start phase of the firing stroke. FIG. 30A illustrates an end effector 2502 comprising a firing member 2520 coupled to an I-beam 2514 comprising a cutting edge 2509. The anvil 2516 is in the closed position and the I-beam 2514 is located in a proximal or parked position 9502 at the bottom of the closure ramp 9506. The parked position 9502 is the position of the I-beam 2514 prior to traveling up the anvil 2516 closure ramp 9506 to the top of the ramp 9506 an into the T-slot 9508 and perhaps a distance beyond over a predetermined fixed initial time interval $T_o$, which is a fixed time period over which the displacement of the displacement member is measured. A top pin 9580 is configured to engage a T-slot 9508 and a lockout pin 9582 is configured to engage a latch feature 9584.

In FIG. 30B the I-beam 2514 is located in a distal position 9504 at the end of time interval $T_o$ with the top pin 2580 engaged in the T-slot 9508 and the bottom pin. As shown in FIGS. 30A-30B, in traveling from the parked position 9502 to the distal position 9504 during the time interval $T_o$, the I-beam 2514 travels a distance indicated as actual measured displacement $\delta_o$ in the horizontal distal direction. During the start phase, the velocity of the I-beam 2514 is set to a predetermined initial velocity $V_o$. A control circuit 2510 measures the actual displacement $\delta_o$ traveled by the I-beam 2514 over a predetermined fixed time interval $T_o$ from the parked position 9502 to the distal position 9504 at the initial velocity $V_o$. In one aspect, at an initial command velocity $V_o$ of 12 mm/s, the actual measured horizontal displacement $\delta_o$ of the I-beam 2512 over a fixed time interval $T_o$=0.8 sec may be $\delta_o$=10.16 mm due to external influences acting on the cutting edge 2509 of the I-beam 2514. As described in more detail below, the time interval $T_o$ is fixed and the actual displacement of the I-beam 2514 over the fixed time interval $T_o$ is measured and is used to set the command velocity of the I-beam 2514 to slow, medium, or fast in subsequent staple cartridge zones $Z_1, Z_2, Z_3 \ldots Z_n$ as the I-beam 2514 advances distally. The number of zones may depend on the length/size of the staple cartridge (e.g., 35 mm, 40 mm, 45 mm, 50 mm, 55 mm, 60 mm, >60 mm). The zones $Z_1$-$Z_n$ are defined in terms of fixed time intervals $T_1$-$T_n$ during which the control circuit 2510 measures the actual displacement of the displacement member.

The command velocity or set velocity is the velocity of the motor 2504 that is applied to the motor 2504 by the control circuit 2510 and the motor control 2508 in order effect a desired velocity of the I-beam 2514. The actual velocity of the I-beam 2514 is determined by the control circuit 2510 by measuring the position of the I-beam 2514 with the position sensor 2534 at fixed time intervals $T_n$ determined by the timer/counter 2531. In accordance with one aspect of the present disclosure, the closed loop feedback control system of the surgical instrument measures the actual displacement $\delta_n$ of the I-beam 2514, or a displacement member, over a predetermined time fixed interval $T_n$. Each zone $Z_n$ may be defined by a predetermined fixed time interval $T_n$ during which the control circuit 2510 measures the actual displacement $\delta_n$ of the displacement member, e.g., the I-beam 2514.

FIG. 31 illustrates the I-beam 2514 firing stroke illustrated by a chart 9509 aligned with the end effector 2502 according to one aspect of this disclosure. As shown, the initial zone $Z_o$, or base zone, is the length of a fixed time interval $T_o$ during which the I-beam 2514 travels from the parked position 9502 to a distal position 9504, which may vary based on external influences acting on the I-beam 2514, such as tissue thickness. The initial time interval $T_o$ is a set fixed time that the I-beam 2514 is enabled to travel up the closure ramp 9506 and to the distal position 9504 an initial set velocity $V_o$. The actual displacement $\delta_o$ of the I-beam 2514 in zone $Z_o$ during the fixed period $T_o$ is used to set the command velocity in subsequent zone $Z_1$.

With reference now to FIGS. 14-15, and 30A-31, at the start phase, e.g., at the beginning of a firing stroke, the control circuit 2510 is configured to initiate firing the displacement member, such as the I-beam 2514, at a predetermined velocity $V_o$ (e.g., 12 mm/s). During the start phase, the control circuit 2510 is configured to monitor the position of the I-beam 2514 and measure the actual displacement $\delta_o$ of the I-beam 2514 over a fixed time interval $T_o$ from the parked position 9502, or at the end of a low power mode of operation. The actual displacement $\delta_o$ of the displacement member over the fixed time interval $T_o$ is used by the control circuit 2510 to determine the firing velocity of the I-beam 2514 through the first zone $Z_1$. For example, in one aspect, if the actual displacement is $\delta_o$>10.0 mm the velocity may be set to fast and if the actual displacement is $\delta_o$≤10.0 mm the velocity may be set to medium. Faster or slower time intervals $T_n$ may be selected based on the length of the staple cartridge 2518. In various aspects, if a lockout condition is encountered, the motor 2504 will stall before the I-beam 2514 reaches the end of the initial time interval $T_o$. When this condition occurs, the display of the surgical instrument indicates the instrument status and may issue a stall warning. The display also may indicate a speed selection.

During the dynamic firing phase, the surgical instrument employs dynamic firing control of the displacement member, where the control circuit 2510 is configured to monitor the position of the I-beam 2514 and measure the actual displacement $\delta_n$ of the I-beam 2514 during the time interval $T_n$, e.g., from the beginning of a zone to the end of a zone, where the time interval $T_n$ may be 0.4 sec or 0.8 sec, for example. In FIG. 31, 51 represents the actual displacement of the I-beam 2514 from the beginning of zone $Z_1$ to the end of zone $Z_1$. Likewise, $\delta_2$ represents the distance traveled by the I-beam 2514 from the beginning of zone $Z_2$ to the end of zone $Z_2$, and so on. Table 1 shows zones that may be defined for staple cartridges 2518 of various sizes.

TABLE 1

Defined Zones For Staple Cartridges Of Various Sizes

| Staple Cartridge | Zones | | | | | |
|---|---|---|---|---|---|---|
| | $Z_1$ | $Z_2$ | $Z_3$ | $Z_4$ | $Z_5$ | $Z_6$ |
| 35 mm | 0-0.4 sec | 0.4-0.8 sec | 0.8-1.2 sec | >1.2 sec | N/A | N/A |
| 40-45 mm | 0-0.4 sec | 0.4-0.8 sec | 0.8-1.2 sec | 1.2-1.6 sec | >1.6 sec | N/A |
| 55-60 mm | 0-0.4 sec | 0.4-0.8 sec | 0.8-1.2 sec | 1.2-1.6 sec | 1.6-2.0 sec | >2.0 sec |

For staple cartridges 2518 over 60 mm, the pattern continues, but during the last 10-15 mm continues at a command or indicated velocity of the previous zone pending other interventions for end of stroke, among others. At the end of each zone $Z_n$, the actual displacement $\delta_n$ of the I-beam 2514 is compared to the values stored in a lookup table (e.g., as shown in Tables 2-5 below) to determine how to set the command velocity $V_{n+1}$ for the next zone $Z_{n+1}$. The command velocity is updated for the next zone and the process continues. Whenever the command velocity is updated in zone $Z_n$, the next zone $Z_{n+1}$ will not be evaluated over the time interval $T_n$. The end of stroke is handled in accordance with a predetermined protocol/algorithm of the surgical instrument including limit switches, controlled deceleration, etc. At the end of stroke, the I-beam 2514 is returned to the initial I-beam park position 9502 at the fast speed. End of return stroke (returning to the parked position 9502) is handled in accordance with the protocol/algorithm of the surgical instrument. Other zones may be defined without limitation.

TABLE 2

Distance Traveled Through Zones At Specified Command Velocity For Various Dynamic Firing Zones

| Dynamic Firing Zone | Distance (mm) Traveled Through Zone at Specified Command Velocity | | |
|---|---|---|---|
| (sec) | Slow | Medium | Fast |
| First Zone ($T_1$ sec long) | $\delta < \delta_1$ | $\delta_1 < \delta < \delta_2$ | $\delta > \delta_2$ |
| Intermediate Zones ($T_2$ sec long) | $\delta < \delta_3$ | $\delta_3 < \delta < \delta_4$ | $\delta > \delta_4$ |
| Last Measured Zone ($T_3$ sec long) | $\delta < \delta_5$ | $\delta_5 < \delta < \delta_6$ | $\delta > \delta_6$ |

TABLE 3

Non-limiting Examples Of Distance Traveled Through Zones At Specified Command Velocity For Various Dynamic Firing Zones

| Dynamic Firing Zone | Distance (mm) Traveled Through Zone at Specified Command Velocity | | |
|---|---|---|---|
| (sec) | Slow | Medium | Fast |
| First Zone (0.4 sec long) | $\delta < 4$ | $4 < \delta < 5$ | $\delta > 5$ |
| Intermediate Zones (0.8 sec long) | $\delta < 8$ | $8 < \delta < 10$ | $\delta > 10$ |
| Last Measured Zone (0.8 sec long) | $\delta < 7$ | $7 < \delta < 9$ | $\delta > 9$ |

TABLE 4

Algorithm To Set Velocity Based On Distance Traveled Over Fixed Time Interval

| Algorithm | $\delta_a$ | $\delta_b$ |
|---|---|---|
| If distance (mm) traveled by I-beam over fixed time interval is . . . | $\delta > \delta_1$ | $\delta \leq \delta_1$ |
| Then initial velocity of I-beam in T-slot is . . . | $V_1$ (mm/sec) | $V_2$ (mm/sec) |
| And automatic velocity is set at . . . | FAST | MEDIUM |

TABLE 5

Non-limiting Example Of Algorithm To Set Velocity Based On Distance Traveled Over Fixed Time Interval

| Algorithm | $\delta_a$ | $\delta_2$ |
|---|---|---|
| If distance (mm) traveled by I-beam over fixed time interval is . . . | $\delta > 10$ mm | $\delta \leq 10$ mm |
| Then initial velocity of I-beam in T-slot is . . . | 30 mm/sec | 12 mm/sec |
| And automatic velocity is set at . . . | FAST | MEDIUM |

In one aspect, Tables 1-5 may be stored in memory of the surgical instrument. The Tables 1-5 may be stored in memory in the form of a look-up table (LUT) such that the control circuit 2510 can retrieve the values and control the command velocity of the I-beam 2514 in each zone based on the values stored in the LUT.

FIG. 32 is a graphical depiction 9600 comparing tissue thickness as a function of set time interval $T_n$ of I-beam stroke 9202 (top graph), force to fire as a function of set time interval $T_n$ of I-beam stroke 9604 (second graph from the top), dynamic time checks as a function of set time interval $T_n$ of I-beam stroke 9606 (third graph from the top), and set velocity of I-beam as a function of set time interval $T_n$ of I-beam stroke 9608 (bottom graph) according to one aspect of this disclosure. The horizontal axis 9610 for each of the graphs 9602, 9604, 9606, 9608 represents set time interval $T_n$ of an I-beam 2514 stroke for a 60 mm staple cartridge, for example. Staple cartridges of different lengths can readily be substituted. With reference also to Table 1, the horizontal axis 9610 has been marked to identify the defined zones $Z_1$-$Z_6$ for a 60 mm staple cartridge. As indicated in Table 1, the defined zones may be marked for staple cartridges of various sizes. With reference also to FIG. 14, in accordance with the present disclosure, the control circuit 2510 samples the displacement of the I-beam 2514 at set time intervals received form the timer/counter circuit 2531 as the I-beam 2514 advances distally along the staple cartridge 2518 during the firing stroke. At the set time intervals, the control circuit 2510 samples the position of the I-beam 2514 from the position sensor 2534 and determines the actual displacement $\delta_n$ of the I-beam 2514 during the time interval $T_n$. In this manner, the control circuit 2510 can determine the actual velocity of the I-beam 2514 and compare the actual velocity to the estimated velocity and make any necessary adjustments to the motor 2504 velocity.

The tissue thickness graph 9602 shows a tissue thickness profile 9620 along the staple cartridge 2518 and an indicated thickness in tissue region 9621 as shown by the horizontal dashed line. The force to fire graph 9604 shows the force to fire profile 9628 along the staple cartridge 2518. The force to fire 9630 remains relatively constant while the tissue thickness in tissue region 9622 remains below the indicated thickness in tissue region 9621 as the I-beam 2514 traverse zones $Z_1$ and $Z_2$. As the I-beam 2514 enters zone $Z_3$, the tissue thickness in tissue region 9624 increases and the force to fire also increase while the I-beam 2514 traverses the thicker tissue in times zones $Z_3$, $Z_4$, and $Z_5$. As the I-beam 2514 exits zone $Z_5$ and enters zone $Z_6$, the tissue thickness 9226 decrease and the force to fire 9234 also decreases.

With reference now to FIGS. 14, 31-32 and Tables 2-3, the velocity $V_1$ in zone $Z_1$ is set to the velocity $V_o$ determined by the control circuit 2510 in zone $Z_o$, which is based on the displacement $\delta_o$ of the I-beam 2514 during the initial set time interval $T_o$ as discussed in reference to FIGS. 30A, 30B. Turning also to the graphs 9606, 9608 in FIG. 32, the initial set velocity $V_o$ was set to Medium and thus the set velocity $V_1$ in zone $Z_1$ is set to Medium such that $V_1=V_o$.

At set time $t_1$ (e.g., 0.4 sec for a 60 mm staple cartridge), as the I-beam 2514 exits zone $Z_1$ and enters zone $Z_2$, the control circuit 2510 measures the actual displacement $\delta_1$ of the I-beam 2514 over the set time interval $T_1$ (0.4 sec long) and determines the actual velocity of the I-beam 2514. With reference to graphs 9606 and 9608 in FIG. 32, at set time $t_1$, the actual displacement $\delta_1$ of the I-beam 2514 over the set time interval $T_1$ is $\delta_1=4.5$ mm. According to Table 3, an actual displacement of 4.5 mm in zone $Z_1$ requires the command or set velocity $V_2$ in zone $Z_2$ to be set to Medium. Accordingly, the control circuit 2510 does not reset the command velocity for zone $Z_2$ and maintains it at Medium.

At set time $t_2$ (e.g., 0.8 sec for a 60 mm staple cartridge), as the I-beam 2514 exits zone $Z_2$ and enters zone $Z_3$, the control circuit 2510 measures the actual displacement $\delta_2$ of the I-beam 2514 over the set time interval $T_2$ (0.8 sec long) and determines the actual velocity of the I-beam 2514. With reference to graphs 9606 and 9608 in FIG. 32, at set time $t_2$, the actual displacement $\delta_2$ of the I-beam 2514 over the set time interval $T_2$ is $\delta_2=9.0$ mm. According to Table 3, an actual displacement of 9.0 mm in zone $Z_2$ requires the command or set velocity $V_3$ in zone $Z_3$ to be set to Medium. Accordingly, the control circuit 2510 does not reset the command velocity for zone $Z_3$ and maintains it at Medium.

At set time $t_3$ (e.g., 2.0 sec for a 60 mm staple cartridge), as the I-beam 2514 exits zone $Z_3$ and enters zone $Z_4$, the control circuit 2510 measures the actual displacement $\delta_3$ of the I-beam 2514 over the set time interval $T_3$ (0.8 sec long) and determines the actual velocity of the I-beam 2514. With reference to graphs 9606 and 9608 in FIG. 32, at set time $t_3$, the actual displacement $\delta_3$ of the I-beam 2514 over the set time interval $T_3$ is $\delta_3=7.5$ mm. According to Table 3, an actual displacement of 7.5 mm in zone $Z_3$ requires the command or set velocity $V_4$ in zone $Z_4$ to be set to Slow. This is because the actual displacement of 7.5 mm is less than 8.0 mm and is outside the previous range. Accordingly, the control circuit 2510 determines that the actual I-beam 2514 velocity in zone $Z_3$ was slower than expected due to external influences such as thicker tissue than expected as shown in tissue region 9624 in graph 9602. Accordingly, the control circuit 2510 resets the command velocity $V_4$ in zone $Z_4$ from Medium to Slow.

In one aspect, the control circuit 2510 may be configured to disable velocity reset in a zone following a zone in which the velocity was reset. Stated otherwise, whenever the velocity is updated in a present zone the subsequent zone will not be evaluated. Since the velocity was updated in zone $Z_4$, the distance traveled by the I-beam will not be measured at the end of zone $Z_4$ at set time $t_4$ (e.g., 2.8 sec for a 60 mm staple cartridge). Accordingly, the velocity in zone $Z_5$ will remain the same as the velocity in zone $Z_4$ and dynamic displacement measurements resume at set time $t_5$ (e.g., 3.6 sec for a 60 mm staple cartridge).

At set time $t_5$, as the I-beam 2514 exits zone $Z_5$ and enters zone $Z_6$, the control circuit 2510 measures the actual displacement $\delta_5$ of the I-beam 2514 over the set time interval $T_5$ (0.8 sec long) and determines the actual velocity of the I-beam 2514. With reference to graphs 9606 and 9608 in FIG. 32, at set time $t_5$, the actual displacement $\delta_5$ of the I-beam 2514 over the set time interval $T_5$ is $\delta_5=9.5$ mm. According to Table 3, an actual displacement of 9.5 mm in zone $Z_5$ requires the command or set velocity $V_6$ in zone $Z_6$ to be set to High. This is because the actual displacement of 9.5 mm is greater than 9.0 mm and is outside the previous range, the control circuit 2510 determines that the actual velocity of the I-beam 2514 in zone $Z_5$ was faster than expected due to external influences such as thinner tissue than expected as shown in tissue region 9626 in graph 9602. Accordingly, the control circuit 2510 resets the command velocity $V_6$ in zone $Z_6$ from Slow to High.

FIG. 33 is a graphical depiction 9700 of force to fire as a function of time comparing slow, medium and fast I-beam 2514 displacement velocities according to one aspect of this disclosure. The horizontal axis 9702 represents time t (sec) that it takes an I-beam to traverse a staple cartridge. The vertical axis 9704 represents force to fire F (N). The graphical depiction shows three separate force to fire curves versus time. A first force to fire curve 9712 represents an I-beam 2514 (FIG. 14) traversing through thin tissue 9706 at a fast velocity and reaching a maximum force to fire $F_1$ at the top of the ramp 9506 (FIG. 30B) at $t_1$. In one example, a fast traverse velocity for the I-beam 2514 is ~30 mm/sec. A second force to fire curve 9714 represents an I-beam 2514 traversing through medium tissue 9708 at a medium velocity and reaching a maximum force to fire $F_2$ at the top of the ramp 9506 at $t_2$, which is greater than $t_1$. In one example, a medium traverse velocity for the I-beam 2514 is ~12 mm/sec. A third force to fire curve 9716 represents an I-beam 2514 traversing through thick tissue 9710 at a slow velocity and reaching a maximum force to fire $F_3$ at the top of the ramp 9706 at $t_3$, which is greater than $t_2$. In one example, a slow traverse velocity for the I-beam 2514 is ~9 mm/sec.

FIG. 34 is a logic flow diagram of a process 9800 depicting a control program or logic configuration for controlling command velocity in an initial firing stage according to one aspect of this disclosure. With reference also to FIGS. 14 and 30A-34, the control circuit 2510 determines 9802 the reference position of the displacement member, such as the I-beam 2514, for example, based on position information provided by the position sensor 2534. In the I-beam 2514 example, the reference position is the proximal or parked position 9502 at the bottom of the closure ramp 9506 as shown in FIG. 30B. Once the reference position has been determined 9802, the control circuit 2510 and motor control 2508 set the command velocity of the motor 2504 to a predetermined command velocity $V_o$ and initiates 9804 firing the displacement member (e.g., I-beam 2514) at the predetermined command velocity $V_o$ for the initial or base zone $Z_o$. In one example, the initial predetermined command velocity $V_o$ is ~12 mm/sec, however, other initial predetermined command velocity $V_o$ may be employed. The control circuit 2510 monitors 9806 the position of the displacement member with position information received from the position sensor 2534 over a predetermined time interval $T_o$ and records the actual displacement $\delta_o$ of the displacement member at the end of the time interval $T_o$ as shown in FIG. 30B. The predetermined displacement $X_o$ is the expected displacement of the displacement member traveling at the current set command velocity $V_o$. The deviation between actual displacement $\delta_o$ and the predetermined displacement $X_o$ is due at least in part to external influences acting on the displacement member such as tissue thickness acting on the cutting edge 2509 of the I-beam 2514.

With timing information received from the timer/counter circuit 2531 and position information received from the position sensor 2534, the control circuit 2510 measures 9808 the actual displacement $\delta_o$ of the of the displacement member over the time interval $T_o$. Based on the actual displacement $\delta_o$ and set time interval $T_o$ the control circuit 210 sets 9810 the command velocity $V_1$ for the first zone $Z_1$. As indicated in Table 1, various zones may be defined for staple cartridges of various sizes. Other zones, however, may be defined. The control circuit 2510 sets 9810 the command velocity $V_1$ for the first zone $Z_1$ by comparing 9812 the actual displacement $\delta_o$ to values stored in memory, such as, for example, stored in a lookup table (LUT). In one example, as indicated in Table 4 generally and in Table 5 by way of specific example, if the actual displacement $\delta_o$ traveled by the displacement member over the fixed time interval $T_o$ (sec) of 0.8 sec is greater than 10 mm, then the command velocity for the first zone $Z_1$ is set 9814 to FAST (e.g., 30 mm/sec). Otherwise, if the actual displacement $\delta_o$ of the displacement member over the fixed time interval $T_o$ (sec) of 0.8 sec is less than or equal to 10 mm, then the command velocity for the first zone $Z_1$ is set 9816 to MEDIUM (e.g., 12 mm/sec). Subsequently, the control circuit 2510 checks 9818 for lockout and stops 9820 the motor 2504 if there is a lockout condition. Otherwise, the control circuit enters 9822 the dynamic firing phase as described below in reference to process 9850 in FIG. 35.

FIG. 35 is a logic flow diagram of a process 9850 depicting a control program or logic configuration for controlling command velocity in a dynamic firing stage according to one aspect of this disclosure. With reference also to FIGS. 14 and 30A-34, the control circuit 2510 sets 9852 the initial command velocity $V_1$ of the motor 2504 for the first zone $Z_1$ based on the displacement $\delta_o$ of the displacement member over the initial set time interval $T_o$, as described in reference to the process 9800 in FIG. 34. As the displacement member traverses the staple cartridge 2518, the control circuit 2510 receives the position of the displacement member from the position sensor 2534 and timing information from the timer/counter 2531 and monitors 9854 the position of the displacement member in a zone $Z_n$ over the predefined set time interval $T_n$. At the end of the zone $Z_n$, the control circuit 2510 measures 9856 the actual displacement $\delta_n$ of the displacement member over the predefined time interval $T_n$ as the displacement member 2514 traverses from the beginning of the zone $Z_n$ to the end of the zone $Z_n$ and compares 9858 the actual displacement $\delta_n$ to a predetermined displacement $X_n$ for a particular zone as shown generally in Table 2 and by way of specific example in Table 3. The predetermined displacement $X_n$ is the expected displacement of the displacement member traveling at the current set command velocity $V_n$. The deviation between actual displacement $\delta_n$ and the predetermined displacement $X_n$ is due at least in part to external influences acting on the displacement member such as tissue thickness acting on the cutting edge 2509 of the I-beam 2514.

For example, with reference to Table 3, the distance traveled by the displacement member through a zone at a specified command velocity over a set time interval $T_n$ is provided for various dynamic firing zones. For example, if the dynamic firing zone is $Z_1$ ($T_1$=0.4 sec long) and the actual displacement $\delta_n$<4 mm, the command velocity for the next zone $Z_2$ is set to FAST; if the actual displacement 4<$\delta_n$<5 mm, the command velocity for the next zone $Z_2$ is set to MEDIUM; and if the actual displacement $\delta_n$>5 mm, the command velocity for the next zone $Z_2$ is set to SLOW.

If, however, the dynamic firing zone is an intermediate zone $Z_2$-$Z_5$ (T=0.8 sec long), for example, located between the first zone $Z_1$ and the last zone $Z_6$ and if the actual displacement $\delta_n$<8 mm, the command velocity for the next zone $Z_2$ is set to FAST; if the actual displacement 8<$\delta_n$<10 mm, the command velocity for the next zone $Z_3$-$Z_5$ is set to MEDIUM; and if the actual displacement $\delta_n$>10 mm, the command velocity for the next zone $Z_3$-$Z_5$ is set to SLOW.

Finally, if the dynamic firing zone is the last measured zone $Z_5$ (T=0.8 sec long) and the actual displacement $\delta_n$<7 mm, the command velocity for the final zone $Z_6$ is set to FAST; if the actual displacement 7<$\delta_n$<9 mm, the command velocity for the final zone $Z_6$ is set to MEDIUM; and if the actual displacement $\delta_n$>9 mm, the command velocity for the final zone $Z_6$ is set to SLOW. Other parameters may be employed not only to define the dynamic firing zones but also to define the time to travel through a zone at specified command velocity for various dynamic firing zones.

Based on the results of the comparison 9858 algorithm, the control circuit 2510 will continue the process 9850. For example, if the results of the comparison 9858 indicate that the actual velocity (FAST, MEDIUM, SLOW) in the previous zone $Z_n$ is the same as the previous command velocity $V_1$ (FAST, MEDIUM, SLOW), the control circuit 2510 maintains 9860 the command velocity for the next zone $Z_{n+1}$ the same as the as the previous command velocity. The process 9850 continues to monitor 9854 the position of the displacement member over the next predefined zone $Z_{n+1}$. At the end of the next zone $Z_{n+1}$, the control circuit 2510 measures 9856 the actual displacement $\delta_n$+1 of the displacement member over the predefined time interval $T_{n+1}$ while traversing from the beginning of the next zone $Z_{n+1}$ to the end of the next zone $Z_{n1}$ and compares 9858 the actual displacement $\delta_n$+1 to a predetermined displacement $X_{n+1}$ for a particular zone as shown generally in Table 2 and by way of specific example in Table 3. If there are no changes required to the command velocity, the process 9850 until the displacement member, e.g., the I-beam 2514, reaches the end of stroke 9866 and returns 9868 the displacement member to the reference position 9502.

If the results of the comparison 9858 indicate that the actual velocity (FAST, MEDIUM, SLOW) in the previous zone $Z_n$ is different as the previous command velocity $V_1$ (FAST, MEDIUM, SLOW), the control circuit 2510 resets 9862 or updates the command velocity to $V_{new}$ for the next zone $Z_{n+1}$ according to the algorithm summarized in Tables 2 and 3. If the command speed is rest reset 9862 or updated, the control circuit 2510 maintains 9864 the command velocity $V_{new}$ for an additional zone $Z_{n+2}$. In other words, at the end of the next zone $Z_{n+1}$, the control circuit 2510 does not evaluate or measure the displacement. The process 9850 continues to monitor 9854 the position of the displacement member over the next predefined zone $Z_{n+1}$ until the displacement member, e.g., the I-beam 2514, reaches the end of stroke 9866 and returns 9868 the displacement member to the reference position 9502.

Various aspects of the subject matter described herein are set out in the following numbered examples:

Example 1. A surgical instrument, comprising: a displacement member configured to translate within the surgical instrument over a plurality of predefined zones; a motor coupled to the displacement member to translate the displacement member; a control circuit coupled to the motor; a position sensor coupled to the control circuit, the position sensor configured to monitor a position of the displacement member; a timer circuit coupled to the control circuit, the timer circuit configured to measure elapsed time; wherein the control circuit is configured to: receive, from the position sensor, a position of the displacement member in a current zone during a set time interval; measure displacement of the displacement member at a set time at the end of the set time interval, wherein the measured displacement is defined as the distance traveled by the displacement member during the set time interval at a set command velocity for the current zone; and set a command velocity of the displacement member for a subsequent zone based on the measured displacement of the displacement member within the current zone.

Example 2. The surgical instrument of Example 1, wherein the control circuit is configured to: determine the set time interval in which the displacement member is located, wherein the set time interval is defined by a beginning time and an ending time; and measure the displacement of the displacement member at the ending time of the set time interval.

Example 3. The surgical instrument of Example 1 through Example 2, wherein the control circuit is configured to: compare the measured displacement to a predetermined displacement stored in a memory coupled to the control circuit; and determine whether to adjust or maintain the command velocity for the current zone based on the comparison.

Example 4. The surgical instrument of Example 3, wherein the control circuit is configured to set the command velocity for the subsequent zone equal to the command velocity of the current zone when the measured displacement is within a range of predetermined displacements.

Example 5. The surgical instrument of Example 3 through Example 4, wherein the control circuit is configured to set the command velocity for the subsequent zone different from the command velocity of the current zone when the measured displacement is outside a range of predetermined displacements.

Example 6. The surgical instrument of Example 5, wherein the control circuit is configured to skip a displacement measurement for a subsequent zone when the command velocity is adjusted.

Example 7. The surgical instrument of Example 1 through Example 6, wherein multiple zones are defined for a staple cartridge configured to operate with the surgical instrument.

Example 8. The surgical instrument of Example 7, wherein at least two zones have different lengths.

Example 9. A surgical instrument, comprising: a displacement member configured to translate within the surgical instrument over a plurality of predefined zones; a motor coupled to the displacement member to translate the displacement member; a control circuit coupled to the motor; a position sensor coupled to the control circuit, the position sensor configured to monitor a position of the displacement member; a timer circuit coupled to the control circuit, the timer/counter circuit configured to measure elapsed time; wherein the control circuit is configured to: receive, from the position sensor, a position of the displacement member in a current zone during an initial set time interval; measure displacement of the displacement member from a parked position to a distal position during the initial set time interval; and set a command velocity of the displacement member for a first dynamic zone based on the measured displacement from the parked position to the distal position.

Example 10. The surgical instrument of Example 9, wherein the control circuit is configured to compare the measured displacement to a predetermined displacement stored in a memory coupled to the control circuit.

Example 11. The surgical instrument of Example 10, wherein the control circuit is configured to set the command velocity for the initial zone to a first velocity when the measured displacement is within a first range of displacements and set the command velocity for the initial zone to a second velocity when the measured time is within a second range of displacements.

Example 12. The surgical instrument of Example 9 through Example 11, wherein the control circuit is configured to determine a lockout condition and stop the motor.

Example 13. A method of controlling motor velocity in a surgical instrument, the surgical instrument comprising a displacement member configured to translate within the surgical instrument over a plurality of predefined zones, a motor coupled to the displacement member to translate the displacement member, a control circuit coupled to the motor, a position sensor coupled to the control circuit, the position sensor configured to monitor the position of the displacement member, a timer circuit coupled to the control circuit, the timer circuit configured to measure elapsed time, the method comprising: receiving, by a position sensor, a position of a displacement member within a current predefined zone defined by a predetermined distance; measuring, by the control circuit, displacement of the displacement member at a set time at the end of the set time interval, wherein the measured displacement is defined as the distance traveled by the displacement member during the set time interval at a set command velocity for the current zone; and setting, by the control circuit, a command velocity of the displacement member for a subsequent zone based on the measured displacement within the current zone.

Example 14. The method of Example 13, further comprising: determining, by the control circuit and the timer circuit, the set time interval in which the displacement member is located, wherein the set time interval is defined by a beginning time and an ending time; measuring, by the timer circuit, the displacement of the displacement member at the ending time of the set time interval.

Example 15. The method of Example 13 through Example 14, further comprising: comparing, by the control circuit, the measured displacement to a predetermined displacement stored in a memory coupled to the control circuit; and determining, by the control circuit, whether to adjust or maintain the command velocity for the current zone based on the comparison.

Example 16. The method of Example 15, further comprising setting, by the control circuit, the command velocity for the subsequent zone equal to the command velocity of the current zone when the measured displacement is within a range of predetermined displacements.

Example 17. The method of Example 15 through Example 16, further comprising setting, by the control circuit, the command velocity for the subsequent zone different from the command velocity of the current zone when the measured displacement is outside a range of predetermined displacements.

Example 18. The method of Example 17, further comprising skipping, by the control circuit, a displacement measurement for a subsequent zone when the command velocity is adjusted.

Example 19. The method of Example 13 through Example 18, further comprising defining, by the control circuit, multiple predefined zones for a staple cartridge configured to operate with the surgical instrument.

Example 20. The method of Example 19, further comprising defining, by the control circuit, at least two predefined zones having different lengths.

Closed Loop Feedback Control of Motor Velocity of a Surgical Stapling and Cutting Instrument Based on Measured Time Over a Specified Number of Shaft Rotations During use of a motorized surgical stapling and cutting instrument it is possible that the velocity of the cutting member or the firing member may need to be measured and adjusted to compensate for tissue conditions. In thick tissue the velocity may be decreased to lower the force to fire experienced by the cutting member or firing member if the force to fire experienced by the cutting member or firing member is greater than a threshold force. In thin tissue the velocity may be increased if the force to fire experienced by the cutting member or firing member is less than a threshold. Therefore, it may be desirable to provide a closed loop feedback system that measures and adjusts the velocity of the cutting member or firing member based on a measurement of time over a specified number of shaft rotations. It may be desirable to measure the number of shaft rotations at a fixed time.

The disclosure now turns to a closed loop feedback system to provide velocity control of a displacement member. The closed loop feedback system adjusts the velocity of the displacement member based on a measurement of actual time over a specified number of shaft rotations. In one aspect, the closed loop feedback system comprises two phases. A start phase defined as the start of a firing stroke followed by a dynamic firing phase while the I-beam 2514 advances distally during the firing stroke. FIGS. 36A and 36B show the I-beam 2514 positioned at the start phase of the firing stroke. FIG. 36A illustrates an end effector 2502 comprising a firing member 2520 coupled to an I-beam 2514 comprising a cutting edge 2509. The anvil 2516 is in the closed position and the I-beam 2514 is located in a proximal or parked position 10002 at the bottom of the closure ramp 10006. The parked position 10002 is the position of the I-beam 2514 prior to traveling up the anvil 2516 closure ramp 10006 to the top of the ramp 10006 to the T-slot 10008 after a predetermined number of shaft rotations. A top pin 10080 is configured to engage a T-slot 10008 and a lockout pin 10082 is configured to engage a latch feature 10084.

In FIG. 36B the I-beam 2514 is located in a target position 10004 at the top of the ramp 10006 with the top pin 10080 engaged in the T-slot 10008. As shown in FIGS. 14, 36A, and 36B and, in traveling from the parked position 10002 to the target position 10004, the I-beam 2514 travels a distance indicated as $X_o$ in the horizontal distal direction after a predetermined number of shaft rotations. During the start phase, the velocity of the I-beam 2514 is set to a predetermined initial velocity $\Phi_o$ rotations per seconds. A control circuit 2510 measures the actual time $t_o$ that it takes the I-beam 2514 to travel up the ramp 10006 from the parked position 10002 to the target position 10004 at the initial velocity $\Phi_o$ rotations per second. In one aspect, the horizontal distance is in the range of 5 mm to 10 mm and in one example is 7.4 mm and the initial velocity $\Phi_o$=5 rotations per second. As described in more detail below, the actual time $t_o$ is used to set the command velocity of the I-beam 2514 in terms of rotations per second of the shaft to slow, medium, or fast in the subsequent staple cartridge zone Z as the I-beam 2514 advances distally. The number of zones may depend on the length/size of the staple cartridge (e.g., 35 mm, 40 mm, 45 mm, 50 mm, 55 mm, 60 mm, >60 mm). The command velocity or set velocity is the velocity of the motor 2504 that is applied to the motor 2504 by the control circuit 2510 and motor control 2508 in order effect a desired velocity of the I-beam 2514. In one aspect, the velocity is determined based on rotations of the shaft of the motor 2504 in terms of rotations per second. The actual velocity of the I-beam 2514 is determined by the control circuit 2510 by measuring the actual time $t_o$ with the timer/counter 2531 circuit that it takes the I-beam 2514 to traverse a specified or fixed distance provided by the position sensor 2534 based on a set rotation interval assuming, in one example, of 60 threads per inch. In accordance with one aspect of the present disclosure, the closed loop feedback control system of the surgical instrument measures the actual time $t_n$ it takes the I-beam 2514, or a displacement member, to travel a predetermined fixed distance or rotation interval $X_n$ after a predetermined set of rotation interval of the motor shaft assuming a 60 threads per inch. A predetermined fixed distance or rotation interval $X_n$ is defined for each zone (e.g., $Z_1, Z_2, Z_3 \ldots Z_n$).

FIG. 37 illustrates a screw drive system 10470 that may be employed with the surgical instrument 10 (FIG. 1) according to one aspect of this disclosure. In one aspect, the longitudinally movable drive member 120 (FIG. 2) may be replaced with the screw drive (sometime referred to as a nut drive) system 10470. The screw drive system 10470 comprises a leadscrew 10472, ball screw or other mechanical linear actuator, adapted and configured to couple to the shaft 10474 of the motor 82 (FIG. 2) via the drive gear 10478 to translate rotational motion to linear motion. The leadscrew 10472 is coupled to the firing member 220 via a nut 1476. The firing member 220 is coupled to firing bar 172, which is coupled to the I-beam 178 as shown and described with reference to FIGS. 2-4. The drive gear 10478, which is driven by the shaft 1474 of the motor 82 is adapted to rotate the screw drive system 10470.

The screw drive system 10470 comprises a leadscrew 10472 and a nut 10476, also known as a power screw or translation screw, and is adapted to couple to the shaft 10474 of the motor 82 via the drive gear 10478 to translate turning motion of the shaft 10474 of the motor 82 into linear motion of the displacement member, such as the I-beam 2514, for example, which is coupled to the nut 10476. The leadscrew 10472 threads are in sliding contact with their counterparts within the nut 10476 such that as the leadscrew 10472 rotates the nut 10476 translates forward and backward according to the rotation of the drive gear 10478 as indicated. A ball screw also may be used for low friction application. In a ball screw, a threaded shaft provides a helical raceway for ball bearings which act as a precision screw. As well as being able to apply or withstand high thrust loads, they can do so with minimum internal friction. Close tolerances make it suitable for use in high precision applications. The ball assembly acts as the nut while the threaded shaft is the screw. The screw drive system 10470, such as the leadscrew 10472 and nut 10476, or ball screw drive, may include a threaded shaft having 60 threads per inch such that a 60 mm staple cartridge can be traversed in approximately 142 rotations of the motor shaft. For example, one rotation of the threaded shaft of the leadscrew 10472 advances the nut 10476 and the displacement member 1 inch (25.4 mm). A 60 mm cartridge is 2.36 inches long and requires ~142 rotations of the leadscrew 10472 to advance the nut 10476 and the displacement member the full 60 mm stroke if there is a 1:1 ratio between the rotation of the shaft 10474 and the rotation of the leadscrew 10472. Other ratios using gear reduction assemblies may be adapted without limitation. The rotation of the shaft 10474 can be measured by a position sensor arrangement comprising one or more magnets and one or more Hall effect sensors to measure the rotation of the shaft 10474 and provide the shaft rotation signals to the control circuit.

In one aspect, with reference to FIG. 37 and also FIGS. 2-4 and 10-12, the rotations of the shaft 10474 of the motor 82 (FIG. 2) or 1116 (FIG. 10) can be measured by measuring the rotation of the shaft 1214 (FIG. 11) coupled to the drive gear 86 (FIG. 2) using the absolute positioning system 1100 (FIGS. 10 and 12) and position sensor 1200 (FIGS. 11, 12). With reference to FIG. 12, the position sensor 1200 for the absolute positioning system 1100 comprising a magnetic rotary absolute positioning system can be employed to measure magnetic rotary position of the shaft of the motor. The position sensor 1200 is interfaced with the controller 1104 to provide an absolute positioning system 1100. Additional details of absolute positioning system 1100 and position sensor 1200 are described above in reference to FIG. 12 and for expedience will not be repeated here.

Turning now to FIG. 38, there is illustrated an I-beam 2514 firing stroke as a chart 9009 aligned with the end effector 2502 according to one aspect of this disclosure. As shown, the initial zone ($Z_o$), or base zone, is defined as the distance traveled by the I-beam 2514 from the parked position 10002 to the target position 10004. The measured time $T_o$ is the time it takes the I-beam 2514 to travel up the closure ramp 10006 to the target position 10004 at an initial set velocity $\Phi_o$ rotations/sec. The measured times $T_1$-$T_5$ are reference periods of time for traversing the corresponding zones $Z_1$-$Z_5$, respectively. The displacement of the I-beam 2514 in zone $Z_o$ is $\Theta_o$ rotations. The period $T_o$, the time it takes for the I-beam 2514 to travel over a distance $\Theta_o$, is used to set the command velocity in the subsequent zone $Z_1$.

With reference now to FIGS. 14-15, and 36A-38, at the start phase, e.g., at the beginning of a firing stroke, the control circuit 2510 is configured to initiate firing the displacement member, such as the I-beam 2514, at a predetermined velocity $\Phi_o$ (e.g., 5 rotations/sec). During the start phase, the control circuit 2510 is configured to monitor the position of the I-beam 2514 and measure the time $t_o$ (sec) it takes for the I-beam 2514 to travel from the I-beam 2514 parked position 10002 to the I-beam 2514 target position 10004, either to the top of the anvil 2516 closure ramp 10006, or at the end of a low power mode of operation. Time $t_o$ in the initial zone 10010 is used by the control circuit 2510 to determine the firing velocity of the I-beam 2514 through the first zone $Z_1$. For example, in one aspect, if time $t_o$ is <0.9 sec the velocity $\Phi_1$ may be set to fast and if time $t_o \geq 0.9$ sec the velocity $\Phi_1$ may be set to medium. Faster or slower times may be selected based on the length of the staple cartridge 2518. The actual time $t_1$-$t_5$ that it takes the I-beam 2514 to traverse a corresponding zone $Z_1$ to $Z_5$ is measured at a corresponding set rotation displacement $\delta_1$-$\delta_5$ and is compared to a corresponding reference time period $T_1$-$T_5$. In various aspects, if a lockout condition is encountered, the motor 2504 will stall before the I-beam 2514 reaches the target position 10004. When this condition occurs, the surgical instrument display indicates the instrument status and may issue a stall warning. The display also may indicate a speed selection.

During the dynamic firing phase, the surgical instrument enters the dynamic firing phase, where the control circuit 2510 is configured to monitor the rotation interval $\delta_n$ of the I-beam 2514 and measure the time $t_n$ that it takes the I-beam 2514 to travel from the beginning of a zone to the end of a zone (e.g., a total distance of 12 rotations or 23 rotations). In FIG. 37, the reference time $T_1$ is the time taken by the I-beam 2514 to travel from the beginning of zone $Z_1$ to the end of zone $Z_1$ at a set velocity $\Phi_1$. Likewise, the reference time $T_2$ is the time it takes the I-beam 2514 to travel from the beginning of zone $Z_2$ to the end of zone $Z_2$ at a set velocity $\Phi_2$, and so on. Table 1 shows zones that may be defined for staple cartridges 2518 of various sizes.

TABLE 1

Defined Zones For Staple Cartridges Of Various Sizes

| Staple Cartridge | Zones | | | | | |
| --- | --- | --- | --- | --- | --- | --- |
| | $Z_1$ | $Z_2$ | $Z_3$ | $Z_4$ | $Z_5$ | $Z_6$ |
| 35 mm | 0-12 rotations | 12-35 rotations | 35-59 rotations | >59 rotations | N/A | N/A |
| 40-45 mm | 0-12 rotations | 12-35 rotations | 35-59 rotations | 59-82 rotations | >82 rotations | N/A |
| 55-60 mm | 0-12 rotations | 12-35 rotations | 35-59 rotations | 59-82 rotations | 82-106 rotations | >106 rotations |

For staple cartridges 2518 over 60 mm, the pattern continues, but the last 10-15 mm continues at a command or indicated velocity of the previous zone pending other interventions for end of stroke, among others. At the end of each zone, the actual time $t_n$ it took the I-beam 2514 to pass through the zone is compared to the values in other tables (e.g., Tables 2-5 below) to determine how to set the command velocity for the next zone. The command velocity is updated for the next zone and the process continues. Whenever the command velocity is updated, the next zone will not be evaluated. The end of stroke is handled in accordance with a predetermined protocol/algorithm of the surgical instrument including limit switches, controlled deceleration, etc. At the end of stroke, the I-beam 2514 is returned to the initial I-beam park position 10002 at the fast speed. End of return stroke (returning to the parked position 10002) is handled in accordance with the protocol/algorithm of the surgical instrument. Other zones may be defined without limitation.

TABLE 2

Time To Travel Through Zones At Specified Command
Velocity For Various Dynamic Firing Zones

| Dynamic Firing Zone | Time (sec) to Travel Through Zone at Specified Command Velocity | | |
|---|---|---|---|
| (rotations) | Fast | Medium | Slow |
| First Zone ($\Theta_1$ rotations) | $t < t_1$ | $t_1 < t < t_2$ | $t > t_2$ |
| Intermediate Zones ($\Theta_2$ rotations) | $t < t_3$ | $t_3 < t < t_4$ | $t > t_4$ |
| Last Measured Zone ($\Theta_3$ rotations) | $t < t_5$ | $t_5 < t < t_6$ | $t > t_6$ |

TABLE 3

Non-limiting Examples Of Time To Travel Through Zones At
Specified Command Velocity For Various Dynamic Firing Zones

| Dynamic Firing Zone | Time (sec) to Travel Through Zone at Specified Command Velocity | | |
|---|---|---|---|
| (rotations) | Fast | Medium | Slow |
| First Zone (5 mm long) | $t < 0.5$ | $0.5 < t < 0.6$ | $t > 0.6$ |
| Intermediate Zones (10 mm long) | $t < 0.9$ | $0.9 < t < 1.1$ | $t > 1.1$ |
| Last Measured Zone (10 mm long) | $t < 1.0$ | $1.0 < t < 1.3$ | $t > 1.3$ |

TABLE 4

Algorithm To Set Velocity Based On Time To Travel Up Ramp

| Algorithm | $t_a$ (sec) | $t_b$ (sec) |
|---|---|---|
| If time t (sec) for I-beam to travel up ramp is . . . | $t_1 < t < t_2$ | $t > t_2$ to $t_3$ |
| Then initial velocity V of I-beam in T-slot is . . . | $V_1$ (mm/sec) | $V_2$ (mm/sec) |
| And automatic velocity is set at . . . | FAST | MEDIUM |

TABLE 5

Non-limiting Example Of Algorithm To Set
Velocity Based On Time To Travel Up Ramp

| Algorithm | $t_a$ (sec) | $t_b$ (sec) |
|---|---|---|
| If time t (sec) for I-beam to travel up ramp is . . . | $t < 0.9$ | $t \geq 0.9$ |
| Then initial velocity of I-beam in T-slot is . . . | 30 mm/sec | 12 mm/sec |
| And automatic velocity is set at . . . | FAST | MEDIUM |

In one aspect, Tables 1-5 may be stored in memory of the surgical instrument. The Tables 1-5 may be stored in memory in the form of a look-up table (LUT) such that the control circuit 2510 can retrieve the values and control the command velocity of the I-beam 2514 in each zone based on the values stored in the LUT.

FIG. 39 is a graphical depiction 10100 comparing the I-beam 2514 stroke rotation interval $\delta_n$ as a function of time 10102 (top graph) and expected force-to-fire the I-beam 2514 as a function of time 10104 (bottom graph) according to one aspect of this disclosure. Referring to the top graph 10102, the horizontal axis 10106 represents time (t) in seconds (sec) from 0-1.00X, where X is a scaling factor. For example, in one aspect, X=6 and the horizontal axis 10106 represents time from 0-6 sec. The vertical axis 10108 represents displacement ($\delta$) of the I-beam 2514 in millimeters (mm). The rotation interval $\delta_1$ represents the I-beam 2615 stroke 10114 or displacement at the top of the ramp 10006 (FIGS. 36A, 36B) for thin tissue and medium thick tissue. The time for the I-beam 2514 to reach the top of ramp stroke 10114 for thin tissue is $t_1$ and the time for the I-beam 2514 to reach the top of ramp stroke 10114 for medium thick tissue is $t_2$. As shown, $t_1 < t_2$, such that it takes less time for the I-beam 2514 to reach the top of the ramp stroke 10114 for thin tissue as it takes for medium or thick tissue. In one example, the top of ramp stroke 10114 rotation interval 51 is about 4.1 mm (01.60 inches) and the time $t_1$ is less than 0.9 sec ($t_1 < 0.9$ sec) and the time $t_2$ is greater than 0.9 sec but less than 1.8 sec ($0.9 < t_2 < 1.8$ sec). Accordingly, with reference also to Table 5, the velocity to reach the top of ramp stroke 10114 is fast for thin tissue and medium for medium thick tissue.

Turning now to the bottom graph 10104, the horizontal axis 10110 represents time (t) in seconds (sec) and has the same scale of the horizontal axis 10106 of the top graph 10102. The vertical axis 10112, however, represents expected force to fire (F) the I-beam 2514 in newtons (N) for thin tissue force to fire graph 10116 and medium thick tissue force to fire graph 10118. The thin tissue force to fire graph 10116 is lower than medium thick tissue force to fire graph 10118. The peak force $F_1$ for the thin tissue force to fire graph 10116 is lower than the peak force $F_2$ for the medium thick tissue to fire graph 10118. Also, with reference to the top and bottom graphs 10102, 10104, the initial velocity of the I-beam 2514 in zone $Z_o$ can be determined based on estimated tissue thickness. As shown by the thin tissue force to fire graph 10116, the I-beam 2514 reaches the peak force $F_1$ top of ramp stroke 10114 at a fast initial velocity (e.g., 30 mm/sec) and as shown by the medium thick tissue force to fire graph 10118, the I-beam 2514 reaches the peak force $F_2$ top of ramp stroke 10114 at a medium initial velocity (e.g., 12 mm/sec). Once the initial velocity in zone $Z_o$ is determined, the control circuit 2510 can set the estimated velocity of the I-beam 2514 in zone $Z_1$, and so on.

FIG. 40 is a graphical depiction 10200 comparing tissue thickness as a function of set rotation interval of I-beam stroke 10202 (top graph), force to fire as a function of set rotation interval of I-beam stroke 10204 (second graph from the top), dynamic time checks as a function of set rotation interval of I-beam stroke 10206 (third graph from the top), and set velocity of I-beam as a function of set rotation interval of I-beam stroke 10208 (bottom graph) according to one aspect of this disclosure. The horizontal axis 10210 for each of the graphs 10202, 10204, 10206, 10208 represents set rotation interval of the shaft of the motor 2504 for a 60 mm staple cartridge, for example. The motor 2504 shaft rotations correspond to a displacement of the displacement member, such as the I-beam 2514, for example. In one example, a 60 mm cartridge 2518 can be traversed by the I-beam 2514 in about 142 rotations of the motor 2504 shaft with a 60 threads per inch screw drive. With reference also to Table 1, the horizontal axis 10210 has been marked to identify the defined zones $Z_1$-$Z_6$ for a 60 mm staple cartridge. As indicated in Table 1, the defined zones may be marked for staple cartridges of various sizes. The horizontal axis 10210 is marked from 0 to 142 rotations for a 60 mm cartridge and 60 threads per inch leadscrew drive. With reference also to FIG. 14, in accordance with the present disclosure, the control circuit 2510 samples or measures the elapsed time from the timer/counter circuit 2531 for a number of motor 2504 shaft rotation intervals corresponding to the displacement of the I-beam 2514 traversing the staple cartridge 2518 during the firing stroke. At set rotation intervals $\delta_n$, 12 rotations, 23 rotations, or other suitable number of shaft rotations for example, received from the position sensor 2534, the control circuit 2510 samples or measures the elapsed time $t_n$ taken by the I-beam 2514 to travel a distance corresponding to the fixed rotation intervals $\delta_n$. For example, a leadscrew with 60 threads per inch corresponds to 0.42 mm per rotation. Thus, 12 rotations of the motor 2504 shaft correspond to a linear displacement of 5.04 mm (~5 mm) and 23 rotations of the motor 2504 shaft corresponds to a displacement of 9.66 mm (~10 mm), for example. In this manner, the control circuit 2510 can determine the actual velocity of the I-beam 2514 and compare the actual velocity to the estimated velocity and make any necessary adjustments to the motor 2504 velocity.

The tissue thickness graph 10202 shows a tissue thickness profile 10220 along the staple cartridge 2518 and an indicated thickness 10221 as shown by the horizontal dashed line. The force to fire graph 10204 shows the force to fire profile 10228 along the staple cartridge 2518. The force to fire 10230 remains relatively constant while the tissue thickness 10222 remains below the indicated thickness 10221 as the I-beam 2514 traverse zones $Z_1$ and $Z_2$. As the I-beam 2514 enters zone $Z_3$, the tissue thickness 10224 increases and the force to fire also increase while the I-beam 2514 traverses the thicker tissue in zones $Z_3$, $Z_4$, and $Z_5$. As the I-beam 2514 exits zone $Z_5$ and enters zone $Z_6$, the tissue thickness 10226 decrease and the force to fire 10234 also decreases.

With reference now to FIGS. 14, 36A-40 and Tables 2-3, the velocity $\Phi_1$ in zone $Z_1$ is set to the command velocity $\Phi_o$ in rotations per second determined by the control circuit 2510 in zone $Z_o$, which is based on the time it takes the I-beam 2514 to travel to the top of the ramp 10006 in zone $Z_o$ as discussed in reference to FIGS. 36A, 36B, and 38. Turning also to the graphs 10206, 10208 in FIG. 39, the initial set velocity $\Phi_o$ was set to Medium and thus the set velocity $\Phi_1$ in zone $Z_1$ is set to Medium such that $\Phi_1=\Phi_o$.

At set rotation position $\delta_1$ (e.g., 12 rotations [5.04 mm] for a 60 mm staple cartridge and 60 threads per inch leadscrew), as the I-beam 2514 exits zone $Z_1$ and enters zone $Z_2$, the control circuit 2510 measures the actual time $t_1$ that it takes the I-beam 2514 to travel a set distance during the set rotation interval $\ominus_1$ (12 rotations, 5.04 mm) and determines the actual velocity of the I-beam 2514. With reference to graphs 10206 and 10208 in FIG. 39, at set rotation position $\delta_1$, the actual time $t_1$ it takes the I-beam 2514 to travel a set distance during the set rotation interval $\ominus_1$ is $t_1=0.55$ sec. According to Table 3, an actual travel time $t_1=0.55$ sec in zone $Z_1$ requires the command or set velocity $\Phi_2$ in zone $Z_2$ to be set to Medium. Accordingly, the control circuit 2510 does not reset the command velocity for zone $Z_2$ and maintains it at Medium.

At set rotation position $\delta_2$ (e.g., 35 rotations [14.7 mm] for a 60 mm staple cartridge and 60 threads per inch leadscrew), as the I-beam 2514 exits zone $Z_2$ and enters zone $Z_3$, the control circuit 2510 measures the actual time $t_2$ it takes the I-beam 2514 to travel a set distance during the set rotation interval $\ominus_2$ (23 rotations, 9.66 mm) and determines the actual velocity of the I-beam 2514. With reference to graphs 10606 and 10608 in FIG. 39, at set rotation position $\delta_2$, the actual time $t_2$ it takes the I-beam 2514 to travel a set distance during the set rotation interval $\ominus_2$ is $t_2=0.95$ sec. According to Table 3, an actual travel time $t_2=0.95$ sec in zone $Z_2$ requires the command or set velocity $\Phi_3$ in zone $Z_3$ to be set to Medium. Accordingly, the control circuit 2510 does not reset the command velocity for zone $Z_3$ and maintains it at Medium.

At set rotation position $\delta_3$ (e.g., 59 rotations [24.78 mm] for a 60 mm staple cartridge and 60 threads per inch leadscrew), as the I-beam 2514 exits zone $Z_3$ and enters zone $Z_4$, the control circuit 2510 measures the actual time $t_3$ it takes the I-beam 2514 to travel a set distance during the set rotation interval $\ominus_3$ (23 rotations, 9.66 mm) and determines the actual velocity of the I-beam 2514. With reference to graphs 10606 and 10608 in FIG. 39, at set rotation position $\delta_3$, the actual time $t_3$ it takes the I-beam 2514 to travel a set distance during the set rotation interval $\ominus_3$ is $t_3=1.30$ sec. According to Table 3, an actual travel time $t_3=1.30$ sec in zone $Z_3$ requires the command or set velocity $\Phi_4$ in zone $Z_4$ to be set to Slow. This is because the actual travel time of 1.3 sec is greater than 1.10 sec and is outside the previous range. Accordingly, the control circuit 2510 determines that the actual I-beam 2514 velocity in zone $Z_3$ was slower than expected due to external influences such as thicker tissue than expected as shown in tissue region 10224 in graph 10202. Accordingly, the control circuit 2510 resets the command velocity $\Phi_4$ in zone $Z_4$ from Medium to Slow.

In one aspect, the control circuit 2510 may be configured to disable velocity reset in a zone following a zone in which the velocity was reset. Stated otherwise, whenever the velocity is updated in a present zone the subsequent zone will not be evaluated. Since the velocity was updated in zone $Z_4$, the time it takes the I-beam 2514 to traverse zone $Z_4$ will not be measured at the end of zone $Z_4$ at the set rotation distance $\delta_4$ (e.g., 82 rotations [34.44 mm] for a 60 mm staple cartridge). Accordingly, the velocity in zone $Z_5$ will remain the same as the velocity in zone $Z_4$ and dynamic time measurements resume at set rotation position $\delta_5$ (e.g., 106 rotations [44.52 mm] for a 60 mm staple cartridge and 60 threads per inch leadscrew).

At set rotation position $\delta_5$ (e.g., 106 rotations [44.52 mm] for a 60 mm staple cartridge and 60 threads per inch leadscrew) as the I-beam 2514 exits zone $Z_5$ and enters zone $Z_6$, the control circuit 2510 measures the actual time $t_5$ it takes the I-beam 2514 to travel a set distance during the set rotation interval $\ominus_5$ (23 rotations, 9.75 mm) and determines the actual velocity of the I-beam 2514. With reference to graphs 10606 and 10608 in FIG. 39, at set rotation position $\delta_5$, the actual time $t_5$ it takes the I-beam 2514 to travel a set distance during the set rotation interval $\ominus_5$ is $t_5=0.95$ sec. According to Table 3, an actual travel time of $t_5=0.95$ sec in zone $Z_5$ requires the command or set velocity $\Phi_6$ in zone $Z_6$ to be set to High. This is because the actual travel time of 0.95 sec is less than 1.00 sec is outside the previous range. Accordingly, the control circuit 2510 determines that the actual velocity of the I-beam 2514 in zone $Z_5$ was faster than expected due to external influences such as thinner tissue than expected as shown in tissue region 10626 in graph 10602. Accordingly, the control circuit 2510 resets the command velocity $\Phi_6$ in zone $Z_6$ from Slow to High.

FIG. 41 is a graphical depiction 10300 of force to fire as a function of time comparing slow, medium and fast I-beam 2514 displacement velocities according to one aspect of this disclosure. The horizontal axis 10302 represents time t (sec) that it takes an I-beam to traverse a staple cartridge. The vertical axis 10304 represents force to fire F (N). The graphical depiction shows three separate force to fire curves versus time. A first force to fire curve 10312 represents an I-beam 2514 (FIG. 14) traversing through thin tissue 10306 at a fast velocity and reaching a maximum force to fire $F_1$ at the top of the ramp 10006 (FIG. 36B) at $t_1$. In one example, a fast traverse velocity for the I-beam 2514 is ~30 mm/sec (~71 rotations/sec). A second force to fire curve 10314 represents an I-beam 2514 traversing through medium tissue 10308 at a medium velocity and reaching a maximum force to fire $F_2$ at the top of the ramp 10006 at $t_2$, which is greater than $t_1$. In one example, a medium traverse velocity for the I-beam 2514 is ~12 mm/sec (~29 rotations/sec). A third force to fire curve 10316 represents an I-beam 2514 traversing through thick tissue 10310 at a slow velocity and reaching a maximum force to fire $F_3$ at the top of the ramp 9006 at $t_3$, which is greater than $t_2$. In one example, a slow traverse velocity for the I-beam 2514 is ~9 mm/sec (~21 rotations/sec).

FIG. 42 is a logic flow diagram of a process 10400 depicting a control program or logic configuration for controlling command velocity in an initial firing stage according to one aspect of this disclosure. With reference also to FIGS. 14 and 36A-40, the control circuit 2510 determines 10402 the reference position of the displacement member, such as the I-beam 2514, based on the number of rotations of the motor 2504 shaft and the number threads per mm or inch of the leadscrew. As discussed previously, a leadscrew having 60 threads per inch advances the displacement member 0.42 mm per rotation of the shaft. The position information based on the shaft rotation information is provided by the position sensor 2534. In the I-beam 2514 example, the reference position is the proximal or parked position 10002 at the bottom of the closure ramp 10006 as shown in FIG. 36B. Once the reference position is determined 10402, the control circuit 2510 and motor control 2508 set the command velocity of the motor 2504 to a predetermined command velocity $\Phi_o$ and initiates 10404 firing the displacement member (e.g., I-beam 2514) at the predetermined command velocity $\Phi_o$ for the initial or base zone $Z_o$. In one example, the initial predetermined command velocity $\Phi_o$ is ~12 mm/sec (29 rotations/sec), however, other initial predetermined command velocity $\Phi_o$ may be employed. The control circuit 2510 monitors 10406 the shaft rotation information received from the position sensor 2534 until the I-beam 2514 reaches a target position at the top of the ramp 10006 as shown in FIG. 36B. The predetermined rotation interval period $T_o$ is the expected period that the displacement member will take to travel a predetermined distance while traveling at the current set command velocity $\Phi_o$. The deviation between actual rotation period $T_n$ and the predetermined rotation period $T_o$ is due at least in part to external influences acting on the displacement member such as tissue thickness acting on the cutting edge 2509 of the I-beam 2514.

With timing information received from the timer/counter circuit 2531 and shaft rotation information received from the position sensor 2534, the control circuit 2510 measures 10408 the time $t_o$ it takes the displacement member to travel from the reference position 10002 to the target position 10004 after a specified number of shaft rotations (e.g., 12 or 24 rotations). The control circuit 210 sets 10410 the command velocity $\Phi_1$ for the first zone $Z_1$ based on the measured time $t_o$. As indicated in Table 1, various defined zones may be defined for staple cartridges of various sizes. Other zones, however, may be defined. The control circuit 2510 sets 10410 the command velocity $\Phi_1$ for the first zone $Z_1$ by comparing 9412 the measured time $t_o$ to values stored in memory, such as, for example, stored in a lookup table (LUT). In one example, as indicated in Table 4 generally and in Table 5 by way of specific example, if the time $t_o$ it takes the I-beam 2514 to travel up the ramp 10006 from the reference positon 10002 to the target position 10004 at κ rotations/sec is less than 0.9 sec ($t_o$<0.9 sec), then the command velocity for the first zone $Z_1$ is set 10414 to FAST (e.g., 30 mm/sec, 71 rotations/sec). Otherwise, if the time $t_o$ (sec) for the I-beam 2514 to travel up the ramp 10006 from the reference positon 10002 to the target position 10004 at 5 rotations/sec is greater than or equal to 0.9 sec (to 0.9), then the command velocity for the first zone $Z_1$ is set 10416 to MEDIUM (e.g., 12 mm/sec, 29 rotations/sec). Subsequently, the control circuit 2510 checks 10418 for lockout and stops 10420 the motor 2504 if there is a lockout condition. Otherwise, the control circuit enters 10422 the dynamic firing phase as described below in reference to process 10450 in FIG. 42.

FIG. 43 is a logic flow diagram of a process 10450 depicting a control program or logic configuration for controlling command velocity in a dynamic firing stage according to one aspect of this disclosure. With reference also to FIGS. 14 and 36A-40, the control circuit 2510 sets 10452 the initial command velocity of the motor 2504 in rotations per second for the first zone $Z_1$ based on the initial time $t_o$, as described in reference to the process 10400 in FIG. 41. As the displacement member traverses the staple cartridge 2518, the control circuit 2510 receives the shaft rotation information from the position sensor 2534 and timing information from the timer/counter 2531 circuit and monitors 10454 the number of shaft rotations that represent the position of the displacement member over the predefined zone $Z_n$. At the end of the zone $Z_n$, the control circuit 2510 measures 10456 the actual time $t_n$ the displacement member took to travel from the beginning of the zone $Z_n$ to the end of the zone $Z_n$ based on a predetermined number of shaft rotations and compares 10458 the actual time $t_n$ to a predetermined time for a particular zone as shown generally in Table 2 and by way of specific example in Table 3. The predetermined rotation period $T_n$ is the expected rotation period of the displacement member traveling at the current set command velocity $\Phi_n$ rotations/sec. The deviation between actual rotation period $t_n$ and the predetermined rotation period $T_n$ is due at least in part to external influences acting on the displacement member such as tissue thickness acting on the cutting edge 2509 of the I-beam 2514.

For example, with reference to Table 3 the time to travel through a zone at a specified command velocity is provided for various dynamic firing zones. For example, if the dynamic firing zone is the zone $Z_1$ (12 rotations) and $t_n$<0.5 sec, the command velocity for the next zone $Z_2$ is set to FAST; if 0.5<$t_n$<0.6 sec, the command velocity for the next zone $Z_2$ is set to MEDIUM; and if $t_n$>0.6 sec, the command velocity for the next zone $Z_2$ is set to SLOW.

If, however, the dynamic firing zone is an intermediate zone $Z_2$-$Z_5$ (24 rotations), for example, located between the first zone $Z_1$ and the last zone $Z_6$ and if $t_n$<0.9 sec, the command velocity for the next zone $Z_2$ is set to FAST; if 0.9<$t_n$<1.1 sec, the command velocity for the next zone $Z_3$-$Z_5$ is set to MEDIUM; and if $t_n$>1.1 sec, the command velocity for the next zone $Z_3$-$Z_5$ is set to SLOW.

Finally, if the dynamic firing zone is the last measured zone $Z_5$ (24 rotations) and $t_n$<1.0 sec, the command velocity for the final zone $Z_6$ is set to FAST; if 1.0<$t_n$<1.3 sec, the command velocity for the final zone $Z_6$ is set to MEDIUM; and if $t_n$>1.3 sec, the command velocity for the final zone $Z_6$ is set to SLOW. Other parameters may be employed not only to define the dynamic firing zones but also to define the time to travel through a zone at specified command velocity for various dynamic firing zones.

Based on the results of the comparison 10458 algorithm, the control circuit 2510 will continue the process 10450. For example, if the results of the comparison 10458 indicate that the actual velocity (FAST, MEDIUM, SLOW) in the previous zone $Z_n$ is the same as the previous command velocity $V_1$ (FAST, MEDIUM, SLOW), the control circuit 2510 maintains 10460 the command velocity for the next zone $Z_{n+1}$ the same as the as the previous command velocity. The process 10450 continues to monitor 10454 the number of shaft rotations over the next predefined zone $Z_{n+1}$. At the end of the next zone $Z_{n+1}$, the control circuit 2510 measures 10456 the time $t_{n+1}$ the displacement member took to travel a distance from the beginning of the next zone $Z_{n+1}$ to the end of the next zone $Z_{n1}$ during the predetermined number of shaft rotations and compares 10458 the actual time $t_{n+1}$ to a predetermined time for a particular zone as shown generally in Table 2 and by way of specific example in Table 3. If there are no changes required to the command velocity, the process 10450 until the number of rotations indicates that the displacement member, e.g., the I-beam 2514, has reached the end of stroke 10466 and returns 10468 the displacement member to the reference position 10002.

If the results of the comparison 10458 indicate that the actual velocity (FAST, MEDIUM, SLOW) in the previous zone $Z_n$ is different as the previous command velocity $\Phi_1$ (FAST, MEDIUM, SLOW), the control circuit 2510 resets 10462 or updates the command velocity for the next zone $Z_{n+1}$ according to the algorithm summarized in Tables 2 and 3. If the command speed is reset 10462 or updated to $\Phi_{new}$, the control circuit 2510 maintains 10464 the command velocity $\Phi_{new}$ for an additional zone $Z_{n+2}$. In other words, at the end of the next zone $Z_{n+1}$, the control circuit 2510 does not evaluate or measure the time. The process 10450 continues to monitor 10454 the number of shaft rotations representative of the position of the displacement member over the next predefined zone $Z_{n+1}$ until the number of rotations indicates that the displacement member, e.g., the I-beam 2514, has reached the end of stroke 10466 and returns 10468 the displacement member to the reference position 10002.

Various aspects of the subject matter described herein are set out in the following numbered examples:

Example 1. A surgical instrument, comprising: a displacement member configured to translate within the surgical instrument over a plurality of predefined zones; a motor comprising a shaft, the motor coupled to the displacement member to translate the displacement member; a control circuit coupled to the motor; a position sensor coupled to the control circuit, the position sensor configured to monitor the rotation of the shaft; a timer circuit coupled to the control circuit, the timer/counter circuit configured to measure elapsed time; wherein the control circuit is configured to: receive, from the position sensor, rotations of the shaft in a current zone defined by a set rotation interval; measure time at a set position of the rotation interval, wherein the measured time is defined as the time taken by the displacement member to traverse the rotation interval based on a predetermined number of shaft rotations; and set a command velocity of the displacement member for a subsequent zone based on the measured time in the current predefined zone.

Example 2. The surgical instrument of Example 1, wherein the control circuit is configured to: determine the set rotation interval in which the displacement member is located, wherein the set rotation interval is defined by a number of rotations of the shaft that result in a linear translation of the displacement member from a beginning position to an ending position; and measure the time when the displacement member reaches the ending position of the rotation interval.

Example 3. The surgical instrument of Example 1, wherein the control circuit is configured to: compare the measured time to a predetermined time stored in a memory coupled to the control circuit; and determine whether to adjust or maintain the command velocity based on the comparison.

Example 4. The surgical instrument of Example 3, wherein the control circuit is configured to maintain the command velocity for the subsequent zone the same as the command velocity of the current zone when the measured time is within a range of predetermined times.

Example 5. The surgical instrument of Example 3, wherein the control circuit is configured to set the command velocity for the subsequent zone different from the command velocity of the current zone when the measured time is outside a range of predetermined times.

Example 6. The surgical instrument of Example 5, wherein the control circuit is configured to skip a time measurement for a subsequent zone when the command velocity is adjusted.

Example 7. The surgical instrument of Example 1, wherein multiple zones are defined for a staple cartridge configured to operate with the surgical instrument.

Example 8. The surgical instrument of Example 7, wherein at least two zones have a different length.

Example 9. The surgical instrument of Example 1, further comprising a screw drive system coupled to the shaft of the motor, the screw drive system comprising a lead screw coupled to a nut, wherein the nut is coupled to the displacement member.

Example 10. A surgical instrument, comprising: a displacement member configured to translate within the surgical instrument over a plurality of predefined zones; a motor comprising a shaft, the motor coupled to the displacement member to translate the displacement member; a control circuit coupled to the motor; a position sensor coupled to the control circuit, the position sensor configured to monitor the rotation of the shaft; a timer circuit coupled to the control circuit, the timer/counter circuit configured to measure elapsed time; wherein the control circuit is configured to: receive, from the position sensor, rotations of the shaft in a current zone defined by a predetermined rotation interval; measure time as the displacement member moves from a parked position to a target position based on a predetermined number of shaft rotations; and set a command velocity of the displacement member for a first dynamic zone based on the measured time.

Example 11. The surgical instrument of Example 10, wherein the control circuit is configured to compare the measured time to a predetermined time stored in a memory coupled to the control circuit.

Example 12. The surgical instrument of Example 11, wherein the control circuit is configured to set the command velocity for the initial zone to a first velocity when the measured time is within a first range of times and set the command velocity for the initial zone to a second velocity when the measured time is within a second range of times.

Example 13. The surgical instrument of Example 10, wherein the control circuit is configured to determine a lockout condition and stop the motor.

Example 14. The surgical instrument of Example 10, further comprising a screw drive system coupled to the shaft of the motor, the screw drive system comprising a lead screw coupled to a nut, wherein the nut is coupled to the displacement member.

Example 15. A method of controlling motor velocity in a surgical instrument, the surgical instrument comprising a displacement member configured to translate within the surgical instrument over a plurality of predefined zones, a motor comprising a shaft, the motor coupled to the displacement member to translate the displacement member, a control circuit coupled to the motor, a position sensor coupled to the control circuit, the position sensor configured to monitor the rotation of the shaft, a timer circuit coupled to the control circuit, the timer/counter circuit configured to measure elapsed time, the method comprising: receiving, from a position sensor, rotations of the shaft in a current zone defined by a set rotation interval; measuring, by a timer circuit, a time at a set position of the of the rotation interval, wherein the measured time is defined by the time taken by the displacement member to traverse the rotation interval based on a predetermined number of shaft rotations; and setting, by the control circuit, a command velocity of the displacement member for a subsequent zone based on the measured time in the current zone.

Example 16. The method of Example 15, further comprising: determining, by the control circuit and the timer circuit, the set rotation interval in which the displacement member is located, wherein the set rotation interval is defined by a number of rotations of the shaft that result in a linear translation of the displacement member from a beginning position to an ending position; and measuring, by the control circuit, the time when the displacement member reaches the ending position of the rotation interval.

Example 17. The method of Example 15, further comprising: comparing, by the control circuit, the measured time to a predetermined time stored in a memory coupled to the control circuit; and determining, by the control circuit, whether to adjust or maintain the command velocity based on the comparison.

Example 18. The method of Example 17, further comprising maintaining, by the control circuit, the command velocity for the subsequent zone the same as the command velocity of the current zone when the measured time is within a range of predetermined times.

Example 19. The method of Example 17, further comprising setting, by the control circuit, the command velocity for the subsequent zone different from the command velocity of the current zone when the measured time is outside a range of predetermined times.

Example 20. The method of Example 19, further comprising skipping, by the control circuit, a time measurement for a subsequent zone when the command velocity is adjusted.

Example 21. The method of Example 15, further comprising defining, by the control circuit, multiple zones are defined for a staple cartridge configured to operate with the surgical instrument.

Example 22. The method of Example 21, further comprising defining, by the control circuit, at least two zones having a different length.

Systems and Methods for Controlling Displaying Motor Velocity for a Surgical Instrument During use of a motorized surgical stapling and cutting instrument it is possible that the user may not know the command velocity or the actual velocity of the cutting member or firing member. Therefore, it may be desirable to communicate information to the user through a display screen to provide information about the firing velocity of the cutting member or firing member where the velocity is related to the size of the zone that is indicated on the display screen. It may be desirable to communicate velocity control to show the command velocity as well as the firing mode in a closed loop feedback automatic mode or manually selected mode.

The disclosure now turns to a closed loop feedback system for controlling motor velocity based on a variety of conditions. The closed loop feedback system as executed by the control circuit 2510 can be configured to implement either a default, e.g., pre-programmed, firing condition or a user-selected firing condition. The user selected firing condition can be selected during the open loop portion or otherwise prior to the closed loop portion of the displacement stroke. In one aspect, the user-selected firing condition is configured to override the execution of the default or pre-programmed firing condition.

Turning now to FIG. 44, there is shown a perspective view of a surgical instrument 10500 according to one aspect of this disclosure. In one aspect, a surgical instrument 10500 comprising an end effector 10504 connected via a shaft 10503 to a handle assembly 10502 further comprises a display 10506. The surgical instrument 10500 comprises a home button 10508, an articulation toggle 10510, a firing trigger and safety release 10512, and a closure trigger 10514.

In the following discussion, reference should also be made to FIG. 14. The display 10506 is operably coupled to the control circuit 2510 such that the control circuit 2510 can cause the display 10506 to show various information associated with the operation of the instrument 10500, such as information determined by or from the position sensor 2534, the current sensor 2536, and/or the other sensors 2538. In one aspect, the display 10506 can be configured to display the velocity at which the I-beam 2514 is set to be translated by the motor 2504, i.e., a command velocity, and/or the actual velocity at which the I-beam 2514 is being translated. The command velocity is the set, target, or desired velocity. The command velocity at which the I-beam 2514 is to be translated can be determined by either receiving the motor set point, which dictates the velocity at which the motor 2504 drives the I-beam 2514, dictated by the motor drive signal 2524 from the motor control 2508 or storing the motor drive signal 2524 that is provided to the motor control 2508 in a memory for subsequent retrieval. The actual velocity at which the I-beam 2514, or other component of the firing drive system, is being translated can be determined by monitoring the position of the I-beam 2514 over a time period, which can be tracked by the control circuit 2510 via input from the timer/counter 2531.

In various aspects, the display 10506 of the surgical instrument 10500 can be positioned directly on the exterior housing or casing of the handle assembly 10502 or otherwise integrally associated with the surgical instrument 10500. In other aspects, the display 10506 can be removably connectable or attachable to the surgical instrument 10500. In still other aspects, the display 10506 can be separate or otherwise distinct from the surgical instrument 10500. The display 10506 can be communicably coupled to the control circuit 2510 via either a wired connection or a wireless connection.

FIG. 45 is a detail view of a display 10506 portion of the surgical instrument 10500 shown in FIG. 44 according to one aspect of this disclosure. The display 10506 includes an LCD display 10516 to communicate velocity control including showing the command velocity as well as if the firing mode is in a closed loop feedback (automatic) mode or manually selected mode. The display 10506 provides transection feedback by displaying a graphic image of an end effector staple cartridge 10518 with a knife 10520 and rows of staples 10522. A left graphic label 10524 indicates the distance 10528 the knife 10520 has traveled (e.g., 10 mm) distally and a right graphic label 10526 indicates the velocity of the knife 10520 as it travels distally where the current velocity is circled (e.g., 3), where 1 is fast, 2 is medium, and 3 is slow velocity. The velocity may be selected manually or automatically based on the conditions of the tissue.

FIG. 46 is a logic flow diagram of a process 10550 depicting a control program or logic configuration for controlling a display according to one aspect of this disclosure. Reference should also be made to FIGS. 14 and 44. Accordingly, the control circuit 2510 first receives 10552 command velocity from the instrument input and sets 10554 the motor 2504 velocity to the command velocity. The control circuit 2510 receives 10556 position information of the displacement member (e.g., I-beam 2514) from the position sensor 2534 and receives 10558 timing information from the timer/counter circuit 2531 and determines 10560 the velocity of the displacement member. The velocity of the I-beam 2514 can include the actual velocity at which the I-beam 2514 is translated or the command velocity at which the I-beam 2514 was set to be translated. The control circuit 2510 then causes the display 10506 to display 10562 an indicia indicative of the actual velocity of the displacement member and/or the command velocity depending on the configuration of the instrument 10500. In one aspect, the control circuit 2510 determines 10560 both the actual and command velocities of the I-beam 2514 and then causes the display 10506 to display 10562 an indicia for each of the actual and command velocities. The control circuit 2510 then compares 10564 the velocity of the displacement member to the command velocity and causes the display 10506 to display 10566 an indicia regarding the comparison. For example, the control circuit 2510 can cause the display 10506 to display indicia that show whether the actual velocity of the displacement member is equal to, greater than, or less than the command velocity. In some aspects, the control circuit 2510 causes the display 10506 to display the actual velocity of the displacement member relative to a range of command velocities such as, for example, low or slow (e.g., 0-7 mm/sec), medium (e.g., 7-12 mm/sec), or high or fast (e.g., 12-30 mm/sec). Furthermore, the control circuit 2510 receives 10568 the operation status of the battery from the energy source 2512 such as voltage, current, impedance, capacity, temperature, and the like, and causes the display 10506 to display 10570 the status of the battery.

The indicia for the velocity or velocities can include a numeral indicating a velocity presented in, e.g., mm/sec, a numeral indicating a value of the velocity relative to a maximum or minimum value, a shape that is altered according to the velocity, a shape that is filled or shaded with a color according to the velocity, a shape or alphanumeric character that flashes according to the velocity, a shape or alphanumeric character that changes in color according to the velocity, a dial indicative of the absolute or relative velocity, a shape or alphanumeric character indicative of a zone in which the velocity falls, an icon or series of icons representing an animal indicative of a velocity, various other indicia configured to represent a velocity, and combinations thereof. These indicia are illustrated and described below in the form of depictions of display feedback screens in reference to FIGS. 47-81, for example.

FIGS. 47-49 illustrate various displays 10600 depicting a velocity feedback screen according to one aspect of this disclosure. The display 10600 depicts a graphic image of an end effector staple cartridge 10618. The display 10600 comprises velocity indicia 10602 to indicate the command or actual velocity of the displacement member (e.g., I-beam 2514). In one aspect, the velocity indicia 10602 comprises a shape or series of shapes that are filled or shaded proportionally to the velocity, such as is depicted in FIGS. 47-49. The shape or shapes of the velocity indicia 10602 can include, e.g., a triangular frustum or any other suitable geometric shape. In one aspect, the velocity indicia 10602 can comprise a plurality of zones that are indicative of the relative value of the velocity. In one such aspect, the velocity indicia 10602 comprises a first zone 10604, a second zone 10606, and a third zone 10608 that correspond respectively to slow, medium, and fast velocity. The control circuit 2510 causes the display 10600 to indicate the zone in which the velocity falls, as determined by the control circuit 2510 as discussed above. Each of the zones 10604, 10606, 10608 may comprise graduations 10610 or marks to provide additional resolution of the command velocity of the I-beam 2514 element. In addition, the velocity indicia 10602 may comprise a graphic that represents slow velocity such as a silhouette of a tortoise 10612 below the first zone 10604 and a graphic that represents fast velocity such as a silhouette of a hare 10614 above the third zone 10608. As illustrated in FIG. 47, the command velocity is set to medium as indicated by the first and second zones 10604, 10606 being filled or shaded while the third zone 16008 is unfilled or unshaded. As illustrated in FIG. 48, the command velocity is set to low as indicated by only the first zone 10604 being filled or shaded while the second and third zones 10606, 16008 are unfilled or unshaded. As illustrated in FIG. 49, the command velocity is set to high as indicated by all three zones 10604, 10606, 10608 being completely filled or shaded. A status bar 10620 at the bottom of the display 10600 indicates operation status as normal (e.g., green) or cautionary (e.g., yellow). In the examples shown in FIGS. 47-49 the status bar 10620 indicates normal operation.

In some aspects, the display 10600 further comprises a mode indicia indicative of the mode to which the surgical instrument 10500 is set. Such modes can include, e.g., an automatic mode 10616 or a manual mode 10622. Such modes and processes for the control circuit 2510 to control the velocity at which the I-beam 2514 is driven and correspondingly cause the display 10600 to indicate the mode of the surgical instrument 10500 are described in U.S. patent application Ser. No. 15/628,077, titled SYSTEMS AND METHODS FOR CONTROLLING MOTOR SPEED ACCORDING TO USER INPUT FOR A SURGICAL INSTRUMENT, filed Jun. 20, 2017, which is herein incorporated by reference in its entirety. In some aspects, the automatic mode 10616 or manual mode 10622 may be flash 10624.

The velocity indicia 10602 can additionally comprise various alphanumeric characters configured to indicate the velocity. The alphanumeric characters can be presented singularly or in combination with other indicia, such as the zones.

In one aspect, the size or relative portion of the display 10600 occupied by the velocity indicia 10602 corresponds to the velocity. For example, the velocity indicia 10602 can be filled or shaded according to the velocity relative to a maximum velocity, as is depicted in FIGS. 47-55. In another aspect wherein the velocity indicia 10602 comprise alphanumeric characters, the size of the alphanumeric character can increase in size according to the velocity determined by the control circuit 2510.

FIGS. 50-52 illustrate various displays 10630 depicting a velocity feedback screen according to one aspect of this disclosure. The display 10630 depicts a graphic image of an end effector staple cartridge 10642. The display 10630 comprises velocity indicia 10632 to indicate the command or actual velocity of the displacement member (e.g., I-beam 2514). In one aspect, the velocity indicia 10632 comprises a shape or series of shapes that are filled or shaded proportionally to the velocity, such as is depicted in FIGS. 50-52. The shape or shapes of the velocity indicia 10632 can include, e.g., a triangular frustum or any other suitable geometric shape. In one aspect, the velocity indicia 10632 can comprise a plurality of zones that are indicative of the relative value of the velocity. In one such aspect, the velocity indicia 10632 comprises a first zone 10634, a second zone 10636, and a third zone 10638 that correspond respectively to slow, medium, and fast velocity. The control circuit 2510 causes the display 10630 to indicate the zone in which the velocity falls, as determined by the control circuit 2510 as discussed above. Each of the zones 10634, 10636, 10638 may comprise graduations 10640 or marks to provide additional resolution of the command velocity of the I-beam 2514 element. In addition, the velocity indicia 10632 may comprise an alphanumeric character 10644 to indicate either automatic or manual modes of operation. In the illustrated examples, the mode is set to AUTO for automatic. A status bar 10646 at the bottom of the display 10630 indicates operation status as normal (e.g., green) or cautionary (e.g., yellow). In the examples shown in FIGS. 50-52 the status bar 10646 indicates normal operation.

As illustrated in FIG. 50, the command velocity is set to medium as indicated by filled or shaded first and second zones 10634, 10636 and unfilled or unshaded third zone 16038. As illustrated in FIG. 51, the command velocity is set to low as indicated by a filled or shaded first zone 10634 and unfilled or unshaded second and third zones 10636, 16038 are unfilled or unshaded. As illustrated in FIG. 52, the command velocity is set to high as indicated by all three zones 10634, 10636, 10638 filled or shaded.

FIGS. 53-55 illustrate various displays 10650 depicting a velocity feedback screen according to one aspect of this disclosure. The display 10650 depicts a graphic image of an end effector staple cartridge 10662. The display 10650 comprises velocity indicia 10652 to indicate the command velocity as well as the actual velocity of the displacement member (e.g., I-beam 2514). In one aspect, the velocity indicia 10652 comprises a shape or series of shapes that are filled or shaded proportionally to the velocity, such as is depicted in FIGS. 53-55. The shape or shapes of the velocity indicia 10652 can include, e.g., a triangular frustum or any other suitable geometric shape. In one aspect, the velocity indicia 10652 can comprise a plurality of zones that are indicative of the relative value of the velocity. In one such aspect, the velocity indicia 10652 comprises a first zone 10654, a second zone 10656, and a third zone 10658 that correspond respectively to slow, medium, and fast actual velocity. The control circuit 2510 causes the display 10650 to indicate the zone in which the velocity falls, as determined by the control circuit 2510 as discussed above. Each of the zones 10654, 10656, 10658 may comprise graduations 10660 or marks to provide additional resolution of the command velocity of the I-beam 2514 element. In addition the velocity indicia 10652 may include an icon comprising an alphanumeric character located within a geometric element to represent low, medium, and high velocity. In the example illustrated in FIGS. 53-55, the velocity indicia 10652 may include an additional alphanumeric character such as a circled "H" icon 10653, a circled "M" icon 10655, and a circled "L" icon 10657 indicate the command velocity. Depending on the command velocity, the H" icon 10653, the "M" icon 10655, or the "L" icon 10657 will be filled, shaded, or lit to indicate the command velocity setting. In addition, the velocity indicia 10652 may comprise an alphanumeric character 10664 to indicate either automatic or manual modes of operation. In the illustrated examples, the mode is set to MANUAL for automatic. A status bar 10666 at the bottom of the display 10650 indicates operation status as normal (e.g., green) or cautionary (e.g., yellow). In the examples shown in FIGS. 53-55 the status bar 10666 indicates normal operation. In one aspect, the fill or shade color of the "H" icon 10653, the "M" icon graphic 10655, and the "L" icon 10657 may be same as the fill or shade color of the status bar 10666 to indicate normal or caution modes of operation.

As illustrated in FIG. 53, the actual velocity is set to medium as indicated by the filled or shaded first and second zones 10654, 1066 and an unfilled or unshaded third zone 16058 and the command velocity is set to medium as indicated by the filled or shaded "M" icon 10655 (and unfilled or unshaded "H" and "L" icons 10653, 10657). As illustrated in FIG. 54, the actual velocity is slow as indicated by the filled or shaded first zone 10654 (and unfilled or unshaded second and third zones 10656, 16058) and the command velocity is set to low as further indicated by the filled "L" icon 10657 (and unfilled or unshaded "H" and "M" icons 10653, 10655). As illustrated in FIG. 55, the actual velocity is fast as indicated by all three zones 10654, 10656, 10658 completely filled or shaded and as the command velocity is set to high as further indicated by the filled or shaded "H" icon 10653 (and unfilled or unshaded circled "M" and circled "L" graphics 10655, 10657).

FIGS. 56-58 illustrate various displays 10670, 10670' depicting various velocity feedback screens according to one aspect of this disclosure. The display 10670, 10670' depicts a graphic image of an end effector staple cartridge 10682. The display 10670, 10670' comprises velocity indicia 10672, 10672' to indicate the command velocity as well as the actual velocity of the displacement member (e.g., I-beam 2514) during the firing cycle. In one aspect, the velocity indicia 10672, 10672' comprises a shape or series of shapes that are filled or shaded proportionally to the velocity, such as is depicted in FIGS. 56-58. The shape or shapes of the velocity indicia 10672, 10672' can include, e.g., an arcuate or any other suitable geometric shape. In one aspect, the velocity indicia 10672, 10672' can comprise an arcuate graphic 10678, 10678' comprising multiple graduations 10680 to indicate the actual velocity from 0-30 mm/sec, for example, of the displacement member. Alphanumeric characters 10684 (0, 7, 12, and 30) are disposed about the perimeter of the arcuate graphic 10678, 10678' to indicate the actual velocity by a filled or shaded region 10686. The display 10670 shown in FIG. 56 is a slightly modified version of the display 10670' shown in FIGS. 57 and 58. For example, the arcuate graphic 10678 of the display 10670 shown in FIG. 62 includes cutouts around the alphanumeric characters 10684 (7 and 12), for example.

In addition, the velocity indicia 10672, 10672' further comprises a filled or shaded circle icon 10676 with one or more white arrows to indicate the command velocity, such that, for example, one arrow refers to low velocity or slow, two arrows refer to medium velocity, and three arrows refer to high velocity or fast. An additional alphanumeric character 10674 indicates the units of velocity, e.g., mm/sec. As the velocity increases or decreases, the shaded region 10686 increases and decreases correspondingly. A status bar 10688 at the bottom of the display 10670 indicates operation status as normal (e.g., green) or cautionary (e.g., yellow). In the examples shown in FIGS. 56-58 the status bar 10688 indicates normal operation. In one aspect, the fill or shade color of the velocity region 10686 may be same as the fill or shade color of the status bar 10688 to indicate normal or caution modes of operation.

As illustrated in FIG. 56, the actual velocity is fast (~12 mm/sec) as indicated by the shaded region 10686 and the command velocity is set to high as indicated by the three arrows in the circle icon 10676. As noted earlier, the alphanumeric characters 10684 "7" and "12" include a cutout. As illustrated in FIG. 57, the actual velocity also is fast (~30 mm/sec) as indicated by the shaded region 10686 and the command velocity is set to high as indicated by the three arrows in the circle icon 10676. As illustrated in FIG. 58, the command velocity is medium (~10 mm/sec) as indicated by the shaded region 10686 and the command velocity is set to medium as indicated by the two arrows in the circle icon 10676.

FIGS. 59-61 illustrate various displays 10690, 10690', 10690" depicting various velocity feedback screens according to one aspect of this disclosure. The display 10690, 10690', 10690" depicts a graphic image of an end effector staple cartridge 10702, 10702', 10702". The display 10690, 10690', 10690" comprises velocity indicia 10692, 10692', 10692" to indicate the command velocity as well as the actual velocity of the displacement member (e.g., I-beam 2514) during the firing cycle. In one aspect, the velocity indicia 10692, 10692', 10692" comprises a shape or series of shapes that are filled or shaded proportionally to the velocity, such as is depicted in FIGS. 59-61. The shape or shapes of the velocity indicia 10692, 10692', 10692" can include, e.g., an arcuate or any other suitable geometric shape. In one aspect, the velocity indicia 10692, 10692', 10692" can comprise an arcuate graphic 10698, 10698', 10698" comprising multiple graduations 10700, 10700', 10700" to indicate the actual velocity from 0-30 mm/sec, for example. Alphanumeric characters 10704, 10704', 10704" (0, 7, 12, and 30) are disposed about the perimeter of the arcuate graphic 10698, 10698', 10698" to indicate the actual velocity by a filled or shaded region 10706, 10706', 10706". The displays 10690, 10690', 10690" are substantially similar but include some slight variations. For example, the arcuate graphic 10678 of the display 10690 depicted in FIG. 59 includes cutouts around the alphanumeric characters 10704 (7 and 12), for example, whereas the arcuate graphic 10678', 10678" of the displays 10690', 10690" depicted in FIGS. 60 and 61 do not. Furthermore, the velocity indicia 10692, 10692" of the displays 10690, 10690" depicted in FIGS. 59 and 61 include an alphanumeric character 10694, 10694" to indicate the units of velocity, e.g., mm/sec, at a bottom portion of the display 10690, 10690" whereas the display 10690' depicted in FIG. 60 includes an alphanumeric character 10694' to indicate the units of velocity, e.g., mm/sec, at a top portion of the display 10690'.

In addition, the velocity indicia 10692, 10692', 10692" further comprises a filled or shaded circle icon 10696, 10696', 10696" with one or more white arrows to indicate the command velocity, such that, for example, one arrow refers to low velocity or slow, two arrows refer to medium velocity, and three arrows refer to high velocity or fast. As the velocity increases or decreases the filled or shaded region 10706, 10706', 10706" increases and decreases correspondingly. A status bar 10708, 10708', 10708" at the bottom of the displays 10690, 10690', 10690" indicates operation status as normal (e.g., green) or cautionary (e.g., yellow). In the example shown in FIG. 59, the status bar 10708 indicates caution operation. In the examples shown in FIGS. 60-61, the bars 10708', 10708" indicate normal operation. In one aspect, the fill or shade color of the velocity region 10706, 10706', 10706" may be same as the fill or shade color of the status bar 10708, 10708', 10708" to indicate normal or caution modes of operation.

As illustrated in FIG. 59, the actual velocity is medium (~12 mm/sec) as indicated by the shaded region 10706 but the command velocity is set to fast as indicated by the three arrows in the circle icon 10696. As noted earlier, the alphanumeric characters 10704 "7" and "12" include a cutout. As illustrated in FIG. 60, the actual velocity is slow (~7 mm/sec) as indicated by the shaded region 10706' and the command velocity is set to low as indicated by the single arrow in the circle icon 10696'. As illustrated in FIG. 61, the actual velocity also is slow (~2 mm/sec) as indicated by the shaded region 10706" and the command velocity is set to low as indicated by the single arrow in the circle icon 10696".

FIGS. 62-64 illustrate various displays 10720, 10720' depicting various velocity feedback screens according to one aspect of this disclosure. The display 10720, 10720' depicts a graphic image of an end effector staple cartridge 10732. The display 10720, 10720' comprises velocity indicia 10722, 10722' to indicate the command velocity as well as the actual velocity of the displacement member (e.g., I-beam 2514) during the firing cycle. In one aspect, the velocity indicia 10722, 10722' comprises a shape or series of shapes that are filled or shaded proportionally to the velocity, such as is depicted in FIGS. 62-64. The shape or shapes of the velocity indicia 10722, 10722' can include, e.g., an arcuate or any other suitable geometric shape. In one aspect, the velocity indicia 10722, 10722' can comprise an arcuate graphic 10728, 10728' comprising multiple graduations 10736 to indicate the actual velocity from 0-30 mm/sec, for example. Alphanumeric characters 10734 (0, 7, 12, and 30) are disposed about the perimeter of the arcuate graphic 10728, 10728' to indicate the actual velocity by a filled or shaded region 10736. The display 10720 shown in FIG. 62 is a slightly modified version of the display 10720' shown in FIGS. 63 and 64. For example, the arcuate graphic 10728 of the display 10720 shown in FIG. 62 includes cutouts around the alphanumeric characters 10734 (7 and 12), for example.

In addition, the velocity indicia 10722, 10722' further comprises a clear or white circle icon 10726 with one or more black or shaded arrows to indicate the command velocity, such that, for example, one arrow refers to low velocity or slow, two arrows refer to medium velocity, and three arrows refer to high velocity or fast. An additional alphanumeric character 10724 indicates the units of velocity, e.g., mm/sec. As the velocity increases or decreases, the shaded region 10736 increases and decreases correspondingly. A status bar 10738 at the bottom of the display 10720, 1072' indicates operation status as normal (e.g., green) or cautionary (e.g., yellow). In the examples shown in FIGS. 62-64 the status bar 10738 indicates normal operation. In one aspect, the fill or shade color of the velocity region 10736 be same as the fill or shade color of the status bar 10738 to indicate normal or caution modes of operation.

As illustrated in FIG. 62, the actual velocity is medium to fast (~12 mm/sec) as indicated by the shaded region 10736 and the command velocity is set to high as indicated by the three arrows in the circle icon 10726. As noted earlier, the alphanumeric characters 10734 "7" and "12" include a cutout. As illustrated in FIG. 63, the actual velocity is fast (~30 mm/sec) as indicated by the shaded region 10736 and the command velocity is set to high as indicated by the three arrows in the circle icon 10726. As illustrated in FIG. 64, the actual velocity is medium (~10 mm/sec) as indicated by the shaded region 10736 and the command velocity is set to medium as indicated by the two arrows in the circle icon 10726.

FIGS. 65-67 illustrate various displays 10740, 10740', 10740" depicting various velocity feedback screens according to one aspect of this disclosure. The display 10740, 10740', 10740" depicts a graphic image of an end effector staple cartridge 10752, 10752', 10752". The display 10740, 10740', 10740" comprises velocity indicia 10742, 10742', 10742" to indicate the command velocity as well as the actual velocity of the displacement member (e.g., I-beam 2514) during the firing cycle. In one aspect, the velocity indicia 10742, 10742', 10742" comprises a shape or series of shapes that are filled or shaded proportionally to the velocity, such as is depicted in FIGS. 65-67. The shape or shapes of the velocity indicia 10742, 10742', 10742" can include, e.g., an arcuate or any other suitable geometric shape. In one aspect, the velocity indicia 10742, 10742', 10742" can comprise an arcuate graphic 10748, 10748', 10748" comprising multiple graduations 10750, 10750', 10750" to indicate the actual velocity from 0-30 mm/sec, for example. Alphanumeric characters 10704, 10704', 10704" (0, 7, 12, and 30) are disposed about the perimeter of the arcuate graphic 10748, 10748', 10748" to indicate the actual velocity by a filled or shaded region 10756, 10756', 10756". The displays 10740, 10740', 10740" are substantially similar but include some slight variations. For example, the arcuate graphic 10748 of the display 10740 depicted in FIG. 65 includes cutouts around the alphanumeric characters 10754 (7 and 12), for example, whereas the arcuate graphic 10748', 10748" of the displays 10740', 10740" depicted in FIGS. 66 and 67 do not. Furthermore, the velocity indicia 10742, 10742" of the displays 10740, 10740" depicted in FIGS. 65 and 67 include an alphanumeric character 10744, 10744" to indicate the units of velocity, e.g., mm/sec, at a bottom portion of the display 10740, 10740" whereas the display 10740' depicted in FIG. 66 includes an alphanumeric character 10744' to indicate the units of velocity, e.g., mm/sec, at a top portion of the display 10740'.

In addition, the velocity indicia 10742, 10742', 10742" further comprises a clear or white circle icon 10746, 10746', 10746" with one or more black or shaded arrows to indicate the command velocity, such that, for example, one arrow refers to low velocity or slow, two arrows refer to medium velocity, and three arrows refer to high velocity or fast. As the velocity increases or decreases the filled or shaded region 10756, 10756', 10756" increases and decreases correspondingly. A status bar 10758, 10758', 10758" at the bottom of the displays 10740, 10740', 10740" indicates operation status as normal (e.g., green) or cautionary (e.g., yellow). In the example shown in FIG. 65, the status bar 10758 indicates caution operation. In the examples shown in FIGS. 66-67, the bars 10758', 10758" indicate normal operation. In one aspect, the fill or shade color of the velocity region 10756, 10756', 10756" may be same as the fill or shade color of the status bar 10758, 10758', 10758" to indicate normal or caution modes of operation.

As illustrated in FIG. 65, the actual velocity is medium (~12 mm/sec) as indicated by the shaded region 10756 and the command velocity is set to high velocity as indicated by the three arrows in the circle icon 10726. As noted earlier, the alphanumeric characters 10734 "7" and "12" include a cutout. As illustrated in FIG. 66, actual velocity is slow (~7 mm/sec) as indicated by the shaded region 10756' and the command velocity is set to low as indicated by the single arrow in the circle icon 10746'. As illustrated in FIG. 67, the actual velocity is slow (~2 mm/sec) as indicated by the shaded region 10756" and the command velocity is set to low as indicated by the single arrow in the circle icon 10746".

FIGS. 68-70 illustrate a display 10760 depicting a velocity feedback screen according to one aspect of this disclosure. The display 10760 depicts a graphic image of an end effector staple cartridge 10772. The display 10760 comprises velocity indicia 10762 to indicate the command velocity as well as the actual velocity of the displacement member (e.g., I-beam 2514). In one aspect, the velocity indicia 10762 comprises a shape or series of shapes that are filled or shaded proportionally to the velocity, such as is depicted in FIGS. 68-70. The shape or shapes of the velocity indicia 10762 can include, e.g., a rectangular shape or any other suitable geometric shape. In one aspect, the velocity indicia 10762 can comprise a rectangular zone 10778 that is filled or shaded to indicate the value of the actual velocity. The control circuit 2510 causes the display 10760 to indicate the zone in which the velocity falls, as determined by the control circuit 2510 as discussed above. The rectangular zone 10778 may comprise graduations or marks to provide additional resolution of the command velocity of the I-beam 2514 element. In addition the velocity indicia 10762 may include an icon 10766 comprising an alphanumeric character located within a geometric element to represent automatic or manual mode of operation. In the illustrated examples, the mode is set to automatic "A" and the command velocity is set to a range of 7 to 12 mm/sec. Thus the automatic icon 10766 is located between the range that the actual velocity can very between. A filled or shaded region 10770 indicates the range that the actual velocity can very between, e.g., 7-12 mm/sec. A bar graph element 10764 indicates the actual velocity of the displacement member. A status bar 10776 at the bottom of the display 10760 indicates operation status as normal (e.g., green) or cautionary (e.g., yellow). In the examples shown in FIGS. 68-70 the status bar 10776 indicates normal operation. In one aspect, the fill or shade color of the filled or shaded region 10770 may be same as the fill or shade color of the status bar 10776 to indicate normal or caution modes of operation. An additional alphanumeric character 10762 indicates the units of velocity, e.g., mm/sec. Additional alphanumeric characters 10768 indicate the command velocity range (e.g., 0-7, 7-12, 12-30).

As illustrated in FIG. 68, the automatic "A" command velocity icon 10766 is located between 7-12 mm/sec and the actual velocity as indicated by the bar graph element 10764 is located toward the upper end of the set range. As illustrated in FIG. 69, the actual velocity is located toward the bottom of the set range of 7-12 mm/sec as indicated by the bar graph element 10764. As illustrated in FIG. 70, the actual velocity is slow as indicated by the bar graph element 10764 and the automatic range is 0-7 mm/sec as indicated by the position of the icon 10766.

FIGS. 71-73 illustrate a display 10780 depicting a velocity feedback screen according to one aspect of this disclosure. The display 10780 depicts a graphic image of an end effector staple cartridge 10792. The display 10780 comprises velocity indicia 10782 to indicate the command velocity as well as the actual velocity of the displacement member (e.g., I-beam 2514). In one aspect, the velocity indicia 10782 comprises a shape or series of shapes that are filled or shaded proportionally to the velocity, such as is depicted in FIGS. 71-73. The shape or shapes of the velocity indicia 10782 can include, e.g., a rectangular shape or any other suitable geometric shape. In one aspect, the velocity indicia 10782 can comprise a rectangular element 10798 that is filled or shaded to indicate the value of the actual velocity. The control circuit 2510 causes the display 10780 to indicate the zone in which the velocity falls, as determined by the control circuit 2510 as discussed above. The rectangular element 10798 may comprise graduations or marks to provide additional resolution of the command velocity of the I-beam 2514 element. In addition the velocity indicia 10782 may include an icon 10786 comprising an alphanumeric character located within a geometric element to represent automatic or manual mode of operation. In the illustrated examples, the mode is set to manual "M" and the command velocity is set to a range of 7 to 12 mm/sec. The icon 10786 is connected to a bar 10792 which indicates the mid point of the range on the rectangular element 10798. Thus the automatic icon 10786 is located between the range that the actual velocity can very between. A filled or shaded region 10790 indicates the range that the actual velocity can very between, e.g., 7-12 mm/sec. A bar graph element 10784 indicates the actual velocity of the displacement member. A status bar 10796 at the bottom of the display 10780 indicates operation status as normal (e.g., green) or cautionary (e.g., yellow). In the examples shown in FIGS. 71-72 the status bar 10796 indicates normal operation and as indicated in FIG. 73, the status bar 10796 indicates the status as cautionary. In one example, the cautionary status may be set because the actual velocity as indicated by the bar graph element 10784 is well below the set range of 12-30 mm/sec, which could indicate that the cutting element encountered thicker tissue than expected. In one aspect, the fill or shade color of the filled or shaded region 10790 may be same as the fill or shade color of the status bar 10796 to indicate normal or caution modes of operation. An additional alphanumeric character 10794 indicates the units of velocity, e.g., mm/sec. Additional alphanumeric characters 10788 indicate the command velocity range (e.g., 0-7, 7-12, 12-30).

As illustrated in FIG. 71, the manual "M" command velocity range icon 10786 is located between 7-12 mm/sec and the actual velocity is indicated by the bar graph element 10784 to be between the set range just above the bar 10792. As illustrated in FIG. 72, the actual velocity is within the set range of 12-30 mm/sec as indicated by the bar graph element 10784 and just below the bar 10792. As illustrated in FIG. 73, the actual velocity is located below the set range of 12-30 mm/sec as indicated by the bar graph 10784 and the bar 10792.

FIGS. 74-76 illustrate a display 10800 depicting a velocity feedback screen according to one aspect of this disclosure. The display 10800 depicts a graphic image of an end effector staple cartridge 10812. The display 10800 comprises velocity indicia 10802 to indicate the command velocity as well as the actual velocity of the displacement member (e.g., I-beam 2514). In one aspect, the velocity indicia 10802 comprises a shape or series of shapes that are filled or shaded proportionally to the velocity, such as is depicted in FIGS. 74-76 The shape or shapes of the velocity indicia 10802 can include, e.g., a rectangular shape or any other suitable geometric shape. In one aspect, the velocity indicia 10802 can comprise a rectangular element 10814 that is divided into two smaller rectangular elements 10804, 10806. The bottom element 10804 indicates the command or "set" velocity (e.g., 30 mm/sec) and the top element 10806 indicates the actual velocity (e.g., 25 mm/sec). An additional alphanumeric character 10808 indicates the units of velocity, e.g., mm/sec. A status bar 10810 at the bottom of the display 10800 indicates operation status as normal (e.g., green) or cautionary (e.g., yellow). In the examples shown in FIGS. 74-75 the status bar 10810 indicates normal operation and as indicated in FIG. 76, the status bar 10810 indicates the status as cautionary. In one example, the cautionary status may be set because the actual velocity 6 mm/sec as indicated by the top rectangular element 10806 is well below the set command velocity of 12 mm/sec, which could indicate that the cutting element encountered thicker tissue than expected.

As illustrated in FIG. 74, the command velocity is set to 30 mm/sec as indicated by the bottom rectangular element 1084 and the actual velocity is 25 mm/sec as indicated by the top rectangular element 10806. As illustrated in FIG. 75, the command velocity is set to 12 mm/sec as indicated by the bottom rectangular element 1084 and the actual velocity is 11 mm/sec as indicated by the top rectangular element 10806. As illustrated in FIG. 76, the command velocity is set to 12 mm/sec as indicated by the bottom rectangular element 1084 and the actual velocity is 6 mm/sec as indicated by the top rectangular element 10806.

FIGS. 77-80 illustrate a display 10820 depicting a velocity feedback screen according to one aspect of this disclosure. The display 10820 depicts a graphic image of an end effector staple cartridge 10832. The display 10820 comprises velocity indicia 10822 to indicate the command velocity as well as the actual velocity of the displacement member (e.g., I-beam 2514). In one aspect, the velocity indicia 10822 comprises a shape or series of shapes that are filled or shaded proportionally to the velocity, such as is depicted in FIGS. 77-80. The shape or shapes of the velocity indicia 10822 can include, e.g., an arcuate shape or any other suitable geometric shape. In one aspect, the velocity indicia 10822 can comprise an arcuate element 10828 that is divided into three smaller elements 10836*a*, 10836*b*, 10836*c*. The smaller elements 10836*a*, 10836*b*, 10836*c* when filled or shaded represent the command velocity range. An icon 10826 comprising an alphanumeric element encompassed in a geometric shape represents automatic "A" or manual "M" mode of operation. A needle 10840 is connected to the icon 10826 and indicates the actual velocity much like a speedometer ad including graduations 10830 for increased resolution. As shown in FIG. 77, the first element 10836*a* is shaded and represents a command velocity between 0-7 mm/sec (low). As shown in FIG. 78, the second element 10836*b* is shaded and represents a command velocity between 7-12 mm/sec (medium). As shown in FIG. 79, the third element 10836*c* is shaded and represents a command velocity between 12-30 mm/sec (high). An additional alphanumeric character 10824 indicates the units of velocity, e.g., mm/sec. A status bar 10838 at the bottom of the display 10820 indicates operation status as normal (e.g., green) or cautionary (e.g., yellow). In the examples shown in FIGS. 77-79 the status bar 10838 indicates normal operation and as indicated in FIG. 80, the status bar 10838 indicates the status as cautionary. In one example, the cautionary status may be set because the actual velocity as indicated by the needle 10840 is above the command velocity range indicated in the first element 10836*a*, which could indicate that the cutting element encountered thinner tissue than expected.

As illustrated in FIG. 77, the command velocity is set to a low range of 0-7 mm/sec as indicated by the first element 10836*a* and the actual velocity is about 3.5 mm/sec as indicated by the needle 10840. As illustrated in FIG. 78, the command velocity is set to a medium range of 7-12 mm/sec as indicated by the second element 10836*b* and the actual velocity is about 9.5 mm/sec as indicated by the needle 10840. As illustrated in FIG. 79, the command velocity is set to a high range of 12-30 mm/sec as indicated by the third element 10836*c* and the actual velocity is about 21 mm/sec as indicated by the needle 10840. In each of the examples illustrated in FIGS. 77-79, the operation is normal and the status bar 10838 indicates normal operation. Turning now to FIG. 80, the command velocity is set to a low range of 0-7 mm/sec as indicated by the first element 10836a and the actual velocity is about 9.5 mm/sec as indicated by the needle 10840, which is outside the command velocity range. Accordingly, the status bar 10838 is set to indicate caution. As previously discussed, the cautionary operation is indicated because the actual velocity as indicated by the needle 10840 is higher than the upper limit of the command velocity range indicating perhaps that the cutting element encountered tissue that is thinner than expected.

FIG. 81 illustrates a display 10860 depicting a battery feedback screen according to one aspect of this disclosure. The display 10860 depicts a graphic image of a battery 10864 communicating an overheated battery 10864. If the battery 10864 is in an overheated state, it may not have the ability complete the firing as requested indicating an overheated battery condition. The display 10860 includes an icon that represents heat 10868 such as the sun, for example. An icon of a thermometer 10866 also may indicate the actual temperature of the battery 10864. A caution icon 10870 and a cautionary status bar 10872 is displayed to indicate the overheated battery 10864 state.

Various aspects of the subject matter described herein are set out in the following numbered examples:

Example 1. A surgical instrument comprising: a displacement member configured to translate within the surgical instrument; a motor coupled to the displacement member to translate the displacement member; a display; a control circuit coupled to the motor and the display; a position sensor coupled to the control circuit, the position sensor configured to monitor a position of the displacement member; and wherein the control circuit is configured to: determine a velocity of the displacement member via the position sensor; cause the display to present a mode indicia that is indicative of a mode of the surgical instrument, wherein the mode comprises an automatic mode and a manual mode, and cause the display to present an indicia that is indicative of the velocity of the displacement member, wherein a portion of the display occupied by the indicia corresponds to the velocity of the displacement member.

Example 2. The surgical instrument of Example 1, wherein the indicia is a first indicia, the control circuit is further configured to: provide a set point velocity to the motor, the motor set point configured to cause the motor to drive the displacement member at a motor velocity; and cause the display to present a second indicia indicative of the motor set point velocity.

Example 3. The surgical instrument of Example 1 through Example 2, wherein the indicia comprises a plurality of zones, each of the plurality of zones indicative of a velocity level.

Example 4. The surgical instrument of Example 3, wherein the plurality of zones comprise a first zone indicative of a low velocity, a second zone indicative of a medium velocity, and a third zone indicative of a fast velocity.

Example 5. A surgical instrument comprising: a displacement member configured to translate within the surgical instrument; a motor coupled to the displacement member to translate the displacement member; a display; a control circuit coupled to the motor and the display; a position sensor coupled to the control circuit, the position sensor configured to monitor a position of the displacement member; and wherein the control circuit is configured to: provide a motor set point to the motor, the motor set point configured to cause the motor to drive the displacement member at a velocity; display an indicia on the display that is indicative of the velocity of the displacement member, wherein a portion of the display occupied by the indicia corresponds to the velocity of the displacement member, and display a second indicia on the display that is indicative of the motor set point velocity.

Example 6. The surgical instrument of Example 5, wherein the control circuit is further configured to cause the display to present a mode indicia that is indicative of a mode of the surgical instrument.

Example 7. The surgical instrument of Example 6, wherein the mode comprises an automatic mode and a manual mode.

Example 8. The surgical instrument of Example 5, wherein the control circuit is further configured to: display an image representative of the displacement member; and display progress of the image representative of the displacement member as the displacement member advances distally.

Example 9. The surgical instrument of Example 5 through Example 8, wherein the control circuit is further configured to cause the display to present a second indicia indicative of the motor set point velocity, wherein the second indicia represents a range of motor set point velocities.

Example 10. The surgical instrument of Example 5 through Example 9, wherein the control circuit is further configured to display a status bar that represents operation status of the surgical instrument.

Example 11. The surgical instrument of Example 10, wherein the status bar represents normal operation when the velocity of the displacement member is within a range of motor set point velocities.

Example 12. The surgical instrument of Example 10 through Example 11, wherein the status bar represents cautionary operation when the velocity of the displacement member is outside a range of motor set point velocities.

Example 13. The surgical instrument of Example 5 through Example 12, wherein the control circuit is further configured to: monitor a condition of a battery; and cause the display to present an image of a battery indicative of the condition of the battery.

Example 14. A method of operating a surgical instrument, the surgical instrument comprising a displacement member configured to translate within the surgical instrument, a motor coupled to the displacement member to translate the displacement member, a display, a control circuit coupled to the motor and the display, a position sensor coupled to the control circuit, the position sensor configured to monitor a position of the displacement member, the method comprising: determining, by the control circuit, a velocity of the displacement member via the position sensor; and presenting, by the control circuit, an indicia on the display that is indicative of the velocity of the displacement member, wherein a portion of the display occupied by the indicia corresponds to the velocity of the displacement member, and wherein the indicia representative of a higher velocity is larger than the indicia representative of a lower velocity.

Example 15. The method of Example 14, wherein the indicia is a first indicia, the method further comprising: providing, by the control circuit, a set point velocity to the motor, the motor set point configured to cause the motor to drive the displacement member at a motor velocity; and presenting, by the control circuit, a second indicia on the display that is indicative of the motor set point velocity.

Example 16. The method of Example 14 through Example 15, further comprising presenting, by the control circuit, on the display a mode indicia that is indicative of a mode of the surgical instrument.

Example 17. The method of Example 16, further comprising presenting, by the control circuit, on the display a mode comprising an automatic mode and a manual mode.

Example 18. The method of Example 14 through Example 17, further comprising presenting, by the control circuit, on the display an indicia comprising a plurality of zones, each of the plurality of zones indicative of a velocity level.

Example 19. The method of Example 18, further comprising presenting, by the control circuit, on the display a plurality of zones comprising a first zone indicative of a low velocity, a second zone indicative of a medium velocity, and a third zone indicative of a fast velocity.

Example 20. The method of claim 14 through Example 19, further comprising: monitoring, by the control circuit, a condition of a battery; and presenting, by the control circuit, on the display an image of a battery indicative of the condition of the battery.

Systems and Methods for Controlling Motor Speed According to User Input for a Surgical Instrument During use of a motorized surgical stapling and cutting instrument it is possible that the user may not know the command velocity or the actual velocity of the cutting member or firing member. Therefore, it may be desirable to provide the user with the ability to control the firing speed through manual selection. It may be desirable to provide a surgical instrument with a first firing condition that is set by the surgical instrument based on a measure of distance traveled by the cutting member or the firing member and a time element and a second firing condition that is predetermined by the user.

The disclosure now turns to a closed loop feedback system for controlling motor velocity based on a variety of conditions. The closed loop feedback system as executed by the control circuit 2510 can be configured to implement either a default, e.g., pre-programmed, firing condition or a user-selected firing condition. The user selected firing condition can be selected during the open loop portion or otherwise prior to the closed loop portion of the displacement stroke. In one aspect, the user-selected firing condition is configured to override the execution of the default or pre-programmed firing condition.

Turning now to FIG. 82, there is shown a perspective view of a surgical instrument 10500 according to one aspect of this disclosure. In one aspect, a surgical instrument 10500 comprising an end effector 10504 connected via a shaft 10503 to a handle assembly 10502 further comprises a display 10506. The surgical instrument 10500 comprises a home button 10508, an articulation toggle 10510, a firing trigger and safety release 10512, and a closure trigger 10514.

In the following discussion, reference should also be made to FIG. 14. The display 10506 is operably coupled to the control circuit 2510 such that the control circuit 2510 can cause the display 10506 to show various information associated with the operation of the instrument 10500, such as information determined by or from the position sensor 2534, the current sensor 2536, and/or the other sensors 2538. In one aspect, the display 10506 can be configured to display the velocity at which the I-beam 2514 is set to be translated by the motor 2504, i.e., a command velocity, and/or the actual velocity at which the I-beam 2514 is being translated. The command velocity is the set, target, or desired velocity. The command velocity at which the I-beam 2514 is to be translated can be determined by either receiving the motor set point, which dictates the velocity at which the motor 2504 drives the I-beam 2514, dictated by the motor drive signal 2524 from the motor control 2508 or storing the motor drive signal 2524 that is provided to the motor control 2508 in a memory for subsequent retrieval. The actual velocity at which the I-beam 2514, or other component of the firing drive system, is being translated can be determined by monitoring the position of the I-beam 2514 over a time period, which can be tracked by the control circuit 2510 via input from the timer/counter 2531.

In various aspects, the display 10506 of the surgical instrument 10500 can be positioned directly on the exterior housing or casing of the handle assembly 10502 or otherwise integrally associated with the surgical instrument 10500. In other aspects, the display 10506 can be removably connectable or attachable to the surgical instrument 10500. In still other aspects, the display 10506 can be separate or otherwise distinct from the surgical instrument 10500. The display 10506 can be communicably coupled to the control circuit 2510 via either a wired connection or a wireless connection.

FIG. 83 is a detail view of a display 10506 portion of the surgical instrument 10500 shown in FIG. 82 according to one aspect of this disclosure. The display 10506 includes an LCD display 10516 to communicate velocity control including showing the command velocity as well as if the firing mode is in a closed loop feedback (automatic) mode or manually selected mode. The display 10506 provides transection feedback by displaying a graphic image of an end effector staple cartridge 10518 with a knife 10520 and rows of staples 10522. A left graphic label 10524 indicates the distance 10528 the knife 10520 has traveled (e.g., 10 mm) distally and a right graphic label 10526 indicates the velocity of the knife 10520 as it travels distally where the current velocity is circled (e.g., 3), where 1 is fast, 2 is medium, and 3 is slow velocity. The velocity may be selected manually or automatically based on the conditions of the tissue.

FIG. 84 is a logic flow diagram of a process 11000 depicting a control program or logic configuration for controlling a display according to one aspect of this disclosure. Reference should also be made to FIGS. 14 and 82. The process 11000 depicted in FIG. 82 relates to the capability for a user to select the speed of the firing stroke. To begin the process 11000, the control circuit 2510 initiates a firing stroke 11010. The firing stroke is initiated 11010 by translating the displacement member a first distance. When the displacement member is moved a first distance, the control circuit is configured to measure the duration of time required for the displacement member to translate the first distance. The measuring of such translation of the displacement member a predetermined first distance, allows the control circuit to be able to calculate the thickness of the tissue being, for example, cut and/or stapled by the surgical instrument. Prior to firing by, for example, translating the knife 10520 of FIG. 83 distally through the surgical instrument 10500, the user is capable of manually selecting the firing speed by choosing a velocity selection from a variety of speeds discussed in more detail below. Based on the calculation of the thickness of tissue from the first distance and the duration of time, the user may able to only select from a variety of speeds appropriate for the procedure. In the alternative, the user may be able to manually choose a velocity selection from all of the variety of speeds. After initiating the firing stroke 11010, the control circuit 2510 assesses whether, by a first time, the user has made a velocity selection 11020. If the user has not made a velocity selection 11020, the control circuit 2510 is configured to determine the position of the displacement member at this time 11022. By determining the position of the displacement member, or knife 10520, the control circuit 2510 can set the motor velocity accordingly 11024. Thus, in the absence of a user input, the control circuit 2510 automatically sets the motor velocity to carry out the firing stroke at a corresponding speed. Alternatively, if a user does make a velocity selection by a first time 11020, the control circuit 2510 is configured to control the motor by setting the motor velocity to correspond with the user selection 11026. After either the user manually selects the firing speed or the control circuit 2510 automatically sets the firing speed, the process for setting the velocity of the firing stroke comes to an end 11028, and the surgical instrument may continue or begin another function.

FIGS. 85 and 86 depict various displays 11100 depicting a user selection menu screen according to one aspect of this disclosure. During a surgical procedure, the information presented on the display 11100 may be communicated throughout the operating room to additional screens, such as, for example, a primary screen connected to a laparoscopic camera. The display 11100 depicts a graphic image of an end effector staple cartridge 11132. An alphanumeric character 11104 indicates the units of velocity, e.g., mm/sec. The display 11100 comprises selection menu indicia 11102 to indicate the available speeds of the displacement member (e.g., I-beam 2514) during a firing stroke. In one such aspect, the selection menu indicia 10602 can comprise four menu options 11112, 11114, 11116, 11118 in the shape of circles. The shape of the selection menu indicia 11102 does not have to be circular, as numerous shapes are envisioned. The shape or shapes of the selection menu indicia 11102 can include, for example, a triangle any other suitable geometric shape. A first menu option 11112 is indicative of an automatic mode of the surgical instrument 10500. The automatic mode is represented in the first menu option 11112 by a capitalized letter "A". The automatic mode may be represented in alternative fashions, including, for example, by the shortened word "auto" or the lowercase letter "a". A second menu option 11114 is indicative of a slow mode of the surgical instrument 10500. The slow mode is represented in the second menu option 11114 by a single arrowhead within a circle. The slow mode may be represented in alternative fashions, such as, for example, by the word "slow" or by a numeric value indicative of the velocity of the displacement member during the slow mode. A third menu option 11116 is indicative of a medium mode of the surgical instrument 10500. The medium mode is represented in the third menu option 11114 by a double arrowhead within a circle. The medium mode may be represented in alternative fashions, such as, for example, by the word "medium" or by a numeric value indicative of the velocity of the displacement member during the medium mode. A fourth menu option 11118 is indicative of a fast mode of the surgical instrument 10500. The fast mode is represented in the fourth menu option 11118 by a triple arrowhead within a circle. The fast mode may be represented in alternative fashions, such as, for example, by the word "fast" or by a numeric value indicative of the velocity of the displacement member during the fast mode. During a firing stroke, a status bar 11138 at the bottom of the display 11100 indicates operation status as normal (e.g., green) or cautionary (e.g., yellow). As the displacement member is not yet being translated in FIGS. 85 and 86, the status bar 11138 is empty.

FIG. 85 is representative of one embodiment of a display 11100 that presents itself for a user to choose the firing speed of a displacement member. In order to trigger the control circuit 2510 to present this display 11100, a user may close the jaws of the end effector (e.g. 10504 in FIG. 82). Without any user input, the motor 2504 operates in an automatic mode. In order to switch out of the automatic mode to a manual mode, the surgeon may press a button, such as the articulation toggle 10510 illustrated in FIG. 87, for a brief period of time. This brief period of time can last, for example, for approximately two seconds. After this brief period of time elapses, the control circuit causes the display to show various information associated with selecting a firing speed as part of an interactive selection menu depicted in FIG. 85. For example, the display can show four menu options relating to the velocity mode: automatic mode; slow mode; medium mode; and fast mode. Additionally, or alternatively, the display 11100 may be a touch screen, wherein the user can simply touch the screen to reach the interactive selection menu.

When the user selects the automatic mode, the control circuit 2510 can control the output of the motor 2504, and thus, the velocity of the I-beam 2514, or displacement member, in response to various conditions. When the user selects the slow mode, the control circuit 2510 slows the velocity of the motor 2504. Reducing the output of the motor 2504 results in a slower translation of the I-beam 2514, and thus, a slower firing speed. When the user selects the fast mode, the control circuit 2510 increases the velocity of the motor 2504. Increasing the output of the motor 2504 results in a faster translation of the I-beam 2514, and thus, a faster firing speed. When the user desires a firing speed that is in between the firing speed offered from the slow mode and the fast mode, the user can select the medium mode. In the medium mode, the control circuit 2510 increases the velocity of the motor 2504 to a point that is greater than the velocity of the motor 2504 in the slow mode but less than the velocity of the motor 2504 in the fast mode. The output of the motor 2504 in the medium mode results in a medium translation of the I-beam 2514, and thus, a medium firing speed.

FIG. 86 is representative of one embodiment of the display 11100 during a user selection process. For example, as the user applies a force F on the articulation toggle 10510, the user is able to cycle through the various menu options 11112, 11114, 11116, 11118 relating to the velocity mode. The upwards arrowhead 11150 located above the articulation toggle 10510 in FIG. 87 indicates that should a user press down on the upper half of the articulation toggle 10510, the user will scroll to the menu option 11112, 11114, 11116, 11118 above the currently highlighted option. The menu options may be configured to be continuous, wherein scrolling beyond the top option 11112 will result in the next highlighted option being the bottom option 11118 when the articulation toggle 10510 is pressed once again. Alternatively, the user may not be able to scroll beyond the top or bottom menu options once they are reached. If the display 11100 possesses the touch screen capabilities mentioned above, the user may simply touch the menu options 11112, 11114, 11116, 11118 to highlight the desired velocity mode instead of, or in combination with, the articulation toggle 10510.

As the user scrolls through the menu options 11112, 11114, 11116, 11118, the menu options change sizes. For example, in FIG. 86, the user has highlighted the slow mode, as the second menu option 11124 has become enlarged. The reader will also recognize that the other three menu options 11122, 11126, 11128 have shrunk in an attempt to add further emphasis to the selected mode. The selected mode may additionally be highlighted and/or illuminated with a color, such as green, upon selection by the scroll menu.

FIG. 88 displays a chart 11200 indicating the various manners in which the menu options 11112, 11114, 11116, 11118 may be highlighted during the selection process discussed above. A menu option may be highlighted when the background of the menu option circle alternates between white and black shading 11210. For example, the menu option is highlighted when the menu option blinks and or flashes 11212. The flash 11212 can be recognized by the user, as a first background 11214 of the menu option has no color or is white, and a second background 11216 of the menu option is black. The flash 11212 alternates between the first background 11214 and the second background 11216. Additionally, the menu option may be highlighted when the background of the menu option circle alternates between white and colored shading 11230. For example, the menu option is highlighted when the menu option blinks and or flashes 11212. The flash 11212 can be recognized by the user, as a first background 11214 of the menu option has no color or is white, and a second background 11232 of the menu option is colored, such as green. The flash 11212 alternates between the first background 11214 and the second background 11232. A third exemplary manner in which a menu option may be highlighted is by size differentiation 11220. For example, while the menu options may all have the same color background 11222, an unselected menu option 11224 may be reduced in size, whereas a highlighted menu option 11226 may be enlarged. These methods of highlighting are not meant to be limiting and can be used in combination or separately.

In order to set and/or activate the highlighted menu option, the user may slightly touch the firing trigger. Alternatively, the user may wait a short period of time without any additional user input, and the control circuit 2510 will automatically activate the highlighted menu option. Once the menu option has been selected, the control circuit 2510 may cause the screen to change to a velocity feedback system to enable the user to monitor the velocity of the firing stroke during use.

FIGS. 89-91 illustrate a display 11300 depicting various velocity feedback screens according to one aspect of this disclosure. The display 11300 depicts a graphic image of an end effector staple cartridge 11312. The display 11300 comprises velocity indicia 11302 to indicate the selected menu option as well as the actual velocity of the displacement member (e.g., I-beam 2514) during the firing cycle. In one aspect, the velocity indicia 11302 comprises a shape or series of shapes that are filled or shaded proportionally to the velocity, such as is depicted in FIGS. 89-91. The shape or shapes of the velocity indicia 11302 can include, e.g., an arcuate or any other suitable geometric shape. In one aspect, the velocity indicia 11302 can comprise an arcuate graphic 11308 comprising multiple graduations 11310 to indicate the actual velocity from 0-30 mm/sec, for example, of the displacement member. Alphanumeric characters 11314 (0, 7, 12, and 30) are disposed about the perimeter of the arcuate graphic 11308 to indicate the actual velocity by a filled or shaded region 11316. The display 11300 shown in FIG. 89 is a slightly modified version of the displays 11300', 11300" shown in FIGS. 90 and 91. The arcuate graphic 11308 of the display 11300 may include cutouts around the alphanumeric character 11314 "12", for example.

In addition, the velocity indicia 11302 further comprises a filled or shaded circle icon 11306 with one or more white arrows to indicate the command velocity, such that, for example, one arrow refers to low velocity or slow, two arrows refer to medium velocity, and three arrows refer to high velocity or fast. On the displays shown in FIGS. 89-91, the user has manually selected the fast mode from the alternate user selection screen as described above. An additional alphanumeric character 11304 indicates the units of velocity, e.g., mm/sec. As the velocity of the displacement member increases or decreases, the shaded region 11316 increases and decreases correspondingly. A status bar 11318 at the bottom of the display 11300 indicates operation status as normal (e.g., green) or cautionary (e.g., yellow). In the examples shown in FIGS. 89 and 90 the status bar 11318 indicates normal operation. In the example shown in FIG. 91, the status bar 11318 indicates cautionary operation. In one aspect, the fill or shade color of the velocity regions 11316, 11316', 11316" may be same as the fill or shade color of the status bars 11318, 11318' to indicate normal or caution modes of operation.

As illustrated in FIG. 89, the actual velocity of the displacement member is fast, approximately 20 mm/sec, as indicated by the shaded region 11316. The command velocity, or the selected menu option, is set to high as indicated by the three arrowheads in the circle icon 11306. For at least the reason that the command velocity and the actual velocity correspond to one another, the status bar 11318 is shaded green, indicating normal operation. As illustrated in FIG. 90, the actual velocity also is fast, approximately 14 mm/sec, as indicated by the shaded region 11316' and the command velocity is set to high as indicated by the three arrows in the circle icon 11306. For at least the reason that the command velocity and the actual velocity correspond to one another, the status bar 11318 is also shaded green, indicating normal operation. Turning to FIG. 91, the command velocity is set to the fast mode as indicated by the three arrows in the circle icon 11306, but the actual velocity is approximately 10 mm/sec as indicated by the shaded region 11316". Due to at least this discrepancy between the command velocity and the actual velocity, the status bar 11318' is shaded yellow, indicating cautionary operation. The status bar 11318' indicating cautionary operation may alert a user, for example, to change the velocity of the firing stroke, as the selected velocity is inappropriate due to, for example, tissue thickness. Additionally, the indication of cautionary operation may alert a user to a defective surgical instrument.

Various aspects of the subject matter described herein are set out in the following numbered examples:

Example 1. A surgical instrument, comprising: a displacement member configured to translate within the surgical instrument; a motor coupled to the displacement member, wherein the motor is configured to translate the displacement member at a velocity, and wherein the velocity is set by a velocity mode; a display; and a control circuit coupled to the motor and the display, wherein the control circuit is configured to: cause the displacement member to translate a first distance; determine a first time period required for the displacement member to translate the first distance; cause the display to present a selection menu indicia that is indicative of the velocity mode, wherein the selection menu indicia displayed is limited by the first distance and the first time period; receive a user input corresponding to the velocity mode; and set the motor velocity based on the user input.

Example 2. The surgical instrument of Example 1, wherein the control circuit is further configured to cause the display to present a velocity indicia that is indicative of the velocity of the displacement member.

Example 3. The surgical instrument of Example 1 through Example 2, wherein the velocity mode comprises an automatic mode, a slow mode, a medium mode, and a fast mode.

Example 4. The surgical instrument of Example 3, wherein the velocity mode is set to the automatic mode in the absence of the user input.

Example 5. The surgical instrument of Example 1 through Example 4, wherein the surgical instrument further comprises a position sensor coupled to the control circuit.

Example 6. The surgical instrument of Example 5, wherein the position sensor is configured to monitor a positon of the displacement member.

Example 7. The surgical instrument of Example 5 through Example 6, wherein the control circuit is further configured to determine a velocity of the displacement member via the position sensor.

Example 8. A surgical instrument, comprising: a displacement member configured to translate within the surgical instrument; a motor coupled to the displacement member, wherein the motor is configured to translate the displacement member at a velocity, wherein the velocity is defined by a velocity mode; a display; and a control circuit coupled to the motor and the display, wherein the control circuit is configured to: cause the displacement member to translate a first distance; determine a first time period required for the displacement member to translate the first distance; receive a first user input; cause the display to present a selection menu indicia that is indicative of the velocity mode in response to the first user input, wherein the selection menu indicia displayed is limited by the first distance and the first time period; receive a second user input corresponding to the velocity mode; and set the motor velocity based on the second user input.

Example 9. The surgical instrument of Example 8, wherein the control circuit is further configured to cause the display to present a velocity indicia that is indicative of the velocity of the displacement member.

Example 10. The surgical instrument of Example 9, wherein the display presents the selection menu indicia during a first time period and the velocity indicia during a second time period.

Example 11. The surgical instrument of Example 10, wherein the first time period is different than the second time period.

Example 12. The surgical instrument of Example 10 through Example 11, wherein the first time period is the same as the second time period.

Example 13. The surgical instrument of Example 8 through Example 12, wherein the velocity mode comprises an automatic mode, a slow mode, a medium mode, and a fast mode.

Example 14. The surgical instrument of Example 13, wherein the velocity mode is set to the automatic mode by default.

Example 15. A method of operating a surgical instrument, the surgical instrument comprising a displacement member configured to translate within the surgical instrument, a motor coupled to the displacement member to translate the displacement member at a velocity, a display, and a control circuit coupled to the motor and the display, the method comprising: causing, by the control circuit, the displacement member to travel a first distance; measuring, by the control circuit, a first time period required for the displacement member to translate the first distance; presenting, by the control circuit, an indicia on the display that is indicative of a velocity mode for the displacement member, wherein the indicia displayed is limited by the first distance and the first time period; receiving, by the control circuit, a user input corresponding to the velocity mode; and setting, by the control circuit, the motor velocity based on the user input.

Example 16. The method of Example 15, further comprising presenting, by the control circuit, a velocity indicia on the display that is indicative of the velocity of the displacement member.

Example 17. The method of Example 15 through Example 16, further comprising presenting, by the control circuit, on the display the velocity mode, wherein the velocity mode comprises an automatic mode, a slow mode, a medium mode, and a fast mode.

Example 18. The method of Example 16 through Example 17, further comprising controlling, by the control circuit, the motor to in the automatic mode in the absence of a user input.

Example 19. The method of Example 16 through Example 18, further comprising presenting, by the control circuit, on the display the velocity mode set to the automatic mode in the absence of a user input.

Example 20. The method of Example 15 through Example 19, further comprising monitoring, by the control circuit, the velocity of the displacement member.

Closed Loop Feedback Control of Motor Velocity of a Surgical Stapling and Cutting Instrument Based on System Conditions During use of a motorized surgical stapling and cutting instrument it is possible that the battery may overheat due to externally applied loads and cause the motor to stall. Therefore, it may be desirable to interrogate the voltage on the battery during a portion of the firing stroke when the system is loaded to assess battery capability and adjusting the firing velocity of the cutting member or the firing member based on this feedback.

The disclosure now turns to a closed loop feedback system for controlling motor velocity based on a variety of conditions. In one aspect, a logic flow diagram of a process of a control program or logic configuration is provided for controlling motor velocity based on battery condition. In another aspect, a logic flow diagram of a process of a control program or logic configuration is provided for controlling motor velocity based on stalled condition during a normal firing cycle. In another aspect, a logic flow diagram of a process of a control program or logic configuration is provided for controlling motor velocity while in manual mode. In another aspect, a logic flow diagram of a process of a control program or logic configuration is provided for controlling motor velocity based on stalled condition during a normal firing cycle and implementing a forced pause in the firing cycle. In another aspect, a logic flow diagram of a process of a control program or logic configuration is provided for controlling motor velocity based on stalled condition during a normal firing and reducing the velocity one level once the firing cycle is restarted. In another aspect, a logic flow diagram of a process of a control program or logic configuration is provided for controlling motor velocity based on stalled condition during a normal firing cycle in manual mode and reducing velocity one level once the firing cycle is restarted. In another aspect, a logic flow diagram of a process depicting a control program or logic configuration is provided for controlling motor velocity based on stalled condition during a normal firing cycle and pausing the firing cycle until the user releases the firing trigger. In another aspect, a logic flow diagram of a process of a control program or logic configuration is provided for controlling motor velocity during transition between velocities. These aspects are described in more detail herein below with reference to FIGS. 92-99.

A motor stall condition is when the rotational output of the motor drops to zero. Stall torque is the torque which is produced by the motor when the output rotational speed is zero. It may also mean the torque load that causes the output rotational speed of the motor to become zero, i.e., to cause stalling. Stalling is a condition when the motor stops rotating. This condition occurs when the load torque is greater than the motor shaft torque, i.e., break down torque condition. In this condition the motor draws maximum current but the motor shaft does not rotate. The current is called the stalling current. Electric motors continue to provide torque when stalled. However, electric motors left in a stalled condition are prone to overheating and possible damage since the current flowing is maximum under these conditions. The maximum torque an electric motor can produce in the long term when stalled without causing damage is called the maximum continuous stall torque.

With reference to FIG. 14, a motor stall condition can be detected using a variety of techniques. In one aspect, a motor stall can be detected by monitoring the energy source 2512 to the motor 2504. If the voltage drops below a predetermined threshold, it may be an indication of a motor stall condition. In another aspect, a motor stall condition can be detected by monitoring the current through the motor 2504 via the current sensor 2536. If the current sensed by the current sensor 2536 increases above a predetermined threshold to a value greater than the stalling current, the motor 2504 may be stalled or stalling. In another aspect, the current sensor 2536 may be placed in series with the ground leg of the motor 2504. In another aspect, a motor stall condition may be detected by monitoring the current applied to the motor 2504 relative to the actual displacement of a displacement member, such as the I-beam 2514, monitored by the position sensor 2534. If the motor current is greater than expected, near or greater than the stalling current, and the actual velocity is lower than the command velocity, the motor may stalled or stalling. The motor 2504 may suffer damage by overheating if a motor stall condition is not corrected in a timely manner.

Accordingly, turning now to FIG. 92, there is illustrated a logic flow diagram of a process 11500 depicting a control program or logic configuration for controlling motor velocity based on battery condition according to one aspect of this disclosure. With reference also to FIGS. 1-15 and in particular FIG. 14, in one aspect, the control circuit 2510 is configured to interrogate the energy source 2512 to determine the voltage on the battery during a portion of the firing cycle when the surgical instrument 2500 is loaded to assess battery capability and adjust the firing velocity of the displacement member (e.g., drive member 120, firing member 220, firing bar 172, I-beam 2514, etc.) based on this feedback. As previously discussed, the firing velocity of the displacement member is controlled by the control circuit 2510 based on various feedback conditions. The control circuit 2510 determines a new velocity of the displacement member and applies a motor set point 2522 to the motor control 2508, which in turn applies the motor drive signal 2524 to the motor 2504. The set or command velocity of the motor 2504 is applied to a transmission 2506. The actual velocity of the displacement member is determined based on feedback from the position sensor 2534, energy source 2512, current sensor 2536, timer/counter 2531, or sensors 2538, alone or in combination. As previously discussed, factors that may affect the actual velocity of the displacement member include external influences such as tissue thickness, tissue, type, or system conditions. The determination of battery condition, such as a battery overheating condition, informs the control circuit 2510 of the firing velocity. As an example, the control circuit 2510 measures the voltage, internal resistance, and/or current in/through the battery during the first 0.080" to 0.12" (2 mm to 3 mm) and in one example 0.09" (2.286 mm) of travel of the displacement member, (e.g., when the system is loaded). If the voltage $V_b$ of a 12V battery is <9V, the internal resistance $R_b$ of the battery is above a threshold, or the current $I_b$ is below a threshold, then it is likely that the battery is in an overheated state. The control circuit 2510 immediately sets the firing velocity to the lowest setting for the entire firing cycle.

With reference now to FIGS. 14 and 92, according to the process 11500, the control circuit 2510 initiates 11502 a firing cycle of the displacement member and continually samples 11504 the energy source 2512 during the initial firing stage (e.g., during the first 0.090" of travel as determined by the position sensor 2534). The sampled voltage is compared 11506 to a threshold voltage. In one example, for a 12V energy source 2512 the threshold is set to 9V. The threshold may be adjusted to accommodate system voltage requirements. If the sampled voltage is greater than or equal to the threshold voltage, the control circuit 2510 continues along the NO branch and continues 11508 the firing cycle until the sampled voltage is less than the threshold voltage, the control circuit 2510 continues along the YES branch and the control circuit 2510 communicates 11510 the weak battery condition via a status indicator such as a display 43, 743 (FIGS. 2, 5B, 6). The status indicator may be an LED, a display, a buzzer, among others. Upon communicating 11510 the weak battery status, the control circuit 2510 determines 11512 if the surgical instrument 2500 device is in automatic mode. If the surgical instrument 2500 is in automatic mode the control circuit 2510 continues along the YES branch and the control circuit 2510 converts 11514 the surgical instrument 2500 to manual mode and reduces 11516 the command velocity of the motor 2504 slow. If the surgical instrument 2500 is not in automatic mode the control circuit 2510 continues along the NO branch and the control circuit 2510 reduces 11516 the command velocity of the motor 2504 slow. In some aspects, a slow command velocity may be less than 10 mm/sec and in some aspects may be less than 5 mm/sec.

FIG. 93 is a logic flow diagram of a process 11520 depicting a control program or logic configuration for controlling motor velocity based on stalled condition during a normal firing cycle according to one aspect of this disclosure. Generally, if the motor stalls during a normal firing cycle, the process 11520 forces the motor to operate in the slowest mode for the rest of the firing cycle. Thus, if the motor stalls, the remaining stroke is executed at a slow velocity.

With reference now to FIGS. 14 and 93, according to the process 11520, the control circuit 2510 initiates 11522 a firing cycle of the displacement member at a medium command velocity such as 12 mm/sec. During the firing cycle, the control circuit 2510 checks 11524 for a motor stall condition and if it determines 11526 that the motor is not stalled, the control circuit 2510 continues along the NO branch and continues 11532 the firing cycle until the motor 2504 stalls. At which time the control circuit 2510 continues along the YES branch and reduces 11528 the command velocity to slow and indicates 11530 the status by way of warning light or other indicator such as display 43, 743 (FIGS. 2, 5B, 6). Upon reducing 11528 the command velocity to slow, the control circuit 2510 continues 11532 the firing cycle and checking 11524 for stalls until the motor 2504 stalls or the displacement member reaches the end of stroke. As previously discussed, a slow command motor velocity may be less than 10 mm/sec and in some aspects may be less than 5 mm/sec. In this example, the command velocity is set to 9 mm/sec.

FIG. 94 is a logic flow diagram of a process 11540 depicting a control program or logic configuration for controlling motor velocity while in manual mode according to one aspect of this disclosure. Generally, while the surgical instrument 2500 is in manual mode, the motor is at risk of stalling and the control circuit displays a warning. If the command velocity of the motor is not paused or reduced by the user, the device will automatically enter into low speed for the remainder of the firing cycle. Accordingly, while the surgical instrument is in manual mode and the risk of stalling is detected by the control circuit, the user is given the opportunity to manually adjust the command velocity to avoid a motor stall.

With reference now to FIGS. 14 and 94, according to the process 11540, the control circuit 2510 selects 11542 manual mode upon receiving a request from the user and initiates 11544 a firing cycle of the displacement member. During the firing cycle, the control circuit 2510 checks 11546 for a motor stall and if the control circuit 2510 does not detect 11548 low velocity, the control circuit 2510 proceeds along the NO branch and the control circuit 2510 continues 11550 the firing cycle until a low velocity is detected 11548. When a low velocity is detected 11548, the control circuit 2510 continues along the YES branch and the control circuit indicates 11552 the low velocity status by way of display 43, 743 (FIGS. 2, 5B, 6), warning light, and display a countdown timer to provide the user some time to manually reduce the motor velocity. This period of time may be a few seconds and up to 10 seconds, for example. After the countdown timer times out, the control circuit 2510 determines 11554 whether the user has selected to manually adjust the velocity of the motor 2504 or pause the motor 2504. If the user selected to manually adjust the velocity of the motor 2504 or pause the motor 2504 the control circuit 2510 continues along the YES branch and the control circuit 2510 detects 11548 for low velocity and the process 11540 continues until the user elects not the manually adjust the velocity of the motor 2504 or pause the motor 2504. At which point, the control circuit 2510 continues along the NO branch and reduces 11556 the velocity of the motor 2504 to slow speed and continues the firing cycle. The process continues until the displacement member reaches the end of stroke. As previously discussed, a slow command motor velocity may be less than 10 mm/sec and in some aspects may be less than 5 mm/sec. In this example, the command velocity is reduced 11556 to 9 mm/sec.

FIG. 95 is a logic flow diagram of a process 11560 depicting a control program or logic configuration for controlling motor velocity based on stalled condition during a normal firing cycle and implementing a forced pause in the firing cycle according to one aspect of this disclosure. Generally, when the motor stalls during a normal firing cycle, the control circuit stops the motor and forces a pause in the firing cycle. The duration of the pause depends on the command velocity of the motor at the time of the stall. Faster motor velocities may require longer pauses, etc. Accordingly, if the motor stalls, the control circuit stops the motor and forces a pause before allowing the motor to restart at the same velocity at the time of the stall.

With reference now to FIGS. 14 and 95, according to the process 11560, the control circuit 2510 initiates 11562 a firing cycle of the displacement member and stores 11564 the current velocity of the motor (e.g., SLOW: 0<V<10 mm/sec; MEDIUM: 10 mm/sec≤V≤12.5 mm/sec; FAST: 12.5 mm/sec<V<15 mm/sec) and checks 11566 for a motor stall condition. The control circuit 2510 then determines 11568 whether the motor 2504 stalled. If the motor 2504 stalled, the control circuit continues along the NO branch and the control circuit 2510 continues 11570 the firing cycle and checks 11566 for a motor stall condition until the motor 2504 stalls. The control circuit 2510 then proceeds along the YES branch and evaluates three conditions. A first evaluation determines 11572 if the previous velocity of the motor 2504 was FAST and if true, the control circuit 2510 sets 11574 a delay greater than or equal to 2 seconds and less than or equal to 5 seconds and continues 11576 the firing cycle at the stored velocity. At the same time, the control circuit 2510 indicates 11578 the status of the surgical instrument 2500 by displaying or showing a warning light, among other feedback techniques such as display 43, 743 (FIGS. 2, 5B, 6). A second evaluation determines 11580 if the previous velocity of the motor 2504 was MEDIUM and if true, the control circuit 2510 sets 11582 a delay greater than or equal to 1 second and less than 2 seconds and continues 11584 the firing cycle at the stored velocity. At the same time, the control circuit 2510 indicates 11586 the status by displaying or showing a warning light, among other feedback techniques such as display 43, 743. A third evaluation determines 11588 if the previous velocity of the motor 2504 was SLOW and if true, the control circuit 2510 sets 11590 a 0 to 1 second delay and preferably a 0 to 0.25 seconds delay and continues 11592 the firing cycle at the stored velocity. At the same time, the control circuit 2510 indicates 11594 the status by displaying or showing a warning light, among other feedback techniques such as display 43, 743. The process 11560 continues until the displacement member reaches the end of stroke.

FIG. 96 is a logic flow diagram of a process 11600 depicting a control program or logic configuration for controlling motor velocity based on stalled condition during a normal firing cycle and reducing the velocity one level once the firing cycle is restarted according to one aspect of this disclosure. Generally, when the motor stalls during a normal firing cycle, the velocity of the motor is reduced one level below the current motor velocity once the firing cycle is restarted. If the motor velocity is already at the slowest speed, a forced pause of a predetermined duration is required before restarting the firing cycle at the slowest speed again. Accordingly, if the motor stalls, the control circuit slows down the motor velocity to one level below stored velocity.

With reference now to FIGS. 14 and 96, according to the process 11600, the control circuit 2510 initiates 11602 a firing cycle of the displacement member and stores 11604 the current velocity of the motor (e.g., SLOW: V<10 mm/sec; MEDIUM: 10 mm/sec≤V≤12.5 mm/sec; FAST: V>12.5 mm/sec) and checks 11606 for a motor stall condition. The control circuit 2510 then determines 11608 whether the motor 2504 stalled. If the motor 2504 stalled, the control circuit 2510 continues along the NO branch and the control circuit 2510 continues 11610 the firing cycle and checks 11606 for a motor stall condition until the motor 2504 stalls. The control circuit 2510 then proceeds along the YES branch and evaluates three conditions. A first evaluation determines 11612 if the previous velocity of the motor 2504 was FAST and if true, the control circuit 2510 autoadjusts 11614 the velocity of the motor 2504 to MEDIUM and reinitiates 11602 the firing cycle at the new MEDIUM velocity. At the same time, the control circuit 2510 indicates 11616 the status of the surgical instrument 2500 by displaying or showing a warning light, among other feedback techniques such as display 43, 743 (FIGS. 2, 5B, 6). A second evaluation determines 11618 if the previous velocity of the motor 2504 was MEDIUM and if true, the control circuit 2510 auto-adjusts 11620 the velocity of the motor 2504 to SLOW and reinitiates 11602 the firing cycle at the new SLOW velocity. At the same time, the control circuit 2510 indicates 11622 the status by displaying or showing a warning light, among other feedback techniques such as display 43, 743. A third evaluation determines 11624 if the previous velocity of the motor 2504 was SLOW and if true, the control circuit 2510 forces a pause 11626 of a predetermined duration. After the predetermined pause, the control circuit 2510 reinitiates 11602 the firing cycle at the SLOW velocity. At the same time, the control circuit 2510 indicates 11628 the status by displaying or showing a warning light, among other feedback techniques such as display 43, 743. The process 11600 continues until the displacement member reaches the end of stroke.

FIG. 97 is a logic flow diagram of a process 11630 depicting a control program or logic configuration for controlling motor velocity based on stalled condition during a normal firing cycle in manual mode and reducing velocity one level once the firing cycle is restarted according to one aspect of this disclosure. Generally, when the motor stalls during a normal firing cycle while in manual mode, the control circuit reduces the velocity of the motor one level once the firing cycle is restarted. If already at the slowest speed, the control circuit forces pause of a predetermined duration before restarting the firing cycle at the slowest speed again. The user can only choose a speed that is slower than the speed at which the stall occurred for the remainder of the firing cycle. Accordingly, if the motor stalls while in manual mode, the control circuit lowers the velocity of the motor one level and locks out the previous higher motor velocities.

With reference now to FIGS. 14 and 97, according to the process 11630, the control circuit 2510 initiates 11632 a firing cycle of the displacement member and stores 11634 the current velocity of the motor (e.g., SLOW: V<10 mm/sec; MEDIUM: 10 mm/sec≤V≤12.5 mm/sec; FAST: V>12.5 mm/sec) and checks 11636 for a motor stall condition. The control circuit 2510 then determines 11638 whether the motor 2504 stalled. If the motor 2504 stalled, the control circuit 2510 continues along the NO branch and the control circuit 2510 continues 11640 the firing cycle and checks 11636 for a motor stall condition until the motor 2504 stalls. The control circuit 2510 then proceeds along the YES branch and evaluates three conditions. A first evaluation determines 11642 if the previous velocity of the motor 2504 was FAST and if true, the control circuit 2510 reduces 11644 the velocity to MEDIUM and disables, inhibits, or blocks the FAST velocity. The control circuit 2510 reinitiates 11632 the firing cycle at the new MEDIUM velocity while blocking FAST. The control circuit 2510 may indicate the status of the surgical instrument 2500 by displaying or showing a warning light, among other feedback techniques. A second evaluation determines 11646 if the previous velocity of the motor 2504 was MEDIUM and if true, the control circuit 2510 reduces 11648 the velocity of the motor 2504 to SLOW and disables, inhibits, or blocks MEDIUM and FAST velocities. The control circuit 2510 reinitiates 11632 the firing cycle at the new SLOW velocity while blocking MEDIUM and FAST velocities. The control circuit 2510 may indicate the status by displaying or showing a warning light, among other feedback techniques. A third evaluation determines 11650 if the previous velocity of the motor 2504 was SLOW and if true, the control circuit 2510 forces a pause 11652 of a predetermined duration. After the predetermined pause, the control circuit 2510 reinitiates 11632 the firing cycle at a velocity that is slower than the SLOW velocity at which the motor stall occurred for the remainder of the firing cycle. At the same time, the control circuit 2510 indicates 11628 the status by displaying or showing a warning light, among other feedback techniques. The process 11600 continues until the displacement member reaches the end of stroke.

FIG. 98 is a logic flow diagram 11660 of a process depicting a control program or logic configuration for controlling motor velocity based on stalled condition during a normal firing cycle and pausing the firing cycle until the user releases the firing trigger according to one aspect of this disclosure. Generally, when the motor stalls during a normal firing cycle, the control circuit pauses until the user (e.g., the surgeon) releases the trigger. When the firing cycle is reinitiated, the control circuit restarts at the same command velocity at which the motor stall occurred.

With reference now to FIGS. 14 and 98, according to the process 11660, the control circuit 2510 initiates 11622 a firing cycle of the displacement member and checks 11664 for a motor stall. If the motor is not stalled 11666, the control circuit 2510 continues along the NO branch and checks 11664 for a motor stall until the motor 2504 stalls. If there is a motor stall, the control circuit 2510 proceeds along the YES branch and pauses 11668 the motor 2504 and halts the firing cycle. The control circuit 2510 indicates 11674 the status and warns of a motor stall condition on a display 43, 743 (FIGS. 2, 5B, 6) and instructs the user (e.g., the surgeon) to release the trigger. The control circuit 2510 then determines 11672 if the trigger is released and continues along the NO branch until the trigger is released. The control circuit 2510 then proceeds along the YES branch and continues 11670 the firing cycle until the motor 2504 stalls or the displacement member reaches the end of stroke.

FIG. 99 is a logic flow diagram of a process 11680 depicting a control program or logic configuration for controlling motor velocity during transition between velocities according to one aspect of this disclosure. Generally, during time, distance, or velocity based control schemes, the transition from one velocity to another likely affects the target value for the next comparison. To avoid constant velocity changes triggered primarily due to changes in command velocity, the zone (or zones) immediately following the latest velocity change are excluded from consideration. In one aspect, the return velocity is always at the fastest velocity.

With reference now to FIGS. 14 and 99, according to the process 11680, the control circuit 2510 initiates 11682 a firing cycle of the displacement member and monitors 11684 the position of the displacement member based on the position sensor 2534 until the displacement member reaches a target for comparison of changes in velocity. When the displacement member reaches a target comparison position, the control circuit 2510 determines 11686 whether the previous zone initiated a change in velocity. If the previous zone initiated a change in velocity, the control circuit 2510 continues along the YES branch and continues firing 11688 at the current command velocity and monitors 11684 if the displacement member has reached a target for comparison. The process continues until the control circuit 2510 determines 11686 that the previous zone did not initiate a change in velocity. The control circuit 2510 proceeds along the NO branch and compares 11690 the expected velocity value of the displacement member with the actual velocity value of the displacement member. The control circuit 2510 sets 11692 the new command velocity of the motor 2504 for the next zone based on the results of the comparison 11690. After setting 11692 the new command velocity of the motor 2504, the control circuit determines 11694 if the displacement member is located in the final zone. If the displacement member is not located in the final zone, the control circuit 2510 continues along the NO branch and continues firing at the new command velocity and the process continues until the displacement member is located in the final zone. At this point, the control circuit 2514 continues firing 11696 until the displacement member reaches the end of stroke. Otherwise, the control circuit 2510 continues 11688 firing the displacement member at the current command velocity.

Various aspects of the subject matter described herein are set out in the following numbered examples:

Example 1. A surgical instrument, comprising: a displacement member configured to translate within the surgical instrument over a plurality of predefined zones; an energy source; a motor coupled to the displacement member to translate the displacement member; a control circuit coupled to the energy source and the motor; a position sensor coupled to the control circuit, the position sensor configured to monitor the position of the displacement member; wherein the control circuit is configured to: initiate firing the displacement member at a predetermined electrical load on the energy source, wherein the predetermined electrical load is applied to the motor to actuate the displacement member; monitor the position of the displacement member via the position sensor; continually sample a voltage of the energy source during a first interval of travel of the displacement member; compare the sampled voltage to a threshold voltage; and continue firing the displacement at the first velocity when the sampled voltage is greater than or equal to the threshold voltage; or adjust the first velocity when the sampled voltage is less than the threshold voltage.

Example 2. The surgical instrument of Example 1, wherein when the sampled voltage is less than the threshold voltage the control circuit is further configured to determine if the surgical instrument is in automatic mode or manual mode.

Example 3. The surgical instrument of Example 2, wherein when the surgical instrument is in automatic mode the control circuit is further configured to convert the operation of the surgical instrument to manual mode.

Example 4. The surgical instrument of Example 3, wherein the control circuit is further configured to reduce the command velocity to a second velocity, wherein the second velocity is slower than the first velocity.

Example 5. The surgical instrument of Example 4, wherein the second velocity is greater than zero and less than 10 mm/sec.

Example 6. The surgical instrument of Example 1 through Example 5, wherein the first interval is between 2 mm and 3 mm.

Example 7. The surgical instrument of Example 1 through Example 6, wherein the control circuit is configured to communicate status of energy source when the sampled voltage is less than the threshold voltage.

Example 8. A surgical instrument, comprising: a displacement member configured to translate within the surgical instrument; a motor comprising a shaft, the motor coupled to the displacement member to translate the displacement member; a control circuit coupled to the motor; wherein the control circuit is configured to: initiate firing the displacement member at a command velocity set to a first velocity, wherein the command velocity is the velocity applied to the motor; check for a motor stall condition; and continue firing the displacement at the first velocity when the motor is not stalled; or reduce the command velocity to a second velocity, wherein the second velocity is slower than the first velocity.

Example 9. The surgical instrument of Example 8, wherein the first velocity is between 10 mm/sec and 12 mm/sec and the second velocity is less than 9 mm/sec.

Example 10. The surgical instrument of Example 8 through Example 9, wherein the control circuit is configured to indicate a motor stall warning.

Example 11. The surgical instrument of Example 10, wherein the control circuit is configured to: set the surgical instrument in manual mode based on a received input; detect a low motor velocity condition; indicate the low motor velocity condition for a predetermined period of time; and monitor for a manual command velocity adjustment or pause; and reduce the command velocity when the manual command velocity adjustment or pause is not detected.

Example 12. The surgical instrument of Example 8 through Example 11, wherein the control circuit is configured to: store a current command velocity in memory as a fast velocity, a medium velocity, or a slow velocity, wherein the fast velocity is greater than the medium velocity and the medium velocity is greater than the slow velocity; and when a motor stall condition is detected, the control circuit is configured to: pause the motor for a first delay when the stored command velocity is a fast velocity and continue firing the displacement member at the fast velocity; pause the motor for a second when the stored command velocity is a medium velocity and continue firing the displacement member at the medium velocity; or pause the motor for a third delay when the stored command velocity is a slow velocity and continue firing the displacement member at the slow velocity; wherein the first delay is greater than second delay and the second delay is greater than the third delay.

Example 13. The surgical instrument of Example 12, wherein: the slow velocity is greater than zero and less 10 mm/sec; the medium velocity is greater than or equal to 10 mm/sec and less than or equal to 12.5 mm/sec; and the fast velocity is greater than 12.5 mm/sec and less than 15 mm/sec.

Example 14. The surgical instrument of Example 12 through Example 13, wherein: the first delay is greater than or equal to 2 seconds and less than five seconds; the second delay is greater than or equal to 1 second and less than two seconds; and the third delay greater than 0 and less than 1 second.

Example 15. The surgical instrument of Example 8 through Example 14, wherein the control circuit is configured to: store a current command velocity in memory as a fast velocity, a medium velocity, or a slow velocity, wherein the fast velocity is greater than the medium velocity and the medium velocity is greater than the slow velocity; and when a motor stall condition is detected, the control circuit is configured to: auto adjust the command velocity to a medium velocity when the stored command velocity is a fast velocity; auto adjust the command velocity to a slow velocity when the stored command velocity is a medium velocity; and pause the motor when the stored command velocity is a slow velocity.

Example 16. The surgical instrument of Example 8 through Example 15, wherein the control circuit is configured to: pause the firing store a current command velocity in memory as a fast velocity, a medium velocity, or a slow velocity, wherein the fast velocity is greater than the medium velocity and the medium velocity is greater than the slow velocity; and when a motor stall condition is detected, the control circuit is configured to: reduce the command velocity to a medium velocity and inhibit a fast velocity when the stored command velocity is a fast velocity; reduce the command velocity to a slow velocity and inhibit a medium velocity and a fast velocity when the stored command velocity is a medium velocity; and pause the motor when the stored command velocity is a slow velocity.

Example 17. The surgical instrument of Example 8 through Example 16, wherein when a motor stall condition is detected, the control circuit is configured to: pause the motor; indicate a warning of motor stall and instruct user to release trigger; monitor release of the trigger; and continue firing the displacement member when the trigger is released.

Example 18. A surgical instrument, comprising: a displacement member configured to translate within the surgical instrument over a plurality of predefined zones; an energy source; a motor coupled to the displacement member to translate the displacement member; a control circuit coupled to the energy source and the motor; a position sensor coupled to the control circuit, the position sensor configured to monitor the position of the displacement member; wherein the control circuit is configured to: initiate firing the displacement member at a command velocity set to a first velocity, wherein the command velocity is the velocity applied to the motor; monitor the position of the displacement member in a current zone until the displacement member reaches a target position for comparison; when the displacement member reaches the target position, determine whether a change in command velocity was initiated in a previous zone prior to the current zone; and continue firing the displacement member at the command velocity when a change in command velocity was initiated in the previous zone.

Example 19. The surgical instrument of Example 18, wherein when a change in command velocity was not initiated in the previous zone, the control circuit is configured to: compare an expected velocity of the displacement member to an actual velocity of the displacement member; and adjust the command velocity based on the results of the comparison.

Example 20. The surgical instrument of Example 19, wherein the control circuit is configured to: determine when the displacement is in a final zone; and continue firing the displacement member until an end of stroke is reached.

Example 21. The surgical instrument of Example 19 through Example 20, wherein the control circuit is configured to continue firing the displacement member at the current command velocity when the displacement member is not in the final zone.

Techniques for Closed Loop Control of Motor Velocity of a Surgical Stapling and Cutting Instrument FIG. 100 is a logic flow diagram depicting a process 8000 of a control program or a logic configuration for adjusting the velocity of a displacement member based on the magnitude of one or more error terms based on the difference between an actual velocity of the displacement member and a command or directed velocity of the displacement member over a specified increment of time or distance according to one aspect of this disclosure. The process 8000 may be executed by the surgical instrument 2500 (e.g., the control circuit 2510). Accordingly, with reference also to FIG. 14, the control circuit 2510 sets 8002 a directed velocity of the displacement member, such as, for example, the I-beam 2514. The directed velocity is the same as the command velocity, which is set by the control circuit 2510. For example, to set the command or directed velocity of the displacement member, the control circuit 2510 applies a motor set point 2522 to a motor control 2508 which applies a motor drive signal 2524 to the motor 2504 to advance the displacement member (e.g., I-beam 2514) through a transmission 2506. The control circuit 2510 determines 8004 the actual velocity of the displacement member utilizing feedback signals from the position sensor 2534 and the timer/counter circuit 2531. The control circuit 2510 determines 8006 the difference between the directed velocity and the actual velocity of the displacement member and controls 8008 the velocity of the displacement member based on a magnitude of the error.

In accordance with the process 8000, the error may be based on at least one of a short term error (S), cumulative error (C), rate of change error (R), and number of overshoots error (N) as described above in connection with FIGS. 16-22. In one aspect, the surgical instrument 2500 further comprises an end effector 2502, where the displacement member (e.g., I-beam 2514) is configured to translate within the end effector 2502. Further, in various aspects, the error may be determined over a predetermined increment of distance or time. In one aspect, the control circuit 2510 is configured to determine a zone in which the displacement member is located.

Various aspects of the subject matter described herein are set out in the following numbered examples:

Example 1. A method of adjusting velocity in a motorized surgical instrument, the surgical instrument comprising a displacement member configured to translate within the surgical instrument over a plurality of predefined zones, a motor coupled to the displacement member to translate the displacement member, a control circuit coupled to the motor, a position sensor coupled to the control circuit, the position sensor configured to measure the position of the displacement member, and a timer circuit coupled to the control circuit, the timer circuit configured to measure elapsed time, the method comprising: setting, by the control circuit, a directed velocity of the displacement member; determining, by the control circuit, an actual velocity of the displacement member; determining, by the control circuit, an error between the directed velocity of the displacement member and the actual velocity of the displacement member; and controlling, by the control circuit, the actual velocity of the displacement member based on the magnitude of the error.

Example 2. The method of Example 1, wherein the error is based on at least one of a short term error (S), cumulative error (C), rate of change error (R), and number of overshoots error (N).

Example 3. The method of Example 1 through Example 2, wherein the surgical instrument further comprises an end effector, wherein the displacement member is configured to translate within the end effector.

Example 4. The method of Example 1 through Example 3, wherein the error is determined over a predetermined increment of time.

Example 5. The method of Example 1 through Example 4, wherein the error is determined over a predetermined increment of distance.

Example 6. The method of Example 1 through Example 5, further comprising determining, by the control circuit, a zone in which the displacement member is located.

The functions or processes 8000, 8600, 8700, 8800, 9400, 9450, 9800, 9850, 10400, 10450, 10550, 11000, 11500, 11520, 11540, 11560, 11600, 11630, 11660, 11680 described herein may be executed by any of the processing circuits described herein, such as the control circuit 700 described in connection with FIGS. 5-6, the circuits 800, 810, 820 described in FIGS. 7-9, the microcontroller 1104 described in connection with FIGS. 10 and 12, and/or the control circuit 2510 described in FIG. 14.

Aspects of the motorized surgical instrument may be practiced without the specific details disclosed herein. Some aspects have been shown as block diagrams rather than detail. Parts of this disclosure may be presented in terms of instructions that operate on data stored in a computer memory. An algorithm refers to a self-consistent sequence of steps leading to a desired result, where a "step" refers to a manipulation of physical quantities which may take the form of electrical or magnetic signals capable of being stored, transferred, combined, compared, and otherwise manipulated. These signals may be referred to as bits, values, elements, symbols, characters, terms, numbers. These and similar terms may be associated with the appropriate physical quantities and are merely convenient labels applied to these quantities.

Generally, aspects described herein which can be implemented, individually and/or collectively, by a wide range of hardware, software, firmware, or any combination thereof can be viewed as being composed of various types of "electrical circuitry." Consequently, "electrical circuitry" includes electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer or processor configured by a computer program which at least partially carries out processes and/or devices described herein, electrical circuitry forming a memory device (e.g., forms of random access memory), and/or electrical circuitry forming a communications device (e.g., a modem, communications switch, or optical-electrical equipment). These aspects may be implemented in analog or digital form, or combinations thereof.

The foregoing description has set forth aspects of devices and/or processes via the use of block diagrams, flowcharts, and/or examples, which may contain one or more functions and/or operation. Each function and/or operation within such block diagrams, flowcharts, or examples can be implemented, individually and/or collectively, by a wide range of hardware, software, firmware, or virtually any combination thereof. In one aspect, several portions of the subject matter described herein may be implemented via Application Specific Integrated Circuits (ASICs), Field Programmable Gate Arrays (FPGAs), digital signal processors (DSPs), Programmable Logic Devices (PLDs), circuits, registers and/or software components, e.g., programs, subroutines, logic and/or combinations of hardware and software components. Logic gates, or other integrated formats. Some aspects disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

The mechanisms of the disclosed subject matter are capable of being distributed as a program product in a variety of forms, and that an illustrative aspect of the subject matter described herein applies regardless of the particular type of signal bearing medium used to actually carry out the distribution. Examples of a signal bearing medium include the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.).

The foregoing description of these aspects has been presented for purposes of illustration and description. It is not intended to be exhaustive or limiting to the precise form disclosed. Modifications or variations are possible in light of the above teachings. These aspects were chosen and described in order to illustrate principles and practical application to thereby enable one of ordinary skill in the art to utilize the aspects and with modifications as are suited to the particular use contemplated. It is intended that the claims submitted herewith define the overall scope.

The invention claimed is:

1. A surgical system, comprising:
an end effector;
a firing driver movable from a proximal position toward a distal position during a firing stroke;
a motor to drive the firing driver toward the distal position during the firing stroke; and
a control circuit, to:
initiate the firing stroke to drive the firing driver in a first mode, wherein, in the first mode, the motor is to drive the firing driver at a first speed;
detect a first motor stall condition in the first mode;
transition from the first mode to a second mode based on the detected first motor stall condition, wherein, in the second mode, the motor is to drive the firing driver at a second speed less than the first speed;
detect a second motor stall condition in the second mode; and
pause driving the firing driver toward the distal position for a period of time based on the detected second motor stall condition.

2. The surgical system of claim 1, wherein the period of time comprises a predetermined period of time.

3. The surgical system of claim 1, further comprising transition from the second mode to a third mode based on the period of time elapsing, wherein, in the third mode, the motor is to drive the firing driver at a third speed less than the second speed.

4. The surgical system of claim 1, further comprising:
an energy source to provide power to the motor; and
a voltage sensor to sense a voltage potential applied to the motor by the energy source;
wherein to detect the first motor stall condition, the control circuit is to compare the sensed voltage potential to a threshold.

5. The surgical system of claim 1, further comprising:
an energy source to provide power to the motor; and
a current sensor to sense a current applied to the motor by the energy source;
wherein to detect the first motor stall condition, the control circuit is to compare the sensed current to a threshold.

6. The surgical system of claim 1, further comprising:
an energy source to provide power to the motor;
a current sensor to sense a current applied to the motor by the energy source; and
a position sensor to measure displacement of the firing driver during the firing stroke;

wherein to detect the first motor stall condition, the control circuit is to:
compare the sensed current to an expected current;
determine a velocity of the firing driver based on the measured displacement; and
compare the determined velocity to an expected velocity.

7. The surgical system of claim 1, wherein the firing driver comprises a knife.

8. A surgical system, comprising:
an end effector;
a firing driver movable from a proximal position toward a distal position during a firing stroke;
a motor to drive the firing driver toward the distal position during the firing stroke;
a memory; and
a control circuit, to:
initiate the firing stroke to drive the firing driver in a first mode, wherein, in the first mode, the motor is to drive the firing driver at a first speed;
store, in the memory, the first speed;
detect a motor stall condition in the first mode; and
select between a first corrective action and second corrective action based on the detected motor stall condition and the stored first speed, wherein the first corrective action comprises transitioning from the first mode to a second mode in which the motor is to drive the firing driver at a second speed less than the first speed, and wherein the second corrective action comprises pausing driving the firing driver toward the distal position for a period of time.

9. The surgical system of claim 8, wherein the control circuit is further to prevent the motor from driving the firing driver at the first speed based on the detected motor stall condition.

10. The surgical system of claim 8, wherein the period of time comprises a predetermined period of time.

11. The surgical system of claim 8, further comprising:
an energy source to provide power to the motor; and
a voltage sensor to sense a voltage potential applied to the motor by the energy source;
wherein to detect the motor stall condition, the control circuit is to compare the sensed voltage potential to a threshold.

12. The surgical system of claim 8, further comprising:
an energy source to provide power to the motor; and
a current sensor to sense a current applied to the motor by the energy source;
wherein to detect the motor stall condition, the control circuit is to compare the sensed current to a threshold.

13. The surgical system of claim 8, further comprising:
an energy source to provide power to the motor;
a current sensor to sense a current applied to the motor by the energy source; and
a position sensor to measure displacement of the firing driver during the firing stroke;
wherein to detect the motor stall condition, the control circuit is to:
compare the sensed current to an expected current;
determine a velocity of the firing driver based on the measured displacement; and
compare the determined velocity to an expected velocity.

14. The surgical system of claim 8, wherein the firing driver comprises a knife.

15. A surgical system, comprising:
an end effector;
a firing driver movable from a proximal position toward a distal position during a firing stroke;
a motor to drive the firing driver toward the distal position during the firing stroke;
a memory; and
a control circuit, to:
initiate the firing stroke to drive the firing driver in a first mode, wherein, in the first mode, the motor is to drive the firing driver at a first speed;
detect a first motor stall condition in the first mode;
transition from the first mode to a second mode based on the detected first motor stall condition, wherein, in the second mode, the motor is to drive the firing driver at a second speed different than the first speed;
store, in the memory, the second speed;
detect a second motor stall condition in the second mode; and
select between a first action and second action based on the second detected motor stall condition and the stored second speed, wherein the first action comprises transitioning from the second mode to a third mode in which the motor is to drive the firing driver at a third speed different than the second speed, and wherein the second action comprises pausing driving the firing driver toward the distal position for a period of time.

16. The surgical system of claim 15, wherein the control circuit is further to:
prevent the motor from driving the firing driver at the first speed based on the detected first motor stall condition; and
prevent the motor from driving the firing driver at the first speed or the second speed based on the detected second motor stall condition.

17. The surgical system of claim 15, wherein the period of time comprises a predetermined period of time.

18. The surgical system of claim 15, further comprising:
an energy source to provide power to the motor; and
a voltage sensor to sense a voltage potential applied to the motor by the energy source;
wherein to detect the first motor stall condition, the control circuit is to compare the sensed voltage potential to a threshold.

19. The surgical system of claim 15, further comprising:
an energy source to provide power to the motor; and
a current sensor to sense a current applied to the motor by the energy source;
wherein to detect the first motor stall condition, the control circuit is to compare the sensed current to a threshold.

20. The surgical system of claim 15, further comprising:
an energy source to provide power to the motor;
a current sensor to sense a current applied to the motor by the energy source; and
a position sensor to measure displacement of the firing driver during the firing stroke;
wherein to detect the first motor stall condition, the control circuit is to:
compare the sensed current to an expected current;
determine a velocity of the firing driver based on the measured displacement; and
compare the determined velocity to an expected velocity.

* * * * *